US006670473B2

(12) United States Patent
Arnaiz et al.

(10) Patent No.: US 6,670,473 B2
(45) Date of Patent: Dec. 30, 2003

(54) N-HETEROCYCLIC DERIVATIVES AS NOS INHIBITORS

(75) Inventors: Damian O. Arnaiz, Hercules, CA (US); John J. Baldwin, Gwynedd Valley, PA (US); David D. Davey, El Sobrante, CA (US); James J. Devlin, Lafayette, CA (US); Roland Ellwood Dolle, III, King of Prussia, PA (US); Shawn David Erickson, New York, NY (US); Kirk McMillan, Trenton, NJ (US); Michael M. Morrissey, Danville, CA (US); Michael H. J. Ohlmeyer, Plainsboro, NJ (US); Gonghua Pan, Groton, CT (US); Vidyadhar Madhav Paradkar, Somerville, NJ (US); John Parkinson, Martinez, CA (US); Gary B. Phillips, Pleasant Hill, CA (US); Bin Ye, Richmond, CA (US); Zuchun Zhao, El Sobrante, CA (US)

(73) Assignees: Berlex Laboratories, Inc., Richmond, CA (US); Pharmacopeia, Inc., Cranbury, NJ (US)

( * ) Notice: Subject to any disclaimer, the term of this patent is extended or adjusted under 35 U.S.C. 154(b) by 0 days.

(21) Appl. No.: 10/121,808

(22) Filed: Apr. 12, 2002

(65) Prior Publication Data

US 2003/0078265 A1 Apr. 24, 2003

Related U.S. Application Data

(60) Division of application No. 09/383,813, filed on Aug. 26, 1999, now Pat. No. 6,432,947, which is a continuation-in-part of application No. 09/025,124, filed on Feb. 17, 1998, now abandoned, which is a continuation-in-part of application No. 08/808,975, filed on Feb. 19, 1997, now abandoned.

(51) Int. Cl.⁷ .................... C07D 473/16; C07D 473/18; C07D 239/47; C07D 239/48
(52) U.S. Cl. ................... 544/118; 544/276; 544/277
(58) Field of Search .............................. 544/277, 276, 544/118

(56) References Cited

U.S. PATENT DOCUMENTS

| | | | |
|---|---|---|---|
| 5,244,865 A | 9/1993 | Seltz et al. ................ 504/239 |
| 5,371,100 A | * 12/1994 | Itoh et al. .................. 514/381 |
| 5,426,110 A | 6/1995 | Gossett et al. ............. 514/275 |
| 5,489,591 A | 2/1996 | Kobayashi et al. ......... 514/245 |
| 5,663,334 A | 9/1997 | Sheldrake et al. .......... 544/122 |
| 6,172,005 B1 | 1/2001 | Selby et al. ................ 504/239 |

FOREIGN PATENT DOCUMENTS

| | | |
|---|---|---|
| EP | 0 257 850 A2 | 3/1988 |
| EP | 0 640 599 A1 | 3/1995 |
| WO | WO96/14842 | 5/1996 |
| WO | WO96/14844 | 5/1996 |
| WO | WO 97/16452 | * 5/1997 |
| WO | WO98/09960 | 3/1998 |

OTHER PUBLICATIONS

Lampe et al. J. Heterocyclic Chem., 31, 287 (1994).*
Feldman et al., "The Surprising Life of Nitric Oxide", *Chemical and Engineering News* (1993) 26–38.
Del Corona et al., "Synthesis and in vitro study of platelet antiaggregant activity of 2(4)–imidazol–1–yl–4(2)–cycloalkylaminopyrimidines", *Eur. J. Med. Chem.* (1991) 26(7):729–733.
Fujisawa et al., "Inducible Nitric Oxide Synthase in a Human Glioblastoma Cell Line", *J. Neurochem.*(1995) 64(1): 85–91.
Damiani et al., "Fluormetric Determination of Nitrite" *Talanta* (1986)33(8): 649–652.
Nathan, "Nitric oxide as a secretory product of mammalian cells", *FASEB Journal* (1992) 6:3052:3064.
Lampe et al., "A Novel Rearrangement of 1–(2–Aminoaryl)imidazoles", *J. Heterocyclic Chem* (1994) 31:287–291.
U.S. patent application Publication No. US2002/0010190 A1 (Davey et al.).

* cited by examiner

*Primary Examiner*—Mark L. Berch
*Assistant Examiner*—Kahsay Habte
(74) *Attorney, Agent, or Firm*—Carol J. Roth; Neil G. Miyamoto; Ronald S. Hermenau

(57) ABSTRACT

N-Heterocyclic derivatives of the formula (I):

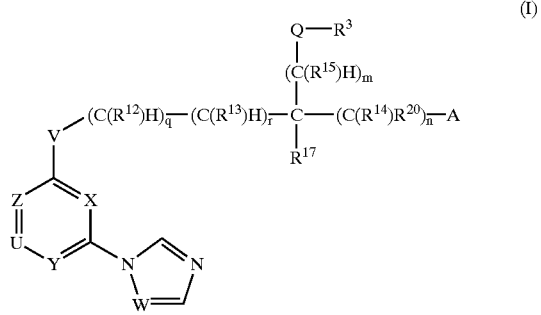

are described herein, as well as other N-heterocycles, as inhibitors of nitric oxide synthase. Pharmaceutical compositions containing these compounds, methods of using these compounds as inhibitors of nitric oxide synthase and processes for synthesizing these compounds are also described herein.

8 Claims, No Drawings

N-HETEROCYCLIC DERIVATIVES AS NOS INHIBITORS

This application is a divisional of application Ser. No. 09/383,813, filed Aug. 26, 1999, now U.S. Pat. No. 6,432,947, which is a continuation-in-part of application Ser. No. 09/025,124, filed Feb. 17, 1998, now abandoned which is a continuation-in-part of application Ser. No. 08/808,975, filed Feb. 19, 1997, now abandoned. The disclosures of these applications are incorporated by reference in full herein.

FIELD OF THE INVENTION

The invention relates to a series of N-heterocyclic compounds and derivatives useful as inhibitors of nitric oxide synthase (NOS) and to methods of therapy for various diseases employing those compounds.

BACKGROUND OF THE INVENTION

Nitrogen monoxide (NO) has been implicated in a number of diverse physiological processes, including smooth muscle relaxation, platelet inhibition, nerve transmission, immune regulation and penile erection. Nitric oxide is produced under various conditions by virtually all nucleated mammalian cells. A number of pathologies are ascribed to abnormalities in NO production including stroke, insulin dependent diabetes, septic shock-induced hypotension, rheumatoid arthritis and multiple sclerosis. Nitric oxide is synthesized in biological tissues by an enzyme called nitric oxide synthase (NOS) which uses NADPH and molecular oxygen to oxidize L-arginine to citrulline and nitric oxide.

Nitric oxide synthase (NOS) exists in at least three isoforms, which fall into two primary categories: constitutive and inducible. Two constitutive isoforms, which are calcium and calmodulin dependent, have been identified, and one inducible isoform has been identified. The constitutive isoforms are (1) a neuronal isoform, NOS-1 or nNOS, which is found in the brain and skeletal muscles and (2) an endothelial isoform, NOS-3 or eNOS, which is expressed in the endothelium of blood vessels, the epithelium of the bronchial tree and in the brain. These constitutive isoforms are not the target of the NOS inhibitors of the present invention.

The inducible isoform (NOS2 or iNOS) is expressed in virtually all nucleated mammalian cells following exposure to inflammatory cytokines or lipopolysaccharide. Its presence in macrophages and lung epithelial cells is particularly noteworthy. The inducible isoform is neither stimulated by calcium nor blocked by calmodulin antagonists. It contains several tightly bound co-factors, including FMN, FAD and tetrahydrobiopterin.

Nitric oxide generated by the inducible form of NOS has been implicated in the pathogenesis of inflammatory diseases. In experimental animals, hypotension induced by lipopolysaccharide or tumor necrosis factor a can be reversed by NOS inhibitors. Conditions which lead to cytokine-induced hypotension include septic shock, hemodialysis and interleukin therapy in cancer patients. It is expected that an iNOS inhibitor would be effective in treating cytokine-induced hypotension. In addition, recent studies have suggested a role for NO in the pathogenesis of inflammation, and NOS inhibitors would therefore have beneficial effects on inflammatory bowel disease, cerebral ischemia and arthritis. Inhibitors of NOS may also be useful in treating adult respiratory distress syndrome (ARDS) and myocarditis, and they may be useful as adjuvants to short term immunosuppression in transplant therapy.

The diversity and ubiquity of NO function in physiology make the specific therapeutic targeting of NO-related phenomena an important consideration. Since endogenous NO production is the result of the actions of related but distinct isozymes, the differential inhibition of NOS isozymes allows more selective therapy with fewer side effects.

SUMMARY OF THE INVENTION

In one aspect, the invention is directed compounds of formula (I):

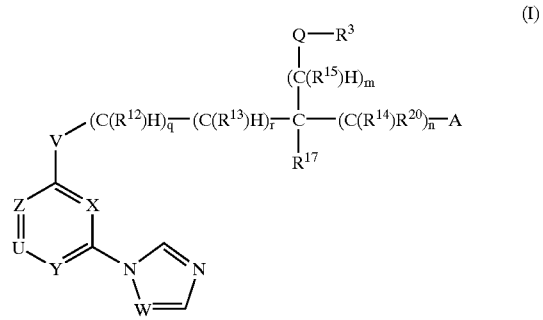

wherein:
A is —$R^1$, —$OR^1$, —C(O)N($R^1$)$R^2$, —P(O)[N($R^1$)$R^2$]$_2$, —N($R^1$)C(O)$R^2$, —N($R^{16}$)C(O)O$R^2$, —N($R^1$)$R^{21}$, —N($R^{16}$)C(O)N($R^1$)$R^{16}$, —S(O)$_t$$R^1$, —SO$_2$NHC(O)$R^1$, —N($R^1$)SO$_2$$R^{22}$, —SO$_2$N($R^1$)H, —C(O)NHSO$_2$$R^{22}$, or —CH=NO$R^1$;
each X, Y and Z are independently N or C($R^{19}$);
each U is N or G($R^5$), provided that U is N only when X is N and Z and Y are C$R^{19}$;
V is N($R^4$), S, O or C($R^4$)H;
each W is N or CH;
Q is chosen from the group consisting of a direct bond, —C(O)—, —O—, —C(=N—$R^1$)—, —S(O)$_t$, and —N($R^6$)—;
m is zero or an integer from 1 to 4;
n is zero or an integer from 1 to 3;
q is zero or one;
r is zero or one, provided that when Q and V are heteroatoms, m, q, and r cannot all be zero; when A is —$OR^1$, —N($R^1$)C(O)$R^2$, —N($R^{16}$)C(O)O$R^2$, —N($R^1$)$R^{21}$, —N($R^{16}$)C(O)N($R^1$)$R^{16}$, —S(O)$_t$$R^1$ (where t is zero), or —N($R^1$)SO$_2$$R^{22}$, n, q, and r cannot all be zero; and when Q is a heteroatom and A is —$OR^1$, —N($R^1$)C(O)$R^2$, —N($R^{16}$)C(O)O$R^2$, —N($R^1$)$R^{21}$, —N($R^{16}$)C(O)N($R^1$)$R^{16}$, —S(O)$_t$$R^1$ (when t is zero) or —N($R^1$)SO$_2$$R^{22}$, m and n cannot both be zero;
t is zero, one or two;
each $R^1$ and $R^2$ are independently chosen from the group consisting of hydrogen, optionally substituted $C_1$–$C_{20}$ alkyl, optionally substituted cycloalkyl, —[$C_0$–$C_8$ alkyl]—$R^9$, —[$C_2$–$C_8$ alkenyl]—$R^9$, —[$C_2$–$C_8$ alkynyl]—$R^9$, —[$C_2$–$C_8$ alkyl]—$R^{10}$ (optionally substituted by hydroxy), —[$C_1$–$C_8$]—$R^{11}$ (optionally substituted by hydroxy), and optionally substituted heterocyclyl;
or $R^1$ and $R^2$ together with the nitrogen atom to which they are attached is an optionally substituted N-heterocyclyl;
$R^3$ is chosen from the group consisting of hydrogen, alkyl, cycloalkyl, optionally substituted aryl, haloalkyl, —[$C_1$–$C_8$ alkyl]—C(O)N($R^1$)$R^2$, —[$C_1$–$C_8$ alkyl]—N($R^1$)$R^2$, —[$C_1$–$C_8$ alkyl]—$R^8$, —[$C_2$–$C_8$ alkyl]—$R^{10}$, —[$C_1$–$C_8$ alkyl]—$R^{11}$, and heterocyclyl (optionally substituted by one or more substituents selected from the group consisting of halo, alkyl, alkoxy and imidazolyl);

or when Q is —N(R$^6$)— or a direct bond to R$^3$, R$^3$ may additionally be aminocarbonyl, alkoxycarbonyl, alkylsulfonyl, monoalkylaminocarbonyl, dialkylaminocarbonyl and —C(=NR$^{18}$)—NH$_2$;

or —Q—R$^3$ taken together represents —C(O)OH, —C(O)N(R$^1$)R$^2$, —C(=NH)—N(R$^1$)R$^2$ or

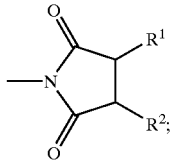

R$^4$ is chosen from the group consisting of hydrogen, alkyl, aryl, aralkyl and cycloalkyl, provided that when A is —R$^1$ or —OR$^1$, R$^4$ cannot be hydrogen, and when V is CH, R$^4$ may additionally be hydroxy;

R$^5$ is chosen from the group consisting of hydrogen, halo, alkyl, haloalkyl, optionally substituted aralkyl, optionally substituted aryl, —OR$^{16}$, —S(O)$_t$R$^{16}$, —N(R$^{16}$)R$^{21}$, —N(R$^{16}$)C(O)N(R$^1$)R$^{16}$, —N(R$^{16}$)C(O)OR$^{16}$, —N(R$^{16}$)C(O)R$^{16}$, —[C$_0$-C$_8$ alkyl]—C(O)OR$^{16}$, —[C$_0$-C$_8$ alkyl]—C(H)[C(O)OR$^{16}$]$_2$, and —[C$_0$-C$_8$ alkyl]—C(O)N(R$^1$)R$^{16}$;

R$^6$ is chosen from the group consisting of hydrogen, alkyl, cycloalkyl, —[C$_1$-C$_8$ alkyl]—R$^8$, —[C$_2$-C$_8$ alkyl]—R$^{10}$, —[C$_1$-C$_8$ alkyl]—R$^{11}$, acyl, —C(O)R$^8$, —C(O)—[C$_1$-C$_8$ alkyl]—R$^8$, alkoxycarbonyl, optionally substituted aryloxycarbonyl, optionally substituted aralkoxycarbonyl, alkylsulfonyl, optionally substituted aryl, optionally substituted heterocyclyl, alkoxycarbonylalkyl, carboxyalkyl, optionally substituted arylsulfonyl, aminocarbonyl, monoalkylaminocarbonyl, dialkylaminocarbonyl, optionally substituted arylaminocarbonyl, aminosulfonyl, monoalkylaminosulfonyl, dialkylaminosulfonyl, arylaminosulfonyl, arylsulfonylaminocarbonyl, optionally substituted N-heterocyclyl, —C(=NH)—N(CN)R$^1$, —C(O)—R$^{23}$—N(R$^1$)R$^2$, —C(O)—R$^{23}$—N(R$^1$)C(O)—R$^{23}$—N(R$^1$)R$^2$, and —C(O)—N(R$^1$)—R$^{23}$—C(O)OR$^1$;

each R$^8$ and R$^9$ are independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each R$^{10}$ is independently chosen from the group consisting of halo, alkoxy, optionally substituted aryloxy, optionally substituted aralkoxy, optionally substituted —S(O)$_t$—R$^{22}$, acylamino, amino, monoalkylamino, dialkylamino, (triphenylmethyl)amino, hydroxy, mercapto, and alkylsulfonamido;

each R$^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each R$^{12}$, R$^{13}$, R$^{14}$, R$^{15}$, R$^{17}$, and R$^{20}$ is independently hydrogen or alkyl;

each R$^{16}$ is independently hydrogen, alkyl, optionally substituted aryl, optionally substituted aralkyl or cycloalkyl;

R$^{18}$ is hydrogen, NO$_2$, or toluenesulfonyl;

each R$^{19}$ is independently hydrogen, alkyl (optionally substituted with hydroxy), cyclopropyl, halo or haloalkyl;

each R$^{21}$ is independently hydrogen, alkyl, cycloalkyl, optionally substituted aryl, optionally substituted aralkyl, —C(O)R$^{22}$ or —SO$_2$R$^{22}$;

or R$^{21}$ taken together with R$^1$ and the nitrogen to which they are attached is an optionally substituted N-heterocyclyl;

or R$^{21}$ taken together with R$^{16}$ and the nitrogen to which they are attached is an optionally substituted N-heterocyclyl;

each R$^{22}$ is independently alkyl, cycloalkyl, optionally substituted aryl or optionally substituted aralkyl; and R$^{23}$ is an amino acid residue;

as a single stereoisomer or mixture thereof, or a pharmaceutically acceptable salt thereof.

In another aspect, the invention is directed to compounds of formula (II):

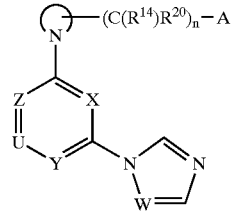

(II)

wherein:

A is —R$^1$, —OR$^1$, —C(O)N(R$^1$)R$^2$, —P(O)[N(R$^1$)R$^2$]$_2$, —N(R$^1$)C(O)R$^2$, —N(R$^{16}$)C(O)OR$^2$, —N(R$^1$)R$^{21}$, —N(R$^{16}$)C(O)N(R$^1$)R$^{16}$, —S(O)$_t$R$^1$, —SO$_2$NHC(O)R$^1$, —N(R$^1$)SO$_2$R$^{22}$, —SO$_2$N(R$^1$)H, —C(O)NHSO$_2$R$^2$, or —CH=NOR$^1$;

each X, Y and Z are independently N or C(R$^{19}$);

each U is N or C(R$^5$), provided that U is N only when X is N and Z and Y are CR$^{19}$;

each W is N or CH;

n is zero or an integer from 1 to 3;

t is zero, one or two;

is an optionally substituted N-heterocyclyl;

each R$^1$ and R$^2$ are independently chosen from the group consisting of hydrogen, optionally substituted C$_1$-C$_{20}$ alkyl, optionally substituted cycloalkyl, —[C$_0$-C$_8$ alkyl]—R$^9$, —[C$_2$-C$_8$ alkenyl]—R$^9$, —[C$_2$-C$_8$ alkynyl]—R$^9$, —[C$_2$-C$_8$ alkyl]—R$^{10}$ (optionally substituted by hydroxy), —[C$_1$-C$_8$]—R$^{11}$ (optionally substituted by hydroxy), optionally substituted heterocyclyl;

or R$^1$ and R$^2$ together with the nitrogen atom to which they are attached is an optionally substituted N-heterocyclyl;

R$^5$ is chosen from the group consisting of hydrogen, halo, alkyl, haloalkyl, optionally substituted aralkyl, optionally substituted aryl, —OR$^{16}$, —S(O)$_t$—R$^{16}$, —N(R$^{16}$)R$^{21}$, —N(R$^{16}$)C(O)N(R$^1$)R$^{16}$, —N(R$^{16}$)C(O)OR$^{16}$, —N(R$^{16}$) C(O)R$^{16}$, —[C$_0$-C$_8$ alkyl]—C(O)OR$^{16}$, —[C$_0$-C$_8$ alkyl]—C(H)[C(O)OR$^{16}$]$_2$, and —[C$_0$-C$_8$ alkyl]—C(O)N(R$^1$)R$^{16}$;

each R$^9$ is independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each R$^{10}$ is independently chosen from the group consisting of halo, alkoxy, optionally substituted aryloxy, optionally substituted aralkoxy, optionally substituted —S(O)$_t$—

$R^{22}$, acylamino, amino, monoalkylamino, dialkylamino, (triphenylmethyl)amino, hydroxy, mercapto, alkylsulfonamido;

each $R^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each $R^{14}$ and $R^{20}$ are independently hydrogen or alkyl;

each $R^{16}$ is independently hydrogen, alkyl, optionally substituted aryl, optionally substituted aralkyl or cycloalkyl;

each $R^{19}$ is independently hydrogen, alkyl (optionally substituted with hydroxy), cyclopropyl, halo or haloalkyl;

each $R^{21}$ is independently hydrogen, alkyl, cycloalkyl, optionally substituted aryl, optionally substituted aralkyl, —C(O)$R^{22}$ or —SO$_2$$R^{22}$;

or $R^{21}$ taken together with $R^1$ and the nitrogen to which they are attached is an optionally substituted N-heterocyclyl;

or $R^{21}$ taken together with $R^{16}$ and the nitrogen to which they are attached is an optionally substituted N-heterocyclyl; and each $R^{22}$ is independently alkyl, cycloalkyl, optionally substituted aryl or optionally substituted aralkyl; as a single stereoisomer or mixture thereof, or a pharmaceutically acceptable salt thereof.

In another aspect, the invention is directed to compounds of formula (III):

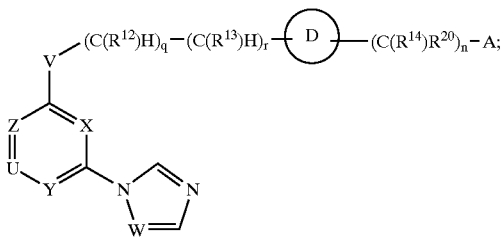

(III)

wherein:
A is —$R^1$, —O$R^1$, —C(O)N($R^1$)$R^2$, —P(O)[N($R^1$)$R^2$]$_2$, —N($R^1$)C(O)$R^2$, —N($R^{16}$)C(O)O$R^2$, —N($R^1$)$R^{21}$—N($R^{16}$)C(O)N($R^1$)$R^{16}$, —S(O)$_t$$R^1$, —SO$_2$NHC(O)$R^1$, —N($R^1$)SO$_2$$R^{22}$, —SO$_2$N($R^1$)H, —C(O)NHSO$_2$$R^{22}$, or —CH=NO$R^1$;

each X, Y and Z are independently N or C($R^{19}$);
each U is N or C($R^5$), provided that U is N only when X is N and Z and Y are CR$^{19}$;
V is N($R^4$), S, O or C($R^4$)H;
each W is N or CH;
n is zero or an integer from 1 to 3;
q is zero or one;
r is zero or one;
t is zero, one or two;

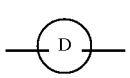

is an optionally substituted carbocyclyl or optionally substituted N-heterocyclyl;

each $R^1$ and $R^2$ are independently chosen from the group consisting of hydrogen, optionally substituted $C_1$–$C_{20}$ alkyl, optionally substituted cycloalkyl, —[$C_0$–$C_8$ alkyl]—$R^9$, —[$C_2$–$C_8$ alkenyl]—$R^9$, —[$C_2$–$C_8$ alkynyl]—$R^9$, —[$C_2$–$C_8$ alkyl]—$R^{10}$ (optionally substituted by hydroxy), —[$C_1$–$C_8$]—$R^{11}$ (optionally substituted by hydroxy), optionally substituted heterocyclyl;

or $R^1$ and $R^2$ together with the nitrogen atom to which they are attached is an optionally substituted N-heterocyclyl;

$R^4$ is chosen from the group consisting of hydrogen, alkyl, aryl, aralkyl and cycloalkyl; provided that when A is —$R^1$ or —O$R^1$, $R^4$ cannot be hydrogen, and when V is CH, $R^4$ may additionally be hydroxy;

$R^5$ is chosen from the group consisting of hydrogen, halo, alkyl, haloalkyl, optionally substituted aralkyl, optionally substituted aryl, —O$R^{16}$, —S(O)$_t$$R^{16}$, —N($R^{16}$)$R^{21}$, —N($R^{16}$)C(O)N($R^1$)$R^{16}$, —N($R^{16}$)C(O)O$R^{16}$, —N($R^{16}$)C(O)$R^{16}$, —[$C_0$–$C_8$ alkyl]—C(O)O$R^{16}$, —[$C_0$–$C_8$ alkyl]—C(H)[C(O)O$R^{16}$]$_2$, and —[$C_0$–$C_8$ alkyl]—C(O)N($R^1$)$R^{16}$;

each $R^9$ is independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each $R^{10}$ is independently chosen from the group consisting of halo, alkoxy, optionally substituted aryloxy, optionally substituted aralkoxy, optionally substituted —S(O)$_t$—$R^{22}$, acylamino, amino, monoalkylamino, dialkylamino, (triphenylmethyl)amino, hydroxy, mercapto, alkylsulfonamido;

each $R^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each $R^{12}$, $R^{13}$, $R^{14}$ and $R^{20}$ are independently hydrogen or alkyl;

each $R^{16}$ is independently hydrogen, alkyl, optionally substituted aryl, optionally substituted aralkyl or cycloalkyl;

each $R^{19}$ is independently hydrogen, alkyl (optionally substituted with hydroxy), cyclopropyl, halo or haloalkyl;

each $R^{21}$ is independently hydrogen, alkyl, cycloalkyl, optionally substituted aryl, optionally substituted aralkyl, —C(O)$R^{22}$ or —SO$_2$$R^{22}$;

or $R^{21}$ taken together with $R^{16}$ and the nitrogen to which they are attached is an optionally substituted N-heterocyclyl;

or $R^{21}$ taken together with $R^{16}$ and the nitrogen to which they are attached is an optionally substituted N-heterocyclyl; and each $R^{22}$ is independently alkyl, cycloalkyl, optionally substituted aryl or optionally substituted aralkyl;

as a single stereoisomer or mixture thereof, or a pharmaceutically acceptable salt thereof.

In another aspect, the invention is directed to compounds of formula (Ya), formula (Yb) and formula (Yc):

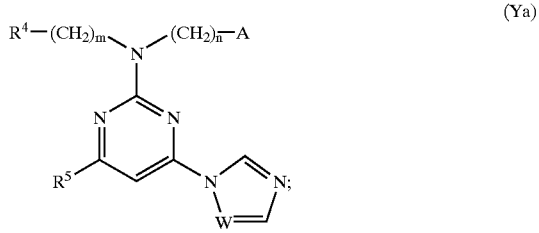

(Ya)

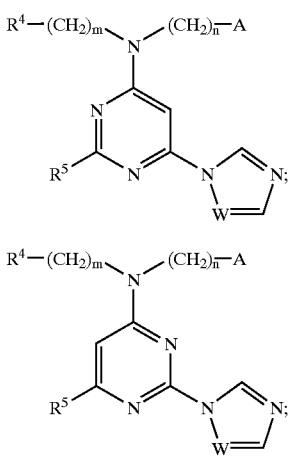

(Yb)

(Yc)

wherein:
n and m are each independently an integer from 1 to 4;
A is —C(O)OR$^1$ or —C(O)N(R$^1$)R$^2$;
each W is N or CH;
each R$^1$ is independently hydrogen, alkyl, aryl or aralkyl;
each R$^2$ is independently hydrogen, C$_0$–C$_{20}$ alkyl, —(CH$_2$)$_n$—N(R$^1$)$_2$, heterocyclylalkyl (optionally substituted by alkyl, halo, haloalkyl or alkoxy), aralkyl (optionally substituted by halo, alkyl, alkoxy, or —N(R$^1$)$_2$);
R$^4$ is hydroxy, cyano, heterocyclyl, —N(R$^1$)R$^2$, —N(R$^1$)—C(O)—R$^1$, —N(R$^1$)—C(O)OR$^1$, —N(R$^1$)—S(O)$_t$—R$^1$, or —N(R$^1$)—C(O)—N(R$^1$)$_2$;
R$^5$ is hydrogen, halo, alkyl, aryl, aralkyl, or haloalkyl;
as a single stereoisomer or mixture thereto, or a pharmaceutically acceptable salt thereof.

In another aspect, the invention is directed to compounds of formula (IV):

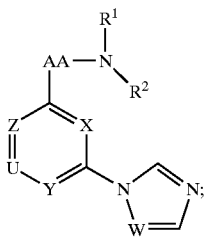

(IV)

wherein:
AA is an amino acid;
X, Y and Z are independently N or C(R$^{19}$);
U is N or C(R$^5$), provided that U is N only when X is N and Z and Y are CR$^{19}$;
W is N or CH;
R$^1$ and R$^2$ are independently chosen from the group consisting of hydrogen, optionally substituted C$_1$–C$_{20}$ alkyl, optionally substituted cycloalkyl, —[C$_0$–C$_8$ alkyl]—R$^9$, —[C$_2$–C$_8$ alkenyl]—R$^9$, —[C$_2$–C$_8$ alkynyl]—R$^9$, —[C$_2$–C$_8$ alkyl]—R$^{10}$ (optionally substituted by hydroxy), —[C$_1$–C$_8$]—R$^{11}$ (optionally substituted by hydroxy), and optionally substituted heterocyclyl;
or R$^1$ and R$^2$ together with the nitrogen atom to which they are attached is an optionally substituted N-heterocyclyl;
R$^5$ is chosen from the group consisting of hydrogen, halo, alkyl haloalkyl, optionally substituted aralkyl, optionally substituted aryl, —OR$^{16}$, —S(O)$_t$—R$^{16}$, —N(R$^{16}$)R$^{21}$, —N(R$^{16}$)C(O)N(R$^1$)R$^{16}$, —N(R$^{16}$)C(O)OR$^{16}$, —N(R$^{16}$)C(O)R$^{16}$, —[C$_0$–C$_8$ alkyl]—C(O)OR$^{16}$, —[C$_0$–C$_8$ alkyl]—C(H)[C(O)OR$^{16}$]$_2$, and —[C$_0$–C$_8$ alkyl]—C(O)N(R$^1$)R$^{16}$;

each R$^9$ is independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each R$^{10}$ is independently chosen from the group consisting of halo, alkoxy, optionally substituted aryloxy, optionally substituted aralkoxy, optionally substituted —S(O)$_t$—R$^{22}$, acylamino, amino, monoalkylamino, dialkylamino, (triphenylmethyl)amino, hydroxy, mercapto, and alkylsulfonamido;

each R$^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each R$^{16}$ is independently hydrogen, alkyl, optionally substituted aryl, optionally substituted aralkyl or cycloalkyl;

R$^{19}$ is hydrogen, alkyl (optionally substituted with hydroxy), cyclopropyl, halo or haloalkyl;

each R$^{21}$ is hydrogen, alkyl, cycloalkyl, optionally substituted aryl, optionally substituted aralkyl, —C(O)R$^{22}$ or —SO$_2$R$^{22}$;

or R$^{21}$ taken together with R$^1$ and the nitrogen to which they are attached is an optionally substituted N-heterocyclyl;

or R$^{21}$ taken together with R$^{16}$ and the nitrogen to which they are attached is an optionally substituted N-heterocyclyl;

each R$^{22}$ is independently alkyl, cycloalkyl, optionally substituted aryl or optionally substituted aralkyl; and t is zero, one or two;

as a single isomer or mixture thereof, or a pharmaceutically acceptable salt thereof.

In another aspect, the invention is directed to compounds of formula (Va), formula (Vb) and formula (Vc):

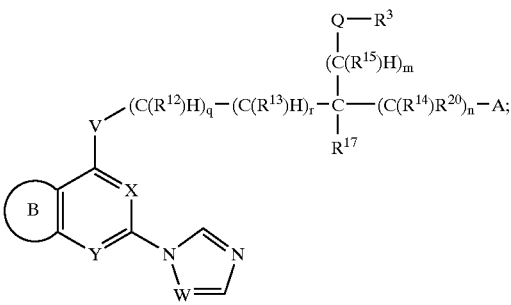

(Va)

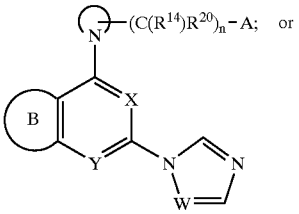

(Vb)

-continued

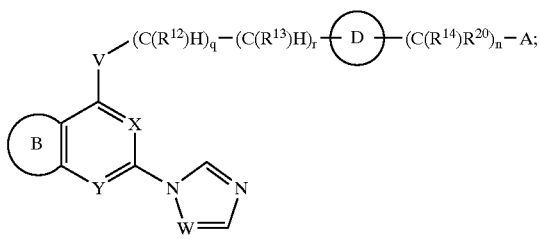

(Vc)

wherein B is a fused 5- or 6-membered optionally substituted carbocyclyl or heterocyclyl; and
wherein:
A is —R$^1$, —OR$^1$, —C(O)N(R$^1$)R$^2$, —P(O)[N(R$^1$)R$^2$]$_2$, —N(R$^1$)C(O)R$^2$, —N(R$^{16}$)C(O)OR$^2$, —N(R$^1$)R$^2$—N(R$^{16}$)C(O)N(R$^1$)R$^{16}$, —S(O)$_t$R$^1$, —SO$_2$NHC(O)R$^1$, —N(R$^1$)SO$_2$R$^{22}$, —SO$_2$N(R$^1$)H, —C(O)NHSO$_2$R$^{22}$, or —CH=NOR$^1$;
each X and Y are independently N or C(R$^{19}$);
V is N(R$^4$), S, O or C(R$^4$)H;
each W is N or CH;
Q is chosen from the group consisting of a direct bond, —C(O)—, —O—, —C(=N—R$^1$)—, —S(O)$_r$, and —N(R$^6$)—;
m is zero or an integer from 1 to 4;
n is zero or an integer from 1 to 3;
q is zero or one;
r is zero or one, provided that when Q and V are heteroatoms, m, q, and r cannot all be zero; when A is —OR$^1$, —N(R$^1$)C(O)R$^2$, —N(R$^{16}$)C(O)OR$^2$, —N(R$^1$)R$^{21}$, —N(R$^{16}$)C(O)N(R$^1$)R$^{16}$, —S(O)$_t$R$^1$ (where t is zero), or —N(R$^1$)SO$_2$R$^{22}$, n, q, and r cannot all be zero; and when Q is a heteroatom and A is —OR$^1$, —N(R$^1$)C(O)R$^2$, —N(R$^{16}$)C(O)OR$^2$, —N(R$^1$)R$^{21}$, —N(R$^{16}$)C(O)N(R$^1$)R$^{16}$, —S(O)$_t$R$^1$ (when t is zero) or —N(R$^1$)SO$_2$R$^{22}$, m and n cannot both be zero;
t is zero, one or two;

is an optionally substituted N-heterocyclyl;

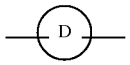

is an optionally substituted carbocyclyl or optionally substituted N-heterocyclyl;
each R$^1$ and R$^2$ are independently chosen from the group consisting of hydrogen, optionally substituted C$_1$–C$_{20}$ alkyl, optionally substituted cycloalkyl, —[C$_0$-C$_8$ alkyl]—R$^9$, —[C$_2$-C$_8$ alkenyl]—R$^9$, —[C$_2$-C$_8$ alkynyl]—R$^9$, —[C$_2$-C$_8$ alkyl]—R$^{10}$ (optionally substituted by hydroxy), —[C$_1$-C$_8$]—R$^{11}$ (optionally substituted by hydroxy), and optionally substituted heterocyclyl;
or R$^1$ and R$^2$ together with the nitrogen atom to which they are attached is an optionally substituted N-heterocyclyl;
R$^3$ is chosen from the group consisting of hydrogen, alkyl, cycloalkyl, optionally substituted aryl, haloalkyl, —[C$_1$-C$_8$ alkyl]—C(O)N(R$^1$)R$^2$, —[C$_1$-C$_8$ alkyl]—N(R$^1$)R$^2$, —[C$_1$-C$_8$ alkyl]—R$^8$, —[C$_2$-C$_8$ alkyl]—R$^{10}$, —[C$_1$-C$_8$ alkyl]—R$^{11}$, and heterocyclyl (optionally substituted by one or more substituents selected from the group consisting of halo, alkyl, alkoxy and imidazolyl);
or when Q is —N(R$^6$)— or a direct bond to R$^3$, R$^3$ may additionally be aminocarbonyl, alkoxycarbonyl, alkylsulfonyl, monoalkylaminocarbonyl, dialkylaminocarbonyl and —C(=NR$^{18}$)—NH$_2$; or —Q—R$^3$ taken together represents —C(O)OH, —C(O)N(R$^1$)R$^2$, —C(=NH)—N(R$^1$)R$^2$ or

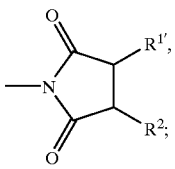

R$^4$ is chosen from the group consisting of hydrogen, alkyl, aryl, aralkyl and cycloalkyl;
provided that when A is —R$^1$ or —OR$^1$, R$^4$ cannot be hydrogen, and when V is CH, R$^4$ may additionally be hydroxy;
R$^6$ is chosen from the group consisting of hydrogen, alkyl, cycloalkyl, —[C$_1$-C$_8$ alkyl]—R$^8$, —[C$_2$-C$_8$ alkyl]—R$^{10}$, —[C$_1$-C$_8$ alkyl]—R$^{11}$, acyl, —C(O)R$^8$, —C(O)—[C$_1$-C$_8$ alkyl]—R$^8$, alkoxycarbonyl, optionally substituted aryloxycarbonyl, optionally substituted aralkoxycarbonyl, alkylsulfonyl, optionally substituted aryl, optionally substituted heterocyclyl, alkoxycarbonylalkyl, carboxyalkyl, optionally substituted arylsulfonyl, aminocarbonyl, monoalkylaminocarbonyl, dialkylaminocarbonyl, optionally substituted arylaminocarbonyl, aminosulfonyl, monoalkylaminosulfonyl, dialkylaminosulfonyl, arylaminosulfonyl, arylsulfonylaminocarbonyl, optionally substituted N-heterocyclyl, —C(=NH)—N(CN)R$^1$, —C(O)—R$^{23}$—N(R$^1$)R$^2$, —C(O)—R$^{23}$—N(R$^1$)C(O)—R$^{23}$—N(R$^1$)R$^2$, and —C(O)—N(R$^1$)—R$^{23}$—C(O)OR$^1$;
each R$^8$ and R$^9$ are independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);
each R$^{10}$ is independently chosen from the group consisting of halo, alkoxy, optionally substituted aryloxy, optionally substituted aralkoxy, optionally substituted —S(O)$_t$R$^{22}$, acylamino, amino, monoalkylamino, dialkylamino, (triphenylmethyl)amino, hydroxy, mercapto, and alkylsulfonamido;
each R$^{11}$ is independently chosen from the group consisting of cyano, di(alkoxy)alkyl, carboxy, alkoxycarbonyl, aminocarbonyl, monoalkylaminocarbonyl and dialkylaminocarbonyl;
each R$^{12}$, R$^{13}$, R$^{14}$, R$^{15}$, R$^{17}$, and R$^{20}$ are independently hydrogen or alkyl;
each R$^{16}$ is independently hydrogen, alkyl, optionally substituted aryl, optionally substituted aralkyl or cycloalkyl;
R$^{18}$ is hydrogen, NO$_2$, or toluenesulfonyl;
each R$^{19}$ is independently hydrogen, alkyl (optionally substituted with hydroxy), cyclopropyl, halo or haloalkyl;
each R$^{21}$ is independently hydrogen, alkyl, cycloalkyl, optionally substituted aryl, optionally substituted aralkyl, —C(O)R$^{22}$ or —SO$_2$R$^{22}$;
or R$^{21}$ taken together with R$^1$ and the nitrogen to which they are attached is an optionally substituted N-heterocyclyl;

or R²¹ taken together with R¹⁶ and the nitrogen to which they are attached is an optionally substituted N-heterocyclyl;

each R²² is independently alkyl, cycloalkyl, optionally substituted aryl or optionally substituted aralkyl; and R²³ is an amino acid residue;

as a single stereoisomer or mixture thereof, or a pharmaceutically acceptable salt thereof.

In another aspect, the invention is directed to compounds of formula (VIa), formula (VIb) or formula (VIc):

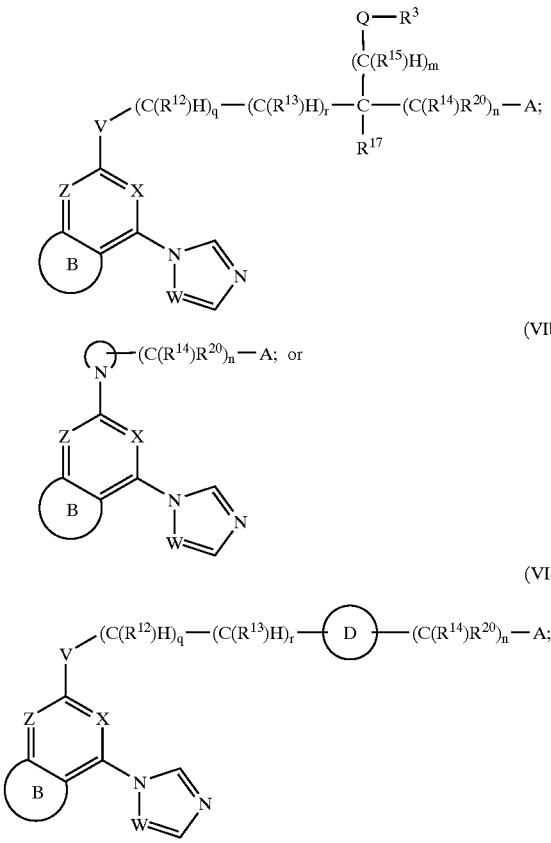

wherein B is a fused 5- or 6-membered optionally substituted carbocyclyl or heterocyclyl; and wherein:

A is —R¹, —OR¹, —C(O)N(R¹)R², —P(O)[N(R¹)R²]₂, —N(R¹)C(O)R², —N(R¹⁶)C(O)OR², —N(R¹)R²¹, —N(R¹⁶)C(O)N(R¹)R¹⁶, —S(O)ₜR¹, —SO₂NHC(O)R¹, —N(R¹)SO₂R²², —SO₂N(R¹)H, —C(O)NHSO₂R²², or —CH=NOR¹;

each X and Z are independently N or C(R¹⁹);

V is N(R⁴, S, O or C(R⁴)H;

each W is N or CH;

Q is chosen from the group consisting of a direct bond, —C(O)—, —O—, —C(=N—R¹)—, —S(O)ₜ, and —N(R⁶)—;

m is zero or an integer from 1 to 4;

n is zero or an integer from 1 to 3;

q is zero or one;

r is zero or one, provided that when Q and V are heteroatoms, m, q, and r cannot all be zero; when A is —OR¹, —N(R¹)C(O)R², —N(R¹⁶)C(O)OR², —N(R¹) R²¹, —N(R¹⁶)C(O)N(R¹)R¹⁶, —S(O)ₜR¹ (where t is zero), or —N(R¹)SO₂R, n, q, and r cannot all be zero; and when Q is a heteroatom and A is —OR¹, —N(R¹)C(O)R², —N(R¹⁶)C(O)OR², —N(R¹)R²¹, —N(R¹⁶)C(O)N(R¹) R¹⁶, —S(O)ₜR¹ (when t is zero) or —N(R¹)SO₂R²², m and n cannot both be zero;

t is zero, one or two;

is an optionally substituted N-heterocyclyl;

is an optionally substituted carbocyclyl or optionally substituted N-heterocyclyl;

each R¹ and R² are independently chosen from the group consisting of hydrogen, optionally substituted C₁–C₂₀ alkyl, optionally substituted cycloalkyl, —[C₀–C₈ alkyl]—R⁹, —[C₂–C₈ alkenyl]—R⁹, —[C₂–C₈ alkynyl]—R⁹, —[C₂–C₈ alkyl]—R¹⁰ (optionally substituted by hydroxy), —[C₁–C₈]—R¹¹ (optionally substituted by hydroxy), and optionally substituted heterocyclyl;

or R¹ and R² together with the nitrogen atom to which they are attached is an optionally substituted N-heterocyclyl;

R³ is chosen from the group consisting of hydrogen, alkyl, cycloalkyl, optionally substituted aryl, haloalkyl, —[C₁–C₈ alkyl]—C(O)N(R¹)R², —[C₁–C₈ alkyl]—N (R¹)R², —[C₁–C₃ alkyl]—R⁸, —[C₂–C₈ alkyl]—R¹⁰, —[C₁–C₈ alkyl]—R¹¹, and heterocyclyl (optionally substituted by one or more substituents selected from the group consisting of halo, alkyl, alkoxy and imidazolyl);

or when Q is —N(R⁶)— or a direct bond to R³, R³ may additionally be aminocarbonyl, alkoxycarbonyl, alkylsulfonyl, monoalkylaminocarbonyl, dialkylaminocarbonyl and —C(=NR¹⁸)—NH₂;

or —Q—R³ taken together represents —C(O)OH, —C(O) N(R¹)R², —C(=NH)—N(R¹)R² or

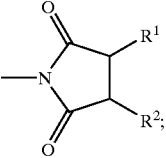

R⁴ is chosen from the group consisting of hydrogen, alkyl, aryl, aralkyl and cycloalkyl;

provided that when A is —R¹ or —OR¹, R⁴ cannot be hydrogen, and when V is CH, R⁴ may additionally be hydroxy;

R⁶ is chosen from the group consisting of hydrogen, alkyl, cycloalkyl, —[C₁–C₈ alkyl]—R⁸, —[C₂–C₈ alkyl]—R¹⁰, —[C₁–C₈ alkyl]—R¹¹, acyl, —C(O)R⁸, —C(O)—[CG–C₈ alkyl]—R⁸, alkoxycarbonyl, optionally substituted aryloxycarbonyl, optionally substituted aralkoxycarbonyl, alkylsulfonyl, optionally substituted aryl, optionally substituted heterocyclyl, alkoxycarbonylalkyl, carboxyalkyl, optionally substituted arylsulfonyl, aminocarbonyl, monoalkylaminocarbonyl, dialkylaminocarbonyl, optionally substituted arylaminocarbonyl, aminosulfonyl, monoalkylaminosulfonyl, dialkylaminosulfonyl, arylaminosulfonyl, arylsulfonylaminocarbonyl, optionally substituted N-heterocyclyl, —C(=NH)—N(CN)R$^1$, —C(O)—R$^{23}$—N(R$^1$)R$^2$, —C(O)—R$^{23}$—N(R$^1$)C(O)—R$^{23}$—N(R$^1$)R$^2$, —C(O)—N(R$^1$)—R$^{23}$—C(O)OR$^1$;

each R$^8$ and R$^9$ are independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each R$^{10}$ is independently chosen from the group consisting of halo, alkoxy, optionally substituted aryloxy, optionally substituted aralkoxy, optionally substituted —S(O)$_t$—R$^{22}$, acylamino, amino, monoalkylamino, dialkylamino, (triphenylmethyl)amino, hydroxy, mercapto, and alkylsulfonamido;

each R$^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each R$^{12}$, R$^{13}$, R$^{14}$, R$^{15}$, R$^{17}$, and R$^{20}$ are independently hydrogen or alkyl;

each R$^{16}$ is independently hydrogen, alkyl, optionally substituted aryl, optionally substituted aralkyl or cycloalkyl;

R$^{18}$ is hydrogen, NO$_2$, or toluenesulfonyl;

each R$^{19}$ is independently hydrogen, alkyl (optionally substituted with hydroxy), cyclopropyl, halo or haloalkyl;

each R$^{21}$ is independently hydrogen, alkyl, cycloalkyl, optionally substituted aryl, optionally substituted aralkyl, —C(O)R$^{22}$ or —SO$_2$R$^{22}$;

or R$^{21}$ taken together with R$^1$ and the nitrogen to which they are attached is an optionally substituted N-heterocyclyl;

or R$^{21}$ taken together with R$^{16}$ and the nitrogen to which they are attached is an optionally substituted N-heterocyclyl;

each R$^{22}$ is independently alkyl, cycloalkyl, optionally substituted aryl or optionally substituted aralkyl; and R$^{23}$ is an amino acid residue;

as a single stereoisomer or mixture thereof, or a pharmaceutically acceptable salt thereof.

In another aspect, the invention is directed to compounds of formula (VIIa), formula (VIIb), or formula (VIIc):

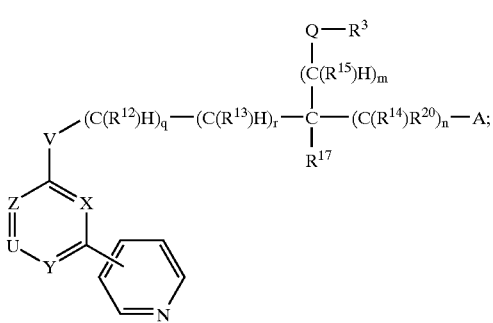

(VIIa)

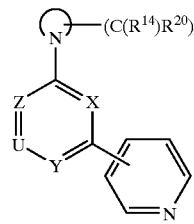

(VIIb)

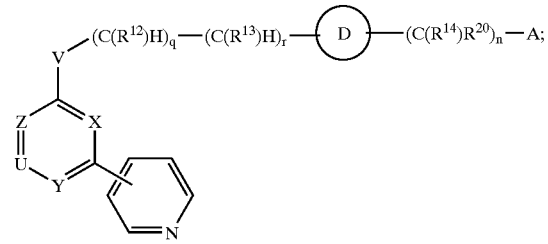

(VIIc)

wherein:

A is —R$^1$, —OR$^1$, —C(O)N(R$^1$)R$^2$, —P(O)[N(R$^1$)R$^2$]$_2$, —N(R$^1$)C(O)R$^2$, —N(R$^{16}$)C(O)OR$^2$, —N(R$^1$)R$^{21}$, —N(R$^{16}$)C(O)N(R$^1$)R$^{16}$, —S(O)$_t$R$^1$, —SO$_2$NHC(O)R$^1$, —N(R$^1$)SO$_2$R$^{22}$, —SO$_2$N(R$^1$)H, —C(O)NHSO$_2$R$^{22}$, or —CH=NOR$^1$;

each X, Y and Z are independently N or C(R$^{19}$);

each U is N or C(R$^5$), provided that U is N only when X is N and Z and Y are CR$^{19}$;

V is N(R$^4$), S, O or C(R$^4$)H;

each W is N or CH;

Q is chosen from the group consisting of a direct bond, —C(O)—, —O—, —C(=N—R$^1$)—, —S(O)$_t$, and —N(R$^6$)—;

m is zero or an integer from 1 to 4;

n is zero or an integer from 1 to 3;

q is zero or one;

r is zero or one, provided that when Q and V are heteroatoms, m, q, and r cannot all be zero; when A is —OR$^1$, —N(R$^1$)C(O)R$^2$, —N(R$^{16}$)C(O)OR$^2$, —N(R$^1$)R$^{21}$, —N(R$^{16}$)C(O)N(R$^1$)R$^{16}$, —S(O)$_t$R$^1$ (where t is zero), or —N(R$^1$)SO$_2$R$^{22}$, n, q, and r cannot all be zero; and when Q is a heteroatom and A is —OR$^1$, —N(R$^1$)C(O)R$^2$, —N(R$^{16}$)C(O)OR$^2$, —N(R$^1$)R$^{21}$, —N(R$^{16}$)C(O)N(R$^1$)R$^{16}$, —S(O)$_t$R$^1$ (when t is zero) or —N(R$^1$)SO$_2$R$^{22}$, m and n cannot both be zero;

t is zero, one or two;

is an optionally substituted N-heterocyclyl;

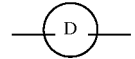

is an optionally substituted carbocyclyl or optionally substituted N-heterocyclyl;

each R$^1$ and R$^2$ are independently chosen from the group consisting of hydrogen, optionally substituted C$_1$–C$_{20}$ alkyl, optionally substituted cycloalkyl, —[C$_0$–C$_8$ alkyl]—R$^9$, —[C$_2$–C$_8$ alkenyl]—R$^9$, —[C$_2$–C$_8$ alkynyl]—R$^9$, —[C$_2$–C$_8$ alkyl]—R$^{10}$ (optionally substituted by hydroxy), —[C$_1$-C$_8$]—R$^{11}$ (optionally substituted by hydroxy), and optionally substituted heterocyclyl;

or R$^1$ and R$^2$ together with the nitrogen atom to which they are attached is an optionally substituted N-heterocyclyl;

R$^3$ is chosen from the group consisting of hydrogen, alkyl, cycloalkyl, optionally substituted aryl, haloalkyl, —[C$_1$-C$_8$ alkyl]—C(O)N(R$^1$)R$^2$, —[C$_1$-C$_8$ alkyl]—N(R$^1$)R$^2$, —[C$_1$-C$_8$ alkyl]—R$^8$, —[C$_2$-C$_8$ alkyl]—R$^{10}$, —[C$_1$-C$_8$ alkyl]—R$^{11}$, and heterocyclyl (optionally substituted by one or more substituents selected from the group consisting of halo, alkyl, alkoxy and imidazolyl);

or when Q is —N(R$^6$)— or a direct bond to R$^3$, R$^3$ may additionally be aminocarbonyl, alkoxycarbonyl, alkylsulfonyl, monoalkylaminocarbonyl, dialkylaminocarbonyl and —C(=NR$^{18}$)—NH$_2$;

or —Q—R$^3$ taken together represents —C(O)OH, —C(O)N(R$^1$)R$^2$, —C(=NH)—N(R$^1$)R$^2$ or

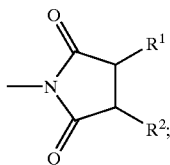

R$^4$ is chosen from the group consisting of hydrogen, alkyl, aryl, aralkyl and cycloalkyl;

provided that when A is —R$^1$ or —OR$^1$, R$^4$ cannot be hydrogen, and when V is CH, R$^4$ may additionally be hydroxy;

R$^5$ is chosen from the group consisting of hydrogen, halo, alkyl, haloalkyl, optionally substituted aralkyl, optionally substituted aryl, —OR$^{16}$, —S(O)$_t$—R$^{16}$, —N(R$^{16}$)R$^{21}$, —N(R$^{16}$)C(O)N(R$^1$)R$^{16}$, —N(R$^{16}$)C(O)OR$^{16}$, —N(R$^{16}$)C(O)R$^{16}$, —[C$_0$-C$_8$ alkyl]—C(O)OR$^{16}$, —[C$_0$-C$_8$ alkyl]—C(H)[C(O)OR$^{16}$]$_2$, and —[C$_0$-C$_8$ alkyl]—C(O)N(R$^1$)R$^{16}$;

R$^6$ is chosen from the group consisting of hydrogen, alkyl, cycloalkyl, —[C$_1$-C$_8$ alkyl]—R$^8$, —[C$_2$-C$_8$ alkyl]—R$^{10}$, —[C$_1$-C$_8$ alkyl]—R$^{11}$, acyl, —C(O)R$^8$, —C(O)—[C$_1$-C$_8$ alkyl]—R$^8$, alkoxycarbonyl, optionally substituted aryloxycarbonyl, optionally substituted aralkoxycarbonyl, alkylsulfonyl, optionally substituted aryl, optionally substituted heterocyclyl, alkoxycarbonylalkyl, carboxyalkyl, optionally substituted arylsulfonyl, aminocarbonyl, monoalkylaminocarbonyl, dialkylaminocarbonyl, optionally substituted arylaminocarbonyl, aminosulfonyl, monoalkylaminosulfonyl, dialkylaminosulfonyl, arylaminosulfonyl, arylsulfonylaminocarbonyl, optionally substituted N-heterocyclyl, —C(=NH)—N(CN)R$^1$, —C(O)—R$^{23}$—N(R$^1$)R$^2$, —C(O)—R$^{23}$—N(R$^1$)C(O)—R$^{23}$—N(R$^1$)R$^2$, and —C(O)—N(R$^1$)—R$^{23}$—C(O)OR$^1$;

each R$^8$ and R$^9$ are independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each R$^{10}$ is independently chosen from the group consisting of halo, alkoxy, optionally substituted aryloxy, optionally substituted aralkoxy, optionally substituted —S(O)$_t$R$^{22}$, acylamino, amino, monoalkylamino, dialkylamino, (triphenylmethyl)amino, hydroxy, mercapto, and alkylsulfonamido;

each R$^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each R$^{12}$, R$^{13}$, R$^{14}$, R$^{15}$, R$^{17}$, and R$^{20}$ are independently hydrogen or alkyl;

each R$^{16}$ is independently hydrogen, alkyl, optionally substituted aryl, optionally substituted aralkyl or cycloalkyl;

R$^{18}$ is hydrogen, NO$_2$, or toluenesulfonyl;

each R$^{19}$ is independently hydrogen, alkyl (optionally substituted with hydroxy), cyclopropyl, halo or haloalkyl;

each R$^{21}$ is independently hydrogen, alkyl, cycloalkyl, optionally substituted aryl, optionally substituted aralkyl, —C(O)R$^{22}$ or —SO$_2$R$^{22}$;

or R$^{21}$ taken together with R$^1$ and the nitrogen to which they are attached is an optionally substituted N-heterocyclyl;

or R$^{21}$ taken together with R$^{16}$ and the nitrogen to which they are attached is an optionally substituted N-heterocyclyl;

each R$^{22}$ is independently alkyl, cycloalkyl, optionally substituted aryl or optionally substituted aralkyl; and R$^{23}$ is an amino acid residue;

as a single stereoisomer or mixture thereof, or a pharmaceutically acceptable salt thereof.

In another aspect, the invention is directed to compounds of formula (VIII):

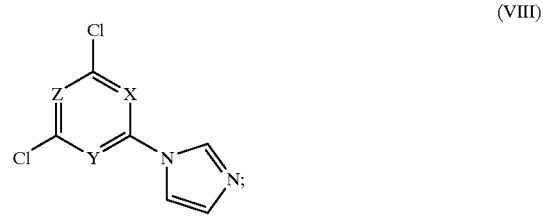

(VIII)

wherein two of X, Y and Z are nitrogen and the third is CH.

In another aspect, the invention provides compounds of formula (IXa), formula (IXb), or formula (IXc):

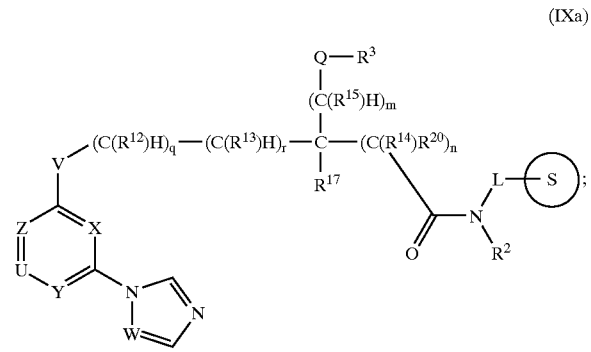

(IXa)

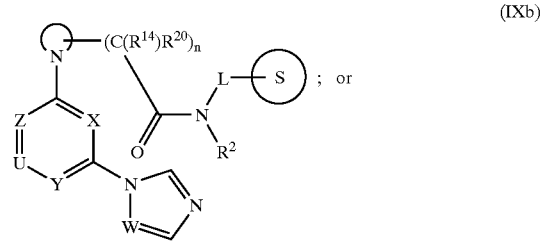

(IXb)

; or

-continued (IXc)

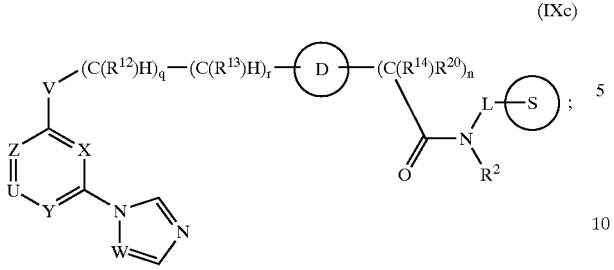

wherein:

is a solid support;
L is a linker residue;
each X, Y and Z are independently N or $C(R^{19})$;
each U is N or $C(R^5)$, provided that U is N only when X is N and Z and Y are $CR^{19}$;
V is $N(R^4)$, S, O or $C(R^4)H$;
each W is N or CH;
Q is chosen from the group consisting of a direct bond, —C(O)—, —O—, —C(=N—$R^1$)—, —S(O)$_t$— and —N($R^6$)—;
m is zero or an integer from 1 to 4;
n is zero or an integer from 1 to 3;
q is zero or one;
r is zero or one, provided that when Q and V are heteroatoms, m, q, and r cannot all be zero;
t is zero, one or two;

is an optionally substituted N-heterocyclyl;

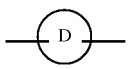

is an optionally substituted carbocyclyl or optionally substituted N-heterocyclyl;
each $R^2$ is independently chosen from the group consisting of hydrogen, optionally substituted $C_1$–$C_{20}$ alkyl, optionally substituted cycloalkyl, —[$C_0$–$C_8$ alkyl]—$R^9$, —[$C_2$–$C_8$ alkenyl]—$R^9$, —[$C_2$–$C_8$ alkynyl]—$R^9$, —[$C_2$–$C_8$ alkyl]—$R^{10}$ (optionally substituted by hydroxy), —[$C_1$–$C_8$]—$R^{11}$ (optionally substituted by hydroxy), and optionally substituted heterocyclyl;
$R^3$ is chosen from the group consisting of hydrogen, alkyl, cycloalkyl, optionally substituted aryl, haloalkyl, —[$C_1$–$C_8$ alkyl]—C(O)N($R^1$)$R^2$, —[$C_1$–$C_8$ alkyl]—N($R^1$)$R^2$, —[$C_1$–$C_8$ alkyl]—$R^8$, —[$C_2$–$C_8$ alkyl]—$R^{10}$, —[$C_1$–$C_8$ alkyl]—$R^{11}$, and heterocyclyl (optionally substituted by one or more substituents selected from the group consisting of halo, alkyl, alkoxy and imidazolyl);
or when Q is —N($R^6$)— or a direct bond to $R^3$, $R^3$ may additionally be aminocarbonyl, alkoxycarbonyl, alkylsulfonyl, monoalkylaminocarbonyl, dialkylaminocarbonyl and —C(=N$R^{18}$)—NH$_2$;
or —Q—$R^3$ taken together represents —C(O)OH, —C(O)N($R^1$)$R^2$, —C(=NH)—N($R^1$)$R^2$ or

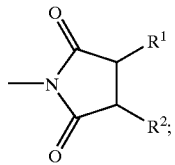

$R^4$ is chosen from the group consisting of hydrogen, alkyl, aryl, aralkyl and cycloalkyl;
provided that when A is —$R^1$ or —O$R^1$, $R^4$ cannot be hydrogen, and when V is CH, $R^4$ may additionally be hydroxy;
$R^5$ is chosen from the group consisting of hydrogen, halo, alkyl, haloalkyl, optionally substituted aralkyl, optionally substituted aryl, —O$R^{16}$, —S(O)$_t$—$R^{16}$, —N($R^{16}$)$R^{21}$, —N($R^{16}$)C(O)N($R^1$)$R^{16}$, —N($R^{16}$)C(O)O$R^{16}$, —N($R^{16}$)C(O)$R^{16}$, —[$C_0$–$C_8$ alkyl]—C(O)O$R^{16}$, —[$C_0$–$C_8$ alkyl]—C(H)[C(O)O$R^{16}$]$_2$, and —[$C_0$–$C_8$ alkyl]—C(O)N($R^1$)$R^{16}$;
$R^6$ is chosen from the group consisting of hydrogen, alkyl, cycloalkyl, —[$C_1$-CB alkyl]—$R^8$, —[$C_2$–$C_8$ alkyl]—$R^{10}$, —[$C_1$–$C_8$ alkyl]—$R^{11}$, acyl, —C(O)$R^8$, —C(O)—[$C_1$–$C_8$ alkyl]—$R^8$, alkoxycarbonyl, optionally substituted aryloxycarbonyl, optionally substituted aralkoxycarbonyl, alkylsulfonyl, optionally substituted aryl, optionally substituted heterocyclyl, alkoxycarbonylalkyl, carboxyalkyl, optionally substituted arylsulfonyl, aminocarbonyl, monoalkylaminocarbonyl, dialkylaminocarbonyl, optionally substituted arylaminocarbonyl, aminosulfonyl, monoalkylaminosulfonyl, dialkylaminosulfonyl, arylaminosulfonyl, arylsulfonylaminocarbonyl, optionally substituted N-heterocyclyl, —C(=NH)—N(CN)$R^1$, —C(O)—$R^{23}$—N($R^1$)$R^2$, —C(O)—$R^{23}$—N($R^1$)C(O)—$R^{23}$—N($R^1$)$R^2$, and —C(O)—N($R^1$)—$R^{23}$—C(O)O$R^1$;
each $R^8$ and $R^9$ are independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);
each $R^{10}$ is independently chosen from the group consisting of halo, alkoxy, optionally substituted aryloxy, optionally substituted aralkoxy, optionally substituted —S(O)$_t$—$R^{22}$, acylamino, amino, monoalkylamino, dialkylamino, (triphenylmethyl)amino, hydroxy, mercapto, and alkylsulfonamido;
each $R^{11}$ is independently chosen from the group consisting of cyano, di(alkoxy)alkyl, carboxy, alkoxycarbonyl, aminocarbonyl, monoalkylaminocarbonyl and dialkylaminocarbonyl;
each $R^{12}$, $R^{13}$, $R^{14}$, $R^{15}$, $R^{17}$, and $R^{20}$ are independently hydrogen or alkyl;
each $R^{16}$ is independently hydrogen, alkyl, optionally substituted aryl, optionally substituted aralkyl or cycloalkyl;
$R^{18}$ is hydrogen, NO$_2$, or toluenesulfonyl;
each $R^{19}$ is independently hydrogen, alkyl (optionally substituted with hydroxy), cyclopropyl, halo or haloalkyl;
each $R^{21}$ is independently hydrogen, alkyl, cycloalkyl, optionally substituted aryl, optionally substituted aralkyl, —C(O)$R^{22}$ or —SO$_2R^{22}$;
or $R^{21}$ taken together with $R^{16}$ and the nitrogen to which they are attached is an optionally substituted N-heterocyclyl;
each $R^{22}$ is independently alkyl, cycloalkyl, optionally substituted aryl or optionally substituted aralkyl; and $R^{23}$ is an amino acid residue;

as a single stereoisomer or mixture thereof, or a pharmaceutically acceptable salt thereof.

In another aspect, the invention is directed to pharmaceutical compositions comprising a compound of formula (I), formula (II), formula (III), formula (IV), formula (Ya), formula (Yb), formula (Yc), formula (Va), formula (Vb), formula (Vc), formula (VIa), formula (VIb), formula (VIc), formula (VIIa), formula (VIIb), or formula (VIIc) as described above, and a pharmaceutically acceptable carrier.

In another aspect, the invention is directed to processes for synthesizing compounds of formula (I), formula (II) and formula (III) as described above: comprising the sequential steps of:

(a) reacting one equivalent of a compound of formula (XI):

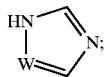
(XI)

where W is N or CH;

with about one equivalent of an chloro-substituted compound of formula (XII):

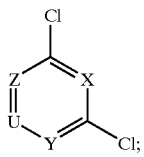
(XII)

where X, Y and Z are independently N or $C(R^{19})$;

U is N or $C(R^5)$, provided that U is N only when X is N and Z and Y are $CR^{19}$, and provided that X, Y and Z can not all be $C(R^{19})$ when U is $C(R^5)$;

$R^5$ is chosen from the group consisting of hydrogen, halo, alkyl, haloalkyl, optionally substituted aralkyl, optionally substituted aryl, —$OR^{16}$, —$S(O)_t$—$R^{16}$, —$N(R^{16})R^{21}$, —$N(R^{16})C(O)N(R^1)R^{16}$, —$N(R^{16})C(O)OR^{16}$, —$N(R^{16})C(O)R^{16}$, —[$C_0$-$C_8$ alkyl]—$C(O)OR^{16}$, —[$C_0$-$C_8$ alkyl]—$C(H)[C(O)OR^{16}]_2$, and —[$C_0$-$C_8$ alkyl]—$C(O)N(R^1)R^{16}$;

each $R^{16}$ is independently hydrogen, alkyl, optionally substituted aryl, optionally substituted aralkyl or cycloalkyl;

each $R^{19}$ is independently hydrogen, alkyl (optionally substituted with hydroxy), cyclopropyl, halo or haloalkyl;

each $R^{21}$ is independently hydrogen, alkyl, cycloalkyl, optionally substituted aryl, optionally substituted aralkyl, —$C(O)R^{22}$ or —$SO_2R^{22}$;

or $R^{21}$ taken together with $R^{16}$ and the nitrogen to which they are attached is an optionally substituted N-heterocyclyl; and each $R^{22}$ is independently alkyl, cycloalkyl, optionally substituted aryl or optionally substituted aralkyl;

to produce a compound of formula (XII):

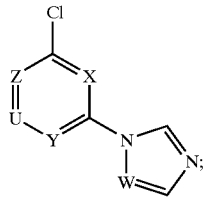
(XIII)

(b) reacting said compound of formula (XIII) with a compound of formula (XIVa), formula (XIVb), or formula (XIVc):

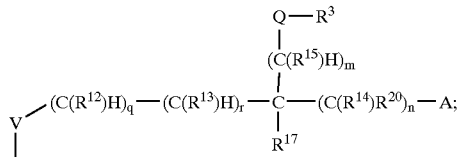
(XIVa)

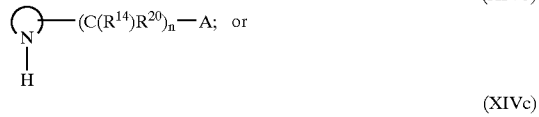
(XIVb)

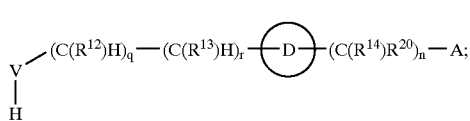
(XIVc)

wherein:

A is —$R^1$, —$OR^1$, —$C(O)N(R^1)R^2$, —$P(O)[N(R^1)R^2]_2$, —$N(R^1)C(O)R^2$, —$N(R^{16})C(O)OR^2$, —$N(R^1)R^{21}$, —$N(R^{16})C(O)N(R^1)R^{16}$, —$S(O)_tR^1$, —$SO_2NHC(O)R^1$, —$N(R^1)SO_2R^{22}$, —$SO_2N(R^1)H$, —$C(O)NHSO_2R^{22}$, or —CH=$NOR^1$;

V is $N(R^4)$, S, or O;

Q is chosen from the group consisting of a direct bond, —C(O)—, —O—, —C(=N—$R^1$)—, —$S(O)_t$, and —$N(R^6)$—;

m is zero or an integer from 1 to 4;

n is zero or an integer from 1 to 3;

q is zero or one;

r is zero or one, provided that when Q and V are heteroatoms, m, q, and r cannot all be zero; when A is —$OR^1$, —$N(R^1)C(O)R^2$, —$N(R^{16})C(O)OR^2$, —$N(R^1)R^{21}$, —$N(R^{16})C(O)N(R^1)R^{16}$, —$S(O)_tR^1$ (where t is zero), or —$N(R^1)SO_2R^{22}$, n, q, and r cannot all be zero; and when Q is a heteroatom and A is —$OR^1$, —$N(R^1)C(O)R^2$, —$N(R^{16})C(O)OR^2$, —$N(R^1)R^{21}$, —$N(R^{16})C(O)N(R^1)R^{16}$, —$S(O)_tR^1$ (when t is zero) or —$N(R^1)SO_2R^{22}$, m and n cannot both be zero;

t is zero, one or two;

is an optionally substituted N-heterocyclyl;

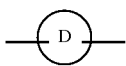

is an optionally substituted carbocyclyl or optionally substituted N-heterocyclyl; each $R^1$ and $R^2$ are independently chosen from the group consisting of hydrogen, optionally substituted $C_1$–$C_{20}$ alkyl, optionally substituted cycloalkyl, —[$C_0$–$C_8$ alkyl]—$R^9$, —[$C_2$–$C_8$ alkenyl]—$R^9$, —[$C_2$–$C_8$ alkynyl]—$R^9$, —[$C_2$–$C_3$ alkyl]—$R^{10}$ (optionally substituted by hydroxy), —[$C_1$–$C_8$]—$R^{11}$ (optionally substituted by hydroxy), and optionally substituted heterocyclyl;

or $R^1$ and $R^2$ together with the nitrogen atom to which they are attached is an optionally substituted N-heterocyclyl;

$R^3$ is chosen from the group consisting of hydrogen, alkyl, cycloalkyl, optionally substituted aryl, haloalkyl, —[$C_1$–$C_8$ alkyl]—C(O)N($R^1$)$R^2$, —[$C_1$–$C_8$ alkyl]—N($R^1$)$R^2$, —[$C_1$–$C_8$ alkyl]—$R^8$, —[$C_2$-CB alkyl]—$R^{10}$, —[$C_1$–$C_8$ alkyl]—$R^{11}$, and heterocyclyl (optionally substituted by one or more substituents selected from the group consisting of halo, alkyl, alkoxy and imidazolyl);

or when Q is —N($R^6$)— or a direct bond to $R^3$, $R^3$ may additionally be aminocarbonyl, alkoxycarbonyl, alkylsulfonyl, monoalkylaminocarbonyl, dialkylaminocarbonyl and —C(=N$R^{18}$)—NH$_2$;

or —Q—$R^3$ taken together represents —C(O)OH, —C(O)N($R^1$)$R^2$, —C(=NH)—N($R^1$)$R^2$ or

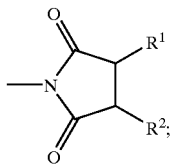

$R^4$ is chosen from the group consisting of hydrogen, alkyl, aryl, aralkyl and cycloalkyl;

provided that when A is —$R^1$ or —O$R^1$, $R^4$ cannot be hydrogen, and when V is CH, $R^4$ may additionally be hydroxy;

$R^4$ is chosen from the group consisting of hydrogen, alkyl, cycloalkyl, —[$C_1$–$C_8$ alkyl]—$R^8$, —[$C_2$–$C_8$ alkyl]—$R^{10}$, —[$C_1$–$C_8$ alkyl]—$R^{11}$, acyl, —C(O)$R^8$, —C(O)—[$C_1$–$C_8$ alkyl]—$R^8$, alkoxycarbonyl, optionally substituted aryloxycarbonyl, optionally substituted aralkoxycarbonyl, alkylsulfonyl, optionally substituted aryl, optionally substituted heterocyclyl, alkoxycarbonylalkyl, carboxyalkyl, optionally substituted arylsulfonyl, aminocarbonyl, monoalkylaminocarbonyl, dialkylaminocarbonyl, optionally substituted arylaminocarbonyl, aminosulfonyl, monoalkylaminosulfonyl, dialkylaminosulfonyl, and arylaminosulfonyl, arylsulfonylaminocarbonyl, optionally substituted N-heterocyclyl, —C(=NH)—N(CN)$R^1$, —C(O)—$R^{23}$—N($R^1$)$R^2$, —C(O)—$R^{23}$—N($R^1$)C(O)—$R^{23}$—N($R^1$)$R^2$, —C(O)—N($R^1$)—$R^{23}$—C(O)O$R^1$;

each $R^8$ and $R^9$ are independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each $R^{10}$ is independently chosen from the group consisting of halo, alkoxy, optionally substituted aryloxy, optionally substituted aralkoxy, optionally substituted —S(O)$_t$—$R^{22}$, acylamino, amino, monoalkylamino, dialkylamino, (triphenylmethyl)amino, hydroxy, mercapto, and alkylsulfonamido;

each $R^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each $R^{12}$, $R^{13}$, $R^{14}$, $R^{15}$, $R^{17}$, and $R^{20}$ are independently hydrogen or alkyl;

each $R^{16}$ is independently hydrogen, alkyl, optionally substituted aryl, optionally substituted aralkyl or cycloalkyl;

$R^{18}$ is hydrogen, NO$_2$, or toluenesulfonyl;

each $R^{21}$ is independently hydrogen, alkyl, cycloalkyl, optionally substituted aryl, optionally substituted aralkyl, —C(O)$R^{22}$ or —SO$_2$$R^{22}$;

or $R^{21}$ taken together with $R^1$ and the nitrogen to which they are attached is an optionally substituted N-heterocyclyl;

or $R^{21}$ taken together with $R^{16}$ and the nitrogen to which they are attached is an optionally substituted N-heterocyclyl;

each $R^{22}$ is independently alkyl, cycloalkyl, optionally substituted aryl or optionally substituted aralkyl; and $R^{23}$ is an amino acid residue;

to produce a compound of formula (I), formula (II) or formula (III) as described above.

In another aspect, the invention is directed to processes for synthesizing a compound of formula (I), formula (II) and formula (III) as described above; comprising photolytically cleaving the compound of formula (IXa), formula (IXb) or formula (IXc):

(IXa)

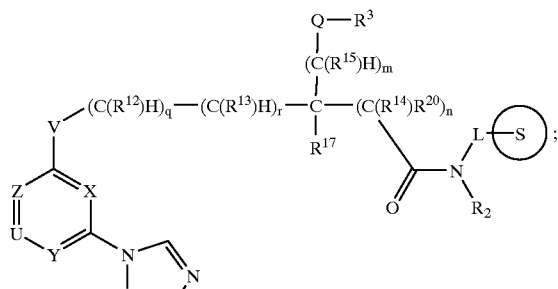

(IXb)

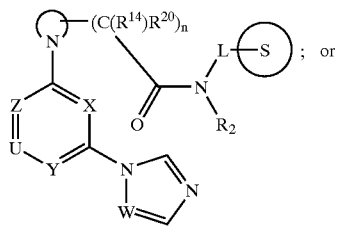

(IXc)

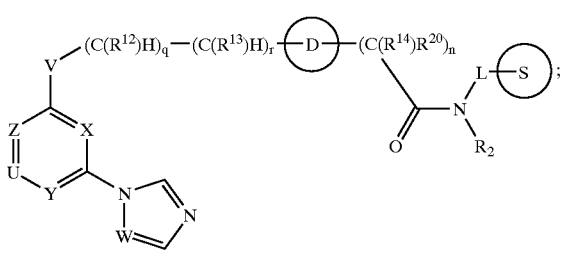

wherein:

U, V, W, X, Y, Z, $R^2$, $R^3$, $R^{12}$, $R^{13}$, $R^{14}$, $R^{15}$, $R^{17}$ and $R^{20}$ are as defined above for compounds of formula (I), formula (II) or formula (III);

is a solid support;
and L is a linker residue of formula (IX):

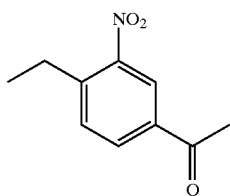

(X)

wherein the unsatisfied valence on the right of the formula represents the point of attachment to the solid substrate and the unsatisfied valence on the left of the formula represents the point of attachment to the ligand;

to form the compound of formula (I), formula (II) and formula (III) as defined above.

In another aspect, the invention is directed to methods of treating a condition resulting from an abnormality in nitric oxide production which comprises administering to a mammal having a condition resulting from an abnormality in nitric oxide production a therapeutically effective amount of compound of formula (I), formula (II), formula (III), formula (IV), formula (Ya), formula (Yb), formula (Yc), formula (Va), formula (Vb), formula (Vc), formula (VIa), formula (VIb), formula (VIc), formula (VIIa), formula (VIIb), or formula (VIIc) as described above.

DETAILED DESCRIPTION OF THE INVENTION

Definitions

As used in this specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Alkyl radicals having more than eight carbon atoms are indicated herein by the notation "[$C_x$–$C_y$ alkyl]" where x and y indicate the number of carbons present. Alkyl radicals may be optionally substituted by one or more substituents independently selected from the group consisting of halo, hydroxy, alkoxy, carboxy, cyano, carbonyl, alkoxycarbonyl, cyano, amino, monoalkylamino, dialkylamino, nitro, alkylthio, amidino, aryl, heterocyclyl, aryloxy, aralkoxy, acylamino, aminocarbonyl, monoalkylaminocarbonyl, and dialkylaminocarbonyl.

"Alkenyl" refers to a straight or branched chain monovalent or divalent radical consisting solely of carbon and hydrogen, containing at least one double bond and having from one to eight carbon atoms, e.g., ethenyl, prop-1-enyl, but-1-enyl, pent-1-enyl, penta-1,4-dienyl, and the like.

"Alkynyl" refers to a straight or branched chain monovalent or divalent radical consisting solely of carbon and hydrogen, containing at least one triple bond and having from one to eight carbon atoms, e.g., ethynyl, prop-1-ynyl, but-1-ynyl, pent-1-ynyl, pent-3-ynyl, and the like.

"Alkoxy" refers to a radical of the formula —$OR_a$ where $R_a$ is an alkyl radical as defined above, e.g., methoxy, ethoxy, propoxy, and the like.

"Alkoxycarbonyl" refers to a radical of the formula —$C(O)OR_a$ where $R_a$ is an alkyl radical as defined above, e.g., methoxycarbonyl, ethoxycarbonyl, n-propoxycarbonyl, and the like.

"Alkoxycarbonylalkyl" refers to a radical of the formula —$R_a$—$C(O)OR_a$ where each $R_a$ is independently an alkyl radical as defined above, e.g., 2-(methoxycarbonyl)ethyl, 3-(ethoxycarbonyl)propyl, 4-(n-propoxycarbonyl)butyl, and the like.

"Alkylsulfonylamino" refers to a radical of the formula —$N(H)S(O)_2$—$R_a$ where $R_a$ is an alkyl radical as defined above, e.g., methylsulfonylamino, ethylsulfonylamino, and the like.

"Alkylsulfonyl" refers to a radical of the formula —$S(O)_2$—$R_a$ where $R_a$ is an alkyl radical as defined above, e.g., methylsulfonyl, ethylsulfonyl, and the like.

"Alkylthio" refers to a radical of the formula —S—$R_a$ where $R_a$ is an alkyl radical as defined above, e.g., methylthio, ethylthio, n-propylthio, and the like.

"Amidino" refers to a radical of the formula —C(NH)—$NH_2$.

"Amino" refers to a radical of the formula —$NH_2$.

"Aminocarbonyl" refers to a radical of the formula —$C(O)NH_2$.

"Aminosulfonyl" refers to a radical of the formula —$S(O)_2NH_2$.

"Aryl" refers to a phenyl or naphthyl radical. The aryl radical may be optionally substituted by one or more substituents selected from the group consisting of hydroxy, mercapto, halo, alkyl, alkenyl, alkynyl, phenyl, phenylalkyl, phenylalkenyl, alkoxy, phenoxy, phenylalkoxy, haloalkyl, haloalkoxy, formyl, nitro, cyano, cycloalkyl, hydroxyalkyl, alkoxyalkyl, phenoxyalkyl, phenylalkoxyalkyl, amidino, ureido, alkoxycarbonyamino, amino, monoalkylamino, dialkylamino, monophenylamino, monophenylalkylamino, sulfonylamino, akylsulfonylamino, aminoalkyl, monoalkylaminoalkyl, dialkylaminoalkyl, monophenylaminoalkyl, monophenylalkylaminoalkyl, acyl, carboxyalkyl, alkoxycarbonylalkyl, aminocarbonyl, monoalkylaminocarbonyl, dialkylaminocarbonyl, aminocarbonylalkyl, monoalkylaminocarbonylalkyl, and dialkylaminocarbonylalkyl, as defined herein.

"Aralkyl" refers to a radical of the formula —$R_aR_b$ where $R_a$ is an alkyl radical as defined above and $R_b$ is an aryl radical as defined above, e.g., benzyl, and the like. The aryl radical may be optionally substituted as described above.

"Aryloxy" refers to a radical of the formula —$OR_b$ where $R_b$ is an aryl radical as defined above, e.g., phenoxy and naphthoxy, and the like. The aryl radical may be optionally substituted as described above.

"Aryloxycarbonyl" refers to a radical of the formula —$C(O)OR_b$ where $R_b$ is an aryl radical as defined above, e.g., phenoxycarbonyl.

"Aralkoxy" refers to a radical of the formula —$OR_c$ where $R_c$ is an aralkyl radical as defined above, e.g., benzyloxy, and the like. The aralkyl radical may be optionally substituted as described above.

"Aralkoxycarbonyl" refers to a radical of the formula —$C(O)OR_c$ where $R_c$ is an aralkyl radical as defined above, e.g., benzyloxycarbonyl, and the like. The aralkyl radical may be optionally substituted as described above.

"Arylaminocarbonyl" refers to a radical of the formula —$C(O)N(R_b)H$ where $R_b$ is an aryl radical as defined above, e.g., phenylaminocarbonyl, and the like. The aryl radical may be optionally substituted as described above.

"Arylaminosulfonyl" refers to a radical of the formula —S(O)$_2$N(R$_b$)H where R$_b$ is an aryl radical as defined above, e.g., phenylaminosulfonyl, and the like. The aryl radical may be optionally substituted as described above.

"Arylsulfonyl" refers to a radical of the formula —S(O)$_2$—R$_b$ where R$_b$ is an aryl radical as defined above, e.g., phenylsulfonyl, and the like. The aryl radical may be optionally substituted as described above. "Arylsulfonylaminocarbonyl" refers to a radical of the formula —C(O)N(H)S(O)$_2$R$_b$ where R$_b$ is an aryl radical as defined above, e.g., phenylsulfonylaminocarbonyl, and the like. The aryl radical may be optionally substituted as described above.

"Acyl" refers to a radical of the formula —C(O)—R$_a$ and —C(O)R$_b$ where R$_a$ is an alkyl radical as defined above and R$_b$ is an aryl radical as defined above, e.g., acetyl, propionyl, benzoyl, and the like.

"Acylamino" refers to a radical of the formula —N(H)—C(O)—R$_a$ and —N(H)—C(O)—R$_b$ where R$_a$ is an alkyl radical as defined above and R$_b$ is an aryl radical as defined above, e.g., acetylamino, benzoylamino and the like.

"Alkylene" refers to straight or branched chain divalent radical consisting solely of carbon and hydrogen, containing no unsaturation and having from one to eight carbon atoms, e.g., methylene, ethylene, propylene, n-butylene, and the like. The alkylene radical may be optionally substituted by one or more substituents selected from the group consisting of alkyl, hydroxy, —N(R$^{16}$)R$^{21}$ or —C(O)N(R$^1$)R$^{16}$ where R$^1$, R$^{16}$ and R$^{21}$ are as defined above in the Summary of the Invention.

"Amino acid" refers to a divalent radical of the formula —N(R$^4$)—R$^{23}$—C(O)— where R$^4$ is as described above in the Summary of the Invention for R$^4$ and R$^{23}$ is an amino acid residue. "Amino acid residue" refers to the alkylene chain between the nitrogen atom and the carboxy group, which is substituted by the various "side chains" of the known amino acids. For example, amino acid residues of α-amino acids include the α-carbon (to which the carboxy group and the nitrogen atom is attached) and the side chain. For example, the amino acid residue of alanine is —C(CH$_3$)—; the amino acid residue of serine is —C(CH$_2$OH)—, and so forth. The term "amino acid" is therefore intended to include α-amino acids, β-amino acids, γ-amino acids, and so forth, and all optical isomers thereof. Examples of such amino acids include alanine, asparagine, N-β-trityl-asparagine, aspartic acid, aspartic acid-β-t-butyl ester, arginine, N$^g$M-Mtr-arginine, cysteine, S-tritylcysteine, glutamic acid, glutamic acid-γ-t-butyl ester, glutamine, N-γ-trityl-glutamine, glycine, histidine, N$^{im}$-trityl-histidine, isoleucine, leucine, lysine, N$^ε$-Boc-lysine, methionine, phenylalanine, proline, serine, O-t-butyl-serine, threonine, tryptophan, N$^{im}$-Boc-tryptophan, tyrosine, valine, sarcosine, L-alanine, chloro-L-alanine, 2-aminoisobutyric acid, 2-(methylamino)isobutyric acid, D,L-3-aminoisobutyric acid, (R)-(−)-2-aminoisobutyric acid, (S)-(+)-2-aminoisobutyric acid, D-leucine, L-leucine, D-norvaline, L-norvaline, L-2-amino-4-pentenoic acid, D-isoleucine, L-isoleucine, D-norleucine, 2,3-diaminopropionic acid, L-norleucine, D,L-2-aminocaprylic acid, β-alanine, D,L-3-aminobutyric acid, 4-aminobutyric acid, 4-(methylamino)butyric acid, 5-aminovaleric acid, 5-aminocaproic acid, 7-aminoheptanoic acid, 8-aminocaprylic acid, 11-aminodecanoic acid, 12-aminododecanoic acid, carboxymethoxyamine, D-serine, D-homoserine, L-homoserine, D-allothreonine, L-allothreonine, D-threonine, L-threonine, D,L-4-amino-3-hydroxybutyric acid, D-,L-3-hydroxynorvaline, (3S,4S)-(−)-statine, 5-hydroxy-D,L-lysine, 1-amino-1-cyclopropanecarboxylic acid, 1-amino-1-cyclopentanecarboxylic acid, 1-amino-1-cyclohexanecarboxylic acid, 5-amino-1,3-cyclohexadiene-1-carboxylic acid, 2-amino-2-norbornanecarboxylic acid, (S)-(−)-2-azetidinecarboxylic acid, cis-4-hydroxy-D-proline, cis-4-hydroxy-L-proline, trans-4-hydroxy-L-proline, 3,4-dehydro-D,L-proline, 3,4-dehydro-L-proline, D-pipecolinic acid, L-pipecolinic acid, nipecotic acid, isonipecotic acid, mimosine, 2,3-diaminopropionic acid, D,L-2,4-diaminobutyric acid, (S)-(+)-diaminobutyric acid, D-ornithine, L-ornithine, 2-methylornithine, N-ε-methyl-L-lysine, N-methyl-D-aspartic acid, D,L-2-methylglutamic acid, D,L-2-aminoadipic acid, D-2-aminoadipic acid, L-2-aminoadipic acid, (+/−)-3-aminoadipic acid, D-cysteine, D-penicillamine, L-penicillamine, D,L-homocysteine, S-methyl-L-cysteine, L-methionine, D-ethionine, L-ethionine, S-carboxymethyl-L-cysteine, (S)-(+)-2-phenylglycine, (R)-(−)-2-phenylglycine, N-phenylglycine, N-(4-hydroxyphenyl)glycine, D-phenylalanine, thienylalanine, (S)-(−)indoline-2-carboxylic acid, α-methyl, D,L-phenylalanine, β-methyl-D,L-phenylalanine, D-homophenylalanine, L-homophenylalanine, D,L-2-fluorophenylglycine, D,L-2-fluorophenylalanine, D,L-3-fluorophenylalanine, D,L-4-fluorophenylalanine, D,L-4-chlorophenylalanine, L4-chlorophenylalanine, 4-bromo-D, L-phenylalanine, 4-iodo-D-phenylalanine, 3,3',5-triiodo-L-thyronine, (+)-3,3',5-triiodo-L-thyronine, D-thyronine, L-thyronine, D,L-m-tyrosine, D-4-hydroxyphenylglycine, D-tyrosine, L-tyrosine, O-methyl-L-tyrosine, 3-fluoro-D,L-tyrosine, 3-iodo-L-tyrosine, 3-nitro-L-tyrosine, 3,5-diiodo-L-tyrosine, D,L-dopa, L-dopa, 2,4,5-trihydroxyphenyl-D,L-alanine, 3-amino-L-tyrosine, 4-amino-D-phenylalanine, 4-amino-L-phenylalanine, 4-amino-D,L-phenylalanine, 4-nitro-L-phenylalanine, 4-nitro-D,L-phenylalanine, 3,5-dinitro-L-tyrosine, D,L-α-methyltyrosine, L-α-methyltyrosine, (−)-3-(3,4-dihydroxyphenyl)-2-methyl-L-alanine, D,L-threo-3-phenylserine, trans-4-(aminomethyl) cyclohexane carboxylic acid, 4-(aminomethyl)benzoic acid, D,L-3-aminobutyric acid, 3-aminocyclohexane carboxylic acid, cis-2-amino-1-cyclohexane carboxylic acid, γ-amino-β-(p-chlorophenyl)butyric acid (Baclofen), D,L-3-aminophenylpropionic acid, 3-amino-3-(4-chlorophenyl) propionic acid, 3-amino-3-(2-nitrophenyl)propionic acid, and 3-amino-4,4,4-trifluorobutyric acid.

"Carbocyclyl" refers to a stable 3- to 15-membered ring radical consisting solely of carbon and hydrogen atoms. For purposes of this invention, the carbocyclyl radical may be a monocyclic, bicyclic or tricyclic ring system, and may include fused or bridged ring systems, and the ring system may be partially or fully saturated or aromatic, and the carbon atoms in the ring system may be optionally oxidized. Examples of such carbocyclyl radicals include, but are not limited to, cycloalkyl radicals (as defined herein), norbornane, norbornene, adamantyl, bicyclo[2.2.2]octane, phenyl, naphthalenyl, insanely, indenyl, azulenyl, fluorenyl, anthracenyl, and the like. The carbocyclyl ring may be substiuted by R$^6$ as described above in the Summary of the Invention, or by one or more substituents selected from the group consisting of hydroxy, mercapto, halo, alkyl, alkenyl, alkynyl, phenyl, phenylalkyl, phenylalkenyl, alkoxy, phenoxy, phenylalkoxy, haloalkyl, haloalkoxy, formyl, nitro, cyano, cycloalkyl, hydroxyalkyl, alkoxyalkyl, phenoxyalkyl, phenylalkoxyalkyl, amidino, ureido, alkoxycarbonyamino, amino, monoalkylamino, dialkylamino, monophenylamino, monophenylalkylamino, sulfonylamino, akylsulfonylamino, aminoalkyl, monoalkylaminoalkyl, dialkylaminoalkyl, monophenylaminoalkyl, monophenylalkylaminoalkyl, acyl, carboxyalkyl, alkoxycarbonylalkyl, aminocarbonyl, monoalkylaminocarbonyl, dialkylaminocarbonyl, aminocarbonylalkyl, monoalkylaminocarbonylalkyl, and dialkylaminocarbonylalkyl, as defined herein.

"Cycloalkyl" refers to a stable 3- to 10-membered monocyclic or bicyclic radical which is saturated, and which consist solely of carbon and hydrogen atoms, e.g., cyclopropyl, cyclobutyl, cyclobutyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, halo, hydroxy, amino, cyano, nitro, alkoxy, carboxy and alkoxycarbonyl.

"Carboxy" refers to the radical of the formula —C(O)OH.

"Carboxyalkyl" refers to a radical of the formula —$R_a$—C(O)OH where $R_a$ is an alkyl radical as defined above, e.g., carboxymethyl, 2-carboxyethyl, 3-carboxypropyl, and the like.

"Di(alkoxy)alkyl" refers to a radical of the formula —$R_a$(—$OR_a$)$_2$ where each $R_a$ is independently an alkyl radical as defined above and where the —$OR_a$ groups may be attached to any carbon in the $R_a$ group, e.g., 3,3-dimethoxypropyl, 2,3-dimethoxypropyl, and the like.

"Dialkylamino" refers to a radical of the formula —N($R_a$)$R_a$ where each $R_a$ is independently an alkyl radical as defined above, e.g., dimethylamino, diethylamino, (methyl)(ethyl)amino, and the like.

"Dialkylaminocarbonyl" refers to a radical of the formula —C(O)N($R_a$)$R_a$ where each $R_a$ is independently an alkyl radical as defined above, e.g., dimethylaminocarbonyl, methylethylaminocarbonyl, diethylaminocarbonyl, dipropylaminocarbonyl, ethylpropylaminocarbonyl, and the like.

"Dialkylaminosulfonyl" refers to a radical of the formula —S(O)$_2$N($R_a$)$R_a$ where each $R_a$ is independently an alkyl radical as defined above, e.g., dimethylaminosulfonyl, methylethylaminosulfonyl, diethylaminosulfonyl, dipropylaminsulfonyl, ethylpropylaminosulfonyl, and the like.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —$OR_d$ where $R_d$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated or aromatic. The heterocyclyl radical may be attached to the main structure at any heteroatom or carbon atom which results in the creation of a stable compound. Examples of such heterocyclyl radicals include, but are not limited to, azepinyl, azetidinyl, acridinyl, benzimidazolyl, benzodioxolyl, benzodioxanyl, benzothiazolyl, benzoxazolyl, benzopyranyl, benzofuranyl, benzothienyl, carbazolyl, cinnolinyl, decahydroisoquinolyl, dioxolanyl, furyl, isothiazolyl, quinuclidinyl, imidazolyl, imidazolinyl, imidazolidinyl, isothiazolidinyl, indolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, perhydroazepinyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, tetrahydropyranyl, tetrahydroisoquinolyl, thienyl, thiomorpholinyl, thiomorpholinyl sulfoxide, and thiomorpholinyl sulfone. The heterocyclyl radical may be optionally substituted by $R^6$ as defined above in the Summary of the Invention or may be optionally substituted by one or more substituents selected from the group consisting of hydroxy, mercapto, halo, alkyl, alkenyl, alkynyl, phenyl, phenylalkyl, phenylalkenyl, alkoxy, phenoxy, phenylalkoxy, haloalkyl, haloalkoxy, formyl, nitro, cyano, amidino, cycloalkyl, hydroxyalkyl, alkoxyalkyl, phenoxyalkyl, phenylalkoxyalkyl, amidino, ureido, alkoxycarbonyamino, amino, monoalkylamino, dialkylamino, monophenylamino, monophenylalkylamino, aminoalkyl, monoalkylaminoalkyl, dialkylaminoalkyl, monophenylaminoalkyl, monophenylalkylaminoalkyl, alkylcarbonyl, carboxyalkyl, alkoxycarbonylalkyl, aminocarbonyl, monoalkylaminocarbonyl, dialkylaminocarbonyl, aminocarbonylalkyl, monoalkylaminocarbonylalkyl, dialkylaminocarbonylalkyl, and imidazolyl, as defined herein.

"Heterocyclylalkyl" refers to a radical of the formula —$R_a$—$R_e$ where $R_a$ is an alkyl radical as defined above and $R_e$ is a heterocyclyl radical as defined above, e.g., 2-(1,3-benzodioxol-5-yl)ethyl, and 3-(1,4-benzodioxan-6-yl)propyl, and the like.

"Linker residue" refers to any component capable of being selectively cleaved to release the residue of the compound of the invention from the solid support. See, e.g., Greene and Wuts, *Protective Groups in Organic Synthesis*, 2nd ed., Wiley (1991). Specific linker residues and cleavage reagents for them are depicted in Table 7 below.

"Monoalkylamino" refers to, a radical of the formula —N(H)$R_a$ where $R_a$ is an alkyl radical as defined above, e.g., methylamino, ethylamino, propylamino, and the like.

"Monoalkylaminocarbonyl" refers to a radical of the formula —C(O)N(H)$R_a$ where $R_a$ is an alkyl radical as defined above, e.g., methylaminocarbonyl, ethylaminocarbonyl, propylaminocarbonyl, and the like.

"Monoalkylaminosulfonyl" refers to a radical of the formula —S(O)$_2$N(H)$R_a$ where $R_a$ is an alkyl radical as defined above, e.g., methylaminosulfonyl, ethylaminosulfonyl, propylaminosulfonyl, and the like.

"N-heterocyclyl" refers to a heterocyclyl radical as defined above which contains at least one nitrogen atom and which is attached to the main structure through the nitrogen atom. The N-heterocyclyl radical may contain up to three additional hetero atoms. Examples include piperidinyl, piperazinyl, pyrrolidinyl, morpholinyl, thiomorpholinyl, azetidinyl, indolyl, pyrrolyl, imidazolyl, tetrahydroisoquinolyl, perhydroazepinyl, tetrazolyl, triazolyl, oxazinyl, and the like, and may be optionally substituted as described above for heterocyclyl radicals. In addition to being optionally substituted by the substituents listed above for a heterocyclyl radical, the N-heterocyclyl radical may also be optionally substituted by $R^6$ as defined above in the Summary of the Invention.

"Phenylalkyl" refers to an alkyl radical as defined above substituted by a phenyl radical, e.g., benzyl, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term "—[$C_2$–$C_8$ alkyl]—$R^{10}$ (optionally substituted by hydroxy)" means that the alkyl has the optional substitution. The same goes for the term "—[$C_1$–$C_8$ alkyl]—$R^{11}$ (optionally substituted by hydroxy)". The term "optionally substituted —S(O)$_r$$R^{22}$" means that the $R^{22}$ substituents all have the optional substitution.

"Phenylalkenyl" refers to an alkenyl radical as defined above substituted by a phenyl radical.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

"Solid support" refers to the material upon which synthesis of the compounds of the invention may be performed, and may be also referred to herein as beads or resins. The term "solid support" is intended to include beads, pellets, disks, fibers, gels, or particles such as celluslose beads, pore-glass beads, silica gels, polysteyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and soluble supports such as low molecular weight non-cross-linked polystyrene.

"Therapeutically effective amount" refers to that amount of a compound of the invention which, when administered to a human in need thereof, is sufficient to effect treatment, as defined below, for conditions resulting from an abnormality in nitric oxide production. The amount of a compound of the invention which constitutes a "therapeutically effective amount" will vary depending on the compound, the condition and its severity, and the age of the human to be treated, but can be determined routinely by one of ordinary skill in the art having regard to his own knowledge and to this disclosure.

"Treating" or "treatment" as used herein covers the treatment of a condition in a human, which condition results from an abnormality in nitric oxide production, and includes:

(i) preventing the condition from occurring in a human, in particular, when such human is predisposed to the condition but has not yet been diagnosed as having it (ii) inhibiting the condition, i.e., arresting its development, or (iii) relieving the condition, i.e., causing regression of the condition.

The yield of each of the reactions described herein is expressed as a percentage of the theoretical yield.

Most of the compounds described herein contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein is a modified form of the I.U.P.A.C. nomenclature system wherein the compounds of the invention are named herein as amide derivatives. For example, the following compound of the invention:

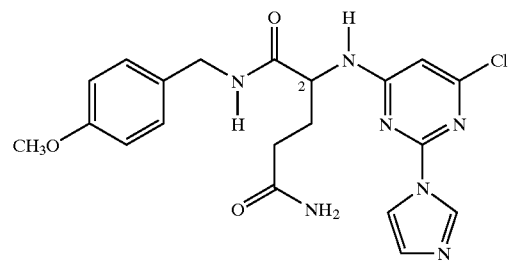

is named herein as 2-[[6-chloro-2-(1H-imidazol-1-yl)pyrimidin-4-yl]amino]-N-[(4-methoxyphenyl)methyl] pentanediamide. Unless otherwise indicated, compound names are intended to include any single stereoisomer, enantiomer, racemate or mixtures thereof.

Utility of the Compounds of the Invention

Nitric oxide generated by the inducible form of nitric oxide synthase (i-NOS) has been implicated in the pathogenesis of numerous inflammatory and autoimmune diseases and also in diseases which are generally not regarded as inflammatory, but nevertheless may involve cytokines which locally up-regulate i-NOS. The compounds of the invention, alone or in combination with other pharmaceutical agents, are therefore useful in treating mammals, preferably humans, having a condition resulting from an abnormality in nitric oxide production. Such conditions include, but are not limited to, the following:

Multiple sclerosis (Parkinson, J. F. et al., *J. Mol. Med.* (1997), Vol. 75, pp. 174–186); stroke or cerebral ischemia (Iadecola, C. et al., *J. Neurosci.* (1997), Vol. 17, pp. 9157–9164); Alzheimer's disease (Smith, M. A. et al., *J. Neurosci.* (1997), Vol. 17, pp.2653–2657; Wallace, M. N. et al., *Exp. Neurol.* (1997), Vol. 144, pp. 266–272); HIV dementia (Adamson D. C. et al., *Science* (1996), Vol. 274, pp. 1917–1921); Parkinson's disease (Hunot, S. et al., *Neuroscience* (1996), Vol. 72, pp. 355–363); meningitis (Koedel, U. et al., *Ann. Neurol.* (1995), Vol. 37, pp. 313–323); dilated cardiomyopathy and congestive heart failure (Satoh M et al.,*J. Am. Coll. Cardiol.* (1997), Vol. 29, pp. 716–724); atherosclerosis (Wilcox, J. N. et al., *Arterioscler. Thromb. Vasc. Biol.* (1997), Vol. 17, pp. 2479–2488); restenosis or graft stenosis, septic shock and hypotension (Petros, A. et al., *Cardiovasc. Res.* (1994), Vol. 28, pp. 34–39); hemorrhagic shock (Thiemermann, C. et al., *Proc. Natl. Acad. Sci.* (1993), Vol. 90, pp. 267–271); asthma (Barnes, P. J.,*Ann. Med.* (1995), Vol. 27, pp. 389–393; Flak, T. A. et al., *Am. J. Respir. Crit. Care Med.* (1996), Vol. 154, pp. S202-S206); adult respiratory distress syndrome, smoke or particulate-mediated lung injury (Ischiropoulos, H. et al., *Am. J. Respir. Crit. Care Med.* (1994), Vol. 150, pp. 337–341; Van Dyke, K., *Agents Actions* (1994), Vol. 41, pp. 4449); pathogen-mediated pneumonias (Adler, H. et al., *J. Exp. Med.* (1997), Vol. 185, pp. 1533–1540); trauma of various etiologies (Thomae, K. R. et al., *Surgery* (1996), Vol. 119, pp. 61–66); rheumatoid arthritis and osteoarthritis (Grabowski, P. S. et al., *Br. J. Rheumatol.* (1997), Vol. 36, pp. 651–655); glomerulonephritis (Weinberg, J. B. et al.,*J. Exp. Med.* (1994), Vol. 179, pp. 651–660); systemic lupus erythematosus (Belmont, H. M. et al., *Arthritis Rheum.* (1997), Vol. 40, pp. 1810–1816); inflammatory bowel diseases such as ulcerative colitis and Crohn's disease (Godkin, A. J. et al., *Eur. J. Clin. Invest.* (1996), Vol. 26, pp. 867–872; Singer, I. I. et al., *Gastroenterology* (1996), Vol. 111, pp. 871–885); insulin dependent diabetes mellitus (McDaniel, M. L., et al., *Proc. Soc. Exp. Biol. Med.* (1996), Vol. 211, pp. 24–32); diabetic neuropathy or nephropathy (Sugimoto, K. and Yagihashi, S., *Microvasc. Res.* (1997), Vol. 53, pp. 105–112; Amore, A. et al., *Kidney Int.* (1997), Vol. 51, pp. 27–35); acute and chronic organ transplant rejection (Worrall, N. K et al., *Transplantation* (1997), Vol. 63, pp. 1095–1101); transplant vasculopathies (Russell, M. E. et al., (1995), Vol. 92, pp. 457464); graft-versus-host disease (Kichian, K. et al., *J. Immunol.* (1996), Vol. 157, pp. 2851–2856); psoriasis and other inflammatory skin diseases (Bruch-Gerharz, D. et al.,*J. Exp. Med.* (1996), Vol. 184, pp. 2007–2012); and cancer (Thomsen, L. L. et al., *Cancer Res.* (1997), Vol. 57, pp. 3300–3304).

The compounds of the current invention may also be useful for the management of male and female reproductive functions when used alone or combined with other drugs commonly used for these indications. Examples, without implied limitation, include: inhibition of fertilization, endometrial receptivity and implantation (alone or in combination with a progesterone antagonist); post-coital contraception (alone or in combination with a progesterone antagonist); induction of abortion (in combination with an antiprogestin and in further combination with a prostaglandin); control and management of labor and delivery; treatment of cervical incompetence (alone or in combination with progesterone or a progestin); treatment of endometriosis (alone or in combination with other drugs, including LHRH-agonists/antagonists, antiprogestins or progestins by either sequential application or by concomitant administration). See, for example, the following references: Chwalisz, K et al., *J. Soc. Gynecol. Invest.* (1997), Vol. 4, No. 1 (Supplement), page 104a, which discusses the inhibition of fertilization, endometrial receptivity and implantation, or post-coital contraception, alone or in combination with a progesterone antagonist; Chwalisz, K. et al., *Prenat. Neonat. Med.* (1996), Vol. 1, pp. 292–329, which discusses the induction of abortion, in combination with an antiprogestin and in further combination with a prostaglandin, and the control and management of labor and delivery; and Chwalisz, K. et al., *Hum. Reprod.* (1997), vol. 12, pp. 101–109, which discusses the treatment of cervial incompetence, alone or in combination with progesterone or a progestin.

Those skilled in the art will also recognize that the compounds of the present invention include 1-substituted imidazoles. This class of compounds has previously been described as mechanism-based, heme-binding inhibitors of the cytochrome P450 family of enzymes (Maurice, M. et al., *FASEB J.* (1992), Vol. 6, pp. 7528) in addition to nitric oxide synthesis (Chabin, R. N M. et al., *Biochemistry* (1996), Vol. 35, pp. 9567–9575). The compounds of the present invention may thus be useful as inhibitors of selected cytochrome P450 family members of therapeutic interest including, but not limited to, P450 enzymes involved in steroid and retinoid biosynthesis (Masamura et al., *Breast Cancer Res. Treat.* (1995), Vol. 33, pp. 19–26; Swart, P. et al., *J. Clin. Endocnnol. Metab.*, Vol. 77, pp. 98–102; Docks, P. et al., *Br. J. Dermatol.* (1995), Vol. 133, pp. 426–32) and cholesterol biosynthesis (Burton, P. M. et al., *Biochem. Pharmacol.* (1995), Vol. 50, pp. 529–544; and Swinney, D. C. et al., *Biochemistry* (1994), Vol. 33, pp. 4702–4713). Imidazole-based compounds may also have antifungal activity (Aoyama, Y. et al., *Biochem. Pharmacol.* (1992), Vol. 44, pp. 1701–1705). The P450 inhibitory activity of the compounds of the present invention can be assessed using appropriate assay systems specific for the P450 isoform of interest. Such assays are included in the references cited above. One additional example of mammalian cytochrome P450 isoform that may be inhibited by the compounds of the present invention is cytochrome P450 3A4 which can be assayed in a manner similar to the method described in Yamazaki et al., *Carcinogenesis* (1995), Vol. 16, pp. 2167–2170.

Testing of the Compounds of the Invention

Nitric oxide synthases are complex enzymes that catalyze the conversion of L-arginine to nitric oxide (NO) and citrulline. Catalysis proceeds through two successive oxidations of the guanidinium group of L-arginine.

A cell-based nitric oxide synthase assay employing the measurement of nitric oxide oxidation product, nitrite, in the conditioned medium of cultured cells was employed for the evaluation of the compounds of the invention. The murine monocytic cell lines RAW 264.7 and J774 are well documented as capable of producing >10 $\mu$M nitrite in response to immunostimulation:

Induction of INOS in RAW 264.7 Mouse Monocytes

RAW 264.7 murine macrophage cells were obtained from American Type Culture Collection (Rockville, Md.) and were maintained in RPMI 1640 containing 10% fetal bovine serum (FBS), 5000 units/mL of penicillin and streptomycin, and 2 mM glutamine (maintenance medium). NOS activity was measured by a fluorescent assay of the nitric oxide oxidation product, nitrite, (Diamani et at., *Talanta* (1986), Vol. 33, pp. 649652). Induction of iNOS (inducible nitric oxide synthase) is stimulated by treatment of the cells with lipopolysaccharide and $\gamma$-interferon. The method of the assay is described below.

Cells are harvested, diluted to 500,000 cells/mL with maintenance medium, and seeded into 96 well plates at 100

μM/well. The plates are incubated overnight at 37° C, under a 5% $CO_2$ atmosphere. The medium is then replaced with 90 μl of BME medium containing 10% FBS, 100 units/mL of penicillin, 100 μl streptomycin, 2 mM glutamine, 100 units/mL of interferon-γ and 2 μg/mL of lipopoly-saccharide. N-guanidino-methyl-L-arginine is added to four wells (negative control) at a final concentration of 200 μM using 10 μl of 2 mM stock solution in 100 mM Hepes, pH 7.3+0.1% DMSO and four wells receive only the 100 mM Hepes/0.1% DMSO buffer (positive control). Compounds for evaluation are dissolved at 10-fold the desired final concentration in Hepes/DMSO and 10 μL of these solutions is transferred to the 96-well plate. The plates are incubated for 17 hrs at 37° C., under a 5% $CO_2$ atmosphere. Nitrite accumulated in the culture medium is determined as follows: add 15 μL of 2,3-diaminonaphthalene (10 μg/mL in 0.75 M HCl) to each well and incubate for 10 minutes at room temperature. Add 15 μl of 1 N NaOH and measure the fluorescence emission at 405 nm, using an excitation wavelength of 365 nm. Enzyme activity in experimental wells is normalized to percent control using the positive and negative control values. The signal to noise ratio is >10 for the assay.

The compounds of the invention, when tested in this assay, demonstrated the ability to inhibit nitric oxide production.

Various in vivo assays may be employed to determine the efficacy of the compounds of the invention in treating a condition resulting from an abnormality in nitric oxide production, such as arthritis. The following is a description of such an assay utilizing rats:

Effects of Compounds of the Invention on Adjuvant-Induced Arthritis in Rats

Male Lewis rats were injected intradermally (proximal quarter of the tail) with 0.1 mL of Mycobacterium butyricum in Incomplete Freund's Adjuvant (10 mg/mL). Either vehicle (acidified saline, 1 mL/kg) or a compound of the invention (3, 10, or 30 mg/kg) were administered subcutaneously (b.i.d.), starting on the day following adjuvant immunization, and continued until the end of the experiment (N=10 rats per treatment group). Clinical scores (see below) were measured in all limbs 3 times per week throughout the study. Rats were euthanized 34–35 days after immunization. At the time of euthanasia, a radiologic evaluation (see below) of the hind paws was performed, a blood sample was collected for clinical blood chemistry and drug levels (high dose group only; 6 or 12 hours post final dose), a section of liver was obtained for measurement of potential toxicity, and the hind limbs were preserved for histopathological determination.

Clinical scoring—each limb was graded according to the following scale:

0 no signs of inflammation
1 moderate redness, first indication of swelling, joint flexible
2 moderate redness, moderate swelling, joint flexible
3 redness, significant swelling and distortion of the paw, joint beginning to fuse
4 redness, gross swelling and distortion of the paw, joint completely fused Radiological scoring—each hind limb was graded on a scale of 0–3 for each of the following parameters:
soft tissue swelling
cartilage loss
erosion
heterotropic ossification The compounds of the invention, when tested in this assay, demonstrated the ability to treat the arthritis present in the rats.

Those skilled in the art will also recognize that numerous assays for the activity of the NOS isoforms (iNOS, nNOS and eNOS) exist which can be used to evaluate the biological activity of the compounds of the current invention. These include assays for native NOS isoforms in tissues studied ex vivo (Mitchell et al., *Br; J. Pharmacol.* (1991), Vol. 104, pp. 289–291; Szabo et al., *Br. J. Pharmacol.* (1993), Vol. 108, pp. 786–792; Joly et al., *Br. J. Pharmacol.* (1995), Vol. 115, pp. 491–497) as well as primary cell cultures and cell lines (Forstermann et al., *Eur. J. Pharmacol.* (1992), Vol. 225, pp. 161–165; Radmoski et al., *Cardiovasc. Res.* (1993), Vol. 27, pp. 1380–1382; Wang et al., *J. Pharmacol. Exp. Ther.* (1994), Vol. 268, pp. 552–557). Those skilled in the art will also recognize that recombinant NOS enzymes can be expressed in heterologous cells by either transient transfection (Karlsen et al., *Diabetes,* (1995), Vol. 44, pp. 753–758), stable transfection (McMillan et al., *Proc. Natl. Acad. Sci.* (1992), Vol. 89, pp. 11141–11145; Sessa et al., *J. Biol. Chem.* (1995), Vol. 270, pp. 17641–17644) or via the use of lytic virus transfection (Busconi & Michel, *Mol. Pharmacol.* (1995), Vol. 47, pp. 655–659; List et al., *Biochem. J.* (1996), Vol. 315, pp. 57–63) using NOS cDNAs. Heterologous expression can be achieved in mammalian cells (McMillan et al., *Proc. Natl. Acad. Sci.* (1992), Vol. 89, pp. 11141–11145), insect cells (Busconi & Michel, *Mol. Pharmacol.* (1995), Vol. 47, pp. 655–459; List et al., *Biochem. J.* (1996), Vol. 315, pp. 5763), yeast (Sari et al., *Biochemistry* (1996), Vol. 35, pp. 7204–7213) or bacteria (Roman et al., *Proc. Natl. Acad. Sci.* (1995), Vol. 92, pp. 8428–8432; Martasek et al., *Biochem. Biophys Res. Commun.* (1996), Vol. 219, pp. 359–365). Any of these heterologous expression systems can be used to establish iNOS, nNOS and eNOS assay systems to evaluate the biological activity of the compounds of the present invention.

Administration of the Compounds of the Invention

Any suitable route of administration may be employed-for providing a patient with an effective dosage of compounds of the invention. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise the compounds of the invention as the active ingredient, and may also contain a pharmaceutically acceptable carrier, and optionally, other therapeutic ingredients. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. Methods for their preparation are well known in the art.

Because of their ease of administration, tablets and capsules represent the most advantageous oral dosage unit forms, in which case solid pharmaceutical carriers are employed. If desired, tablets may be coated by standard aqueous or nonaqueous techniques. In addition to the common dosage forms set out above, the compounds of the present invention may also be administered by controlled or sustained release means and delivery devices.

Pharmaceutical compositions of the present invention suitable for oral administration may be presented as discrete units such as capsules, cachets, or tablets, each containing a predetermined v amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

Preferred Embodiments

Of the compounds of formula (I), as described above in the Summary of the Invention, the following group of compounds having the formula (Ia), formula (Ib) or formula (Ic) are preferred:

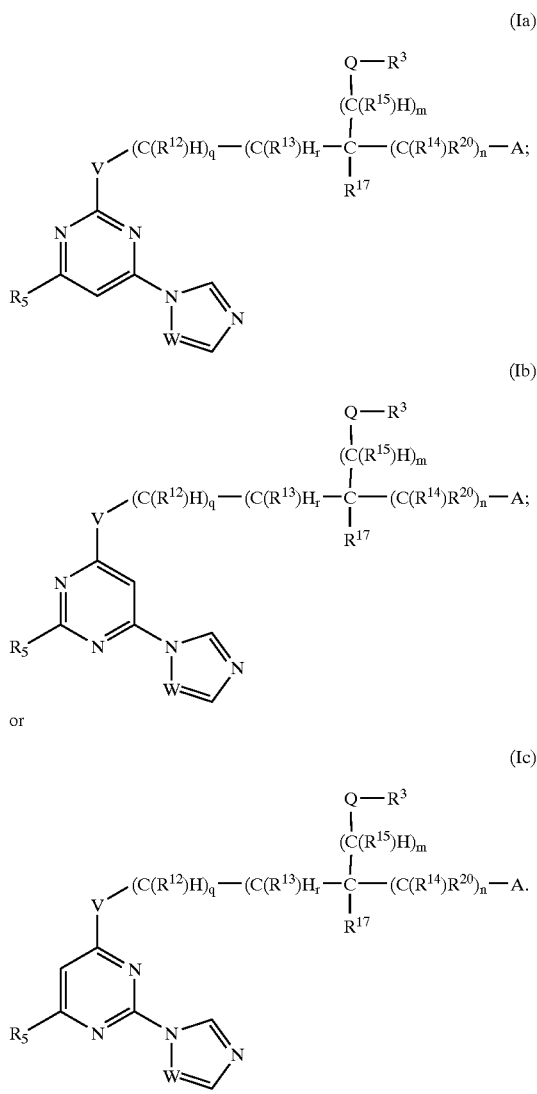

Of this group of compounds, a preferred subgroup of compounds are those compounds wherein A is $R^1$, —$OR^1$, —$C(O)N(R^1)R^2$, —$N(R^1)C(O)N(R^1)R^{16}$, —$NR^1C(O)R^2$ or —$N(R^1)R^{21}$; V is $N(R^4)$; and W is CH.

Of this subgroup of compounds, a preferred class of compounds are those compounds wherein A is —C(O)N($R^1$)$R^2$; $R^1$ is hydrogen; and $R^2$ is alkyl or —[$C_1$—$C_8$]—$R^9$; $R^4$ is hydrogen or alkyl; $R^5$ is hydrogen, halo, alkyl, or alkoxy; and $R^9$ is optionally substituted phenyl, tolyl, anisyl, 1,4-benzodioxan-6-yl, 1,3-benzodioxol-5-yl, 2-thienyl, pyridinyl or morpholinyl.

Of this class of compounds, a preferred subclass of compounds are those compounds wherein A is —C(O)N ($R^1$)$R^2$; q, r, n and m are each zero; Q is a direct bond to $R^3$; and $R^3$ is hydrogen.

Of this subclass of compounds, a preferred compound is 2-[[2-(1H-imidazol-1-yl)-6-methylpyrimidin-4-yl](methyl)amino]-N-[(1,3-benzodioxol-5-yl)ethyl]acetamide.

Of the subclass of compounds, other preferred compounds are selected from the group consisting of:

2-[[6-chloro-2-(1H-imidazol-1-yl)pyrimidin-4-yl]amino]-N-[2–3,4-dimethoxyphenyl) ethyl]acetamide;

2-[[6-chloro-2-(1H-imidazol-1-yl)pyrimidin-4-yl](methyl)amino]-N-[(1,3-benzodioxol-5-yl) methyl]acetamide;

2-[[6-chloro-2-(1H-imidazol-1-yl)pyrimidin-4-yl](methyl)amino]-N-[(pyridin-4-yl)methyl]acetamide;

2-[[2-(1H-imidazol-1-yl)-6-methylpyrimidin-4-yl](methyl)amino]-N-[2-(1,3-benzodioxol-5-yl) ethyl]acetamide;

2-[[2-(1H-imidazol-1-yl)-6-methylpyrimidin-4-yl]amino]-N-[2-1,3-benzodioxol-5-yl) ethyl]acetamide;

2-[[2-(1H-imidazol-1-yl)pyrimidin-4-yl]amino]-N-[2-(1,3-benzodioxol-5-yl)ethyl]acetamide;

2-[[2-(1H-imidazol-1-yl)-6-methylpyrimidin-4-yl](methyl)amino]-N-octylacetamide;

2-[[2-(1H-imidazol-1-yl)-6-methylpyrimidin-4-yl](phenylmethyl)amino]-N-[2-(1,3-benzodioxol-5-yl) ethyl]acetamide;

2-[[2-(1H-imidazol-1-yl)-6-(methylethyl)pyrimidin-4-yl]amino]-N-[2-(1,3-benzodioxol-5-yl) ethyl]acetamide;

2-[[2-(1H-imidazol-1-yl)-6-methylpyrimidin-4-yl](methyl)amino]-N-[2-3,4-dimethoxyphenyl)ethyl]-acetamide;

2-[[2-(1H-imidazol-1-yl)pyrimidin-4-yl](methyl)amino]-N-[2-(1,3-benzodioxol-5-yl) ethyl]acetamide;

2-[[2-(1H-imidazol-1-yl)-6-methylpyrimidin-4-yl](methylethyl)amino]-N-[2-(1,3-benzodioxol-5-yl) ethyl]acetamide;

2-[[2-(1H-imidazol-1-yl)-6-methylpyrimidin-4-yl](methyl)amino]-N-[2-1,3-benzodioxol-5-oxy) ethyl]acetamide;

2-[[4-(1H-imidazol-1-yl)-(methylethyl)pyrimidin-2-yl]amino]-N-[2-(1,3-benzodioxol-5-yl) ethyl]acetamide;

2-[[4-(1H-imidazol-1-yl)-6-methylpyrimidin-2-yl]amino]-N-[2-(1,3-benzodioxol-5-yl) ethyl]acetamide;

2-[[2-(1H-imidazol-1-yl)-6-methylpyrimidin-4-yl]amino]-N-[2-(3-chloro-4-methoxyphenyl) ethyl]acetamide;

2-[[2-(1H-imidazol-1-yl)-6-methylpyrimidin-4-yl]amino]-N-[2-(1,4-benzodioxan-6-yl) ethyl]acetamide;

2-[[2-(1H-imidazol-1-yl)-6-methylpyrimidin-4-yl]amino]-N-[2-(4-methoxyphenyl)ethyl]acetamide;

2-[[2-(1H-imidazol-1-yl)-6-methylpyrimidin-4-yl](methyl)amino)-N-[2-(1,4-benzodioxan-6-yl) ethyl]acetamide;

2-[[2-(1H-imidazol-1-yl)-6-methylpyrimidin-4-yl]amino]-N-[(1,3-benzodioxol-5-yl) methyl]acetamide; and 2-[[2-(1H-imidazol-1-yl)-6-methylpyrimidin-4-yl]amino]-N-[(1,4-benzodioxan-6-yl) methyl]acetamide.

Of the compounds of formula (II) as described above in the Summary of the Invention, a preferred group of compounds are those compounds having the formula (IIa), formula (IIb) or formula (IIc):

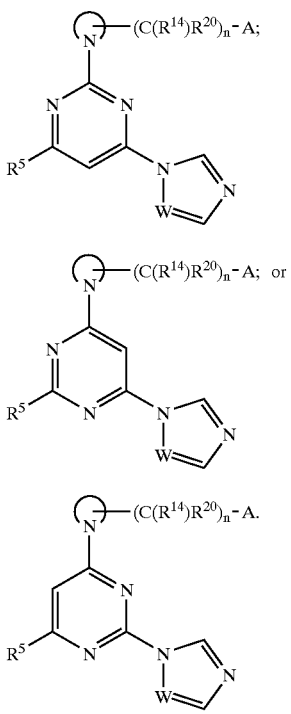

(IIa)

(IIb)

(IIc)

Of this group of compounds, a preferred subgroup of compounds are those compounds wherein the N-heterocyclyl is selected from the group consisting of imidazolyl, piperidinyl, piperazinyl, pyrrolidinyl, morpholinyl, thiomorpholinyl, azetidinyl, indolyl, pyrrolyl, imidazolyl, tetrahydroisoquinolyl, and perhydroazepinyl.

Of this subgroup of comounds, a preferred class of compounds are those compounds wherein the N-heterocyclyl is piperazinyl substituted by $R^6$, i.e., the compound of formula (IId), formula.(IIe) or formula

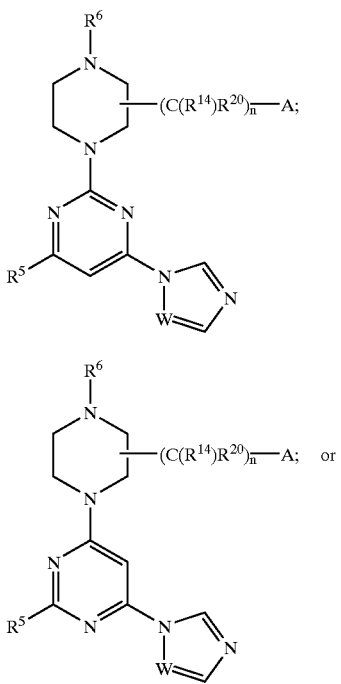

(IId)

(IIe)

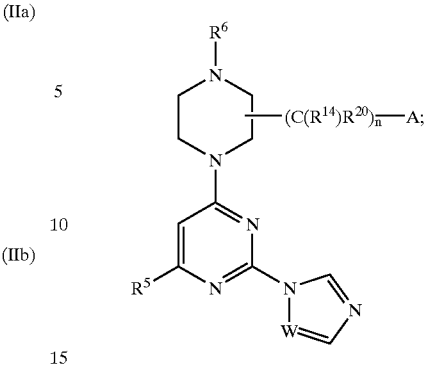

(IIf)

where $R^6$ is chosen from the group consisting of hydrogen, alkyl, cycloalkyl, —[$C_1$–$C_8$ alkyl]—$R^8$, —[$C_2$–$C_8$ alkyl]—$R^{10}$, —[$C_1$–$C_8$ alkyl]—$R^{11}$, acyl, —C(O)$R^8$, —C(O)—[$C_1$–$C_8$ alkyl]—$R^8$, alkoxycarbonyl, optionally substituted aryloxycarbonyl, optionally substituted aralkoxycarbonyl, alkylsulfonyl, optionally substituted aryl, optionally substituted heterocyclyl, alkoxycarbonylalkyl, carboxyalkyl, optionally substituted arylsulfonyl, aminocarbonyl, monoalkylaminocarbonyl, dialkylaminocarbonyl, optionally substituted arylaminocarbonyl, aminosulfonyl, monoalkylaminosulfonyl, dialkylaminosulfonyl, arylaminosulfonyl, arylsulfonylaminocarbonyl, optionally substituted N-heterocyclyl, —C(=NH)—N(CN)$R^1$, —C(O)—$R^{23}$—N($R^1$)$R^2$, —C(O)—$R^{23}$—N($R^1$)C(O)—$R^{23}$—N($R^1$)$R^2$, and —C(O)—N($R^1$)—$R^{23}$—C(O)O$R^1$; each $R^8$ is independently selected from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy); and each $R^{23}$ is an amino acid residue.

Of this class of compounds, a preferred subclass of compounds are those compounds where A is —O$R^1$, —C(O)N($R^1$)$R^2$, —N($R^{16}$)C(O)N($R^1$)$R^{16}$, —N$R^1$C(O)$R^2$ or —N($R^1$)$R^{21}$; and W is CH.

Of this subclass of compounds, a preferred set of compounds are those compounds where A is —C(O)N($R^1$)$R^2$; $R^1$ is hydrogen; $R^2$ is lower alkyl, —[$C_1$–$C_8$ alkyl]—$R^9$, or —[$C_1$–$C_8$]—$R^{10}$; $R^6$ is hydrogen, acetyl, t-butoxycarbonyl, 4-methoxyphenylaminocarbonyl, 4-methoxyphenyl-methyl, methoxycarbonyl, methyl or benzyl; $R^5$ is hydrogen, halo, alkyl, or alkoxy; and n is 0 or 1.

Of this set of compounds, a preferred subset of compounds are those compounds where $R^2$ is —CH$_2$—$R^9$ or —[$C_1$–$C_8$]—$R^{10}$; $R^9$ is optionally substituted carbocyclyl or optionally substituted heterocyclyl; and $R^{10}$ is methylthio.

Of this preferred subset of compounds, preferred compounds are those compounds where $R^2$ is —CH$_2$—$R^9$; $R^6$ is hydrogen, acetyl or t-butoxycarbonyl; and $R^9$ is optionally substituted phenyl, tolyl, anisyl, 1,4-benzodioxan-6-yl, 1,3-benzodioxol-5-yl, or 2-thienyl.

Even more preferred are those compounds where $R^5$ is chloro, $R^6$ is acetyl and $R^9$ is p-tolyl.

Also preferred are those compounds where $R^5$ is chloro, $R^6$ is hydrogen and $R^9$ is p-tolyl.

Also preferred are those compounds where $R^5$ is chloro, $R^6$ is hydrogen and $R^9$ is 1,4-benzodioxan-6-yl or 1,3-benzodioxol-5-yl.

Also preferred are those compounds where $R^5$ is chloro, $R^6$ is t-butoxycarbonyl and $R^9$ is 1,4-benzodioxan-6-yl or 1,3-benzodioxol-5-yl.

Of this class of compounds, the most preferred compounds are those compounds selected from the group consisting of:

N-[(1,3-benzodioxol-5-yl)ethyl]-4-[2-(1H-imidazol-1-yl)-methylpyrimidin-4-yl]-1-(2-methyl-1-oxopropyl)piperazine-2-acetamide;

N-[(1,3-benzodioxol-5-yl)methyl]-1-[2-(1H-imidazol-1-yl)pyrimidin-4-yl-4-(methoxycarbonyl)piperazine-2-acetamide;

N-[(1,4-benzodioxan-6-yl)methyl]-1-[2-(1H-triazol-1-yl)pyrimidin-4-yl]-4-[(dimethylethoxy)carbonyl]piperazine-2-acetamide;

N-[(1,3-benzodioxol-5-yl)methyl]-4-[2-(1H-imidazol-1-yl)-6-methoxypyrimidin-4-yl]-1-(methoxycarbonyl)piperazine-2-acetamide;

1-(acetyl)-N-[(1,3-benzodioxol-5-yl)methyl]-4-[6-chloro-2-(1H-imidazol-1-yl)pyrimidin-4-yl]piperazine-2-acetamide;

1-[6-chloro-2-(1H-imidazol-1-yl)pyrimidin-4-yl]-N-[(4-methoxy-3chlorophenyl)methyl-4-(methylsulfonyl)piperazine-2-acetamide; and 1-[2-(1H-imidazol-1-yl)pyrimidin-4-yl]-N-[(pyridin-3-yl)methyl]-4-(tetrahydro-3-furanoyl)piperazine-2-carboxamide.

Of the preferred subgroup of compounds of formula (II), another preferred class of compounds are those compounds wherein the N-heterocyclyl is optionally substituted piperidinyl, i.e., the compound of formula (IIg), formula (IIh) or formula (IIi):

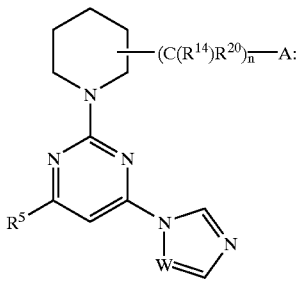

(IIg)

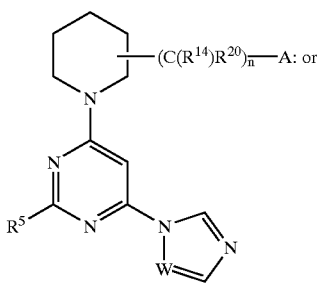

(IIh)

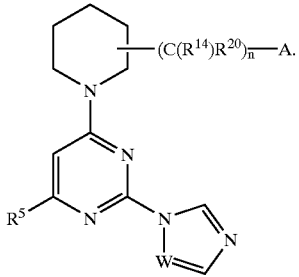

(IIi)

Of this class of compounds, a preferred subclass of compounds are those compounds wherein A is —OR$^1$, —C(O)N(R$^1$)R$^2$, —N(R$^{16}$)C(O)N(R$^1$)R$^{16}$, —NR$^1$C(O)R$^2$ or —N(R$^1$)R$^{21}$; and W is CH.

Of this subclass of compounds, a preferred set of compounds are those compounds wherein A is —C(O)N(R$^1$)R$^2$; R$^1$ is hydrogen; R$^2$ is lower alkyl or —[C$_1$–C$_8$ alkyl]—R$^9$; R$^5$ is hydrogen, halo, alkyl, or alkoxy; and n is zero or one.

Of this set of compounds, a preferred subset of compounds are those compounds wherein R$^2$ is lower alkyl or —CH$_2$—R$^9$ and R$^9$ is 4-methoxyphenyl, 1,4-benzodioxan-6-yl, 1,3-benzodioxol-5-yl or 3,4-dimethoxyphenyl.

Of this class of compounds, preferred compounds are those compounds selected from the group consisting of:

N-[(1,3-benzodioxol-5-yl)methyl]-1-[2-(1H-imidazol-1-yl)pyrimidin-4-yl]piperidine-2-ethanamine;

1-[2-(1H-imidazol-1-yl)pyrimidin-4-yl]-N-[(3-methoxyphenyl)methyl]piperidine-2-acetamide;

1-[2-(1H-imidazol-1-yl)-6-methylethylpyrimidin-4-yl]-N-[2-(morpholin-4-yl)ethyl]piperidine-2-acetamide;

1-[2-(1H-imidazol-1-yl)-6-methylpyrimidin-4-yl]-N-(1-methylhexyl)piperidine-2-acetamide;

1-[2-(1H-imidazol-1-yl)pyrimidin-4-yl]-N-[(4-methylsulfonylphenyl)methyl]piperidine-2-acetamide;

N-[(4-chlorophenyl)methyl]-1-[2,6-bis(1H-imidazol-1-yl)pyrimidin-4-yl]piperidine-2-acetamide;

1-(4-fluorophenyl)-4-[1-[2-(1H-imidazol-1-yl)pyrimidin-4-yl]piperidine-2-acetyl]piperazine;

1-[(1,3-benzodioxol-5-yl)methyl]-4-[1-[2-(1H-imidazol-1-yl)pyrimidin-4-yl]piperidine-2-acetyl]piperazine;

1-(phenylmethyl)-4-[1-[2-(1H-imidazol-1-yl)pyrimidin-4-yl]piperidine-2-acetyl]piperazine;

4-[1-[2-(1H-imidazol-1-yl)pyrimidin-4-yl]piperidine-2-acetyl]piperazine-1-carboxylic acid, ethyl ester;

1-(4-chlorophenyl)-4-[1-[2-(1H-imidazol-1-yl)pyrimidin-4-yl]piperidine-2-acetyl-]-4-hydroxypiperidine;

4-[[1-[2-(1H-imidazol-1-yl)pyrimidin-4-yl]piperidine-2-acetyl]amino]piperidine-1-carboxylic acid, ethyl ester;

4-[[1-[2-(1H-imidazol-1-yl)-6-methylethylpyrimidin-4-yl]piperidine-2-acetyl]amino]piperidine-1-carboxylic acid, ethyl ester;

4-[[1-[2-(1H-imidazol-1-yl)-6-methylpyrimidin-4-yl]piperidine-2-acetyl]amino]piperidine-1-carboxylic acid, ethyl ester;

4-[2-[[(1,3-benzodioxol-5-yl)methoxy]ethyl]piperidin-1-yl]-2-(1H-imidazol-1-yl)pyrimidine;

1-6-chloro-2-(1H-imidazol-1-yl)pyrimidin-4-yl]piperidine-2-ethanol;

4-chloro-2-(1H-imidazol-1-yl)-6-piperidin-1-yl)pyrimidine;

4-chloro-2-(1H-imidazol-1-yl)-6-(2-ethylpiperidin-1-yl)pyrimidine;

N-[(1,3-benzodioxol-5-yl)methyl]-1-[2-(1H-imidazol-1-yl)pyrimidin-4-yl]-N-methylpiperidine-2-ethanamine;

N-acetyl-N-[(1,3-benzodioxol-5-yl)methyl]-1-[2-(1H-imidazol-1-yl)pyrimidin-4-yl]piperidine-2-ethanamine;

N-[(1,3-benzodioxol-5-yl)methyl]-1-[2-(1H-imidazol-1-yl)pyrimidin-4-yl]-N-(methylsulfonyl)piperidine-2-ethanamine;

1-[2-(1H-imidazol-1-yl)pyrimidin-4-yl]-N-[2-(4-methoxyphenyl)ethyl]piperidine-2-acetamide; and N-[(1,3-benzodioxol-5-yl)methyl]-4-[2-(1H-imidazol-1-yl)-6-methoxypyrimidin-4-yl]piperidine-2-acetamide.

Of the preferred subgroup of compounds of formula (II), another preferred class of compounds are those compounds wherein the N-heterocyclyl is optionally substituted pyrrolidinyl, i.e., the compound of formula (IIj), formula (IIk) or formula (IIm):

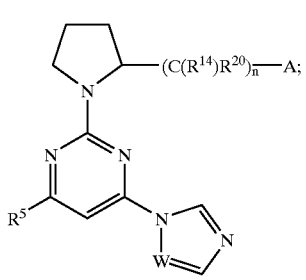
(IIj)

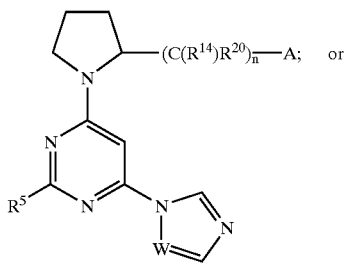
(IIk)

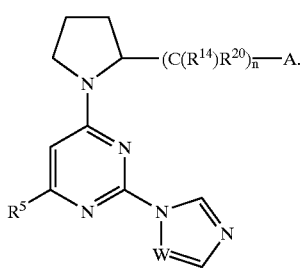
(IIm)

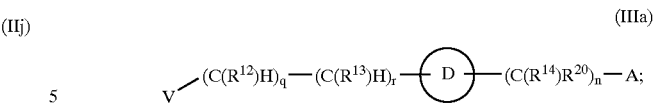
(IIIa)

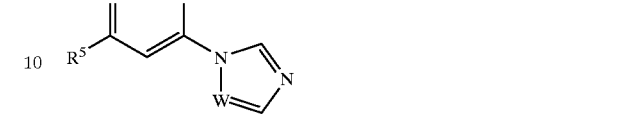
(IIIb)

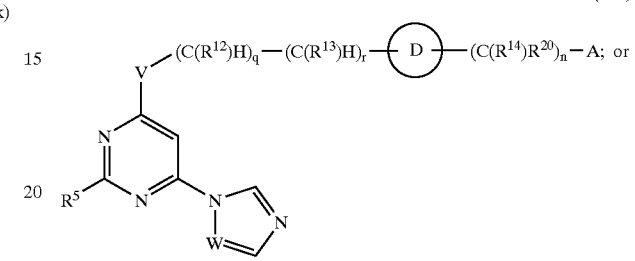
(IIIc)

Of this class of compounds, a preferred subclass of compounds are those compounds wherein A is —OR$^1$, —C(O)N(R$^1$)R$^2$, —N(R$^{16}$)C(O)N(R$^1$)R$^{16}$, —NR$^1$C(O)R$^2$ or —N(R$^1$)R$^{21}$; and W is CH.

Of this subclass of compounds, a preferred set of compounds are those compounds wherein A is —C(O)N(R$^1$)R$^2$; R$^1$ is hydrogen; R$^2$ is lower alkyl or —[C$_1$-C$_8$ alkyl]—R$^9$; R$^5$ is hydrogen, halo, alkyl, or alkoxy; and n is zero or one.

Of this set of compounds, a preferred subset of compounds are those compounds having the R-configuration at C-2 of the pyrrolidinyl ring.

Of this set of compounds, preferred compounds are those compounds selected from the group consisting of.

N-[(1,3-benzodioxol-5-yl)ethyl]-1-[2-(1H-imidazol-1-yl)-6-methylpyrimidin-4-yl]pyrrolidine-2-carboxamide;

N-[(1,3-benzodioxol-5-yl)ethyl]-1-[2-(1H-imidazol-1-yl)-6-ethylpyrimidin-4-yl]pyrrolidine-2-carboxamide;

N-(3,4-dimethoxyphenyl)methyl]-1-[2-(1H-imidazol-1-yl)pyrimidin-4-yl]pyrrolidine-2-acetamide;

N-[(4-methoxyphenyl)ethyl]-1-[2-(1H-imidazol-1-yl)-6-methylpyrimidin-4-yl]pyrrolidine-2-carboxamide; and N-[(1,3-benzodioxol-5-yl)methyl]-1-[2-(1H-imidazol-1-yl)-6-ethylpyrimidin-4-yl]pyrrolidine-2-acetamide.

Of the compounds of formula (III) as described above in the Summary of the Invention, a preferred group of compounds are those compounds having the formula (IIIa), formula (IIIb) or formula (IIIc):

Of this group of compounds, a preferred subgroup of compounds are those compounds wherein

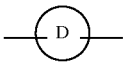

is optionally substituted phenyl or optionally substituted naphthyl.

Of the compounds of formula (Ya), formula (Yb) and formula (Yc) as described above in the Summary of the invention, a preferred group of compounds are those compounds having the formula (Yc) wherein n is 1; m is 2 or 3; A is —C(O)OR$^1$ or —C(O)N(R$^1$)R$^2$; each W is CH; R$^1$ is hydrogen or alkyl; and R$^2$ is hydrogen, alkyl, —(CH)$_n$—N(R$^1$)$_2$, optionally substituted heterocyclylalkyl or optionally substituted aralkyl.

Of this subgroup of compounds, a preferred class of compounds are those compounds wherein R$^4$ is —N(R$^1$)R$^2$ where R$^1$ is hydrogen or alkyl and R$^2$ is heterocyclylalkyl selected from the group consisting of (1,3-benzodioxol-5-yl)methyl or (1,4-benzodioxan-4-yl)methyl.

Of this class of compounds, preferred compounds are selected from the group consisting of:

2-[[3-[[(1,3-benzodioxol-5-yl)methyl](methyl)amino]propyl][2-(1H-imidazol-1-yl)-6-methylpyrimidin-4-yl]amino]acetic acid, ethyl ester;

2-[[3-[[(1,3-benzodioxol-5-yl)methyl](methyl)amino]propyl][2-(1H-imidazol-1-yl)-6-methylpyrimidin-4-yl]amino]-N,N-diethylacetamide;

2-[[3-[[(1,3-benzodioxol-5-yl)methyl](methyl)amino]propyl][2-(1H-imidazol-1-yl)-6-methylpyrimidin-4-yl]amino]-N-(2-dimethylaminoethyl)acetamide;

2-[[3-[[(1,3-benzodioxol-5-yl)methyl](methyl)amino] propyl][2-(1H-imidazol-1-yl)-6-methylpyrimidin-4-yl] amino]acetamide;
2-[[3-[(1,3-benzodioxol-5-yl)methyl]aminopropyl][2-(1H-imidazol-1-yl)-6-methylpyrimidin-4-yl]amino]-N,N-diethylacetamide;
2-[[3-[(1,3-benzodioxol-5-yl)methyl]aminopropyl][2-(1H-imidazol-1-yl)-6-methylpyrimidin-4-yl]amino]-N-methylacetamide;
2-[[3-[(1,4-benzodioxan-6-yl)methyl]aminopropyl][2-(1H-imidazol-1-yl)-6-methylpyrimidin-4-yl]amino]-N-methylacetamide;
2-[[3-[(1,4-benzodioxan-6-yl)methyl]aminopropyl][2-(1H-imidazol-1-yl)-6-methylpyrimidin-4-yl]amino]-N,N-diethylacetamide;
2-[[3-[(1,4-benzodioxan-6-yl)methyl]aminopropyl][2-(1H-imidazol-1-yl)-6-methylpyrimidin-4-yl]amino] acetamide; and
2-[[3-[(1,3-benzodioxol-5-yl)methyl]aminopropyl][2-(1H-imidazol-1-yl)-6-methylpyrimidin-4-yl]amino] acetamide.

Of the preferred subgroup of compounds, a preferred class of compounds are those compounds wherein $R^4$ is heterocyclyl.

Of this class of compounds, preferred compounds are selected from the group consisting of:
2-[[pyridin-3-ylmethyl][2-(1H-imidazol-1-yl)-6-methylpyrimidin-4-yl]amino]-N-[2-(1,3-benzodioxol-5-yl)ethyl]acetamide;
2-[[2-(1H-imidazol-1-yl)-6-methylpyrimidin-4-yl][(1,3-benzodioxol-5-yl)methyl]amino]-N-[2-(1,3-benzodioxol-5-yl)ethyl]acetamide; and
2-[[2-(1H-imidazol-1-yl)-6-methylpyrimidin-4-yl][2-(morpholin-4-yl)ethyl]amino]-N-[2-(1,3-benzodioxol-5-yl)ethyl]acetamide.

Of this subgroup of compounds, another preferred class of compounds are those compounds wherein $R^4$ is hydroxy, cyano, —N($R^1$)$R^2$, —N($R^1$)—C(O)—$R^1$, —N($R^1$)—C(O)O$R^1$, —N($R^1$)—S(O)$_t$$R^1$, or —N($R^1$)—C(O)—N($R^1$)$_2$, where each $R^1$ and each $R^2$ is independently hydrogen, alkyl or aralkyl.

Of this class of compounds, preferred compounds are selected from the group consisting of:
2-[[3-hydroxypropyl][2-(1H-imidazol-1-yl)-6-methylpyrimidin-4-yl]amino]-N-[2-(1,3-benzodioxol-5-yl)ethyl]acetamide;
2-[[2-cyanoethyl][2-(1H-imidazol-1-yl)-6-methylpyrimidin-4-yl]amino]-N-[2-(1,3-benzodioxol-5-yl)ethyl]acetamide;
2-[[3-(dimethylamino)propyl][2-(1H-imidazol-1-yl)-6-methylpyrimidin-4-yl]amino]-N-[2-(1,3-benzodioxol-5-yl)ethyl]acetamide;
2-[[3-(acetylamino)propyl][2-(1H-imidazol-1-yl)-6-methylpyrimidin-4-yl]amino]-N-[2-(1,3-benzodioxol-5-yl)ethyl]acetamide;
2-[[3-(methylsufonylamino)propyl][2-(1H-imidazol-1-yl)-6-methylpyrimidin-4-yl]amino]-N-[2-(1,3-benzodioxol-5-yl)ethyl]acetamide;
2-[[3-(methoxycarbonylamino)propyl][2-(1H-imidazol-1-yl)-6-methylpyrimidin-4-yl]amino]-N-[2-(1,3-benzodioxol-5-yl)ethyl]acetamide;
2-[[3-(phenylmethylamino)propyl][2-(1H-imidazol-1-yl)-6-methylpyrimidin-4-yl]amino]-N-[2-(1,3-benzodioxol-5-yl)ethyl]acetamide;
2-[[3-aminopropyl][2-(1H-imidazol-1-yl)-6-methylpyrimidin-4-yl]amino]-N-[2-(1,3-benzodioxol-5-yl)ethyl]acetamide;
2-[[3-aminopropyl][2-(1H-imidazol-1-yl)-6-methylpyrimidin-4-yl]amino]-N-[2-(4-methoxyphenyl)ethyl]acetamide;
2-[[3-(methylsufonylamino)propyl][2-(1H-imidazol-1-yl)-6-methylpyrimidin-4-yl]amino]-N-[2-(4-methoxyphenyl)ethyl]acetamide;
2-[[3-(methoxycarbonylamino)propyl][2-(1H-imidazol-1-yl)-6-methylpyrimidin-4-yl]amino]-N-[2-(4-methoxyphenyl)ethyl]acetamide;
2-[[3-(phenylmethylamino)propyl][2-(1H-imidazol-1-yl)-6-methylpyrimidin-4-yl]amino]-N-[2-(4-methoxyphenyl)ethyl]acetamide;
2-[3-(acetylamino)propyl][2-(1H-imidazol-1-yl)-6-methylpyrimidin-4-yl]amino]-N-[2-(4-methoxyphenyl)ethyl]acetamide;
2-[[3-aminopropyl][2-(1H-imidazol-1-yl)-6-methylpyrimidin-4-yl]amino]-N-[2-(1,4-benzodioxan-6-yl)ethyl]acetamide;
2-[[3-(methoxycarbonylamino)propyl][2-(1H-imidazol-1-yl)-6-methylpyrimidin-4-yl]amino]-N-[2-(1,4-benzodioxan-6-yl)ethyl]acetamide;
2-[[3-(di(phenylmethyl)amino)propyl][2-(1H-imidazol-1-yl)-6-methylpyrimidin-4-yl]amino]-N-[2-(1,4-benzodioxan-6-yl)ethyl]acetamide;
2-[[3-(acetylamino)propyl][2-(1H-imidazol-1-yl)-6-methylpyrimidin-4-yl]amino]-N-[2-(1,4-benzodioxan-4-yl)ethyl]acetamide;
2-[[3-(methylsufonylamino)propyl][2-(1H-imidazol-1-yl)-6-methylpyrimidin-4-yl]amino]-N-[2-(1,4-benzodioxan-6-yl)ethyl]acetamide;
2-[[3-(dimethylamino)propyl][2-(1H-imidazol-1-yl)-6-methylpyrimidin-4-yl]amino]-N-[2-(1,4-benzodioxan-6-yl)ethyl]acetamide;
2-[[3-(dimethylamino)propyl][2-(1H-imidazol-1-yl)-6-methylpyrimidin-4-yl]amino]-N-[2-(4-methoxyphenyl)ethyl]acetamide;
2-[[3-(ureido)propyl][2-(1H-imidazol-1-yl)-6-methylpyrimidin-4-yl]amino]-N-[2-(4-methoxyphenyl)ethyl]acetamide;
2-[[3-(phenylmethylamino)propyl][2-(1H-imidazol-1-yl)-6-methylpyrimidin-4-yl]amino]-N-[2-(1,4-benzodioxan-6-yl)ethyl]acetamide;
2-[[3-(phenylmethylamino)propyl][2-(1H-imidazol-1-yl)-6-methylpyrimidin-4-yl]amino]-N-2-(2,3-dihydrobenzofuran-5-yl)ethyl]acetamide;
2-[[3-aminopropyl][2-(1H-imidazol-1-yl)-6-methylpyrimidin-4-yl]amino]-N-[2-(2,3-dihydrobenzofuran-5-yl)ethyl]acetamide;
2-[[3-(dimethylamino)propyl][2-(1H-imidazol-1-yl)-6-methylpyrimidin-4-yl]amino]-N-[2-(2,3-dihydrobenzofuran-5-yl)ethyl]acetamide;
2-[[3-(acetylamino)propyl][2-(1H-imidazol-1-yl)-6-methylpyrimidin-4-yl]amino]-N-[2-(2,3-dihydrobenzofuran-5-yl)ethyl]acetamide;
2-[[3-(methoxycarbonylamino)propyl][2-(1H-imidazol-1-yl)-6-methylpyrimidin-4-yl]amino]-N-[2-(2,3-dihydrobenzofuran-5-yl)ethyl]acetamide;
2-[[3-(methylsufonylamino)propyl][2-(1H-imidazol-1-yl)-6-methylpyrimidin-4-yl]amino]-N-[2-(2,3-dihydrobenzofuran-5-yl)ethyl]acetamide;
2-[[3-(ureido)propyl][2-(1H-imidazol-1-yl)-6-methylpyrimidin-4-yl]amino]-N-[2-(1,4-benzodioxane-6-yl)ethyl]acetamide; and
2-[[3-(ureido)propyl][2-(1H-imidazol-1-yl)-6-methylpyrimidin-4-yl]amino]-N-[2-(2,3-benzofuran-5-yl)ethyl]acetamide.

Of the compounds of formula (IV) as described above in the Summary of the Invention, a preferred group of compounds are those compounds having the formula (IVa), formula (IVb) or formula (IVc):

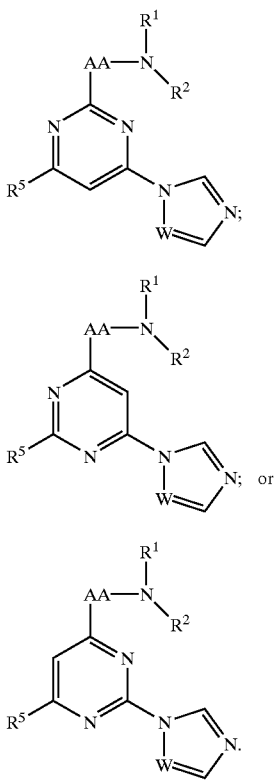

(IVa)

(IVb)

(IVc)

Of this group of compounds, a preferred subgroup of compounds are those compounds wherein said amino acid is an α-aminoacid of the L configuration at the carbon a to the acid.

Of this group of compounds, another preferred subgroup of compounds are those compounds wherein said amino acid is an α-aminoacid of the D configuration at the carbon a to the acid.

Of this group of compounds, another preferred subgroup of compounds are those compounds wherein $R^1$ is hydrogen; $R^2$ is lower alkyl or —[$C_1$-$C_8$ alkyl]—$R^9$; and $R^5$ is hydrogen, halo, alkyl, or alkoxy.

Of this subgroup of compounds, a preferred class of compounds are those compounds wherein $R^9$ is phenyl, tolyl, anisyl, 1,4-benzodioxan-6-yl, 1,3-benzodioxol-5-yl, chlorophenyl, carboxyphenyl, 2-thienyl, dimethoxyphenyl or morpholinyl.

Of the compounds of formula (Va), formula (Vb) and formula (Vc) as described above in the Summary of the Invention, a preferred group of compounds are those compounds wherein each X and each Y is N; each W is CH; and B is a fused optionally substituted heterocyclyl Of this group of compounds, a preferred subgroup of compounds are those compounds having the formula (Vba):

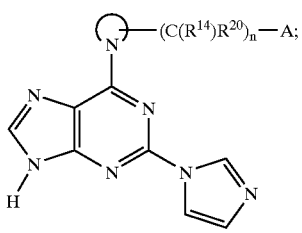

(Vba)

where A is —$OR^1$, —$C(O)N(R^1)R^2$, —$N(R^{16})C(O)N(R^1)$ $R^{16}$, —$NR^1C(O)R^2$ or —$N(R^1)R^{21}$; and

is an N-heterocyclyl selected from group consisting of piperidinyl, piperazinyl, pyrrolidinyl or morpholinyl.

Of this subgroup of compounds, a preferred compound is N-[(1,3-benzodioxol-5-yl)methyl]-1-[2-(1H-imidazol-1-yl)purin-6-yl]piperidine-2-acetamide.

Of the compounds of formula (VIIa), formula (VIIb) and formula (VIIc) as described above in the Summary of the Invention, a preferred compounds is N-[(1,3-benzodioxol-5-yl)methyl]-1-[6-chloro-2-(pyridin-3-yl)pyrimidin-4-yl]piperidine-2-acetamide.

Of the compounds of formula (VIII) as described above in the Summary of the Invention, preferred compounds are 4,6-dichloro-2-(1H-imidazol-1-yl)pyrimidine and 2,4-dichloro-6-(1H-imidazol-1-yl)pyrimidine.

Of the compounds of formula (Ixa), formula (Ixb) and formula (Ixc), a preferred group of compounds are those compounds wherein L is a photolytically cleavable linkage of formula (X):

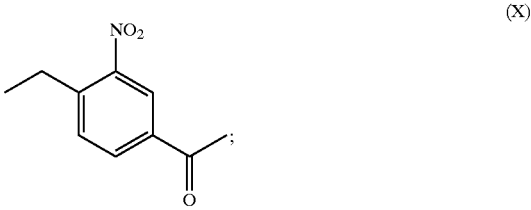

(X)

wherein the unsatisfied valence on the-right of the formula represents the point of attachment to the solid substrate and the unsatisfied valence on the left of the formula represents the point of attachment to the ligand.

In addition to the preferred embodiments described above, other compounds of the invention of interest-are those compounds of formula (I), formula (II) or formula (III) wherein each X, Y or Z is $C(R^{19})$, and each U is $C(R^5)$ where each $R^{19}$ and $R^5$ is as described above in claim 1. Also of interest are those compounds of formula (I), formula (II) or formula (III) wherein each X, Y or Z is N, and each U is $C(R^5)$ where each $R^5$ is as described above in claim 1. Also of interest are those compounds of formula (I), formula (II) or formula (II) wherein each X is N, each Z or Y is $C(R^{19})$, and each U is N where each $R^{19}$ is as described above in claim 1. Also of interest are those compounds of formula (I), formula (II) or formula (II) wherein in each formula, one of X, Y, and Z is N and the others are $C(R^{19})$, and U is $C(R^5)$ where each $R^{19}$ and each $R^5$ is as described above in claim 1.

Preparation of the Compounds of the Invention

The compounds of the invention may be synthesized by two general approaches, one of which solid phase) could be thought of as a variant of the other (solution phase). The solution phase generic synthesis is shown in the following Reaction Scheme 1 which, for illustration purposes only, illustrates the synthesis of a compound of formula (I) where A is —$C(O)N(R^1)R^2$. It is understood that other compounds of the invention may be prepared in a similar manner. In the following Reaction Scheme 1, PG is a suitable protecting group; m, n, q, r, Q, U, W, X, Y and Z are as described above in the Summary of the Invention; V is $N(R^4)$, S or O (where $R^4$ is as described in the Summary of the Invention); and $R^1$, $R^2$, $R^3$, $R^{12}$, $R^{13}$, $R^{14}$, $R^{15}$, $R^{17}$, and $R^{20}$ are as described above in the Summary of the Invention for compounds of formula (I):

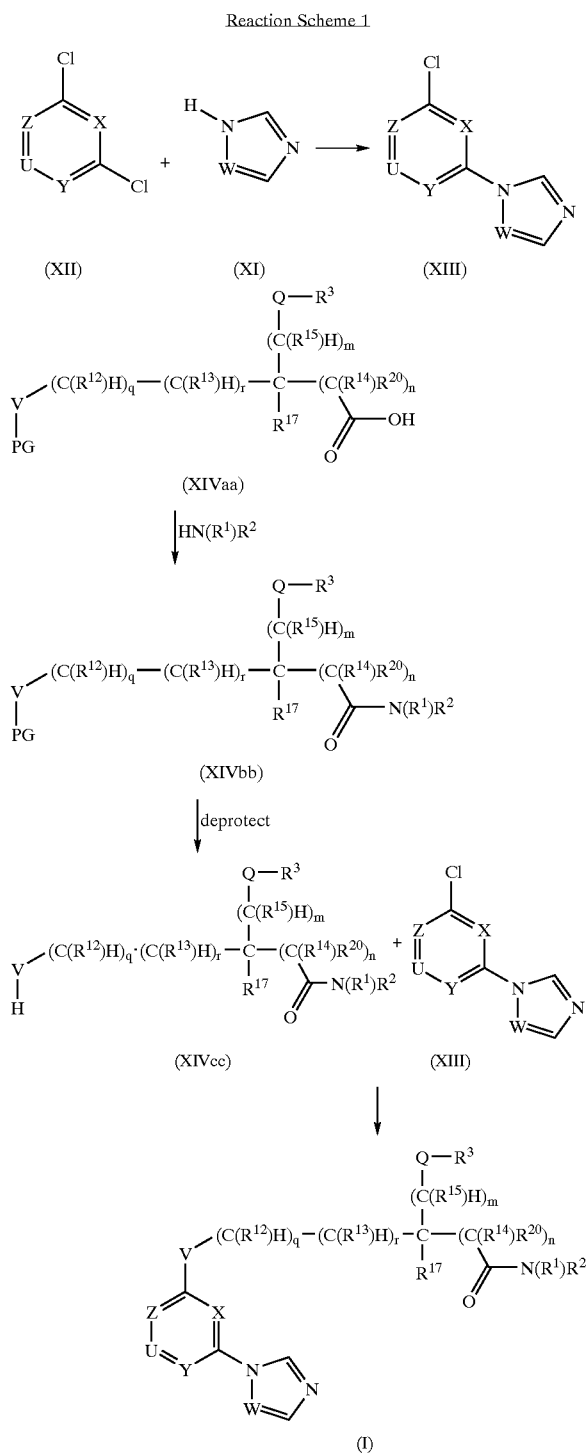

In general, the compounds of formula (I) are prepared by first adding one equivalent of a compound of formula (XI) in one portion to a solution of one equivalent of a compound of formula (XII) having at least two substituents displaceable by a nucleophile and 1.1 equivalents of a trialkyl amine base (such as triethylamine) in a polar, nonprotic solvent such as THF or methylene chloride to provide the compound of formula (XIII). Upon completion of the reaction, the mixture is purified by conventional methods.

The compounds of formula (XIVcc) are synthesized by methods well known in the amino acid and peptide synthetic art from the appropriate compound of formula (XIVaa), wherein PG is a standard protecting group for the V substituent. Compounds of formula (XIVaa) are commercially available, usually in protected form, or are readily synthesized by procedures well-known in the art. Preferred protecting groups are Boc (t-butoxycarbonyl) and Fmoc (fluorenylmethoxy-carbonyl), although others, such as CBZ (benzyloxycarbonyl), and Troc (trichloroethoxycarbonyl), could be used for particular circumstances. Side chain functionalities may be protected, as is well known in the peptide art, by Trt (triphenylmethyl), tBu (t-butyl), Acm (acetamidomethyl) etc. The protected compounds of formula (XIVaa) are reacted with the appropriate amine to produce the compounds of formula (XIVbb) and deprotected to produce the compound of formula (XIVcc), once again by methods well known in the peptide art.

One equivalent of the compound of formula (XIVcc) is added to a solution of one equivalent of the compound of formula (XIII) and one equivalent of base in a polar, aprotic solvent such as THF. The reaction is heated to a temperature at which the reaction proceeds cleanly to completion in less than 16 hours. Upon completion of the reaction, the compound of formula (I) is purified and characterized by conventional methods.

Compounds of formula (I) having the so-called "reverse amide", i.e., where A is —N(R$^1$)C(O)R$^2$ can be made from the appropriate acid of formula (XIVaa) by Hofmann rearrangement of the acid to an amine, followed by acylation with an appropriate acid under the conditions described above. In many cases, the desired diamine can be obtained commercially.

The compounds of formula (I) in which A is a urea may be prepared by reacting a compound of formula (I) where A is —N(R$^1$)R$^{21}$ (where R$^1$ is hydrogen and R$^{21}$ is hydrogen, alkyl, aryl or aralkyl) with an isocyanate. Similarly, the compounds of formula (I) in which A is a carbamate may be prepared by reacting a compound of formula (I) (where A is —N(R$^1$)R$^{21}$ where R$^1$ is hydrogen and R$^{21}$ is hydrogen, alkyl, aryl or aralkyl) with an alkyl chloroformate or by Curtius rearrangement of the carboxylic acid azide of the compound of formula (XIVaa) in the presence of the appropriate alcohol.

A specific embodiment of the generic synthesis of a compound of the invention is shown below in Reaction Scheme 2 as applied to a 6-chloro-2-(1-imidazolyl)-4-pyrimidinamine that incorporates the residue of D-β-thienylalanine piperonylamide:

Reaction Scheme 2

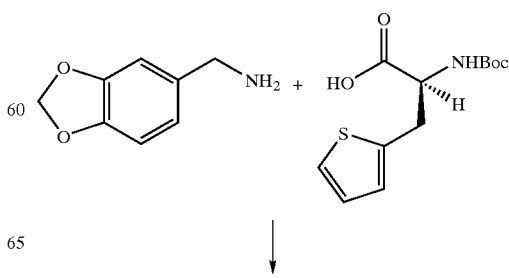

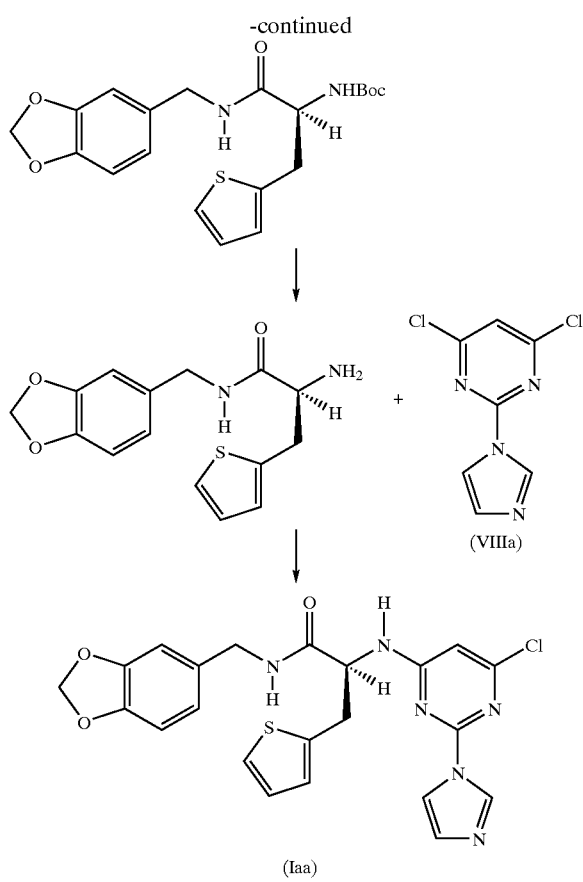

One equivalent of isobutyl chloroformate is added to a solution of N-Boc-D-β-thienylalanine and one equivalent of a base such as N-methyl morpholine in THF. After two minutes, one equivalent of piperonylamine is added and the mixture allowed to warm to room temperature. After thirty minutes, the reaction mixture is passed through a bed of Celite and all volatiles are removed under reduced pressure to yield N-Boc-D-β-thienylalanine piperonylamide.

The N-Boc-D-β-thienylalanine piperonylamide in methanol is treated with acetyl chloride. After 45 minutes, all volatiles are removed under reduced pressure to yield D-β-thienylalanine piperonylamide hydrochloride.

One equivalent of imidazole is added in one portion to a solution of one equivalent of trichloropyrimidine and 1.5 equivs of triethylamine in THF. After reaction is complete, the reaction mixture is poured into saturated, aqueous ammonium chloride and extracted three times with ethyl acetate. The combined organic layers are washed with brine and dried. The reaction mixture is filtered and all volatiles removed under reduced pressure. The product, 2-imidazolyl-4,6-dichloropyrimidine (the compound of formula (VIIIa)) is isolated by flash chromatography (20% ethyl acetate in hexane) as an off-white solid.

Two equivalents of D-β-thienylalanine piperonylamide hydrochloride are added to a solution of one equivalent of 2-imidazolyl-4,6-dichloropyrimidine (the compound of formula (VIIIa)) and three equivalents of Hünig's base (diisopropylethylamine) in THF. After reaction is complete, all volatiles are removed and the product (the compound of formula (Iaa)) is isolated.

A specific example of the synthesis as applied to sarcosine piperonylamide hydrochloride is provided:

Isobutyl chloroformate (226 μL, 1.73 mmol) was added to a solution of N-Boc sarcosine (1.73 mmol) and N-methylmorpholine (192 μL, 1.73 mmol) in THF. After two minutes, piperonylamine (216 mL, 1.73 mmol) was added and the mixture allowed to warm to room temperature. After thirty minutes, the reaction mixture was passed through a bed of Celite and all volatiles were removed under reduced pressure to yield N-Boc sarcosine piperonyl amide (531 mg, 95%) as a white solid. $^1$H NMR: (CDCl$_3$)δ 2.41 (s,3), 3.28 (s,2), 4.39 (d,2), 5.95 (s,2), 6.80 (m,3), 7.43 (bs,1), 9.04 (bs,1).

N-Boc sarcosine piperonylamide (500 mg, 1.54 mmol) in methanol (10 mL) was treated with acetyl chloride (1 mL). After 45 minutes, all volatiles were removed under reduced pressure to yield sarcosine piperonyl amide hydrochloride (395 mg, quant.) as a sticky solid.

Imidazole (9.5 g, 140 mmol) was added in one portion to a solution of trichloropyrimidine (24.7 g, 135 mmol) and triethylamine (30 mL, 216 mmol) in THF (500 mL). After 16 hrs, the reaction mixture was poured into saturated, aqueous ammonium chloride and extracted three times with ethyl acetate. The combined organic layers were washed with brine and dried over MgSO$_4$. The reaction mixture was filtered and all volatiles were removed under reduced pressure. 2-Imidazolyl-4,6-dichloropyrimidine (the compound of formula (VIIIa)) (9.61 g, 33%) was isolated by flash chromatography (20% ethyl acetate in hexane) as an off-white solid. $^1$H NMR: (CDCl$_3$) δ 7.13 (s,1), 7.25 (s,1), 7.76 (s,1), 8.50 (s, 1).

Sarcosine piperonyl amide hydrochloride (50 mg, 0.19 mmol) was added to a solution of 2-imidazolyl-4,6-dichloropyrimidine (VIIIa) (20 mg, 0.093 mmol) and Hünig's base (50 μL, 0.29 mmol) in THF (1 mL). After 16 hrs, all volatiles were removed and the product was isolated as a waxy solid (29 mg, 78%). $^1$H NMR (CDCl$_3$) δ 3.2 (s,3), 4.25 (s,2), 4.38 (s,2), 5.88 (s,2), 6.30 (bs,1), 6.42 (bs,2), 6.65 (m,3), 7.05 (s,1), 8.40 (s,1).

Another specific example of the synthesis of a compound of (XIc) is provided:

Boc-pyrrolidine (3.0 g, 17.5 mmol) was dissolved in ether (35 ml) and tetramethylethylenediamine (TMEDA) (2.03 g, 17.5 mmol), cooled to −78° C. and s-butyllithium (1.3 M, 13.5 mL, 18 mmol) was added. After stirring for 1 hour, allyl bromide was added in ether (5 mL). After warming to room temperature, the reaction was quenched with water and the organic layer was separated. The organic layer was washed with 1 M solution of NaH$_2$PO$_4$ and water, then dried over MgSO$_4$. The solvent was removed in vacuo and the residue was purified by chromatography on silica gel (hexanes/ethyl acetate (9:1) to give the olefin (0.50 g, 14%, $^1$H NMR (CDCl$_3$) δ 5.65–5.85 (m, 1), 5.00–5.20 (m, 2), 3.70–3.90 (m, 1), 3.20–3.45 (m, 2), 2.35–2.60 (M, 1), 2.00–2.20 (m, 1), 1.60–2.00 (m, 4), 1.45 (s, 9)). The olefin (500 mg, 2.37 mmol), 5-bromo-1,3-benzodioxolane (476 mg, 2.37 mmol), triethylamine (478 mg, 4.74 mmol), tri-o-tolylphosphine (96 mg. 0.31 mmol) and Pd(OAc)$_2$ (26 mg, 0.12 mmol) was dissolved in CH$_3$CN and refluxed overnight under argon. An additional 1 equivalent (476 mg) of the bromide and Pd(OAC)$_2$ (52 mg, 0.24 mmol) was added and refluxing continued for 4.5 hours. The reaction was filtered and the solvent was evaporated. The residue was taken up in ether and washed successively with water, 1 M $NaH_2PO_4$, water, and brine. After drying, the solvent was removed and the product was purified by chromatography (silica gel. hexane-:ethyl acetate, 4:1) to yield 152 mg (19%) of the Boc-protected [(1,3-benzodiox-5-yl)prop-2-enyl]pyrrolidine ($^1$H NMR (CDCl$_3$) δ 6.90 (s, 1), 6.70–6.80 (m, 2), 6.35 (d, 1). 3.80–3.95 (m, 1), 3.25–3.50 (m. 2), 2.45–2.70 (m, 1), 2.20–2.35 (m, 1), 1.70–2.00 (M, 4), 1.45 (s, 9)). The Boc group was removed under standard conditions.

Another specific embodiment of the generic syntheis as applied to a compound of the invention follows:

To butyl alchohol (3 ml) was added 2-fluoro-4-chloropurine (41 mg, 0.24 mmol), N-[(1,3-benzodioxol-5-yl)methyl]piperidine-2-acetamide (66 mg, 0.24 mmol), and Hünig's's base (diisopropylethylamine) (0.042 mL, 0.24 mmol). After stirring at 90° C for 6 hours, the reaction was diluted with ethyl acetate. The organic material was washed with saturated NH$_4$Cl and brine, dried (MgSO$_4$), and the solvent was removed in vacuo. Chromatography of the residue (CH$_2$Cl$_2$/MeOH, 10/1) gave 42 mg of the fluoropurine. The fluoropurine (18.9 mg, 0.046 mmol) was dissolved in DMSO and reacted with TMS-imidazole (0.10 g, 0.66 mmol) and CsF (61 mg, 0.40 mmol). After stirring at 130° C for 72 hours, the reaction was diluted with ethyl acetate and washed with saturated NH$_4$Cl and brine. The organic layer was dried (MgSO$_4$), the solvent removed in vacuo, and the residue chromatographed (CH$_2$Cl$_2$/MeOH, 19/1) to give 12 mg of N-[(1,3-benzodioxol-5-yl)methyl]-1-[2-(1H-imidazol-1-yl)purin-6-yl]piperidine-2-acetamide.

Another specific example of the synthesis is provided:

To THF (10 mL) was added cyanuric chloride (158 mg, 0.85 mmol), N-[(1,3-benzodioxol-5-yl)methyl]piperidine-2-acetamide (47 mg, 0.17 mmol), and imidazole (58 mg, 0.85 mmol). After stirring for 12 hours, the reaction was diluted with ethyl acetate. The organic material was washed with saturated NH$_4$Cl and brine, dried (MgSO$_4$), and the solvent was removed in vacuo. Chromatography of the residue (hexanes/ethyl acetate, 4/1) gave 60 mg of the dichlorotriazine. The dichlorotriazine (20 mg, 0.047 mmol) was dissolved in THF and reacted with TMS-imidazole (0.009 mL, 0.06 mmol) and CsF (11 mg, 0.07 mmol) at 0° C. After warming to room temperature and stirring for 4 hours, the reaction was diluted with ethyl acetate and washed with saturated NH$_4$Cl, water, and brine. The organic layer was dried (MgSO$_4$), the solvent removed in vacuo, and the residue chromatographed (ethyl acetate/hexanes/MeOH, 4/4/1) to give 6.5 mg of N-[(1,3-benzodioxol-5-yl)methyl]-1-[3-chloro-5-(1H-imidazol-1-yl)triazin-2-yl]piperidine-2-acetamide.

Another specific example of the synthesis is provided:

To a solution of indole-5-carboxylic acid (0.50 g, 3.1 mmol) in MeOH (25 mL) was added trimethylsilyidiazomethane until no gas evolution was observed. The solution was concentrated, dissolved in CH$_2$Cl$_2$, and washed with saturated NaHCO$_3$ and brine. The organic layer was dried (MgSO$_4$) and the solvent was removed in vacuo to give 0.54 g of the ester ($^1$H NMR (CDCl$_3$) δ 3.95 (s, 3), 6.63 (s, 1), 7.25 (m, 1), 7.40 (d, 1), 7.95 (d, 1), 8.25–8.4 (br s, 1), 8.45 (s, 1)). The ester (100 mg, 0.58 mmol) was dissolved in DMF (10 mL) and 4-chloro-2-imidazol-1-ylpyrimidine (113 mg, 0.63 mmol) was added. After heating at 60° C for 18 hours, the solvent was removed in vacuo, the residue was dissolved in CH$_2$Cl$_2$, and washed with saturated NaHCO$_3$ and brine. The organic layer was dried (MgSO$_4$), the solvent was removed in vacuo and the residue was chromatographed (CH$_2$Cl$_2$/MeOH, 19/1) to give 68 mg (37%) of the pyrimidine ($^1$H NMR (CDCl$_3$) δ 3.95 (s, 3), 6.90 (s, 1), 7.25 (m, 2), 7.80 (m, 1), 7.95 (s, 1), 8.10 (d, 1), 8.4 (s, 1), 8.50 (d, 1), 8.70 (m, 2)). The pyrimidine was dissolved in THF/water (1/1) and LiOH (6 mg, 0.21 mmol) was added. After heating at 60° C for 3 hours, the solvent was removed in vacuo and acidified with methanolic HCl. The solvent was removed in vacuo, dissolved in DMF and treated with HATU (42 mg, 0.11 mmol), DIEA (37 mg, 0.21 mmol), and piperonylamine (26 mL, 0.21 mmol). After stirring for 18 hours, the solvent was removed in vacuo, the residue was dissolved in CH$_2$Cl$_2$, and washed with saturated NaHCO$_3$ and brine. The organic layer was dried (MgSO$_4$), the solvent was removed in vacuo, and the residue was chromatographed (CH$_2$Cl$_2$/MeOH, 19/1) to give 2 mg (4%) of N-[(1,3-benzodioxol-5-yl)methyl]-1-[2-(1H-imidazol-1-yl)pyrimidin-4-yl]indole-6-carboxamide; $^1$H NMR (CDCl$_3$) δ 3.75 (s, 2), 5.95 (s, 2), 6.80–6.90 (m, 2), 7.05–7.15 (m, 2), 7.25 (m, 2), 7.75–7.85 (m, 2), 8.00 (s, 2), 8.50–8.60 (m, 2), 8.70–8.80 (m, 1); MS: (439.2 M+H)$^+$.

Another specific embodiment of the generic synthesis as applied to a compound of the invention is N-[(1,3-benzodioxol-5-yl)ethyl]-1-[2-(1H-imidazol-1-yl)pyrimidin-4-yl]pyrrole-2-carboxamide [MS: (403.2 M+H)$^+$, which was prepared in a similar manner described above for N-[(1,3-benzodioxol-5-yl)methyl]-1-[2-(1H-imidazol-1-yl)pyrimidin-4-yl]indole-6-carboxamide.

The following Reaction Scheme 3 depicts a method of preparing the compounds of the invention where U is CR$^5$ (where R$^5$ is hydrogen) and X, Y and Z are CR$^{19}$ (where R$^{19}$ is hydrogen):

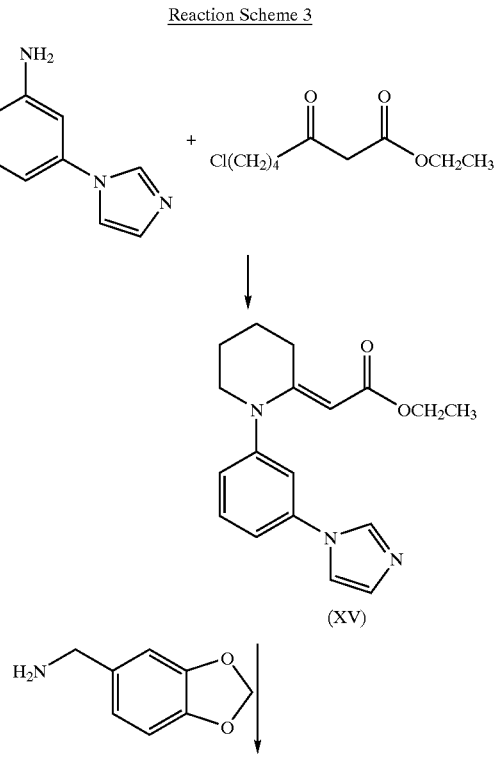

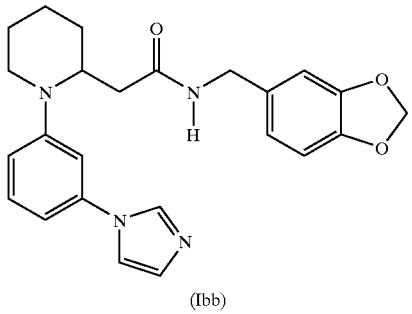

(Ibb)

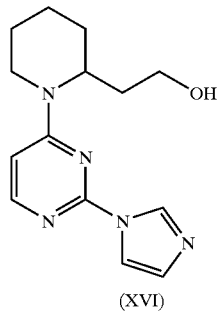

(XVI)

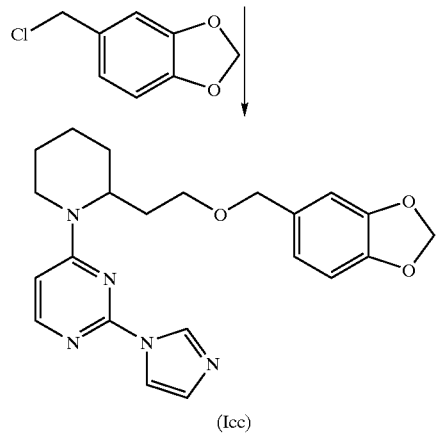

(Icc)

The above synthesis may be carried out as follows: To benzene (20 mL) was added 1-(3-aminophenyl)imidazole (755 mg, 4.7 mmol), 7-chloro-3-oxoheptanoic acid ethyl ester (982 mg, 4.7 mmol), $Na_2HPO_4$ (667 mg, 4.7 mmol), $I_2$ (60 mg, 0.23 mmol), and 4 Å molecular sieves (500 mg). After refluxing for 6 hours, more $I_2$ (60 mg) was added. After stirring for 16 hours, the reaction was filtered, the solvent was removed in vacuo, and the residues chromatographed ($CH_2Cl_2$/MeOH, 98/2) to give 120 mg (8%) of 1-[3-(1H-imidazol-1-yl)phenyl]piperidine-2-acrylic acid ethyl ester ($^1$H NMR ($CDCl_3$) δ 7.85 (s, 1), 7.05–7.50 (m, 6), 4.80 (s, 1), 4.15 (q, 2), 3.45 (t, 2), 2.4 (t, 2), 1.5–1.8 (m, 6), 1.30 (t, 3)). This ester (120 mg, 0.38 mmol) was dissolved in MeOH (20 mL) and reacted with 10% Pd/C (60 mg) and 1 atm of $H_2$. After reacting for 60 hours, the reaction was filtered, the solvent removed in vacuo, and the residue chromatographed (ethyl acetate/hexanes, 1/1) to give 24 mg of 1-[3-(1H-imidazol-1-yl)phenyl]piperidine-2-acetic acid ethyl ester (compound of formula (XV)). This ester (24 mg, 0.076 mmol) was dissolved in 5% methanolic NaOH. After stirring for 16 hours, the reaction was acidified with methanolic HCl, the solvent removed in vacuo, and the residue dissolved in DMF. Piperonylamine (1 eq), Hünig's base (2 eq) and HATU (1 eq) were added. After reaction completion the reaction mixture was partitioned with water and ethyl acetate. The organic layer was separated, washed with water, and dried. The solvent was removed in vacuo and the residue was chromatographed (ethyl acetate/MeOH, 98/2) to give 6 mg of the compound of formula (Ibb), N-[(1,3-benzodioxol-5-yl)methyl]-1-[3-(1H-imidazol-1-yl)phenyl]piperidine-2-acetamide: $^1$H NMR ($CDCl_3$) δ 7.80 (s, 1), 7.10–7.30 (m, 4), 6.50–6.70 (m, 5), 5.90 (s, 2), 4.20–4.35 (m, 2), 3.85 (brs, 1), 3.50 (t, 2), 2.95 (d, 1), 2.35–2.55 (m, 2), 1.4–1.9 (m, 6); MS: (419 M+H)$^+$.

The following Reaction Scheme 4 depicts a method of preparing compounds of the invention where A is —OR$^1$:

Reaction Scheme 4

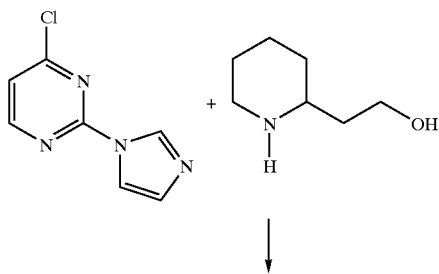

The above synthesis may be carried out as follows: To DMF (100 ml) was added 4-chloro-2-imidazol-1-ylpyrimidine (0.50 g, 2.77 mmol), 2-piperidineethanol (0.359 g, 2.77 mmol), and Hünig's base (0.536 g, 4.15 mmol). After heating at 80° C for 5 hours, the solvent was removed in vacuo and the residue was chromatographed ($CH_2Cl_2$/MeOH, 19/1) to give 349 mg (46%) of 1-[(1H-imidazol-1-yl)pyrimidin-4-yl]piperidine-2-ethanol (the compound of formula (XVI)), ($^1$H NMR ($CDCl_3$) δ 8.54 (s, 2), 8.11 (d, 1), 7.82 (t, 1), 7.11 (d, 1), 6.44 (d, 1), 3.60 (m, 2), 3.03 (m, 1), 1.77 (m); MS: 274 (M+H)$^+$). To a solution of 1-[(1H-imidazol-1-yl)pyrimidin-4-yl]piperidine-2-ethanol (25 mg, 0.092 mmol) dissolved in DMF (5 ml) was added NaH (60% dispersion in oil, 5.5 mg, 0.14 mmol) followed by piperonyl chloride (17 mg, 0.10 mmol) and t-butyl ammonium chloride. After stirring for 16 hours at 80° C., the solvent was removed in vacuo and the residue was partitioned with saturated $NH_4Cl$ and $CH_2Cl_2$. The organic layer was separated, dried ($MgSO_4$), the solvent removed in vacuo, and the residue chromatographed ($CH_2Cl_2$/MeOH, 19/1) to give 13 mg (35%) of 4-[2-[[(1,3-benzodioxol-5-yl)methoxy]ethyl]piperidin-1-yl]-2-(1H-imidazol-1-yl)pyrimidine (the compound of formula (Icc)); $^1$H NMR ($CDCl_3$) δ 8.52 (s, 1), 8.05 (d, 1), 7.80 (s, 1), 7.09 (s, 1), 6.73 (m, 3), 6.45 (d, 1), 5.93 (s, 2), 4.30 (s, 2), 3.45 (m, 2), 2.95 (m, 1), 1.55 (m); MS: 408.7 (M+H)$^+$.

Compounds of formula (XVI) may be used to prepare other compounds of the invention as depicted below in Reaction Scheme 5 where R$^{1b}$ is hydrogen or —CH$_3$, Ms is mesyl and Ac is acetyl:

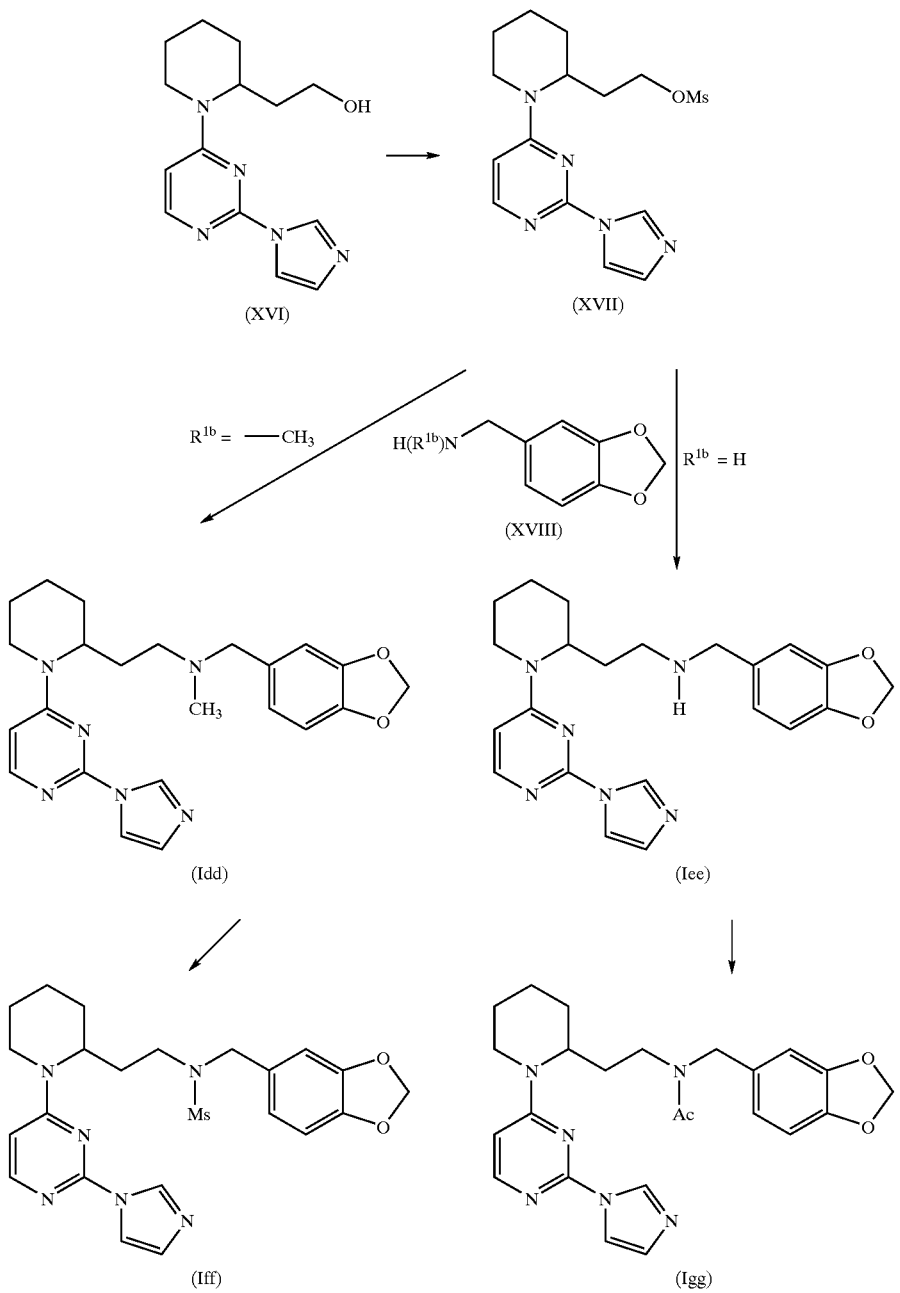

Reaction Scheme 5

The above synthesis may be carried out as follows: To a solution of 1-[(1H-imidazol-1-yl)pyrimidin-4-yl]piperidine-2-ethanol (the compound of formula (XVI)) (236 mg, 0.86 mmol) and methanesulfonyl chloride (99 mg, 0.87 mmol) dissolved in $CH_2Cl_2$ (20 mL) was added TEA (87.5 mg, 0.87 mmol). After stirring for 16 hours at 0° C, methanesulfonyl chloride (99 mg, 0.87 mmol) and TEA (87.5 mg, 0.87 mmol) were added and the solution was warmed to ambient temperature. After stirring for 1 hour, the solution was washed with saturated $NH_4Cl$ and brine; dried ($MgSO_4$), and the solvent removed in vacuo to give 276 mg (91%) of the compound of formula (XVII) ($^1$H NMR (CDCl$_3$) δ 8.72 (s, 1), 8.15 (d, 1), 7.89 (s, 1), 7.18 (s, 1), 6.46 (d, 1), 4.24 (m, 3), 2.95 (s, 3), 2.18 (m, 6), 1.76 (m). MS: 352.5 (M+H)$^+$. A solution of the compound of formula (XVII) (100 mg, 028 mmol) and a compound of formula (XVIII) (429 mg, 2.84 mmol) dissolved in $CH_2Cl_2$ (7.5 ml) was stirred for 16 hours, and then DMF (7.5 ml) was added. After stirring for 2 hours, the solvent was removed in vacuo and the residue was partitioned with saturated $NH_4Cl$ and $CH_2Cl_2$. The organic layer was separated, washed with brine, dried ($MgSO_4$), the solvent removed in vacuo, and the residue chromatographed ($CH_2Cl_2$/MeOH, 19/1) to give 6.6 mg (21%) of N-[(1,3-benzodioxol-5-yl)methyl]-1-[2-(1H-imidazol-1-yl)pyrimidin-4-yl]piperidine-2-ethanamine (the compound of formula (Iee)): $^1$H NMR (CDCl$_3$) δ 8.50 (s, 1), 8.08 (d, 1), 7.77 (s, 1), 7.08 (s, 1), 6.66 (m, 3), 6.43 (d, 1), 5.91 (s, 2), 3.60 (d, 2), 3.00 (m, 1), 2.57 (m, 2), 2.02 (m, 1), 1.65 (m). MS: 407.8 (M+H)$^+$.

To THF (3 mL) was added N-[(1,3-benzodioxol-5-yl)methyl]-1-[2-(1H-imidazol-1-yl)pyrimidin-4-yl]piperidine-2-ethanamine (8 mg, 0.03 mmol), Hünig's base (8 mg, 0.06 mmol), and acetic anhydride (4 mg, 0.04 mmol). After stirring for 16 hours, the solvent was removed in vacuo and the residue was chromatographed (CH$_2$Cl$_2$/MeOH. 19/1) to give 8 mg (60%) of N-acetyl-N-[(1,3-benzodioxol-5-yl)methyl]-1-[2-(1H-imidazol-1-yl)pyrimidin-4-yl]piperidine-2-ethanamine (the compound of formula (Igg)): $^1$H NMR (CDCl$_3$) δ 8.48 (s, 1), 8.08 (d, 1), 7.76 (s, 1), 7.09 (s, 1), 6.66 (m, 3), 6.33 (m, 1), 5.94 (s, 1), 5.91 (s, 1), 4.43 (m,3), 3.40 (m, 2), 2.11 (d, 3), 1.14 (m); MS: 450.0 (M+H)$^+$.

Alternatively, to THF (3 mL) was added N-[(1,3-benzodioxol-5-yl)methyl]-1-[2-(1H-imidazol-1-yl)pyrimidin-4-yl)piperidine-2-ethanamine (8 mg, 0.03 mmol), Hünig's base (8 mg, 0.06 mmol), and methanesulfonyl chloride (4.5 mg, 0.04 mmol). After stirring for 16 hours, the solvent was removed in vacuo and the residue was chromatographed (CH$_2$Cl$_2$/MeOH. 19/1) to give 7 mg (51%) of N-[(1,3-benzodioxol-5-yl)methyl]-1-[2-(1H-imidazol-1-yl)pyrimidin-4-yl]-N-(methylsulfonyl)piperidine-2-ethanamine (the compound of formula (Iff)); $^1$H NMR (CDCl$_3$) δ 8.10 (s, 1), 7.78 (d, 1), 7.13 (s, 1), 6.82 (s, 1), 6.72 (s, 2), 6.30 (d, 1), 5.94 (s, 2), 4.23 (m, 3), 3.20 (m, 2), 2.80 (s, 3), 1.14 (m); MS: 485.7 (M+H)$^+$.

To DMF (5 ml) was added the compound of formula (XVII) (50 mg, 0.14 mmol), Hünig's base (28 mg, 0.21 mmol), and N-methylpiperonylamine (28 mg, 0.17 mmol). After stirring at 80° C for 16 hours, the solvent was removed in vacuo and the residue was partitioned with saturated NH$_4$Cl and CH$_2$Cl$_2$. The organic layer was separated, washed with brine, dried (MgSO$_4$), the solvent removed in vacuo, and the residue was partitioned with ethyl acetate and water. The organic layer was separated, washed with brine, dried (MgSO$_4$), the solvent was removed in vacuo, and the residue was chromatographed (ethyl acetate/MeOH, 19/1) to give 7 mg (12%) of N-[(1,3-benzodioxol-5-yl)methyl]-1-[2-(1H-imidazol-1-yl)pyrimidin-4-yl]-N-methylpiperidine-2-ethanamine (the compound of formula (Idd)); $^1$H NMR (CDCl$_3$) δ 8.53 (s, 1), 8.07 (d, 1), 7.80 (s, 1), 7.10 (s, 1), 6.78 (s, 1), 6.69 (m, 2), 6.43 (d, 1), 5.92 (s, 2), 3.40 (m, 2), 2.97 (m, 1), 1.80 (m); MS: 422.0 (M+H)$^+$.

Reaction Scheme 6 depicts another method of preparing compounds of the invention where V is C(R$^4$)H:

Reaction Scheme 6

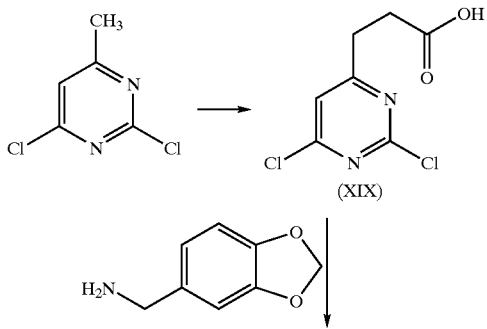

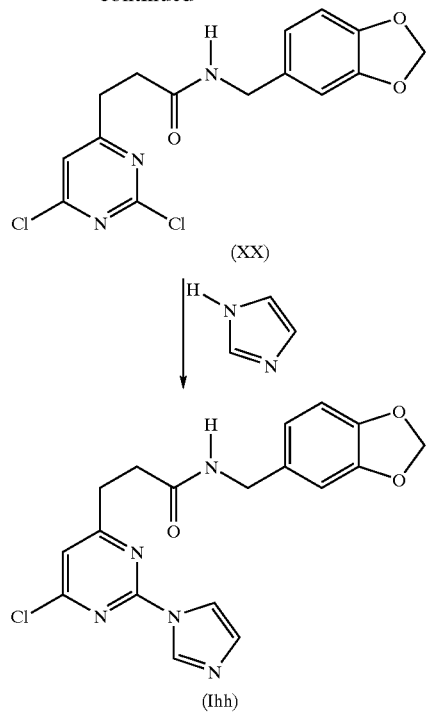

The above synthesis may be carried out as follows: To a solution of LDA (1.28 g, 12 mmol) in THF (30 mL) at −78° C. was added 2,4-dichloro-6-methylpyrimidine (1.96 g, 12 mmol) in THF (15 mL). After stirring for 15 minutes, 3,3-dimethylallyl bromide (1.79 g, 12 mmol) in THF (5 mL) was added dropwise. After the reaction warmed to ambient temperature, water and ethyl acetate was added. The organic layer was separated, the solvent was removed in vacuo, and the residue was chromatographed (ethyl acetate/hexane, 1/19) to give 2.06 g (74%) of 2,4-dichloro-6-(4-methyl-3-pentenyl)pyrimidine ($^1$H NMR (CDCl$_3$) δ 7.15 (s, 1), 5.10 (t, 1), 2.80 (t, 2), 2.45 (m, 21, 1.70 (s, 3), 1.55 (s, 3)). To a solution of NaIO$_4$ (17 g, 81 mmol) and KMnO$_4$ (251 mg, 1.59 mmol) in water was added K$_2$CO$_3$ (1.29 g, 9.38 mmol) and 2,4dichloro-6-(4-methyl-3-pentenyl)pyrimidine (2.06 g, 8.9 mmol) in t-butanol. After stirring for 16 hours, the reaction was acidified to pH 3 and extracted with ethyl acetate. The organic layer was extracted with aqueous NaHCO$_3$. The aqueous layer was acidified to pH 3 and extracted with ethyl acetate. The organic layer was dried and the solvent removed in vacuo to give 980 mg of 3-(2,4-dichloropyrimidin-6-yl)propionic acid (the compound of formula (XIX)), $^1$H NMR (CDCl$_3$) δ 7.30 (s, 1), 3.05 (t, 2), 2.90 (t, 2). The acid was coupled to piperonylamine under standard conditions with isobutyl chloroformate and N-methylmorpholine to give the compound of formula (XX). Imidazole was added under standard conditions (1-trimethylsilylimidazole and CsF in DMF at 60° C.) to give N-[(1,3-benzodioxol-5-yl)ethyl]-6-chloro-2-(1H-:imidazol-1-yl)pyrimidine-4-propionamide (the compound of formula (Ihh)); MS: 386 (M+H)$^+$.

Reaction Schemes 6a through 6d depict methods of preparing compounds of formula (Yc). Compounds of formula (Ya) and formula (Yc) may be similarly prepared:

Reaction Scheme 6a

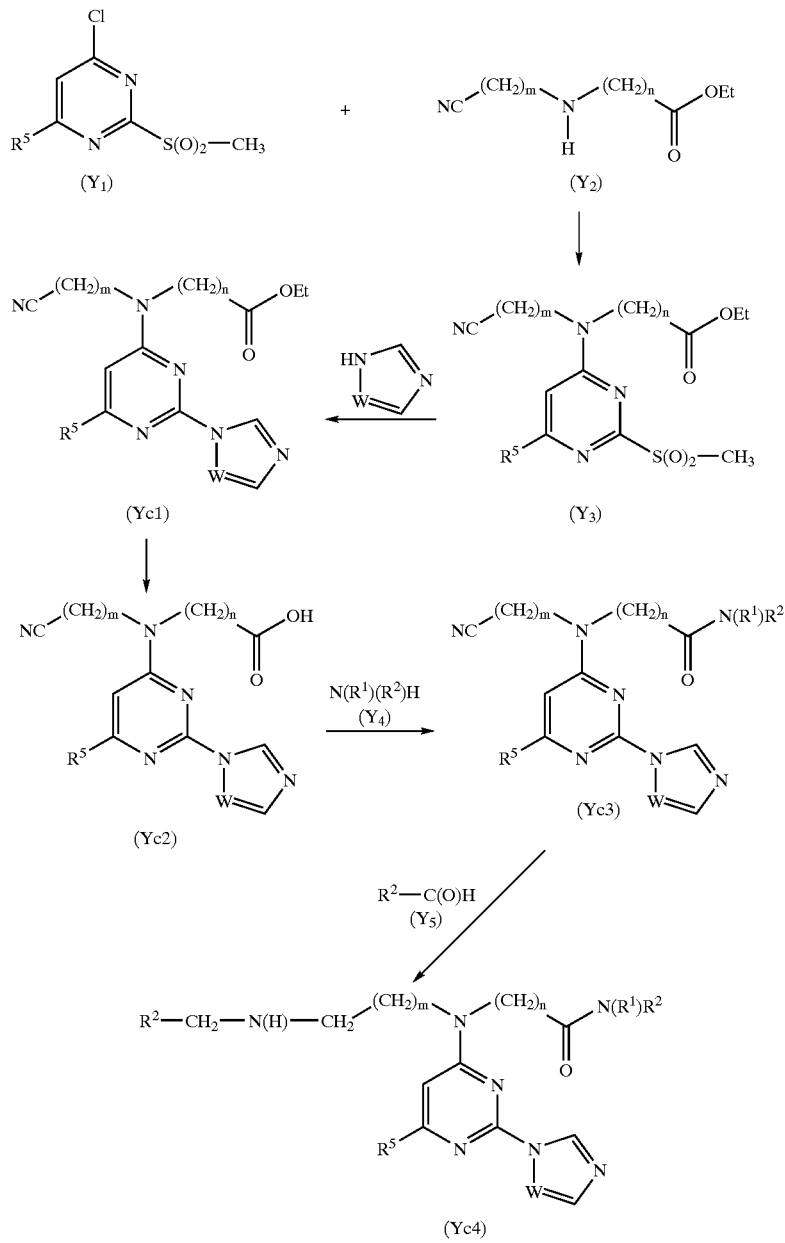

Compounds of formulae ($Y_1$), ($Y_2$), ($Y_4$) and ($Y_5$) are commercially available or may be prepared by methods disclosed herein or by methods known to those of ordinary skill in the art. Each $R^1$, $R^2$, m and n are independently as described above in the Summary of the Invention for compounds of formula (Ya), formula (Yb) and formula (Yc); and $R^5$ and W are also as described above in the Summary of the Invention for compounds of formula (Ya), formula (Yb) and formula (Yc).

The above synthesis may be carried out as follows:

To N-cyanoethylglycine, ethyl ester (15.9 g, 102 mmol) (a compound of formula ($Y_2$)) dissolved in DMSO (70 mL) was added 4-chloro-6-methyl-2-methylsulfonylpyrimidine (18.8 g, 91 mmol) (a compound of formula ($Y_1$)) and diisopropylethylamine (18 mL, 100 mmol). After stirring for 16 hours, the reaction temperature was raised to 70° C. and imidazole (26.5 g, 0.39 mol) was added. After stirring for 1 day, the reaction was cooled to ambient temperature and added to ice water. The solid that formed was suction filtered and collected on paper to give 9.9 g of 2-[(2-cyanoethyl)[2-(1H-imidazol-1-yl)-6-methyl-4-pyrimidinyl]amino]acetic acid, ethyl ester (a compound of formula (Yc1)).

To 2–1(2-cyanoethyl)[2-(1H-imidazol-1-yl)-6-methyl-4-pyrimidinyl]amino]acetic acid, ethyl ester (4.51 g, 14.4 mmol) dissolved in THF (250 mL) was added LiOH (0.91 g, 21.7 mmol) and water (30 mL). After stirring for 18 hours, most of the solvent was removed in vacuo and 1 N HCl (21.7 mL, 21.7 mmol) was added. The solid that formed was suction filtered and collected on paper to give 3.17 g of 2-[(2-cyanoethyl)[2-(1H-imidazol-1-yl)-6-methyl-4-pyrimidinyl]amino]acetic acid (a compound of formula (Yc2)).

To 2-[(2-cyanoethyl)[2-(1H-imidazol-1-yl)-6-methyl-4-pyrimidinyl]amino]acetic acid (1.53 g, 5.3 mmol) slurried in DMF (25 mL) was added carbonyldiimidazole (0.87 g, 5.4 mmol). After stirring for 2 hours, diethylamine (1.0 mL, 9.7 mmol) (a compound of formula $Y_4$)) was added. After stirring for 18 hours, the reaction was partitioned with ethyl acetate and water. The organic layer was separated, dried ($Na_2SO_4$), and the solvent was removed in vacuo to give 0.91 g of 2-[(2-cyanoethyl)[2-(1H-imidazol-1-yl)-6methyl-4-pyrimidinyl]amino)-N,N-diethylacetamide (a compound of formula (Yc3)).

The following compounds of formula (Yc3) and derivatives thereof were prepared in a similar manner with the appropriately substituted starting materials:
2-[(2-cyanoethyl)[2-(1H-imidazol-1-yl)-6-methyl-4-pyrimidinyl]amino]-N-methylacetamide;
2-[(2-cyanoethyl)[2-(1H-imidazol-1-yl)-6-methyl-4-pyrimidinyl]amino]-N-[2-(1,4-benzodioxan-4-yl)ethyl]acetamide.

Ammonia (g) was bubbled into 2-[(2-cyanoethyl)[2-(1H-imidazol-1-yl)-6-methyl-4-pyrimidinyl]amino]-N,N-diethylacetamide (0.22 g, 0.65 mmol) dissolved in MeOH (25 mL). Raney Nickel (0.8 g) was added and the mixture was placed under nitrogen at 50 psi. When the reaction was determined to be complete by TLC, the reaction mixture was suction filtered through celite and the solvent was removed in vacuo. To the residue dissolved in MeOH (10 mL) was added piperonal (0.29 g, 1.9 mmol) and $NaBH(OAc)_3$ (0.40 g, 1.9 mmol). After stirring for 18 hours, the solvent was evaporated and the residue was partitioned between ethyl acetate and aqueous bicarbonate solution. The organic layer was separated, dried ($Na_2SO_4$), and the solvent was removed in vacuo. Chromatography on silica with acetonitrile/ammonium hydroxide (19/1) gave 2-[3-[(1,3-benzodioxol-5-ylmethyl)amino]propyl][2-(1H-imidazol-1-yl)-6-methyl-4-pyrimidinyl]amino]-N,N-diethylacetamide, a compound of formula (Yc4); NMR ($CDCl_3$) 8.4 (s, 1), 7.65 (s, 1), 7.0 (s, 1), 6.85 (s, 1), 6.75 (d, 1), 6.5 (d, 1), 6.05 (br, 1), 5.85 (s, 2), 4.3 (s, 2), 3.85 (s, 2), 3.65 (br, 2), 3.4 (m, 4), 2.95 (t, 2), 2.3 (s, 3), 2.2 (m, 2), 1.25 (t, 3), 1.1 (t, 3) ppm.

The following compounds of formula (Yc4) and derivatives thereof were prepared in a similar manner with appropriately substituted starting materials:
2-[[3-[[1,4-benzodioxan-6-yl)methyl]amino]propyl][2-(1H-imidazol-1-yl)-6-methyl-4-pyrimidinyl]amino]-N-methylacetamide; NMR ($CDCl_3$) 8.5 (s, 1), 7.8 (s, 1), 7.1 (s, 1), 6.75 (m, 3), 6.25 (br, 1), 4.25 (s, 4), 4.15 (br, 2), 3.7 (s, 2), 3.6 (s, 2), 2.8 (d, 3), 2.75 (m, 2), 2.4 (s, 3), 1.85 (m, 2) ppm;
2-[[3-[(1,3-benzodioxol-5-ylmethyl)amino]propyl][2-(1H-imidazol-1-yl)-6-methyl-4-pyrimidinyl]amino]-N-methylacetamide; NMR (DMSO-$d_6$) 8.4 (s, 1), 8.0 (m, 1), 7.8 (s, 1), 7.05 (s, 1), 6.9 (s, 1), 6.8 (m, 2), 6.65 (s, 1), 6.3 (br, 1), 5.95 (s, 2), 4.1 (br, 2), 3.6 (s, 2), 3.55 (br, 2), 3.3 (br, 3), 2.6 (m, 2), 2.3 (s, 3), 1.75 (m, 2) ppm;
2-[[3-[[(1,4-benzodioxan-6-yl)methyl)amino]propyl][2-(1H-imidazol-1-yl)-6-methyl-4-pyrimidinyl]amino]-N,N-diethylacetamide; NMR ($CDCl_3$) 8.4 (s, 1), 7.7 (s, 1), 7.05 (s, 1), 6.85 (s, 1), 6.6 (m, 2), 6.3 (br, 1), 4.4 (s, 2), 4.25 (s, 4), 3.7 (s, 2), 3.6 (m, 2), 3.4 (q, 4), 2.7 (t, 2), 2.35 (s, 3), 1.9 (m, 2), 1.35 (t, 3), 1.15 (t, 3) ppm;
2-[[3-[[(1,4-benzodioxan-6-yl)methyl]amino]propyl][2-(1H-imidazol-1-yl)-6-methyl-4-pyrimidinyl]amino]acetamide; NMR ($CDCl_3$) 8.5 (s, 1), 7.8 (s, 1), 7.1 (s, 1), 6.75 (m, 3), 6.3 (br, 1), 6.0 (br, 1), 4.2 (s, 4), 4.15 (s, 2), 3.65 (m, 4), 2.75 (m, 2), 2.4 (s, 3), 1.85 (m, 2) ppm;
2-[[3-[(1,3-benzodioxol-5-ylmethyl)amino]propyl](2-(1H-imidazol-1-yl)-6-methyl-4-pyrimidinyl]amino]acetamide; NMR ($CDCl_3$) 8.5 (s, 1), 7.75 (s, 1), 7.05 (s, 1), 6.75 (m, 3), 6.3 (br, 1), 5.95 (s, 2), 5.4 (br, 1), 4.15 (s, 2), 3.7 (br, 2), 3.6 (s, 2), 2.75 (t, 2), 2.4 (s, 3), 1.85 (m, 2) ppm.

Compounds of formula ($Y_4$) wherein $R^2$ is 2-(1,4-benzodioxan-6-yl)ethyl may be prepared as follows and reacted with the compound of formula (Yc2) to prepare compounds of formula (Yc3), which may be further reacted as described above to form compounds of formula (Yc4):

To 1,4-benzodioxane-6-carboxaldehyde (10.0 g, 60 mmol) in acetic acid (50 mL) was added nitromethane (6.3 mL, 1.9 eq.) and ammonium acetate (5.1 g, 1.1 eq.). After heating at 110° C for 4 hours the mixture was cooled to ambient temperature, water (150 mL) was added, and the solid precipitate was collected by filtration. The solid was crystallized from methylene chloride-hexane (1:1, 45 mL) to obtain 7.6 g (61%) of 6(2-nitroethenyl)-1,4-benzodioxane. To a portion of the solid (3.58 g) dissolved in MeOH-EtOH-AcOEt (1:1:1, 450 mL) was added 10% Pd/C (1.7 g) and concentrated HCl (3.3 mL, 2.3 eq). After shaking on a Parr hydrogenator at 45 psi for 5 hours, the catalyst was removed by filtration through Celite and washed with methanol. Evaporation of the filtrate gave 3.59 g (96%) of 1,4-benzodioxan-6-ethanamine, hydrochloride.

Alternatively, compounds of formula ($Y_3$) may be reacted as follows to form compounds of formula (Yc3) wherein $R^1$ and $R^2$ are both hydrogen, which may be further reacted with a compound of formula (Y5) to form compounds of formula (Yc4):

To 2-[(2-cyanoethyl)[2-(1H-imidazol-1-yl)-6-methyl-4-pyrimidinyl]amino]acetic acid, ethyl ester (2.3 g, 7.3 mmol) slurried in MeOH (50 mL) and cooled in a dry ice/acetone bath was bubbled $NH_3$. The bomb was sealed and heated in an oil bath at 65° C for 2 days. The reaction was cooled in a dry ice/acetone bath and the seal was broken. The solid was suction filtered to give 1.7 g of 24(2-cyanoethyl)[2-(1H-imidazol-1-yl)-6-methyl-4-pyrimidinyl]amino]acetamide.

Reaction Scheme 6b depicts another method of preparing compounds of formula (Yc). Compounds of formula (Ya) and formula (Yb) may be similarly prepared:

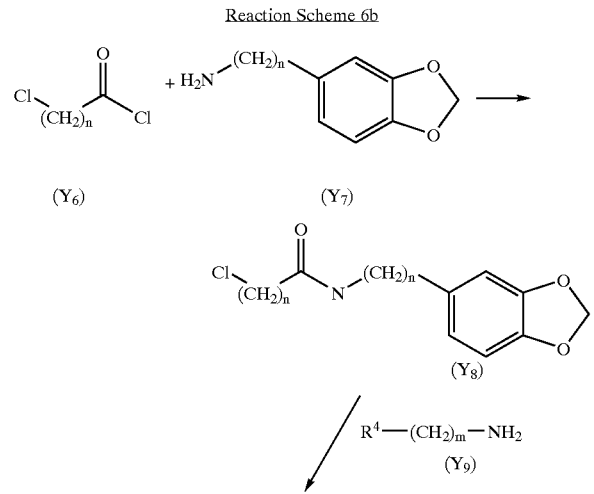

Reaction Scheme 6b

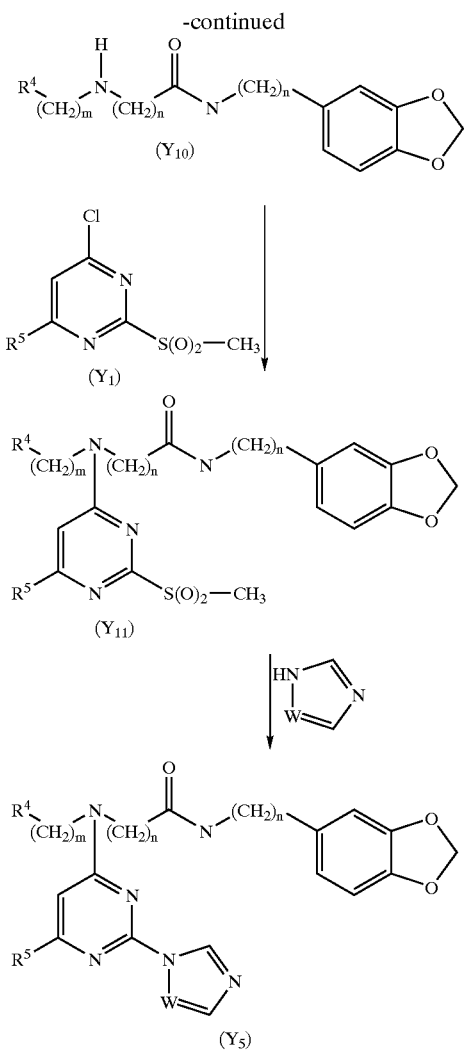

Compounds of formulae (Y₁), (Y₆), (Y₇), (Y₉) and (Y₅) are commercially available or may be prepared by methods disclosed herein or by methods known to those of ordinary skill in the art. Each $R^1$ $R^2$, m and n are independently as described above in the Summary of the Invention for compounds of formula (Ya), formula (Yb) and formula (Yc); and $R^4$, $R^5$ and W are also as described above in the Summary of the Invention for compounds of formula (Ya), formula (Yb) and formula (Yc).

The above synthesis may be carried out as follows:

To homopiperonylamine hydrochloride (2.14 g, 10.6 mmol) (a compound of formula (7)) in CH₂Cl₂ (20 mL) in an ice bath was added triethylamine (3.1 mL, 21 mmol) and chloroacetyl chloride (0.85 mL, 10 mmol) (a compound of formula Y₆)). After warming to ambient temperature and stirring for 16 hours, the reaction was partitioned with 1 N HCl. The organic layer was separated, washed with aqueous bicarbonate, dried (Na₂SO₄), and the solvent was removed in vacuo to give 1.8 g of 2-chloro-N-[2-(1,3-benzodioxol-5-yl)ethyl]acetamide, a compound of formula 8).

To 2-chloro-N-[2-(1,3-benzodioxol-5-yl)ethyl]acetamide (0.45 g, 1.9 mmol) in ethanol (10 mL) was added 3-aminopropanol (0.72 mL, 9.4 mmol) (a compound of formula (Y₉)). After heating the reaction in an oil bath at 60° C for 1 day, the reaction was partitioned with ethyl acetate and water. The organic layer was separated, washed with brine, dried (Na₂SO₄), and the solvent was removed in vacuo to give 0.44 g of 2-[(3-hydroxypropyl)amino]-N-[2-(1,3-benzodioxol-5-yl)ethyl]acetamide, a compound of formula (Y₁₀).

The following compounds of formula (Y₁₀) were prepared in a similar manner from the appropriately substituted starting materials:

2-[(3-pyridinylmethyl)amino]-N-[2-(1,3-benzodioxol-5-yl)ethyl]acetamide;

2-[[2-(4-morpholinyl)ethyl]amino]-N-[2-(1,3-benzodioxol-5-yl)ethyl]acetamide;

2-[(1,3-benzodioxol-5-ylmethyl)amino]-N-[2-(1,3-benzodioxol-5-yl)ethyl]acetamide.

To 2-[(3-hydroxypropyl)amino]-N-1,3-benzodioxol-5-ylmethyl)acetamide (0.44 g, 1.6 mmol) dissolved in DMSO (5 mL) was added 4-chloro-6-methyl-2-methylsulfonylpyrimidine (0.31 g, 1.5 mmol) (a compound of formula (Y₁) and diisopropylethylamine (0.55 mL, 3.1 mmol). After stirring for 16 hours, the reaction temperature was raised to 70° C and imidazole (0.47 g, 6.9 mol) was added. After stirring for 1 day, the reaction was cooled to ambient temperature and partitioned with water and ethyl acetate. The organic layer is separated, dried (Na₂SO₄), and the solvent was removed in vacuo. Chromatography on silica with CH₂Cl₂/MeOH gave 2-[(3-hydroxypropyl)[2-(1H-imidazol-1-yl)-6-methyl-4-pyrimidinyl]amino)-N-[2-(1,3-benzodioxol-5-yl)ethyl]acetamide, a compound of formula (Yc5).

The following compounds of formula (Yc5) and derivatives thereof were prepared in a similar manner with the appropriately substituted starting materials:

2-[(3-pyridinylmethyl)[2-(1H-imidazol-1-yl)-6-methyl-4-pyrimidinyl]amino]-N-[2-(1,3-benzodioxol-5-yl)ethyl]acetamide; NMR (CDCl₃) 8.6 (s, 1), 8.45 (s, 2), 8.15 (t, 1), 7.8 (s, 1), 7.7 (d, 1), 7.35 (br, 1), 7.05 (s, 1), 6.8 (br, 2), 6.6 (br, 2), 6.0 (s, 2), 4.8 (m, 2), 4.2 (m, 2), 3.3 (m, 2), 2.6 (m, 2), 2.3 (s, 3) ppm;

2-[(2-cyanoethyl)[2-(1H-imidazol-1-yl)-6-methyl-4-pyrimidinyl]amino]N-[2-(1,3-benzodioxol-5-yl)ethyl]acetamide; NMR(CDCl₃) 8.5 (s, 1), 7.8 (s, 1), 7.1 (s, 1), 6.6 (d, 1), 6.55 (d, 1), 6.3 (t, 1), 6.2 (s, 1), 5.9 (s, 2), 4.2 (s, 2), 3.9 (t, 2), 3.55 (t, 2), 2.8 (t, 2), 2.75 (t, 2), 2.45 (s, 3) ppm;

2-[[3-[[(1,3-benzodioxol-5-yl)methyl)(methyl)amino]propyl][2-(1H-imidazol-1-yl)-6-methylpyrimidin-4-yl]amino]acetic acid, ethyl ester; NMR (CDCl₃) 8.5 (s, 1), 7.8 (s, 1), 7.05 (s, 1), 6.85 (s, 1), 6.75 (m, 2), 6.4 (br, 1), 5.9 (s, 2), 4.2 (m, 4), 3.6 (m, 2), 3.4 (s, 2), 2.4 (t, 2), 2.35 (s, 3), 2.2 (s, 3), 1.9 (t, 3), 1.2 (t, 3) ppm;

2-[[2-(4-morpholinyl)ethyl][2-(1H-imidazol-1-yl)-6-methyl-4-pyrimidinyl]amino]-N-[2-(1,3-benzodioxol-5-yl)ethyl]acetamide; NMR (CDCl₃) 8.5 (s, 1), 7.8 (s, 1), 7.1 (s, 1), 6.5 (d, 1), 6.3 (br, 1), 6.15 (s, 2), 5.7 (br, 2), 4.0 (m, 4), 3.45 (m, 8), 2.6 (m, 2), 2.4 (s, 3), 2.35 (m, 4) ppm; and 2-[(1,3-benzodioxol-5-ylmethyl)[2-(1H-imidazol-1-yl)-6-methyl-4-pyrimidinyl]amino]-N-[2-(1,3-benzodioxol-5-yl)ethyl]acetamide; NMR (CDCl₃) 8.75 (s, 1), 8,15 (t, 1), 7.8 (s, 1), 7.15 (s, 1), 6.75 (d, 1), 6.7 (m, 2), 6.55 (d, 1), 6.4 (m, 2), 6.2 (br, 1), 6.0 (s, 2), 5.9 (s, 2), 4.65 (br, 2), 4.1 (br, 2), 3.4 (m, 2), 2.3 (s, 3) ppm.

Alternatively, compounds of formula (Y₁₀) and derivatives thereof are prepared as follows:

In a manner similar to the preparation of compounds of formula (Yc3) above, to 2-[(2-cyanoethyl)(dimethylethoxycarbonyl)amino]acetic acid (8.3 g, 39 mmol) dissolved in CH₂Cl₂ (100 mL) was added carbonyldiimidazole (6.2 g., 38 mmol). After stirring for 30 minutes, homopiperonylamine, hydrochloride (8.0 g, 41 mmol) and diisopropylethylamine (7.5 mL, 43 mmol) were added. After stirring for 18 hours, most of the solvent was removed in vacuo and the residue was partitioned with ethyl acetate and 1 N HCl. The organic layer was separated, washed with aqueous bicarbonate and brine, dried ($Na_2SO_4$), and the solvent was removed in vacuo to give 13 g of 2-[(2-cyanoethyl)(dimethylethoxycarbonyl)amino]-N-[2-(1,3-benzodioxol-5-yl)ethyl]acetamide.

To 2-[(2-cyanoethyl)(dimethylethoxycarbonyl)amino]-N-[2-(1,3-benzodioxol-5-yl)ethyl]acetamide (14 g, 37 mmol) in $CH_2Cl_2$ (75 mL) cooled in an ice bath was added trifluoroacetic acid (50 mL). After stirring for 1 hour the ice bath was removed and the solvent was removed in vacuo. The residue was triturated with ether and a solid formed. The solid was collected by filtration to give 12 g of 2-[(2-cyanoethyl)amino]-N-[2-(1,3-benzodioxol-5-yl)ethyl]acetamide, trifluoroacetic acid salt, a compound of formula ($Y_{10}$).

Alternatively, compounds of formula ($Y_{10}$) and derivatives thereof are prepared as follows:

To N-methyl-β-alaninenitrile (50 g, mmol in acetonitrile was added piperonyl chloride (50 g, mmol). After stirring for 18 h, the solvent was removed in vacuo. The residue was dissolved in $CH_2Cl_2$, washed with aqueous carbonate, dried ($MgSO_4$), and the solvent was removed in vacuo. The residue was dissolved in methanol saturated with ammonia (600 mL) and Raney nickel (10 g) was added. After shaking under an atmosphere of hydrogen at 20 psi for 6 h, the reaction was filtered through celite and the solvent was removed in vacuo to give 65 g of N-(1,3-benzodioxol-5-ylmethyl)-N-methyl-1,3-propanediamine.

To N-(1,3-benzodioxol-5-ylmethyl)-N-methyl-1,3-propanediamine (33 g, 0.15 mol) in $CH_2Cl_2$ (500 mL) was added ethyl glyoxalate (30 mL of a 50% toluene solution, 0.15 mol) and sodium triacetoxyborohydride (40 g, 0.19 mol). After stirring for 4 hours, the reaction was washed with aqueous potassium carbonate and the solvent removed in vacuo. Chromatography on silica with $CH_2Cl_2$/MeOH/ammonium hydroxide gave 14 g of 2-([3-[(1,3-benzodioxol-5-ylmethyl)amino]propyl]amino]acetic acid, ethyl ester, a compound of formula ($Y_{10}$)

Reaction Scheme 6c depicts another method of preparing compounds of formula (Yc). Compounds of formula (Ya) and formula (Yb) may be similarly prepared with the appropriately substituted starting materials.

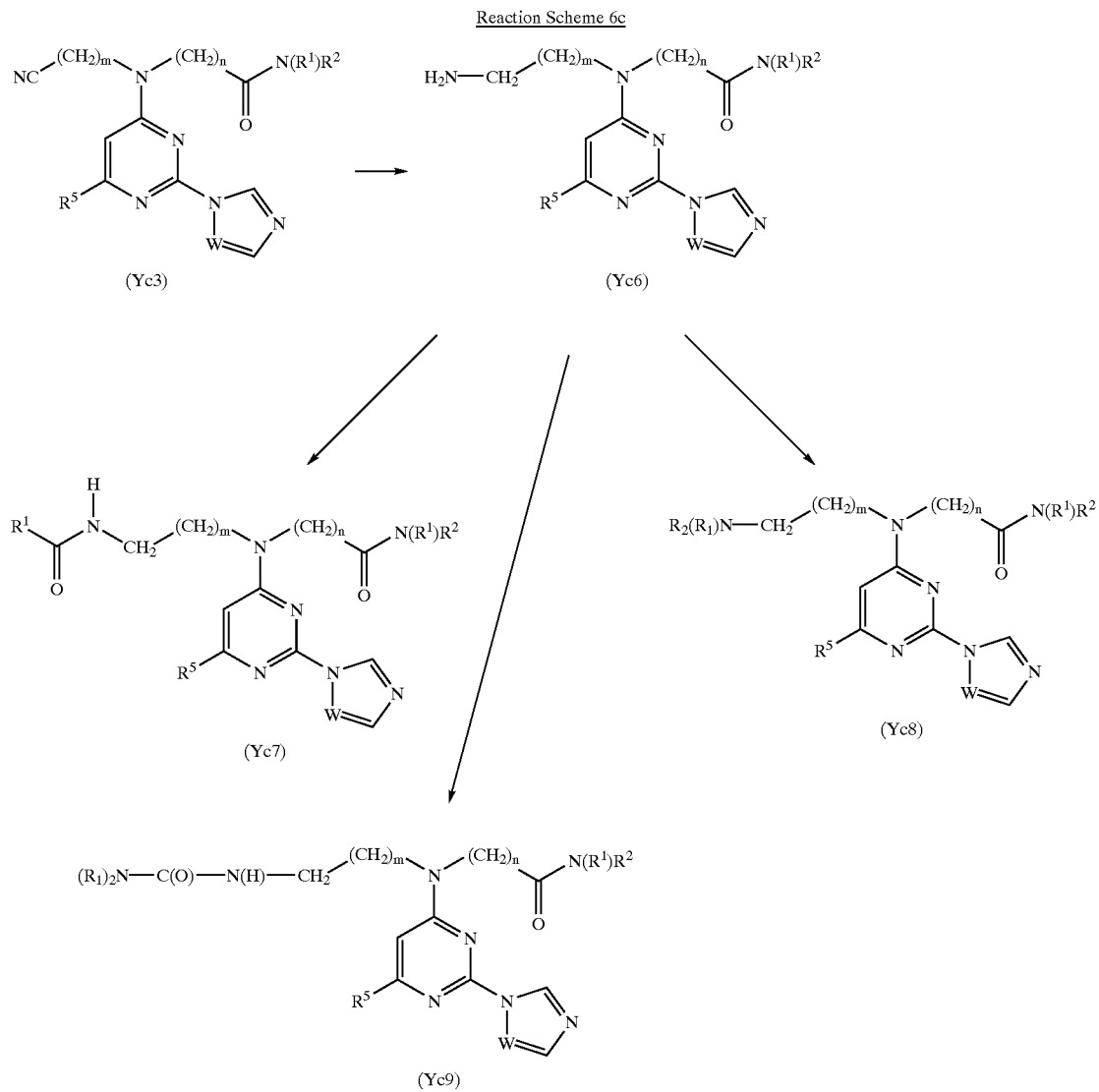

Reaction Scheme 6c

Compounds of formulae (Yc3) are prepared by methods disclosed herein. Each $R^1$, $R^2$, m and n are independently as described above in the Summary of the Invention for compounds of formula (Ya), formula (Yb) and formula (Yc); and $R^5$ and W are also as described above in the Summary of the Invention for compounds of formula (Ya), formula (Yb) and formula (Yc).

The above synthesis may be carried out as follows:

To 2–1(2-cyanoethyl)[2-(1H-imidazol-1-yl)-6-methyl-4-pyrimidinyl]amino]-N-[2-1,3-benzodioxol-5-yl)ethyl] acetamide (2.5 g, 5.8 mmol) (a compound of formula (Yc3)) in MeOH (50 mL) was bubbled ammonia. Raney nickel (1.0 g of a 50% slurry) was added and the reaction was placed on a Parr hydrogenator at 50 psi. After shaking for 16 hours, the pressure was released and the reaction mixture was suction filtered through Celite. The solvent was removed in vacuo and the residue was chromatographed on silica gel (9:1 $CH_3CN/NH_4OH$) to afford 2-[(3-aminopropyl)[2-(1H-imidazol-1-yl)-6-methyl-4-pyrimidinyl]amino]-N-[2-1,3-benzodioxol-5-yl)ethyl]acetamide, a compound of formula (Yc6); as a white solid; NMR (DMSO-$d_6$, 90° C) 8.4 (s, 1), 7.8 (s, 1), 7.0 (s, 1), 6.75 (d, 1), 6.7 (s, 1), 6.6 (d, 1), 5.9 (s, 2), 4.1 (s, 2), 3.6 (br, 2), 3.3 (m, 2), 2.75 (t, 2), 2.6 (t, 2), 2.3 (s, 3), 1.8 (m, 2) ppm.

The following compounds of formula (Yc6) and derivatives thereof were prepared in a similar manner with appropriately substituted starting materials:

2-[(3-aminopropyl)[(2-(1H-imidazol-1-yl)-6-methyl-4-pyrimidinyl]amino]-N-[2-(4-methoxyphenyl)ethyl] acetamide; NMR (DMSO-$d_6$, 90° C.) 8.4 (s, 1), 7.8 (s, 1), 7.05 (m, 3), 6.75 (d, 2), 6.45 (s, 1), 4.1 (s, 2), 3.7 (s, 3), 3.55 (t, 2), 3.3 (m, 2), 3.2 (s, 2), 3.6 (m, 4), 2.3 (s, 3) ppm;

2-[(3-aminopropyl)[2-(1H-imidazol-1-yl)-6-methyl-4-pyrimidinyl]amino]-N-[2-(1,4-benzodioxan-6-yl)ethyl] acetamide; NMR (DMSO-$d_6$) 8.42 (br, 1), 8.08 (br, 1), 7.80 (br, 1), 7.02 (s, 1), 6.65 (m, 4), 4.16 (m, 6), 4.05 (br, 1), 3.65 (br, 1), 3.45 (br, 2), 3.15 (br, 2), 2.59 (m, 4), 2.35 (s, 3), 1.62 (m, 2) ppm; and 2-[(3-aminopropyl)[2-(1H-imidazol-1-yl)-6-methyl-4-pyrimidinyl]amino]-N-[2-2,3-dihydrobenzofuran-5-yl) ethyl]acetamide; NMR (CDCl$_3$) 8.46 (s, 1), 7.75 (s, 1), 7.06 (s, 1), 6.80 (s, 1), 6.70 (d, 1), 6.52 (d, 1), 6.18 (br, 1), 4.46 (t, 2), 4.06 (br, 2), 3.60 (br, 2), 3.45 (m, 2), 3.05 (m, 2), 2.78 (br, 2), 2.65 (m, 2), 2.39 (s, 3), 1.70 (br, 4) ppm.

Compounds of formula (Yc6) may be used to prepare compounds of formula (Yc7), (Yc8) and (Yc9) as set forth below:

To 2-[(3-aminopropyl)[2-(1H-imidazol-1-yl)-6-methyl-4-pyrimidinyl]amino]-N-[2-(1,3-benzodioxol-5-yl)ethyl] acetamide (0.3 g, 0.7 mmol) (a compound of formula (Yc6)) dissolved in MeOH (10 mL) was added formalin (0.15 mL, 2.0 mmol) and sodium triacetoxyborohydride (0.37 g, 1.7 mmol). After stirring for 16 hours, the solvent was removed in vacuo. The residue was partitioned with ethyl acetate and aqueous bicarbonate. The organic layer was separated, washed with brine, dried (Na$_2$SO$_4$), and the solvent was removed in vacuo. Chromatography on silica with acetonitrile/ammonium hydroxide gave 0.14 g of 2-[[3-(dimethylamino)propyl][2-(1H-imidazol-1-yl)-6-methyl-4-pyrimidinyl]amino]-N-[2-(1,3-benzodioxol-5-yl)ethyl] acetamide, a compound of formula (Yc8); NMR (CDCl$_3$) 8.5 (s, 1), 7.8 (s, 1), 7.1 (s, 1), 6.5 (d, 1), 6.45 (s, 2), 6.4 (d, 1), 6.2 (m, 1), 5.9 (s, 2), 4.15 (s, 2), 3.55 (m, 2), 3.5 (q, 2), 2.6 (t, 2), 2.4 (s, 3), 2.3 (t, 2), 2.25 (s, 6), 1.7 (m, 2) ppm.

To 2-[(3-aminopropyl)[2-(1H-imidazol-1-yl)-6-methyl-4-pyrimidinyl]amino]-N-[2-1,3-benzodioxol-5-yl)ethyl] acetamide (50 mg, 0.11 mmol) (a compound of formula (Yc6)) in methanol (2 mL) was added benzaldehyde (0.2 M in methanol, 68 μL, 0.14 mmol). After stirring for 15 minutes, borane-pyridine complex (0.2 M in methanol, 0.14 mmol) was added. After 2 hours, the solution was evaporated. The residue was partitioned into water and ethyl acetate. The aqueous layer was extracted twice with ethyl acetate. The combined ethyl acetate fractions were washed with brine, dried over sodium sulfate and concentrated. The residue was purified by chromatography on silica gel (2:1 ethyl acetate/hexanes) to provide 2-[[3-(phenylmethylamino)propyl][2-(1H-imidazol-1-yl)-6-methyl-4-pyrimidinyl]amino]-N-[2-(1,3-benzodioxol-5-yl) ethyl]acetamide, a compound of formula (Yc8); as a white solid; NMR (CDCl$_3$) 8.65 (s, 1), 7.7 (s, 1), 7.2 (br, 5), 7.1 (s, 1), 6.6 (d, 1), 6.55 (s, 1), 6.5 (d, 1), 6.1 (br, 2), 5.9 (s, 2), 3.95 (br, 2), 3.5 (br, 6), 2.7 (m, 3), 2.35 (s, 6) ppm.

The following compounds of formula (Yc8) and derivatives thereof were prepared in a similar manner with appropriately substituted starting materials:

2-[[3(phenylmethylamino)propyl][2-(1H-imidazol-1-yl)-6-methyl-4-pyrimidinyl]amino]-N-[2-(4-methoxyphenyl) ethyl]acetamide; NMR (CDCl$_3$) 8.45 (s, 1), 7.75 (s, 1), 7.2 (br, 5), 7.05 (s, 1), 6.9 (d, 2), 6.65 (d, 2), 6.4 (br, 1), 4.1 (s, 2), 3.75 (s, 2), 3.7 (s, 3), 3.6 (br, 2), 3.45 (dd, 2), 2.7 (m, 4), 2.35 (s, 3), 1.8 (s, 2) ppm;

2-[[3-(dimethylamino)propyl][2-(1H-imidazol-1-yl)-6-methyl-4-pyrimidinyl]amino]-N-[2-4-methoxyphenyl) ethyl]acetamide; NMR (CDCl$_3$) 8.45 (s, 1), 7.75 (s, 1), 7.05 (s, 1), 6.85 (d, 2), 6.6 (d, 2), 6.3 (br, 1), 6.25 (br, 1), 4.1 (s, 2), 3.7 (s, 3), 3.5(m, 4), 2.7 (t, 2), 2.4 (s, 3), 2.3 (t, 2), 2.2 (s, 6), 1.75 (m, 2) ppm;

2-[[3-bis(phenylmethylamino)propyl][2-(1H-imidazol-1-yl)-6-methyl-4-pyrimidinyl]amino]-N-[2-(1,4-benzodioxan-6-yl)ethyl]acetamide; NMR (CDCl$_3$) 8.45 (s, 1), 7.70 (s, 1), 7.35 (m, 10), 7.04 (s, 1), 6.62 (d, 1), 6.45 (s, 1), 6.40 (d, 1), 6.06 (br, 1), 5.96 (br, 1), 4.15 (br, 4), 3.92 (br, 2), 3.60 (s, 4), 3.45 (m, 4), 2.62 (t, 2), 2.50 (t, 2), 2.30 (s, 3),1.72 (m, 2) ppm;

2-[[3-(phenylmethylamino)propyl][2-(1H-imidazol-1-yl)-6-methyl-4-pyrimidinyl]amino]-N-[2-(1,4-benzodioxan-6-yl)ethyl]acetamide; NMR (CDCl$_3$) 8.45 (s, 1), 7.75 (s, 1), 7.25 (m, 6), 7.05 (s, 1), 6.60 (d, 1), 6.45 (s, 1), 6.40 (d, 1), 6.20 (br, 1), 4.10 (m, 6), 3.70 (br, 4), 3.40 (m, 2), 2.65 (t, 2), 2.60 (t, 2), 2.40 (s, 3), 1.90 (br, 1), 1.76 (m, 2) ppm;

2-[[3-(dimethylamino)propyl][2-(1H-imidazol-1-yl)-6-methyl-4-pyrimidinyl]amino]-N-[2-1,4-benzodioxan-6-yl)ethyl]acetamide; NMR (CDCl$_3$) 8.45 (s, 1), 7.75 (s, 1), 7.05 (s, 1), 6.65 (d, 1), 6.50 (s, 1), 6.42 (s, 1), 6.30 (t, 1), 6.16 (br, 1), 4.12 (m, 6), 3.50 (m, 4), 2.75 (m, 2), 2.62 (t, 2), 2.56 (s, 6), 2.40 (s, 3), 2.10 (m, 2) ppm;

2-[[3-(phenylmethylamino)propyl][2-(1H-imidazol-1-yl)-6-methyl-4-pyrimidinyl]amino]-N-[2-(2,3-dihydrobenzofuran-5-yl)ethyl]acetamide; NMR (CDCl$_3$) 8.46 (s, 1), 7.75 (s, 1), 7.30 (m, 6), 7.10 (s, 1), 6.82 (s, 1), 6.68 (d, 1), 6.54 (d, 1), 6.25 (br, 1), 4.46 (t, 2), 4.10 (br, 2), 3.70 (br, 2), 3.62 (br, 2), 3.45 (m, 2), 3.05 (t, 2), 2.65 (m, 4), 2.40 (s, 3), 1.78 (m, 2) ppm; and 2-[[3-(dimethylamino)propyl][2(1H-1-imidazol-1-yl)-6-methyl-4-pyrimidinyl]amino]-N-[2-(2,3-dihydrobenzofuran-5-yl)ethyl]acetamide; NMR (CDCl$_3$) 8.45 (s, 1), 7.76 (s, 1), 7.06 (s, 1), 6.85 (s, 1), 6.70 (d, 1), 6.50 (d, 1), 6.16 (br, 2), 4.50 (t, 2), 4.10 (s, 2), 3.52 (m, 4), 3.05 (t, 2), 2.76 (m, 2), 2.68 (m, 2), 2.62 (s, 6), 2.42 (s, 3), 2.10 (m, 2) ppm.

To 2-[(3-aminopropyl)[2-(1H-imidazol-1-yl)-6-methyl-4-pyrimidinyl]amino]-N-[2-(1,3-benzodioxol-5-yl)ethyl] acetamide (0.3 g, 0.7 mmol) (a compound of formula (Yc6)) dissolved in pyridine (5 mL) was added acetic anhydride (0.10 mL, 1.0 mmol). After stirring for 16 hours, the reaction was partitioned with ethyl acetate and water. The organic layer was separated, washed with water and brine, dried (Na$_2$SO$_4$), and the solvent was removed in vacuo. Chromatography on silica with CH$_2$Cl$_2$ gave 0.14 g of 2-[[3-(acetylamino)propyl][2-(1H-imidazol-1-yl)-6-methyl-4-pyrimidinyl]amino]-N-[2-(1,3-benzodioxol-5-yl)ethyl] acetamide, a compound of formula (Yc7); NMR (DMSO-$d_6$) 8.4 (s, 1), 8.05 (t, 2), 7.85 (t, 1), 7.8 (s, 1), 7.05 (s, 1), 6.7 (m, 2), 6.6 (m, 1), 6.2 (s, 1), 5.9 (s, 2), 4.1 (m, 2), 3-3.6 (m, 6), 2.6 (m, 2), 2.3 (m, 3), 1.8 (s, 3), 1.65 (m, 2) ppm.

The following compounds of formula (Yc7) and derivatives thereof were prepared in a similar manner with appropriately substituted starting materials:

2-[[3-(methylsulfonylamino)propyl][2-(1H-imidazol-1-yl)-6-methyl-4-pyrimidinyl]amino]-N-[2-(1,3-benzodioxol-5-yl)ethyl]acetamide; NMR (CDCl$_3$) 8.45 (s, 1), 7.65 (s, 1), 7.0 (s, 1), 6.55 (m, 2), 6.5 (s, 1), 6.45 (d, 1), 6.15 (br, 1), 5.95 (br, 1), 5.85 (s, 2), 4.1 (s, 2), 3.65 (br, 2), 3.45 (m, 2), 3.2 (dd,2), 2.9 (s, 3), 2.65 (t, 2), 2.35 (s, 3), 1.9 (m, 2) ppm;

2-[[3-(methoxycarbonylamino)propyl)[241 H-imidazol-1-yl)-6-methyl-4-pyrimidinyl]amino]-N-[2-1,3-benzodioxol-5-yl)ethyl]acetamide; NMR (CDCl$_3$) 8.45 (s, 1), 7.7 (s, 1), 7.1(s, 1), 6.55 (d, 1), 6.5 (s, 1), 6.45 (d, 1), 6.3 (br, 1), 6.1 (br, 1), 5.9 (s, 2), 4.1 (s, 2), 3.7 (s, 3), 3.5 (m, 2), 3.2 (dd, 2), 2.7 (t, 2), 2.4 (s, 3), 1.85 (m, 4) ppm;

2-[[3-methylsulfonylamino)propyl][2-(1H-imidazol-1-yl)-6-methyl-4-pyrimidinyl]amino]-N-[2-4-methoxyphenyl)ethyl]acetamide; NMR (CDCl$_3$) 8.45 (s, 1), 7.75 (s, 1), 7.1 (s, 1), 6.95 (d, 2), 6.7 (d, 2), 6.25 (br, 1), 6.15 (br, 1), 4.1 (s, 2), 3.75 (s, 3), 3.6 (br, 2), 3.5 (m, 2), 3.2 (dd, 2), 2.95 (s, 3), 2.7 (t, 2), 2.4 (s, 3), 1.85 (m, 2) ppm;

2-[[3-(methoxycarbonylamino)propyl][2-(1H-imidazol-1-yl)-6-methyl-4-pyrimidinyl]amino]-N-[2-(4-methoxyphenyl)ethyl]acetamide; NMR (CDCl$_3$) 8.45 (s, 1), 7.75 (s, 1), 7.1 (s, 1), 6.9 (d, 2), 6.7 (d, 2), 6.2 (br, 1), 6.1 (br, 1), 4.05 (s, 2), 3.75 (s, 3), 3.65 (s, 2), 3.5 (s, 3), 3.2 (m, 2), 2.7 (t, 2), 2.4 (s, 3), 1.8 (m, 4) ppm;

2-[[3-(acetylamino)propyl][2-(1 H-imidazol-1-yl)-6-methyl-4-pyrimidinyl]amino]-N-[2-(4-methoxyphenyl) ethyl]acetamide; NMR (CDCl$_3$) 8.45 (s, 1), 7.7 (s, 1), 7.05 (s, 1), 6.9 (d, 2), 6.65 (d, 2), 6.4 (br, 1), 6.1 (s, 1), 4.05 (s, 2), 3.7 (s, 3), 3.5 (m, 4), 3.25 (dd, 2), 2.7 (t, 2), 2.4 (s, 3), 1.9 (s, 3), 1.8 (m, 2) ppm;

2-[[3-(methoxycarbonylamino)propyl][2-(1H-imidazol-1-yl)-6-methyl-4-pyrimidinyl]amino]-N-[2-(1,4-benzodioxan-6-yl)ethyl]acetamide; NMR (CDCl$_3$) 8.60 (s, 1), 7.78 (s, 1), 7.08 (s, 1), 6.64 (d, 1), 6.45 (s, 1), 6.44 (d, 1),=6.25 (br, 1), 6.15 (s, 1), 5.05 (br, 1), 4.12 (m, 6), 3.65 (s, 3), 3.45 (m, 4), 3.20 (m, 2), 2.65 (t, 2), 2.40 (s, 3), 1.80 (m, 2) ppm;

2-[3-(acetylamino)propyl][2-(1H-imidazol-1-yl)-6-methyl-4-pyrimidinyl]amino]-N-[2-(1,4-benzodioxan-6-yl)ethyl] acetamide; NMR (CDCl$_3$) 8.50 (s, 1), 7.75 (s, 1), 7.06 (s, 1), 6.62 (d, 1), 6.58 (br, 1), 6.45 (s,1), 6.42 (d, 1), 6.15 (s, 1), 4.10 (m, 6), 3.55 (m, 4), 3.30 (m, 2), 2.64 (t, 2), 2.40 (s, 3), 1.92 (s, 3), 1.82 (m, 2) ppm;

2-[[3-methylsulfonylamino)propyl][2-(1H-imidazol-1-yl)-6-methyl-4-pyrimidinyl]amino]-N-[2-(1,4-benzodioxan-6-yl)ethyl]acetamide; NMR (CDCl$_3$) 8.46 (s, 1), 7.76 (s, 1), 7.03 (s, 1), 6.65 (d, 1), 6.50 (s, 1), 6.42 (d, 1), 6.18 (br, 1), 5.80 (br, 1), 4.20 (m, 6), 3.65 (br, 2), 3.48 (m, 2), 3.20 (m, 2), 2.92 (s, 3), 2.65 (m, 2), 2.40 (s, 3), 1.90 (m, 2) ppm;

2-[[3-(acetylamino)propyl][2-(1H-imidazol-1-yl)-6-methyl-4-pyrimidinyl]amino]-N-[2-(2,3-dihydrobenzofuran-5-yl)ethyl]acetamide; NMR (CDCl$_3$) 8.46 (s, 1), 7.76 (s, 1), 7.05 (s, 1), 6.86 (s, 1), 6.72 (d, 1), 6.55 (d, 1), 6.45 (br, 2), 6.13 (s, 1), 4.50 (t, 2), 4.08 (s, 2), 3.55 (m, 4), 3.30 (q, 2), 3.06 (t, 2), 2.66 (t, 2), 2.40 (s, 3), 1.93 (s, 3), 1.85 (m, 2) ppm;

2-[[3-(methoxycarbonylamino)propyl][2-(1H-imidazol-1-yl)-6-methyl-4-pyrimidinyl]amino]-N-[2-(2,3-dihydrobenzofuran-5-yl)ethyl]acetamide; NMR (CDCl$_3$) 8.46 (s, 1), 7.76 (s, 1), 7.05 (s, 1), 6.84 (s, 1), 6.70 (d, 1), 6.54 (d, 1), 6.26 (br, 2), 6.10 (s, 1), 5.08 (br, 1), 4.50 (t, 2), 4.06 (s, 2), 3.65 (s, 3), 3.50 (m, 4), 3.22 (q, 2), 3.04 (t, 2), 2.66 (t, 2), 2.42 (s, 3), 1.80 (m, 2) ppm; and 2-[[3-(methylsulfonylamino)propyl][2-(1H-imidazol-1-yl)-6-methyl-4-pyrimidinyl]amino]-N-[2-(2,3-dihydrobenzofuran-5-yl)ethyl]acetamide; NMR (CDCl$_3$) 8.44 (s, 1), 7.74 (s, 1), 7.02 (s, 1), 6.86 (m, 1), 6.72 (d, 1), 6.52 (m, 2), 6.19 (s, 1), 5.80 (br, 1), 4.50 (t, 2), 4.10 (s, 2), 3.62 (br, 2), 3.46 (q, 2), 3.20 (q, 2), 3.06 (t, 2), 2.95 (s, 3), 2.66 (t, 2), 2.38 (s, 3), 1.86 (m, 2) ppm.

To 2-[(3-aminopropyl)[2-(1H-imidazol-1-yl)-6-methyl-4-pyrimidinyl]amino]-N-[2-(4-methoxyphenyl)ethyl] acetamide (135 mg, 0.32 mmol) (a compound of formula (Yc6)) in pyridine (1.5 mL) was added water (1.5 mL) solution of potassium cyanate (64 mg, 0.76 mmol). The mixture was stirred and heated in an oil bath at 80° C overnight. The mixture was poured into water and extracted with ethyl acetate (3×20 mL). The combined ethyl acetate fractions were washed with brine, dried over sodium sulfate and concentrated. The residue was purified by chromatography on silica gel (9:1 CH$_3$CN/NH$_4$OH) to afford 2-[[3-ureido)propyl][2-(1H-imidazol-1-yl)-6-methyl-4-pyrimidinyl]amino]-N-[2-(4-methoxyphenyl)ethyl] acetamide, a compound of formula (Yc9); as a white solid; NMR (DMSO-d$_6$, 90° C.) 8.4 (s, 1), 7.8 (s, 1), 7.05 (d, 2), 7.0 (s, 1), 6.75 (d, 2), 6.4 (s, 1), 4.1 (s, 2), 3.7 (s, 3), 3.5 (m, 2), 3.25 (m, 2), 3.05 (m, 2), 2.65 (t, 2), 2.3 (s, 3), 1.7 (m, 2) ppm.

The following compounds of formula (Yc9) and derivatives thereof were prepared in a similar manner with the appropriately substituted starting materials:

2-[[3-(ureido)propyl][2-(1H-imidazol-1-yl)-6-methyl-4-pyrimidinyl]amino]-N-[2-(1,4-benzodioxan-4-yl)ethyl] acetamide; NMR (DMSO-d$_6$) 8.42 (br, 1), 8.08 (t, 1), 7.80 (br, 1), 7.05 (s, 1), 6.60 (m, 3), 6.03 (br, 1), 5.45 (br, 1), 4.18 (br, 6), 3.40 (m, 6), 3.00 (m, 2), 2.55 (m, 2), 2.35 (br, 3), 1.70 (m, 2) ppm; and 2-[[3-(ureido)propyl][2-(1H-imidazol-1-yl)-6-methyl-4-pyrimidinyl]amino]-N-[2-(2,3-dihydrobenzofuran-5-yl) ethyl]acetamide; NMR (DMSO-d$_6$) 8.45 (br, 1), 8.12 (br, 1), 7.80 (br, 1), 7.00 (m, 2), 6.82 (m, 1), 6.60 (br, 1), 6.10 (br, 1), 5.42 (br, 1), 4.42 (t, 2), 4.14 (m, 2), 3.00–3.60 (m, 10), 2.60 (m, 2), 2.30 (s, 3), 1.68 (m, 2) ppm.

Reaction Scheme 6d depicts another method of preparing compounds of formula (Yc). Compounds of formula (Ya) and formula (Yb) may be similarly prepared.

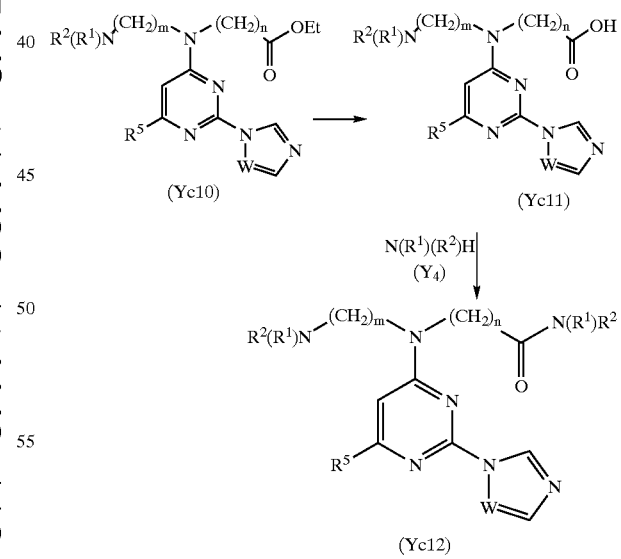

Reaction Scheme 6d

Compounds of formulae (Yc10) are prepared by methods disclosed herein. Each R$^1$, R$^2$, m and n are independently as described above in the Summary of the Invention for compounds of formula (Ya), formula (Yb) and formula (Yc); and R$^5$ and W are also as described above in the Summary of the Invention for compounds of formula (Ya), formula (Yb) and formula (Yc).

The above synthesis may be carried out as follows:

To 2-[[3-[(1,3-benzodioxol-5-ylmethyl)amino](methyl)propyl][2-(1H-imidazol-1-yl)-6-methyl-4-pyrimidinyl]amino]acetic acid, ethyl ester (2.2 g, 4.6 mmol) (a compound of formula (Yc10)) dissolved in THF (50 mL) was added LiOH (0.34 g, 8.1 mmol) and water (10 mL). After stirring for 16 hours, the solvent was removed in vacuo and 1 N HCl (8.1 mL, 8.1 mmol) was added. The solvent was removed in vacuo to give 2-[[3-[(1,3-benzodioxol-5-ylmethyl)(methyl)amino]propyl][2-(1H-imidazol-1-yl)-6-methyl-4-pyrimidinyl]amino]acetic acid, a compound of formula (Yc11).

To 2-[[3-[(1,3-benzodioxol-5-ylmethyl)(methyl)amino]propyl][2-(1H-imidazol-1-yl)-6-methyl-4-pyrimidinyl]amino]acetic acid (0.35 g, 0.8 mmol) (a compound of formula (Yc11)) slurried in DMF (5 mL) was added carbonyldiimidazole (0.14 g, 0.8 mmol). After stirring for 20 minutes, diethylamine (0.25 mL, 2.4 mmol) was added. After stirring for 18 hours, the reaction was partitioned with ethyl acetate and water. The organic layer was separated, washed with water, dried ($Na_2SO_4$), and the solvent was removed in vacuo to give 0.91 g of the desired product Chromatography on silica with $CH_2Cl_2$/MeOH gave 2-[[3-[[(1,3-benzodioxol-5-yl)methyl)(methyl)amino]propyl][2-(1H-imidazol-1-yl)-6-methylpyrimidin-4-yl]amino]-N,N-diethylacetamide; NMR ($CDCl_3$) 8.4 (s, 1), 7.85 (s, 1), 7.1 (m, 1), 6.85 (s, 1), 6.75 (m, 2), 6.4 (br, 1)i 5.95 (s, 2), 4.4 (br, 2), 3.6 (br, 2), 3.4 (m, 6), 2.45 (t, 2), 2.35 (s, 3), 2.2 (s, 3), 1.9 (m, 2), 1.3 (t, 3), 1.15 (t, 3) ppm.

The following compounds of formula (Yc12) and derivatives thereof were prepared in a similar manner:

2-[[3-[[(1,3-benzodioxol-5-yl)methyl](methyl)amino]propyl][2-(1H-imidazol-1-yl)-6-methylpyrimidin-4-yl]amino]-N-(2-dimethylaminoethyl)acetamide; NMR ($CDCl_3$) 8.5 (s, 1), 7.8 (s, 1), 7.1 (s, 1), 6.8 (5, 1), 6.75 (m, 2), 6.25 (br, 1), 5.95 (s, 2), 4.15 (br, 2), 3.6 (br, 2), 3.4 (s, 2), 3.35 (m, 2), 2.4 (t, 2), 2.4 (s, 3), 2.35 (t, 2), 2.2 (s, 3), 2.0 (br, 6), 1.8 (m, 2), 1.6 (m, 2) ppm; and 2-[[3-[(1,3-benzodioxol-5-yl)methyl](methyl)amino]propyl][2-(1H-imidazol-1-yl)-6-methylpyrimidin-4-yl]amino]acetamide; NMR (DMSO-$d_6$) 8.4 (s, 1), 7.8 (s, 1), 7.5 (s, 1), 7.1 (m, 2), 6.8 (m, 3), 6.3 (br, 1), 6.0 (s, 2), 5.4 (br, 1), 4.1 (m, 2), 3.4 (m, 4), 2.4 (t, 2), 2.3 (s, 3), 2.1 (s, 3), 1.75 (m, 2) ppm.

The solid phase generic synthesis of the compounds of the invention may be conceptualized as the generic synthesis of Reaction Scheme 1 in which $R^1$ has been replaced by a cleavable attachment to a derivatized polymer resin. At the end of the synthetic scheme, the resin is cleaved and $R^1$ becomes hydrogen. The solid phase synthetic scheme is illustrated in Reaction Scheme 7 as applied to the specific example, as before, of a piperonylamide, but in this case the amino acid is piperazine-2-acetic acid:

Reaction Scheme 7

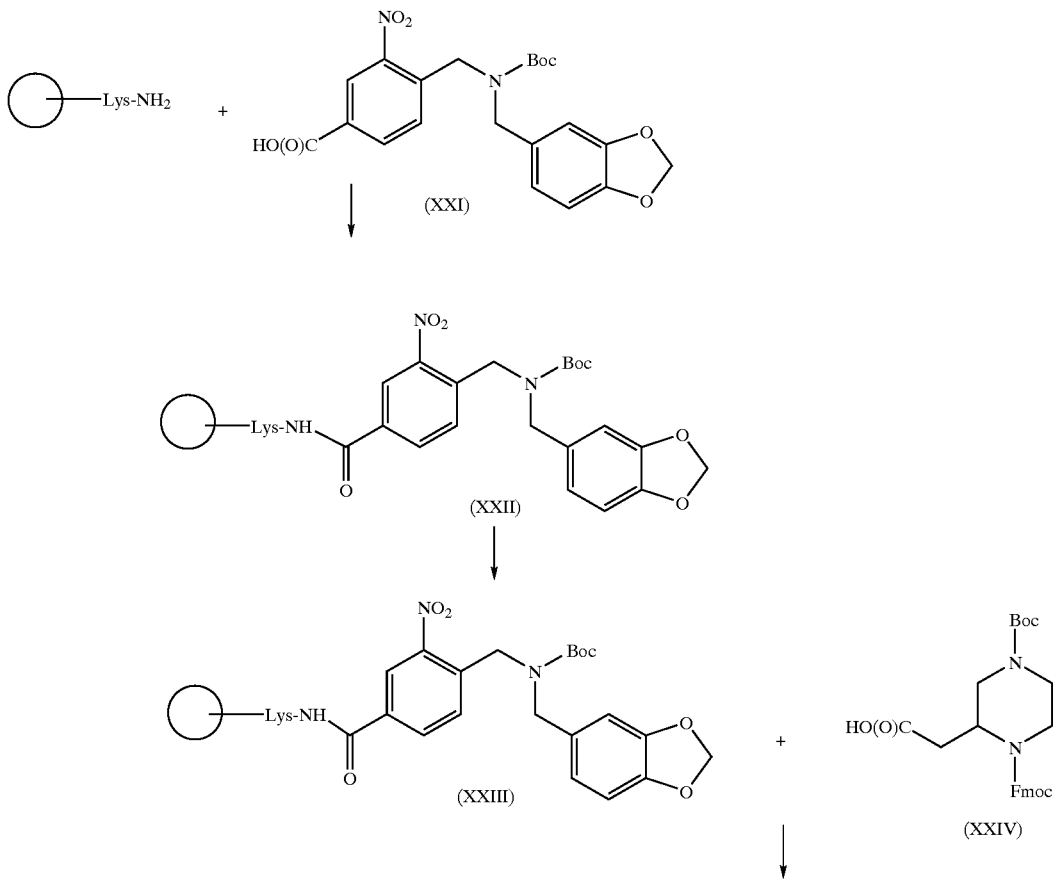

-continued

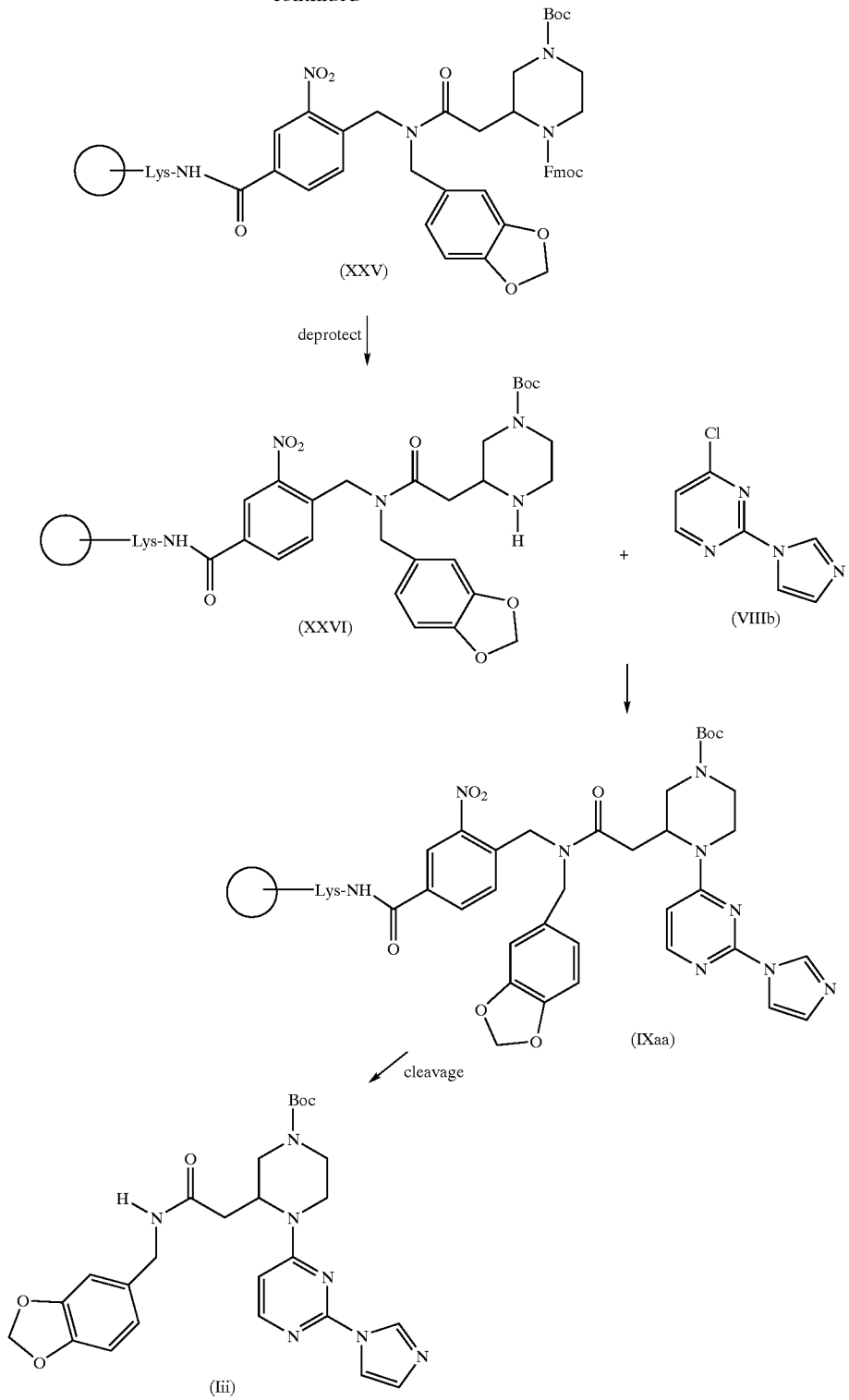

In the solid phase synthesis, the group which is to become $R^1$ is attached to the resin through a cleavable linkage, such as the 2-nitrobenzyl residue, which can be photolytically cleaved. In the example shown, the piperonylamine (see above) has been protected with Boc and reacted with 4-(bromomethyl)-3-nitrobenzoic acid to produce the Boc-protected compound of formula (XXI), which is then attached to a free amine of the lysine-derivatized, amino-functionalized synthetic support. In this case, a polyethyleneglycol-grafted crossliked polystyrene, 1% DVB crosslinked polystyrene or crosslinked polydimethy-lacrylamide is suspended in a polar aprotic solvent such as methylene chloride, DMF or THF. An excess of the suitably protected linker-synthon is added to the suspended support followed by a coupling reagent such as diisopropylcarbodiimide (DIC), dicyclohexylcarbodiimide (DCC), bis(2-oxo-3-oxazolidinyl) phosphinic chloride (BOP), or O-7-azabenzotriazol-1-yl)-1,1,3,3-tetramethyluronium-hexafluorophosphate (HATU) and optionally an acylation catalyst such as dimethylaminopyridine (DMAP) or hydroxybenzotriazole (HOBT). The mixture is agitated at ambient temperature for 1 to 24 hours or until the reaction is complete as judged by a ninhydrin test The resin is washed with an appropriate solvent or solvents multiple times to remove excess reagents and by-products to give the resin-compound of formula (XXII).

The resin-compound of formula (XXII) is deprotected to liberate the compound of formula (XXIII), which is then suspended in a polar aprotic solvent such as methylene chloride or DMF. An excess of an appropriately protected compound of formula (XXIV) is added followed by a coupling agent such as HATU, BOP or DIC with the optional addition of an acylation catalyst such as DMAP or HOBT. Alternatively an excess of an activated form of the compound of formula (XXIV), such as the symmetrical anhydride or acyl fluoride may be added to the resin. The mixture is shaken for 1 to 24 hours at ambient temperature and then washed multiple times with an appropriate solvent or solvents to remove excess reagents and by-products to give the resin-compound of formula (XXV).

Resin-compound of formula (XXV) is deprotected to liberate the compound of formula (XXVI), which is then suspended in a polar aprotic solvent such as DMF or THF. An excess of the appropriate compound of formula (VIIIb) is added followed by an excess of a base such as triethylamine or diisopropylethylamine. The mixture is agitated and heated to 50–100° C for 1 to 24 hours, then cooled and washed multiple times with an appropriate solvent to remove excess reagents and by products to give resin-compound of formula (IXaa). The resin-compound of formula (IXaa) is optionally treated to liberate protected functionality incorporated as part of a synthon to produce the compound of formula (Iii).

For those compounds in which the substitution pattern of the piperazine is reversed (e.g., examples 95–102 below), the procedure of the preceding paragraph may be slightly modified. Resin-compound of formula (XXV) is deprotected with piperidine to liberate an amine and then dissolved or suspended in an inert solvent, such as methylene dichloride. An excess of an appropriately protected acid that will furnish $R^6$ is added followed by a coupling agent such as HATU, BOP or DIC with the optional addition of an acylation catalyst such as DMAP or HOBT. Alternatively an excess of an activated form of the acid, such as the symmetrical anhydride or acyl fluoride may be added to the resin. The mixture is shaken for 1 to 24 hours at ambient temperature and then washed multiple times with an appropriate solvent or solvents to remove excess reagents. The product is suspended in a polar aprotic solvent, such as DMF or THF. An excess of the appropriate compound of formula (VIIIb) is added followed by an excess of a base such as triethylamine or diisopropylethylamine. The mixture is agitated and heated to 50–100° C for 1 to 24 hours, then cooled and washed multiple times with an appropriate solvent to remove excess reagents and by products to give resin compounds analogous to the resin-compound of formula (IXaa), but having the pyrimidine attached to the piperazineacetic acid at the 4-position.

This resin compound analogus to the resin-compound of formula (IXaa) is then suspended in a protic solvent such as methanol or acetonitrile-water and stirred and photolyzed to cleave the product from the resin. Filtration, and evaporation of the filtrate gives the crude product, which is then purified and characterized by standard techniques.

In a specific example, 1.57 g of an amino-functionalized TentaGel resin (0.80 mmole) was suspended in 20 mL of methylene chloride and treated with 1.05 g of linker acid (2.4 mmole), 0.50 mL of DIC (3.2 mmole), and 20 mg of DMAP (0.16 mmole). The mixture was shaken at room temperature for 20 hours and then washed with methylene chloride ten times to give a resin-compound of formula (XXII). The resin-compound of formula (XXII) was treated with 50% trifluoroacetic acid (TFA) in methylene chloride at room temperature for 2 hours and then washed with methylene chloride ten times, 15% triethylamine in methylene chloride for 10 minutes, and again methylene chloride for 5 times. The deprotected resin-compound of formula (XXIII) was then suspended in 12 mL of methylene chloride and treated with 1.444 g of the compound of of formula (XXIV) (3.2 mmole), 1.216 g of HATU (3.2 mmole), and 1.3 mL of diisopropylethylamine (7.2 mmole). The mixture was shaken for 16 hours at ambient temperature and then washed 5 times to give resin-compound of formula (XXV). The Fmoc was removed by treatment with 30% piperidine in DMF and 777 mg of the resulting resin-bound compound of formula (XXVI) (0.35 mmole) was then reacted with 320 mg of 2-imidazolyl-4-chloropyrimidine (the compound of formula (VIIIb)), in the presence of 0.61 mL of diisopropylethylamine (3.5 mmole) in 12 mL of DMF at 80° C for 15 hours and then cooled to room temperature and washed with DMF and methylene chloride to give the resin-compound of formula (IXaa). The final product was cleaved from the resin by photolysis in methanol (MeOH) for 17 hours to give 54.6 mg of product, a compound of formula (Iii) (31%). The crude product was purified by flash chromatography (eluted with 4:4:1 ethyl acetate:hexanes:MeOH). The Boc-protected amine product was treated with 3 mL of 30% TFA-methylene chloride for 1 hour and was dried in vacuo to give quantitative amount of product.

The piperazineacetic acid compound of formula (XXIV) employed in the synthesis above and many others in this application was synthesized as follows: Twelve milliliters (50 mmol) of N,N'-dibenzylethylene-diamine, 14 mL (100 mmol) of $Et_3N$ and 250 mL toluene were combined at 0° C, and 7 mL (50 mmol) of methyl 4-bromocrotonate (7 mL, 50 mmol) was added. The reaction was slowly warmed to room temperature, stirred for 24 hours, filtered, concentrated in vacuo to a residue and treated with 10% aqueous HCl (300 mL). The mixture was filtered again and the filtrate washed with ethyl acetate (2×100 mL). The filtrate was made basic with $K_2CO_3$ and extracted with ethyl acetate (3×150 mL). The combined extracts were washed with brine, dried over $MgSO_4$ and concentrated in vacuo to give 13.7 g of methyl 1,4-4-dibenzylpiperazine-2-acetate. $^1H$ NMR ($CDCl_3$) δ 2.28–2.50 (m,4), 2.5–2.75 (m,4), 3.1 (bs, 1), 3.42 (d,2), 3.52 (d,1), 3.6 (s,3), 3.75 (d,1), 7.15–7.35 (m,1).

The 13.7 g (40 mmol) of methyl 1,4-dibenzylpiperazine-2-acetate, 150 mL of MeOH, 50 mL of 1 N HCl (aqueous) and 3 g of 10% Pd/C were combined and hydrogenated with $H_2$ (50 psi) for 24 hours. The reaction was filtered, the filtrate was concentrated in vacuo to remove most of the MeOH, and the residue was made basic with $K_2CO_3$ to pH=9–10, and 9.8 g (40 mmol) of BOC-ON was added slowly at 0° C. The reaction was stirred at 0° for 1 hour, allowed to warm up to room temperature, stirred for 2 hours, and extracted with ethyl acetate (2×200 mL). The combined extracts were treated with 50 mL of 10% HCl (aqueous). The aqueous layer was washed with ethyl acetate, basified with $K_2CO_3$ and extracted three times with ethyl acetate. The combined organic layers were washed with brine, dried over $MgSO_4$ and concentrated in vacuo to give 7.89 g of methyl 4-Boc-piperazine-2-acetate; $^1H$ NMR ($CDCl_3$) δ 1.4 (s,9), 2.31 (dd,1), 2.37 (dd, 1), 2.55 (b, 1), 2.69–3.02 (m,4), 3.75 (s,3), 3.88 (b,2).

A portion (5.2 g; 20 mmol) of the methyl 4-Boc-piperazine-2-acetate product from the previous step was combined with 60 mL of THF and 60 mL of 1 N NaOH (aqueous) and stirred at room temperature for 6 hours to saponify the methyl ester. The reaction was cooled to 0° C., adjusted to pH 9–10 with 10% HCl(aqueous), and 5.2 g (20 mmol) of FMOC-Cl was added. The reaction was stirred at room temperature for 6 hours, (adding 1 N NaOH (aqueous) to maintain pH=9–10) 1 hour, then acidified with 10% HCl to pH=1. The reaction was extracted twice, the combined organic layers were washed with brine, dried over $MgSO_4$ and concentrated in vacuo to give 8.56 g of the desired 4-Boc-1-Fmoc-piperazine-2-acetic acid (the compound of formula (XXIV)); $^1H$ NMR ($CDCl_3$) δ 1.4 (s,9), 2.5–3.0 (m,5), 3.94.2 (m,6), 4.5 (m,1), 7–25 (t,4), 7.32 (t,4), 7.48 (d,4), 7.75 (d,4).

In the cases in which 4-Boc-1-Fmoc-piperazine-2-acetic acid (the compound of formula (XXIV)) was replaced by 4-Boc-1-Fmoc-piperazine-2-carboxylic acid, the starting material was prepared by dissolving 5.25 g (25.85 mmol) of 2-piperazine carboxylic acid-2HCl in 160 mL of 1:1 dioxane/$H_2O$, and adjusting the pH to 11 with 50% NaOH (aq.). A solution of 7.21 g (29.28 mmol) of BOC-ON in 40 mL of dioxane was slowly added (in portions) while maintaining the pH at 11 with 50% NaOH (aq.) during the addition. The reaction was stirred at room temperature for 5 hours, then cooled to 0° C and adjusted to pH 9.5 with 50% NaOH (aq.). A solution of 7.34 g (28.37 mmol) of FMOC-CL in 40 mL of dioxane was slowly added (in portions), maintaining a pH of 9.5 during the addition with 50% NaOH (aq.). The mixture was warmed to room temperature, stirred for 20 hours, washed with ethyl ether (3×150 mL), adjusted to pH=2–3 with 6N HCl (aq.), and extracted with toluene (3×150 mL). The combined extracts were dried over $Na_2SO_4$, concentrated in vacuo to a volume of 150 mL and chilled at −20° C overnight. The resulting solids were filtered off, washed with hexane and dried in vacuo to give 5.4 g of the desired 4-Boc-1-Fmoc-piperazine-2-carboxylic acid.

Alternatively, 4-Boc-morpholine-3-carboxylic acid, which can be substituted for the compound of formula (XXIV) in Reaction Scheme 7 above to prepare other compounds of the invention, can be prepared in the following manner: To a solution of 4-phenylmethylmorpholin-5-one-3-carboxylic acid methyl ester (5.1 g. 20.5 mmol) in 100 mL of THF was added borane/DMS (10M, 2.6 mL) slowly while cooling at 0° C. The solution was allowed to warm to ambient temperature and stirred for 18 hours. Water (100 mL) was then added and the mixture extracted with ethyl acetate. The organic layers were dried over $MgSO_4$ and concentrated. The resulting oil was purified on a silica gel column eluted with 3:7 ethyl:hexanes to yield the morpholine (3.0 g, 64%). The morpholine (3.0 g. 12.75 mmol) was dissolved in 50 mL MeOH and 10% Pd/C (10 mg) was added. The mixture was stirred at-ambient temperature under a $H_2$ atmosphere for 16 hours. The mixture was then filtered through celite and concentrated. The resulting oil was dissolved in $CH_2Cl_2$ (25 mL) and di-t-butyldicarbonate (2.8 g, 12.75 mmol) was added. After stirring for 4 hours, the mixture was concentrated and taken up in $CH_2Cl_2$ and washed with water, saturated $NaHCO_3$, and brine. The organic layer was dried over $MgSO_4$ and concentrated to yield 2.8 g (89%) of the ester. The ester was dissolved in MeOH (30 mL) and NaOH (1.4 g, 35 mmol) was added. After stirring for 4 hours at reflux, the solution was concentrated, acidified with 1 N HCl and extracted with $CH_2Cl_2$. The organic layer was dried ($MgSO_4$) and concentrated to yield 4-Boc-morpholine-3-carboxylic acid as a white solid (2.4 g, 90%). $^1H$ NMR ($CDCl_3$) δ 1.40 (m, 9). 3.20–350 (m, 2), 3.70(m, 2), 3.90 (m, 1), 4.30–4.65 (m, 2).

1-Boc-perhydroazepine-2-acetic acid can also be substituted for the compound of formula (XXIV) in Reaction Scheme 7 and can be prepared in the following manner: N-Boc-perhydroazepine (1.06 g, 6.16 mmol) in ether is treated with TMEDA (715 mg, 6.16 mmol) followed by sec-butyllithium (1.3 M. 4.74 ml, 6.16 mmol) at −78° C. The reaction was slowly warmed to 40° C, stirred for 1 hour, cooled to −78° C. and treated with a solution of 3,3-dimethylallyl bromide (918 mg. 6.16 mmol) in ether. After warming to room temperature and quenching with water, the organic layer is washed with water, 1 M $NaH_2PO_4$, water, and brine. After drying ($MgSO_4$), the solvent is removed and the product is purified by chromatography (silica gel, hexane:ethyl acetate 95:5), to yield the olefin (300 mg, 21%, $^1H$ NMR ($CDCl_3$) δ 5.05–5.20 (m, 1), 3.55–3.80 (m, 2), 2.60–2.75 (m, 1), 1.90–2.20 (m, 3), 1.10–1.80 (m, 22). To a solution of $NaIO_4$ (2.17 g, 10.2 mmol) and $KMnO_4$ (32 mg, 0.2 mmol) in 45 mL of water was added $K_2CO_3$ (162 mg, 1.18 mmol) and the olefin (300 mg, 1.12 mmol) dissolved in t-butanol (11 ml). After stirring for three days, the reaction was acidified to pH 3 and extracted with ethyl acetate. The organic layer was washed with water and brine, dried ($MgSO_4$), and the solvent was removed in vacuo to give 1-Boc-perhydroazepine-2-acetic acid (250 mg, 87%): $^1H$ NMR ($CDCl_3$) δ 4.20–4.45 (m, 1), 3.55–3.80 (m, 1), 2.00–2.80 (m, 4), 1.10–1.80 (m, 16).

4-Boc-morpholine-3-acetic acid can also be substituted for the compound of formula (XXIV) in Reaction Scheme 7, and can be prepared in the following manner from 4-benzylmorpholine-3-acetic acid ethyl ester (Brown, G. R; Foubister. A. J.; Stribling. D. J. *Chem. Soc. Perkin Trans.* 1 (1987), p. 547). After hydrogenolysis (Pd(OH)$_2$, $H_2$) of the benzyl group, the N-Boc derivative is prepared by treatment with di-t-butyldicarbonate and the ethyl ester is hydrolyzed by aqueous base to provide 4-Boc-morpholine-3-acetic acid.

1-Boc-pyrrolidine-2-propionic acid can also be substituted for the compound of formula (XXIV) in Reaction Scheme 7 and can be prepared in the following manner: Boc-pyrrolidine (5.0 g, 29.2 mmol) was dissolved in ether (35 ml) and TMEDA (3.0 g, 20 mmol), cooled to −78° C and s-butyllithium (1.3 M, 17 ml, 22 mmol) was added. After stirring for 1 hour, allyl bromide (5.1 mL, 57 mmol) was added. After warming to room temperature, the reaction was quenched with water and the organic layer was separated. The organic layer was dried ($MgSO_4$) and the solvent was removed in vacuo to give the olefin (2.9 g, 47%, $^1H$ NMR ($CDCl_3$) δ 5.65–5.85 (m. 1), 5.00–5.20 (m, 2), 3.70–3.90 (m 1). 3.20–3.45 (m, 2). 2.35–2.60 (M, 1). 2.00–2.20 (m, 1), 1.60–2.00 (m, 4), 1.45 (s, 9)). To the olefin (1.0 g, 4.7 mmol) in THF (20 mL) at 0° C was added borane/THF. After warming to room temperature and stirring for 1 hour, $H_2O_2$ (30%, 14 mL) and 3N NaOH (3.2 mL) were added. The reaction was partitioned with ethyl acetate and separated. The organic layer was dried and concentrated in vacuo. The residue was added to $NaIO_4$ (1.2 g, 5.4 mmol) and $RuO_4$ (10 mg, 0.08 mmol) in water (100 mL) and acetone (10 mL).

After stirring for 1 hour, the reaction was concentrated and extracted with $CH_2Cl_2$. The organic layer was extracted with 1 N NaOH. The aqueous layer was washed with $CH_2Cl_2$, made acidic with 1 N HCl, and extracted with $CH_2Cl_2$. The organic layer was dried ($MgSO_4$) and concentrated to give 0.14 g (26%) of 1-Boc-pyrrolidine-2-propionic acid: $^1H$ NMR ($CDCl_3$) δ 1.40 (m, 9), 1.60–2.00 (m, 6), 2.20 (m, 2). 2.40 (m, 2), 3.30 (m. 2), 3.90 (m, 1).

4-Boc-thiomorpholine-3-carboxylic acid can also be substituted for the compound of formula (XXIV) in Reaction Scheme 7 and can be prepared in the following manner: To THF was added cysteine ethyl ester hydrochloride (1.15 g, 6.18 mmol), triethylamine (4.17 mL, 30 mmol) and dibromoethane (2.51 mL, 6.2 mmol). After stirring for 1 hour and refluxing for 16 hours, the solids were removed by filtration. The solvent was removed in vacuo and the residue was chromatographed on silica to give thiomorpholinecarboxylic acid ethyl ester (0.94 g, 87%). The ester (15.3 g, 95 mmol) was dissolved in dioxane/water (1/1) and di-t-butyldicarbonate (24 g, 110 mmol) and LiOH were added. After stirring for 3 hours, the solvent was removed in vacuo and the pH was adjusted to 3 with $KHSO_3$ and extracted with ethyl acetate. The organic layer was separated, washed with brine, dried ($MgSO_4$), and the solvent was removed in vacuo to give 17.4 g (78%) 4-Boc-thiomorpholine-3-carboxylic acid: $^1H$ NMR ($CDCl_3$) δ 1.45 (m, 9), 2.45 (m, 1), 2.71 (m, 1). 2.93(m, 1), 3.10 (m. 1), 3.29 (m, 1), 4.11 (m, 1), 4.19 (m, 1), 5.20 (m, 1). 4-Boc-thiomorpholine-3-acetic acid can also be substituted for the compound of formula (XXIV) in Reaction Scheme 7 and can be prepared in the following manner: To THF (50 mL) was added methyl bromocrotonate (1.0 mL, 8.6 mmol), Hünig's base (1.5 mL, 8.6 mmol), and N-Boc-2-aminoethanethiol (1.5 g, 8.6 mmol). After stirring for 3 hours, the reaction was poured into saturated $NH_4Cl$ and extracted with ethyl acetate. The organic layer was washed with brine, dried ($MgSO_4$), and the solvent was removed in vacuo. Chromatography (hexane/ethyl acetate, 6/1) gave N-Boc-2-aminoethanethiocrotonic acid methyl ester. The ester was dissolved in $CH_2Cl_2$ (80 mL) and TFA (20 mL) was added. After stirring for 1 hour, the solvent was removed in vacuo. The residue was added to a solution of toluene and TEA (2.5 ml). After stirring for 16 hours, the solvent was removed in vacuo and the residue was chromatographed to give the thiomorpholine. The ester (18.0 g, 95 mmol) was dissolved in dioxane/water (1/1) and di-t-butyldicarbonate (19.6 g, 90 mmol) and LiOH were added. After stirring for 12 hours, the solvent was removed in vacuo and the pH was adjusted to 3 with $KHSO_3$ and extracted with ethyl acetate. The organic layer was separated, washed with brine, dried ($MgSO_4$), and the solvent was removed in vacuo to give 20.3 g (86%) 4-Boc-thiomorpholine-3-acetic acid: $^1H$ NMR ($CDCl_3$) δ 1.45 (m, 9), 2.45 (m, 1), 2.51 (m, 1), 2.68 (m, 1), 2.82 (m, 1), 3.05 (m. 4), 4.24 (s, 1), 4.93 (s, 1).

4-Boc-thiomorpholine-2-acetic acid can also be substituted for the compound of formula (XXIV) in Reaction Scheme 7 and can be prepared in the following manner: To THF (100 mL) was added diethyl fumarate (3.27 mL, 820 mmol), DBU (7.22 mL, 50 mmol), and aminoethanethiol hydrochloride (2.26 g, 20 mmol). After refluxing for 16 hours, the reaction was poured into saturated $NaHCO_3$, and extracted with ethyl acetate. The organic layer was washed with brine, dried ($MgSO_4$), and the solvent was removed in vacuo. Chromatography (ethyl acetate) gave thiomorpholinone (2.61 g, 70%). The ester was dissolved in THF (50 mL) and borane/DMS (3 mL, 30 mmol) was added. After stirring for 16 hours, ethanol was added to quench the reaction. HCl gas was bubbled into the reaction and the mixture was refluxed for 2 hours. The solvent was removed in vacuo and the residue was suspended in 0.5 M NaOH and $CH_2Cl_2$. The organic layer was separated, dried ($Na_2SO_4$), and the solvent was removed in vacuo. Chromatography on silica (MeOH/ethyl acetate) afforded starting material (0.71 g, 29%) and the thiomorpholine (1.26 g, 56%). The ester (3.0 g, 11.4 mmol) was dissolved in dioxane/water (1/1) and di-t-butyldicarbonate (2.29 g, 10.5 mmol) and LiOH were added. After stirring for 12 hours, the solvent was removed in vacuo and the pH was adjusted to 3 with $KHSO_4$ and partitioned with ethyl acetate. The organic layer was separated, washed with brine, dried ($MgSO_4$), and the solvent was removed in vacuo to give 2.20 g (81%) 4-Boc-thiomorpholine-2-acetic acid: $^1H$ NMR ($CDCl_3$) δ 1.44 (m, 9), 2.59 (m, 4), 3.17 (m, 1). 3.24.0 (m, 4).

Reaction Scheme 7 depicts a synthesis in which a preformed, protected compound of formula (XXI) is coupled to the resin and deprotected to allow reaction with the protected compound of formula (XXIV). It will be apparent to the artisan that the sequence of this reaction series could be altered to provide the same deprotected piperonylamino-methyl benzoyl resin. An example of such a sequence follows. This example also illustrates how one would reverse the substitution pattern in the piperazineacetic acid ring.

4-Bromomethyl-3-nitrobenzoic acid (819 mg, 3.15 mmol) and HOBt (426 mg, 3.15 mmol) were taken up in 15 mL of DMF, DIC (795 mg, 6.30 mmol) was added and the contents were stirred for 30 min at ambient temperature. The mixture was then added to the resin and shaken overnight. The resin was filtered, washed and dried as before. The resin showed negative ninhydrin stain. The resin was taken in 15 mL of THF containing piperonyl amine (1.51 g, 10 mmol), and shaken over the weekend. The resin was filtered, washed and dried (1.507 g). $N^1$-Fmoc-$N^4$-Boc-piperazine-2-acetic acid (978 mg, 2.1 mmol), HATU (798 mg, 2.1 mmol) and DIEA (542 mg, 4.2 mmol) were mixed in 15 mL of DMF; and then added to the resin. After shaking for 24 hours, the resin was filtered, washed and dried as usual; the resin weighed 1.693 g. The resin was taken in 15 mL of 30% v/v piperidine in DMF, and shaken for 2 hours to cleave the Fmoc protecting group. After filtration, the resin was subjected to the usual wash and dry cycle; the resin weighed 1.588 g. The resin, acetic anhydride (591 mg, 5.8 mmol) and DIEA (748 mg, 5.8 mmol) were taken in 15 mL of methylene chloride and shaken overnight to acetylate at $N^1$. After filtration, the resin was washed with methylene chloride and dried in a vacuum desiccator for 5 hours. The resin was shaken with 15 mL of 1:1 TFA:methylene chloride for 1 hour to cleave the tBoc protecting group at $N^4$. After filtration, the resin was washed with methylene chloride (5×15 mL), followed by 20% triethyl amine in methylene chloride (5×15 mL) and then again with methylene chloride (5×5 mL). After drying, the resin weighed 1.294 g. 669 Mg of the resin from the previous step, DIEA (116 mg., 0.9 mmol) and 4-chloro-2-(1-imidazolyl)-6-iso-propylpyrimidine (200 mg, 0.9 mmol) were taken up in 6 mL of DMF and heated to 80° C for 24 hours. After filtration the resin was washed (DMF, methanol and methylene chloride) and dried. A portion (377 mg) of the resin from the previous step was suspended in methanol and photolyzed at 50° C for 6 hours. The solution was filtered, the solvent was removed and the residue was purified by chromatography (silica, methylene chloride:methanol, 95.5), yield 14 mg. $^1H$ NMR and MS were consistent with the proposed structure.

The following compounds, shown in Table 1 through Table 7 are representative of the compounds of the inventions and were synthesized by the foregoing methods. All exhibited iNOS inhibitory activity at concentrations less than 25 μM.

TABLE 1
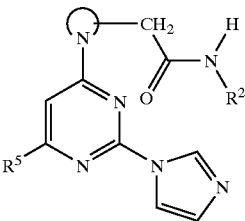
| Ex. # | R² | [N ring] | R⁵ | R⁶ | R⁹ |
|---|---|---|---|---|---|
| 1 | —CH₂R⁹ | 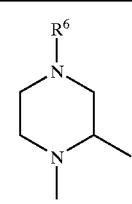 | H | H | 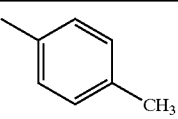 |
| 2 | —CH₂R⁹ | 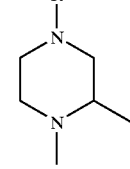 | Cl | Ac | 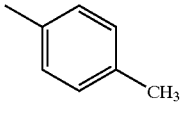 |
| 3 | —CH₂R⁹ | 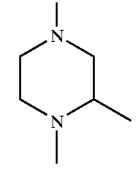 | H | Boc | 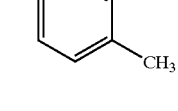 |
| 4 | —CH₂R⁹ | 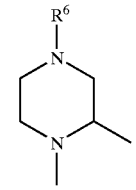 | Cl | Boc | 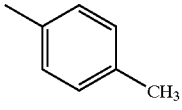 |
| 5 | —CH₂R⁹ | 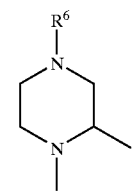 | F | Boc | 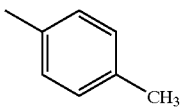 |
| 6 | —CH₂R⁹ | 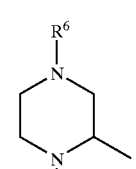 | Cl | H | 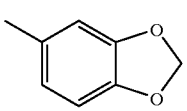 |

TABLE 1-continued
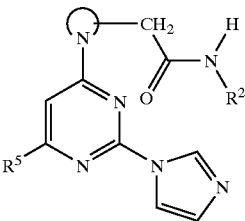
| Ex. # | R² | 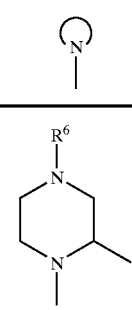 | R⁵ | R⁶ | R⁹ |
|---|---|---|---|---|---|
| 7 | —CH₂R⁹ | 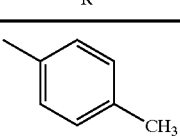 | Cl | H | 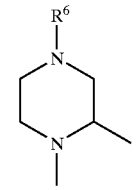 |
| 8 | —CH₂R⁹ | 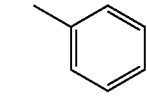 | Cl | H | 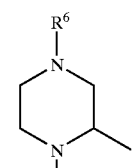 |
| 9 | —CH₂R⁹ | 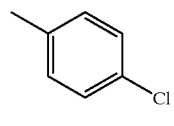 | Cl | H | 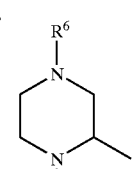 |
| 10 | —(CH₂)₂—R⁹ | 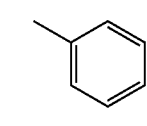 | Cl | H | 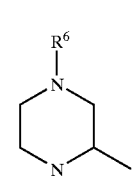 |
| 11 | —CH₃ | 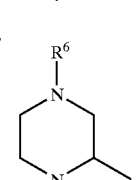 | Cl | H | |
| 12 | —(CH₂)₃—R⁹ | 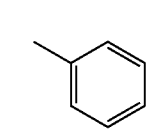 | Cl | H | |

TABLE 1-continued
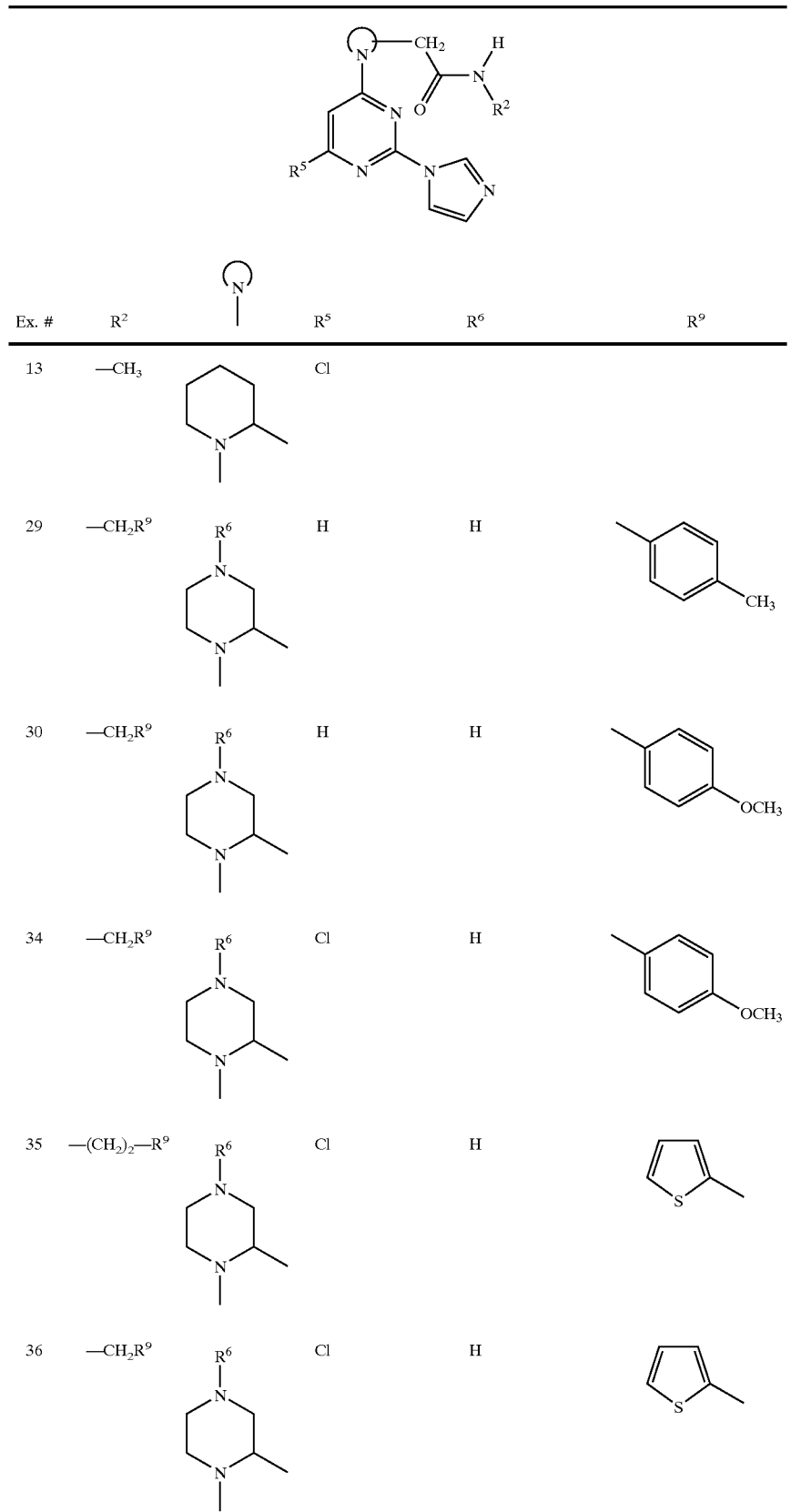
| Ex. # | R² | ⟨N⟩ | R⁵ | R⁶ | R⁹ |
|---|---|---|---|---|---|
| 13 | —CH₃ | 1,2-dimethylpiperidine | Cl | | |
| 29 | —CH₂R⁹ | R⁶-3-methylpiperazine (N4-methyl) | H | H | 4-methylphenyl |
| 30 | —CH₂R⁹ | R⁶-3-methylpiperazine (N4-methyl) | H | H | 4-methoxyphenyl |
| 34 | —CH₂R⁹ | R⁶-3-methylpiperazine (N4-methyl) | Cl | H | 4-methoxyphenyl |
| 35 | —(CH₂)₂—R⁹ | R⁶-3-methylpiperazine (N4-methyl) | Cl | H | 2-thienyl |
| 36 | —CH₂R⁹ | R⁶-3-methylpiperazine (N4-methyl) | Cl | H | 2-thienyl |

TABLE 1-continued
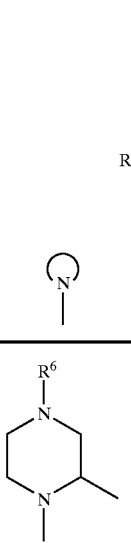
| Ex. # | R² | 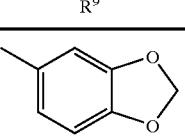 | R⁵ | R⁶ | R⁹ |
|---|---|---|---|---|---|
| 52 | —CH₂R⁹ | 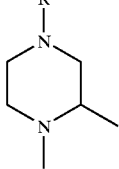 | H | H | 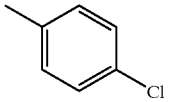 |
| 58 | —CH₂R⁹ | 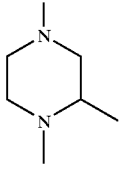 | Cl | Boc | 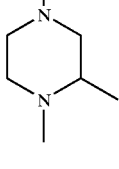 |
| 59 | —CH₃ | 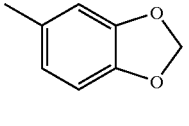 | Cl | Boc | |
| 60 | —CH₂R⁹ | 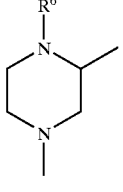 | Cl | Boc | 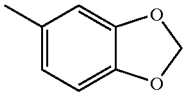 |
| 76 | —(CH₂)₂—R⁹ | 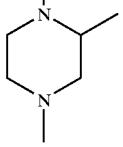 | Cl | —C(O)CH₂OCH₃ | |
| 77 | —(CH₂)₂—R⁹ | 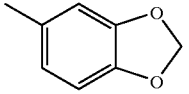 | H | —C(O)O(CH₂)₃CH₃ | |

TABLE 1-continued
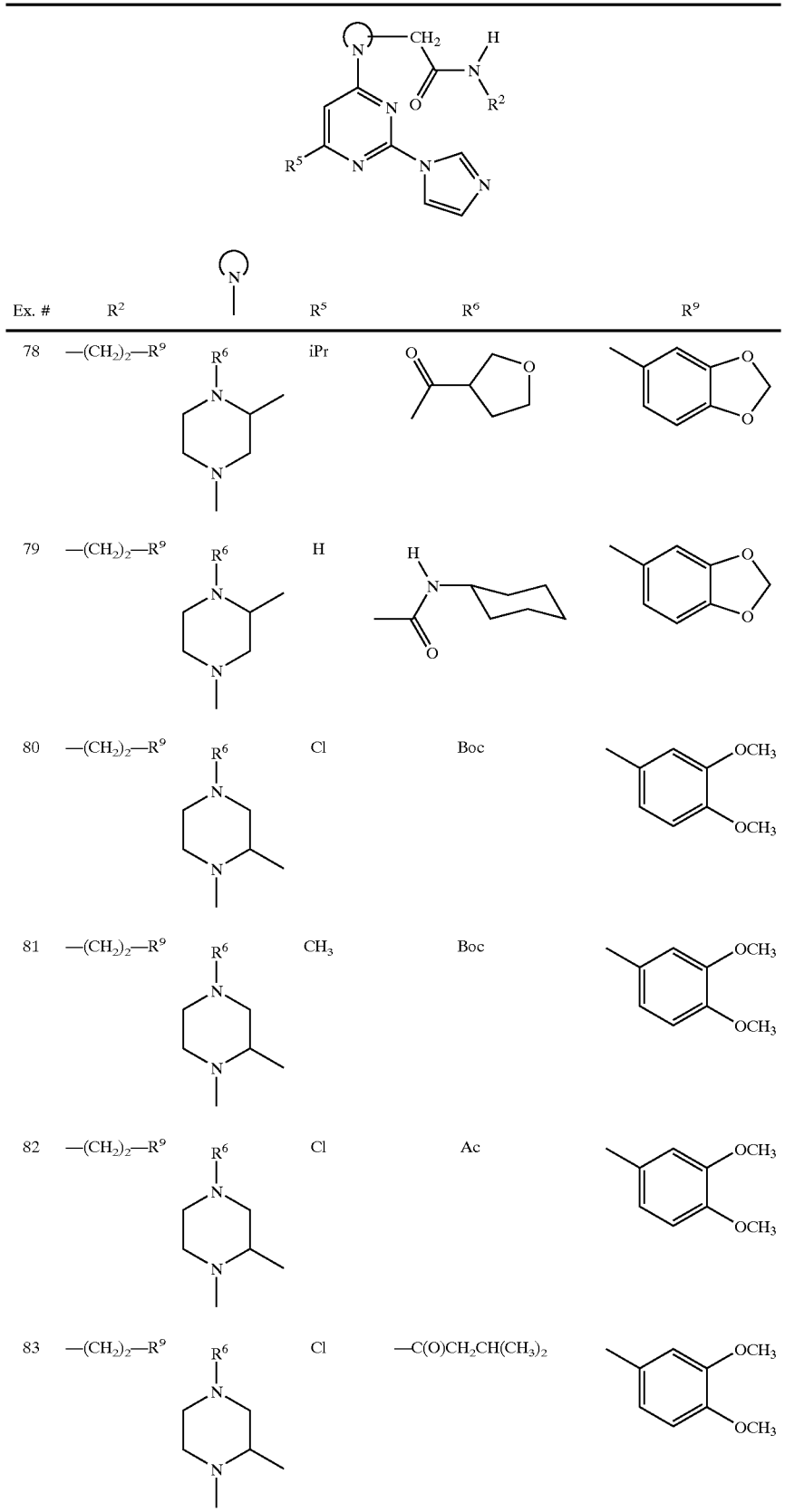

TABLE 1-continued
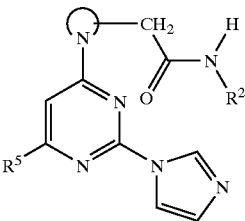
| Ex. # | R² | (N ring) | R⁵ | R⁶ | R⁹ |
|---|---|---|---|---|---|
| 84 | —(CH₂)₂—R⁹ | 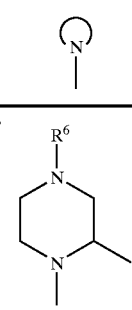 | Cl | H | 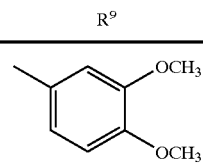 |
| 85 | —(CH₂)₂—R⁹ | 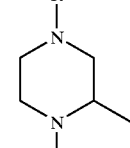 | CH₃ | H | 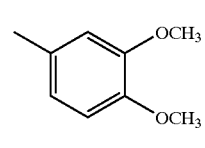 |
| 86 | —(CH₂)₂—R⁹ | 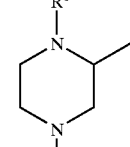 | Cl | Ac | 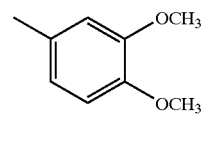 |
| 87 | —(CH₂)₂—R⁹ | 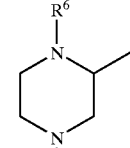 | Cl | —C(O)CH₂CH(CH₃)₂ | 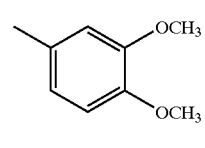 |
| 88 | —(CH₂)₂—R⁹ | 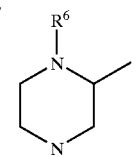 | CH₃ | Ac | 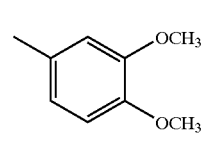 |
| 89 | —(CH₂)₂—R⁹ | 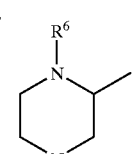 | CH₃ | —C(O)CH₂CH(CH₃)₂ | 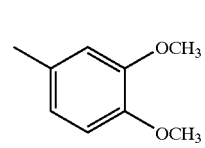 |

TABLE 1-continued
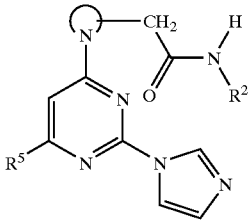
| Ex. # | R² | 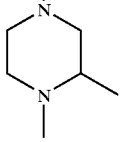 | R⁵ | R⁶ | R⁹ |
|---|---|---|---|---|---|
| 90 | —CH₂R⁹ | 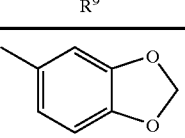 | Cl | —C(O)OCH₃ | 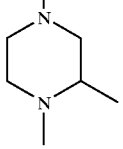 |
| 91 | —CH₂R⁹ | 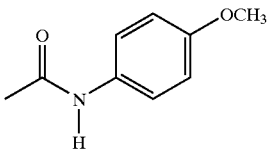 | Cl | 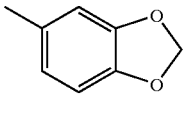 | 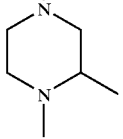 |
| 92 | —CH₂R⁹ | 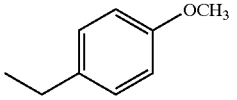 | Cl | 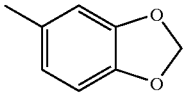 | 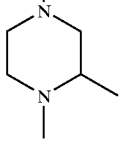 |
| 93 | —CH₂R⁹ | 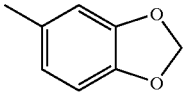 | Cl | —S(O)₂NH(CH₃) | 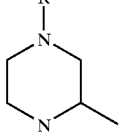 |
| 94 | —CH₂R⁹ | 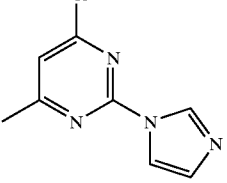 | Cl | 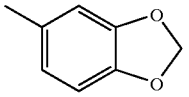 | 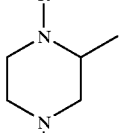 |
| 95 | —CH₂R⁹ | 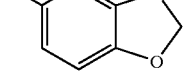 | iPr | —C(O)OCH₃ | 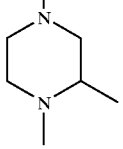 |

TABLE 1-continued
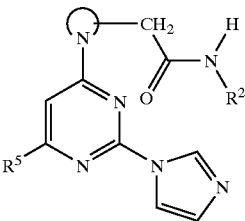
| Ex. # | R² | 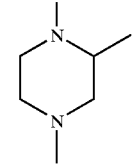 | R⁵ | R⁶ | R⁹ |
|---|---|---|---|---|---|
| 96 | —CH₂R⁹ | 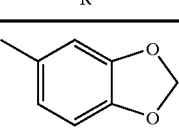 | CH₃ | —C(O)OCH₃ | 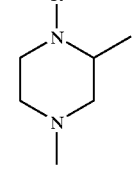 |
| 97 | —CH₂R⁹ | 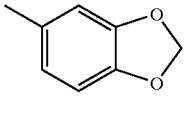 | Cl | —C(O)OCH₃ | 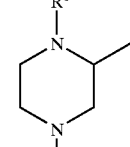 |
| 98 | —CH₂R⁹ | 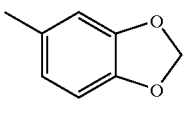 | H | —C(O)OCH₃ | 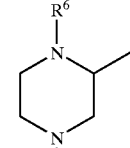 |
| 99 | —CH₂R⁹ | 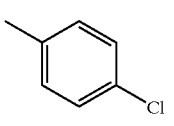 | Cl | —C(O)OCH₃ | 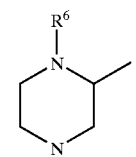 |
| 100 | —CH₂R⁹ | 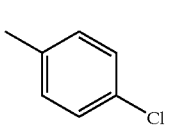 | H | —C(O)OCH₃ | 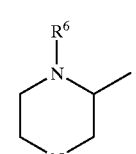 |
| 101 | —CH₂R⁹ | 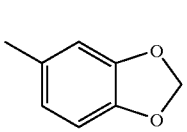 | CF₃ | Ac | (benzo[1,3]dioxole) |

TABLE 1-continued
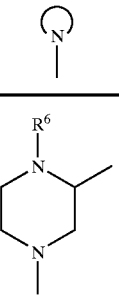
| Ex. # | R² | 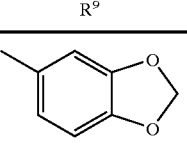 | R⁵ | R⁶ | R⁹ |
|---|---|---|---|---|---|
| 102 | —CH₂R⁹ | 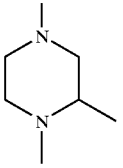 | iPr | Ac | 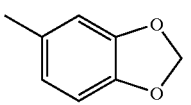 |
| 103 | —CH₂R⁹ | 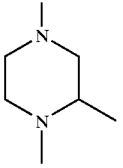 | CH₃ | —C(O)OC(CH₃)₃ | 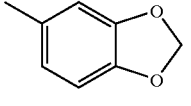 |
| 104 | —CH₂R⁹ | 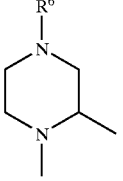 | iPr | —C(O)OC(CH₃)₃ | 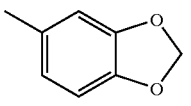 |
| 105 | —CH₂R⁹ | 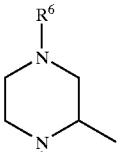 | CF₃ | Ac | 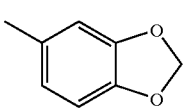 |
| 106 | —CH₂R⁹ | 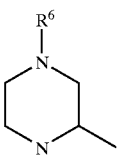 | iPr | Ac | 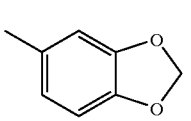 |
| 107 | —CH₂R⁹ | | Et | Ac | |

TABLE 1-continued

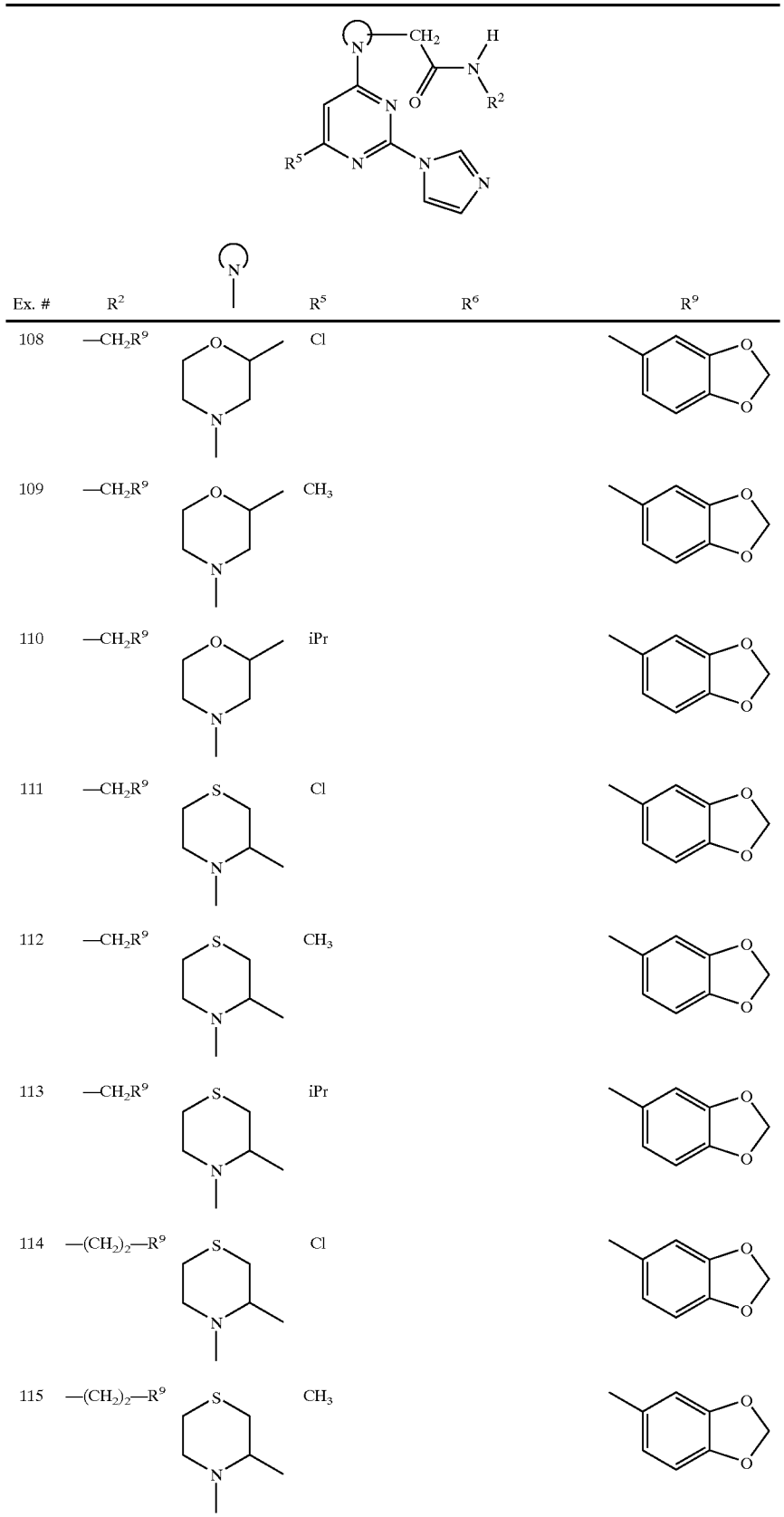

| Ex. # | R² | ⌒N- | R⁵ | R⁶ | R⁹ |
|---|---|---|---|---|---|
| 108 | —CH₂R⁹ | 2-methylmorpholine | Cl | | methylenedioxyphenyl |
| 109 | —CH₂R⁹ | 2-methylmorpholine | CH₃ | | methylenedioxyphenyl |
| 110 | —CH₂R⁹ | 2-methylmorpholine | iPr | | methylenedioxyphenyl |
| 111 | —CH₂R⁹ | 3-methylthiomorpholine | Cl | | methylenedioxyphenyl |
| 112 | —CH₂R⁹ | 3-methylthiomorpholine | CH₃ | | methylenedioxyphenyl |
| 113 | —CH₂R⁹ | 3-methylthiomorpholine | iPr | | methylenedioxyphenyl |
| 114 | —(CH₂)₂—R⁹ | 3-methylthiomorpholine | Cl | | methylenedioxyphenyl |
| 115 | —(CH₂)₂—R⁹ | 3-methylthiomorpholine | CH₃ | | methylenedioxyphenyl |

TABLE 1-continued

| Ex. # | R² | ⟨N⟩ | R⁵ | R⁶ | R⁹ |
|---|---|---|---|---|---|
| 116 | —(CH₂)₂—R⁹ | 2,4-dimethyl-thiomorpholinyl | iPr | | benzo[1,3]dioxol-5-yl |
| 117 | —CH₂R⁹ | 2-methyl-4-methyl-thiomorpholinyl | Cl | | benzo[1,3]dioxol-5-yl |
| 118 | —CH₂R⁹ | 2-methyl-4-methyl-thiomorpholinyl | CH₃ | | benzo[1,3]dioxol-5-yl |
| 119 | —CH₂R⁹ | 2-methyl-4-methyl-thiomorpholinyl | iPr | | benzo[1,3]dioxol-5-yl |
| 120 | —(CH₂)₂—R⁹ | 2-methyl-4-methyl-thiomorpholinyl | Cl | | benzo[1,3]dioxol-5-yl |
| 121 | —(CH₂)₂—R⁹ | 2-methyl-4-methyl-thiomorpholinyl | CH₃ | | benzo[1,3]dioxol-5-yl |
| 122 | —(CH₂)₂—R⁹ | 2-methyl-4-methyl-thiomorpholinyl | iPr | | benzo[1,3]dioxol-5-yl |

TABLE 2
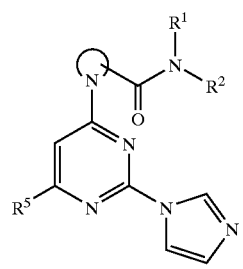
| Ex. # | R² | 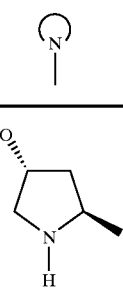 | R⁵ | R⁶ | R⁹ |
|---|---|---|---|---|---|
| 19 | —CH₂—R⁹ | 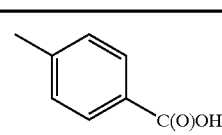 | Cl | | 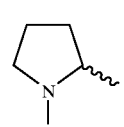 |
| 42 | —(CH₂)₂—R⁹ | 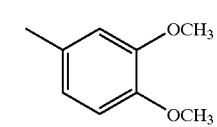 | Cl | | 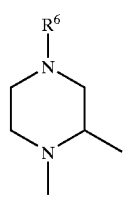 |
| 123 | —(CH₂)₂—R⁹ | 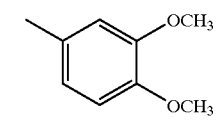 | Cl | —C(O)CH₂CH(CH₃)₂ | 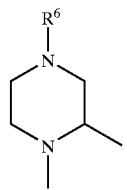 |
| 124 | —(CH₂)₂—R⁹ | 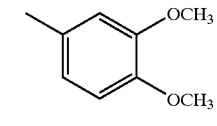 | Cl | Boc | 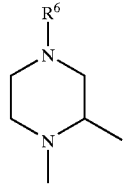 |
| 125 | —(CH₂)₂—R⁹ | 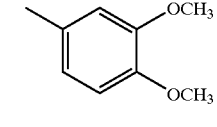 | Cl | H | 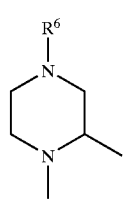 |
| 126 | —(CH₂)₂—R⁹ | 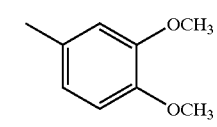 | Cl | Ac | |

TABLE 2-continued
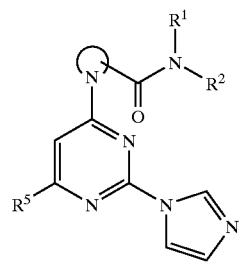
| Ex. # | R² | 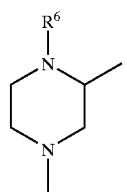 | R⁵ | R⁶ | R⁹ |
|---|---|---|---|---|---|
| 127 | —(CH₂)₂—R⁹ | 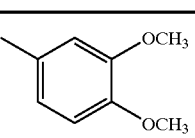 | Cl | Ac | 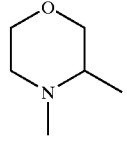 |
| 128 | —(CH₂)₂—R⁹ | 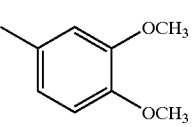 | Cl |  | 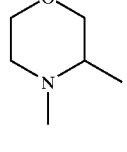 |
| 129 | —(CH₂)₂—R⁹ | 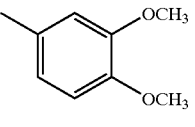 | iPr |  | 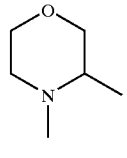 |
| 130 | —(CH₂)₂—R⁹ | 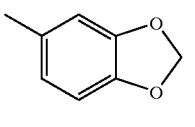 | Cl |  | 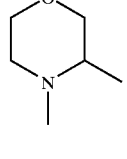 |
| 131 | —(CH₂)₂—R⁹ | 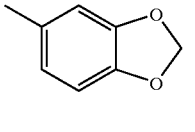 | iPr |  | 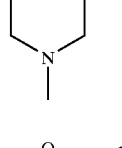 |
| 132 | —(CH₂)₂—R⁹ | 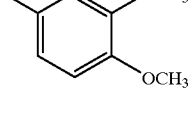 | Cl |  | 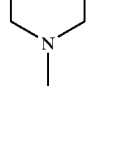 |
| 133 | —(CH₂)₂—R⁹ | 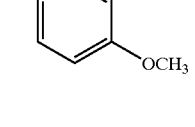 | iPr |  | |

TABLE 2-continued

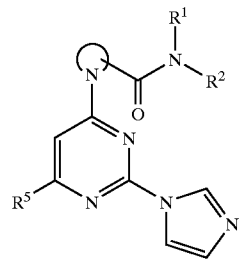

| Ex. # | R² | (N-ring) | R⁵ | R⁶ | R⁹ |
|---|---|---|---|---|---|
| 134 | —(CH₂)₂—R⁹ | N-methyl-2-methylmorpholine | Cl | | benzo[1,3]dioxol-5-yl |
| 135 | —(CH₂)₂—R⁹ | N-methyl-2-methylmorpholine | iPr | | benzo[1,3]dioxol-5-yl |
| 136 | —CH₂—R⁹ | (3,5)-N-methyl-3-acetamido-5-methylpyrrolidine | CH₃ | | benzo[1,3]dioxol-5-yl |
| 137 | —CH₂—R⁹ | (3,5)-N-methyl-3-acetamido-5-methylpyrrolidine | iPr | | benzo[1,3]dioxol-5-yl |
| 138 | —CH₂—R⁹ | (3,5)-N-methyl-3-acetamido-5-methylpyrrolidine | Cl | | benzo[1,3]dioxol-5-yl |
| 139 | —CH₂—R⁹ | (2S)-2-methylpyrrolidine | CH₃ | | benzo[1,3]dioxol-5-yl |
| 140 | —CH₂—R⁹ | (2S)-2-methylpyrrolidine | Et | | benzo[1,3]dioxol-5-yl |

TABLE 2-continued
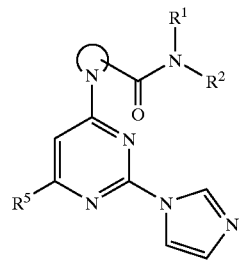
| Ex. # | R² | [N ring] | R⁵ | R⁶ | R⁹ |
|---|---|---|---|---|---|
| 141 | —CH₂—R⁹ | 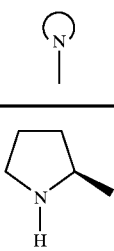 | iPr | | 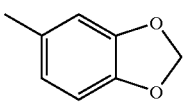 |
| 142 | —CH₂—R⁹ | 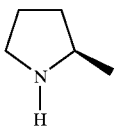 | Cl | | 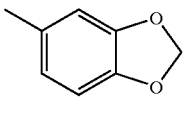 |
| 143 | —(CH₂)₂—R⁹ | 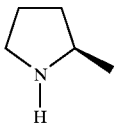 | CH₃ | | 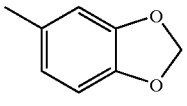 |
| 144 | —(CH₂)₂—R⁹ | 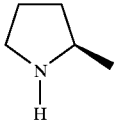 | Et | | 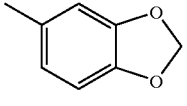 |
| 145 | —(CH₂)₂—R⁹ | 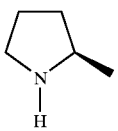 | iPr | | 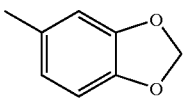 |
| 146 | —(CH₂)₂—R⁹ | 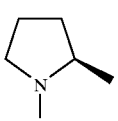 | Cl | | 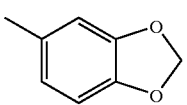 |

TABLE 3
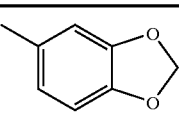
| Ex. # | R² | R⁴ | R⁵ | Q—R³ | R⁹ or R¹⁰ (from R²) | m | n | p | AA |
|---|---|---|---|---|---|---|---|---|---|
| 14 | —CH₂R⁹ | H | Cl | —SCH₃ | 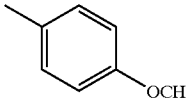 | 2 | 0 | 0 | D-Met |
| 15 | —CH₂R⁹ | H | Cl | —SCH₃ | 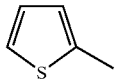 | 2 | 0 | 0 | D-Met |
| 16 | —(CH₂)₂R⁹ | H | Cl | 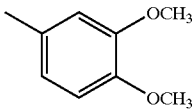 | 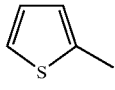 | 1 | 0 | 0 | [D] |
| 17 | —(CH₂)₃CH₃ | H | Cl | 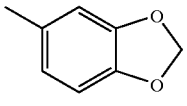 |  | 1 | 0 | 0 | [D] |
| 18 | —CH₂R⁹ | H | Cl | H | 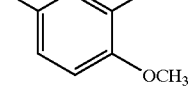 | 0 | 2 | 2 | Acp |
| 20 | —(CH₂)₂R⁹ | H | Cl | H | 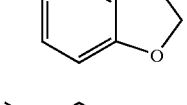 | 0 | 0 | 0 | Gly |
| 21 | —CH₂R⁹ | H | Cl | —OH | 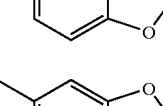 | 1 | 0 | 0 | D,L-Ser |
| 22 | —CH₂R⁹ | CH₃ | Cl | H | 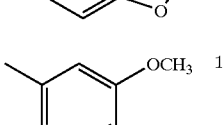 | 0 | 0 | 0 | Sar |
| 23 | —CH₂R⁹ | H | Cl | —CONH₂ |  | 2 | 0 | 0 | L-Gln |
| 24 | —(CH₂)₂R⁹ | H | Cl | H | 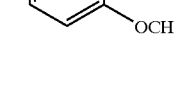 | 1 | 0 | 0 | D,L-Ala |

TABLE 3-continued
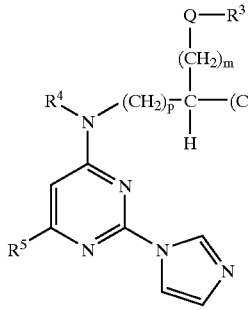
| Ex. # | R² | R⁴ | R⁵ | Q—R³ | R⁹ or R¹⁰ (from R²) | m | n | p | AA |
|---|---|---|---|---|---|---|---|---|---|
| 25 | —CH₂R⁹ | H | Cl | —CONH₂ | 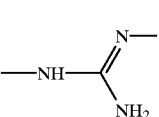 | 2 | 0 | 0 | D-Gln |
| 26 | —CH₂R⁹ | H | Cl | 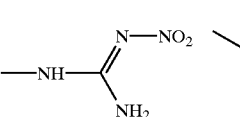 | 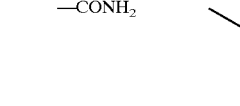 | 3 | 0 | 0 | L-Arg (NO₂) |
| 27 | —(CH₂)₂R⁹ | H | Cl | —CONH₂ |  | 2 | 0 | 0 | D-Gln |
| 28 | —CH₂R⁹ | H | Cl | —NH₂ | 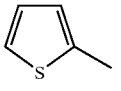 | 3 | 0 | 0 | D,L-Orn |
| 31 | —(CH₂)₃R⁹ | H | H | 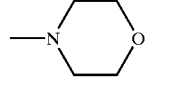 | 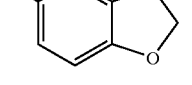 | 1 | 0 | 0 | [D] |
| 32 | —CH₂R⁹ | H | H | —CONH₂ | 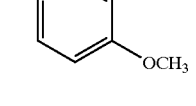 | 2 | 0 | 0 | L-Gln |
| 37 | —CH₂R⁹ | H | Cl | —SCH₃ | 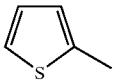 | 2 | 0 | 0 | D-Met |
| 38 | —CH₃ | H | Cl | —SCH₃ | | 2 | 0 | 0 | D-Met |
| 39 | —(CH₂)₂R¹⁰ | H | Cl | —StBu | —SCH₃ | 1 | 0 | 0 | L-Cys |
| 40 | —(CH₂)₃R⁹ | H | Cl | —StBu | phenyl | 1 | 0 | 0 | D-Cys |
| 41 | —CH₂R⁹ | H | Cl | 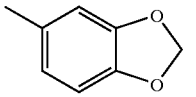 | 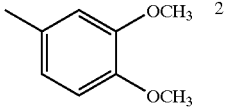 | 1 | 0 | 0 | [D] |
| 43 | —CH₂R⁹ | H | Cl | —CONH₂ | 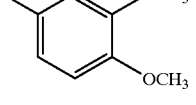 | 2 | 0 | 0 | D-Gln |
| 44 | —CH₂R⁹ | H | Cl | —CONH₂ | 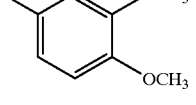 | 2 | 0 | 0 | L-Gln |

TABLE 3-continued

| Ex. # | $R^2$ | $R^4$ | $R^5$ | Q—$R^3$ | $R^9$ or $R^{10}$ (from $R^2$) | m | n | p | AA |
|---|---|---|---|---|---|---|---|---|---|
| 45 | —$CH_2R^9$ | H | Cl | —NH–C(=N–NO$_2$)–NH$_2$ | 4-methoxyphenyl | 3 | 0 | 0 | L-Arg (NO$_2$) |
| 46 | —$CH_2R^9$ | H | Cl | —NH–C(=NH)–NH$_2$ | 4-methoxyphenyl | 3 | 0 | 0 | D-Arg |
| 48 | —$(CH_2)_3CH_3$ | H | Cl | —$NH_2$ | | 3 | 0 | 0 | D,L-Orn |
| 49 | —$(CH_2)_2R^{10}$ | H | Cl | —COOH | —COOH | 1 | 0 | 0 | D,L-Asp |
| 50 | —$(CH_2)_3R^9$ | H | Cl | phenyl | —$S(O)_2CH_3$ | 1 | 0 | 0 | D,L-Phe |
| 51 | —$CH_2R^9$ | $CH_3$ | Cl | H | 4-pyridyl | 0 | 0 | 0 | Sar |
| 53 | —$CH_2R^9$ | H | H | —OH | benzo[1,3]dioxol-5-yl | 1 | 0 | 0 | D,L-Ser |
| 54 | —$CH_2R^9$ | H | H | —NH–C(=N–NO$_2$)–NH$_2$ | benzo[1,3]dioxol-5-yl | 3 | 0 | 0 | L-Arg (NO$_2$) |
| 56 | —$(CH_2)_2R^9$ | H | Cl | 2-thienyl | 3,4-dimethoxyphenyl | 1 | 0 | 0 | [L] |
| 57 | —$CH_2R^9$ | H | Cl | 2-thienyl | benzo[1,3]dioxol-5-yl | 1 | 0 | 0 | [L] |
| 61 | —$(CH_2)_2R^9$ | $CH_3$ | Cl | H | benzo[1,3]dioxol-5-yl | 0 | 0 | 0 | Sar |
| 62 | —$(CH_2)_2R^9$ | H | Cl | H | 3,4-dimethoxyphenyl | 1 | 0 | 0 | D-Ala |

TABLE 3-continued
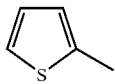
| Ex. # | R² | R⁴ | R⁵ | Q—R³ | R⁹ or R¹⁰ (from R²) | m | n | p | AA |
|---|---|---|---|---|---|---|---|---|---|
| 64 | —(CH₂)₃R⁹ | H | Cl | 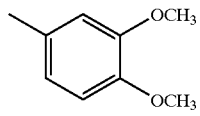 | 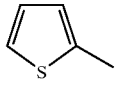 OCH₃ OCH₃ | 1 | 0 | 0 | [D] |
| 65 | —(CH₂)₄R⁹ | H | Cl | 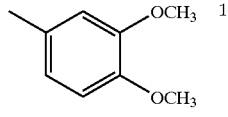 | 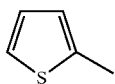 OCH₃ OCH₃ | 1 | 0 | 0 | [D] |
| 66 | —(CH₂)₂R⁹ | H | H | 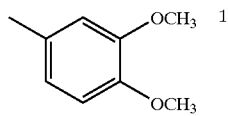 | 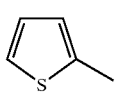 OCH₃ OCH₃ | 1 | 0 | 0 | [D] |
| 67 | —(CH₂)₃R⁹ | H | H | 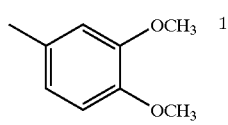 | OCH₃ OCH₃ | 1 | 0 | 0 | [D] |
| 68 | —CH₂R⁹ | H | Cl | —SCH₃ | 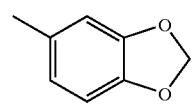 | 2 | 0 | 0 | L-Met |
| 69 | —CH₂R⁹ | H | Cl | —NHTrt | 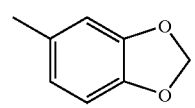 | 2 | 0 | 0 | Nᵞ-trityl L-Gln |
| 70 | —CH₂R⁹ | H | Cl | —NHTrt | 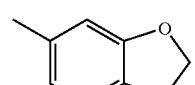 | 2 | 0 | 0 | Nᵞ-trityl D-Gln |

TABLE 4
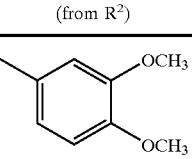
| Ex # | R² | R⁴ | R⁵ | Q-R³ | R⁹ or R¹⁰ (from R²) | m | n | p | AA |
|---|---|---|---|---|---|---|---|---|---|
| 71 | —(CH₂)₂R⁹ | H | Cl | H | 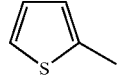 3,4-dimethoxyphenyl | 1 | 0 | 0 | D-Ala |
| 72 | —(CH₂)₃R⁹ | H | Cl | 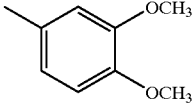 2-thienyl | 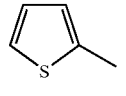 3,4-dimethoxyphenyl | 1 | 0 | 0 | [D] |
| 73 | —(CH₂)₄R⁹ | H | Cl | 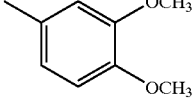 2-thienyl | 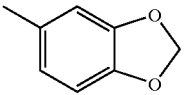 3,4-dimethoxyphenyl | 1 | 0 | 0 | [D] |
| 74 | —CH₂R⁹ | CH₃ | Cl | H | 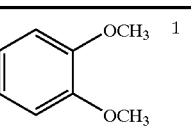 benzo[1,3]dioxol-5-yl | 0 | 0 | 0 | Sar |
TABLE 5
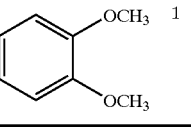
| Ex. # | R² | R⁴ | R⁵ | Q—R³ | R⁹ or R¹⁰ (from R²) | m | n | p | AA |
|---|---|---|---|---|---|---|---|---|---|
| 75 | —(CH₂)₂R⁹ | H | Cl | H | 3,4-dimethoxyphenyl | 1 | 0 | 0 | D-Ala |
| 63 | —(CH₂)₂R⁹ | H | H | H | 3,4-dimethoxyphenyl | 1 | 0 | 0 | D-Ala |

TABLE 6

Physical Data for Compounds of the Invention

| Ex.# | Formula | FABMS | Definitive $^1$H NMR (ppm) |
|---|---|---|---|
| 1 | $C_{21}H_{24}N_7O$ | 392 | 9.6(1H), 8.3(1H), 8.2(1H)6.9–7.5 (6H), 2.2(3H) |
| 2 | $C_{23}H_{26}ClN_7O$ | 468 | 8.5(1H), 7.6–7.8(1H)6.9–7.2 (6H), 2.3(3H), 2.1(3H) |
| 3 | $C_{26}H_{32}N_7O_3$ | 492 | 8.5(1H), 8.2(1H), 7.8(1H), 7.0–7.2 (5H), 6.6(1H), 2.3(3H), 1.5(9H) |
| 4 | $C_{26}H_{32}ClN_7O_3$ | 526 | 8.5(1H), 7.8(1H), 7.0–7.2(6H), 2.3 (3H), 1.5(9H) |
| 5 | $C_{26}H_{32}FN_7O_3$ | 510 | 8.5(1H), 7.8(1H), 7.0–7.2 (6H), 2.3(3H), 1.5(9H) |
| 6 | $C_{21}H_{22}ClN_7O_3$ | 456 | ND |
| 7 | $C_{21}H_{24}ClN_7O$ | ND | 9.6(1H), 8.3(1H), 8.2(1H), 6.9–7.5 (6H) |
| 9 | $C_{20}H_{21}Cl_2N_7O$ | 446 | 9.6(1H), 8.1(1H), 7.4(1H), 7.0(4H), 6.9(1H) |
| 11 | $C_{14}H_{18}ClN_7O$ | 336 | 9.7(1H), 8.2(1H), 7.5(1H), 6.9 (1H), 2.6(3H) |
| 14 | $C_{20}H_{21}ClN_6O_3S$ | 461 | 2.0(SCH$_3$) |
| 16 | $C_{23}H_{23}ClN_6O_3S$ | ND | 2.65(m,2H), 3.36(m,2H), 3.55(m, 2H), 3.79(s,3H), 3.80(m,2H), 3.83 (s,3H), 4.77(m,1H), 6:30(s,1H), 6.32 (bs,1H), 6.55–6.95(m,5H), 7.08(s, 1H), 7.18(d,1H), 7.78(s,1H), 8.45(s, 1H). |
| 18 | $C_{21}H_{23}ClN_6O_3$ | 443 | 8.4(1H), 7.8(1H), 7.2(1H), 7.0(1H), 6.7(2H), 5.9(1H)4.2(2H), 2.2(2H) |
| 22 | $C_{18}H_{17}ClN_6O_3$ | ND | 3.2(s,3H), 4.25(s,2H), 4.38(s,2H), 5.88(s,2H), 6.30(brs,1H), 6.42(bs, 2H), 6.65(m,3H), 7.05(s,1H), 8.40 (s,1H). |
| 56 | $C_{24}H_{25}ClN_6O_3S$ | ND | 8.5(1H), 7.8(1H), 7.2(1H), 7.1(1H), 3.9(6H) |
| 57 | $C_{22}H_{19}ClN_6O_3S$ | ND | 8.5(1H), 7.8(1H), 7.2(1H), 7.1(1H), 4.3(2H) |
| 58 | $C_{25}H_{29}Cl_2N_7O_3$ | 546 | 8.5(1H), 7.8(1H), 7.2–7.4(5H), 6.6(1H), 1.4(9H) |
| 59 | $C_{19}H_{26}ClN_7O_3$ | 436 | 8.5(1H), 7.8(1H), 7.1(1H), 6.6 (2H), 1.5(9H) |
| 60 | $C_{26}H_{30}ClN_7O_5$ | 556 | 8.5(1H), 7.8(1H), 7.1(1H), 6.7(4H), 5.9(2H), 1.5(9H) |
| 61 | $C_{19}H_{20}N_6O_3$ | ND | 3.22(s,3H), 4.24(bs,2H), 4.32(d,2H), 5.92(s,2H), 6.30(bs,1H), 6.47(d, 1H), 6.65(m,3H), 7.04(s,1H), 7.68 (s,1H), 7.95(d,1H), 8.41(s,1H). |
| 62 | $C_{20}H_{23}ClN_6O_3$ | ND | 1.48(d,3H), 2.78(m,2H), 3.58(2H,m), 3.80(6H,s), 4.60(1H,m), 5.9–6.25 (3H,m), 6.55–6.8(3H,m), 7.12 (1H,s), 7.78(1H,s), 8.44(1H,s). |
| 63 | $C_{20}H_{24}N_6O_3$ | ND | 1.40(d,3H) |
| 64 | $C_{24}H_{25}ClN_6O_3S$ | ND | 1.75(m,2H), 2.50(m,2H), 3.2–3.5(m, 4H), 3.82(s,6H), 4.78(m,1H), 6.21 (m,1H), 6.36(m,2H), 6.60–6.95(m, 5H), 7.10(s,1H), 7.21(d,1H), 7.80(s, 1H), 8.53(s,1H). |
| 65 | $C_{25}H_{27}ClN_6O_3S$ | ND | 1.47(m,4H), 2.52(m,2H), 3.2–3.45 (m,4H), 3.83(s,6H), 4.78(m,1H), 6.08(m,1H)6.17(m,2H), 6.64(m,2H), 6.77(m,3H), 7.13(s,1H), 7.19(d,1H), 7.80(s,1H), 8.51(s,1H). |
| 66 | $C_{23}H_{24}N_6O_3S$ | ND | 3.35–3.6(m), 3.83(s,6H), 4.62(m, 1H), 5.75(m,1H), 6.18(m,1H), 6.50–6.95(m,7H), 7.17(s,1H), 7.19(d,1H), 7.57(s,1H), 8.27(s,1H). |
| 67 | $C_{24}H_{26}N_6O_3S$ | ND | 1.70(m,2H), 2.48(m,2H), 3.1–3.5 (m,4H), 3.82(s,6H), 4.77(s,1H), 5.90 (d,1H), 6.03(m,1H), 6.29(d,1H), 6.60 (m,1H), 6.61(m,1H), 6.75–6.95(m, 3H), 7.12(s,1H), 7.20(d,1H), 7.82(s, 1H), 8.14(d,1H), 8.57(s,1H). |
| 68 | $C_{20}H_{21}ClN_6O_3S$ | 461 | 2.0(SCH$_3$) |
| 69 | $C_{39}H_{34}ClN_7O_4$ | 700 | 8.4(1H), 7.6(1H), 6.8–7.5(16H), 6.5 (3H), 5.8–5.9(3H) |
| 70 | $C_{39}H_{34}ClN_7O_4$ | 700 | 8.4(1H), 7.6(1H), 6.8–7.5 (16H), 6.5(3H), 5.8–5.9(3H) |
| 71 | $C_{20}H_{23}ClN_6O_3$ | ND | 1.43(d,3H), 2.79(m,2H), 3.57(m,2H), 3.80(s,3H), 3.82(s,3H), 4.60(m,1H), 5.95–6.20(m,3H), 6.60–6.80(m, 3H), 7.18(s,1H), 7.51(s,1H), 8.28 (s,1H). |
| 72 | $C_{24}H_{25}ClN_6O_3S$ | ND | 1.75(m,2H), 2.50(m,2H), 3.2–3.5 (4H), 3.82(s,6H), 4.78(m,1H), 5.85 (m,1H), 6.10–6.25(m,2H), 6.6–7.0 (m,3H), 6.8–7.0(m,2H), 7.57(s,1H), 8.38(s,1H). |
| 73 | $C_{25}H_{27}ClN_6O_3S$ | ND | 1.47(m,4H), 2.52(m,2H), 3.2–3.45 (m,4H), 3.83 (s,6H), 4.78(m,1H), 5.80(m,1H), 6.22(m,2H), 6.63–6.95 (m,5H), 7.20(m,2H), 7.50(s,1H), 8.33(m,1H). |
| 74 | $C_{18}H_{17}ClN_6O_3$ | ND | 3.22(s,3H), 4.24(s,2H), 4.37(d,2H), 5.96(s,2H), 6.29(s,1H), 6.76(s,2H), 7.17(s,1H), 7.56(s,1H), 8.37(s,1H). |
| 75 | $C_{20}H_{23}ClN_6O_3$ | ND | 1.43(d,3H), 2.80(m,2H), 3.57(m,2H), 3.80(s,3H), 3.82(s,3H), 4.60(m,1H), 6.20(m,1H), 6.4–6.5(m,2H), 6.60–6.80(m,3H), 7.18(s,1H), 7.51(s,1H), 8.28(s,1H). |
| 76 | $C_{25}H_{28}ClN_7O_5$ | 542 | 8.5(1H), 7.8(1H), 7.1(1H), 6.4–6.8 (3H), 5.9(2H), 3.4(3H) |
| 77 | $C_{27}H_{33}N_7O_5$ | 536 | 8.5(1H), 8.2(1H), 7.8(1H), 7.1(1H), 5.9(2H) |
| 78 | $C_{30}H_{37}N_7O_5$ | 576 | 8.5(1H), 7.8(1H), 7.1(1H), 6.4(3H), 5.9(2H), 1.3(6H) |
| 79 | $C_{29}H_{36}N_8O_4$ | 561 | 8.5(1H), 8.2(1H), 7.8(1H), 7.1(1H), 5.9(2H) |
| 80 | $C_{28}H_{36}ClN_7O_5$ | 586 | 8.5(1H), 7.8(1H), 6.7–6.8(4H), 3.8 (6H), 1.5(9H) |
| 81 | $C_{29}H_{39}N_7O_5$ | 566 | 8.5(1H), 7.8(1H), 7.1(1H), 6.6–6.8 (4H), 3.8(6H), 2.4(3H), 1.4(9H) |
| 82 | $C_{25}H_{30}ClN_7O_4$ | 528 | 8.5(1H), 7.8(1H), 7.1(1H), 6.6–6.8 (4H), 3.8(6H), 2.2(3H) |
| 83 | $C_{28}H_{36}ClN_7O_4$ | 570 | ND |
| 84 | $C_{23}H_{28}ClN_7O_3$ | 486 | 9.5(1H), 8.0(1H), 3.9(6H) |
| 85 | $C_{24}H_{31}N_7O_3$ | 466 | 9.6(1H), 8.1(1H), 2.4(3H) |
| 86 | $C_{25}H_{30}ClN_7O_4$ | 528 | 8.5(1H), 7.8(1H), 7.1(1H), 3.9(6H), 2.2(3H) |
| 87 | $C_{28}H_{36}ClN_7O_4$ | 570 | 8.5(1H), 7.8(1H), 7.1(1H), 3.9(6H), 1.0(6H) |
| 88 | $C_{26}H_{33}N_{74}$ | 508 | 8.5(1H), 7.8(1H), 7.1(1H), 3.9(6H), 2.4(3H), 2.2(3H) |
| 89 | $C_{29}H_{39}N_7O_4$ | 550 | 8.5(1H), 7.8(1H), 7.1(1H), 3.9(6H), 2.4(3H), 1.0(6H) |
| 90 | $C_{23}H_{24}ClN_7O_5$ | 514 | 8.5(1HO,7.8(1H), 7.1(1H), 6.4–6.8 (4H), 5.9(2H), 3.7(3H) |
| 91 | $C_{29}H_{29}ClN_8O_5$ | 605 | 8.4(1H), 7.6(1H), 7.2(1H), 6.9(1H), 6.5–6.8(5H), 5.8(2H), 3.7(3H) |
| 92 | $C_{29}H_{30}ClN_7)_4$ | 576 | 8.4(1H), 7.7(1H), 7.0(1H), 5.8(2H), 3.7(3H) |
| 93 | $C_{23}H_{37}ClN_8O_5S$ | 563 | 8.5(1H), 7.8(1H), 7.5(3H), 7.1(1H), 5.9(2H), 2.8(6H) |
| 94 | $C_{28}H_{25}Cl_2N_{11}O_3$ | 634 | 8.5(1H), 8.3(1H), 7.8(1H), 7.5(1H), 7.0(2H), 6.6–6.8(3H), 6.4(2H), 5.9(2H) |
| 95 | $C_{26}H_{31}N_7O_5$ | 522 | 8.6(1H), 7.8(1H), 7.1(1H), 6.6–6.8 (2–3H), 5.9(2H), 3.7(3H), 1.2(6H) |
| 96 | $C_{26}H_{31}N_7O_5$ | 494 | 8.6(1H), 7.8(1H), 7.1(1H), 5.9(2H), 3.7(3H), 2.4(3H) |
| 97 | $C_{23}H_{24}ClN_7O_5$ | 514 | 8.5(1H), 7.8(1H), 5.9(2H), 3.8(3H) |
| 98 | $C_{23}H_{25}N_7O_5$ | 480 | 8.6(1H), 8.2(1H), 7.8(1H), 5.9(2H), 3.7(3H) |
| 99 | $C_{22}H_{23}Cl_2N_7O_3$ | 504 | 8.4(1H), 7.7(1H), 7.0–7.3(6H), 3.7(3H) |
| 100 | $C_{22}H_{24}ClNO_3$ | 470 | 8.5(1H), 8.1(1H), 7.8(1H), 7.1–7.3 (6H), 3.8(3H) |
| 101 | $C_{24}H_{24}F_3N_7O4$ | 532 | 8.4(1H), 7.6(1H), 7.2(1H), 5.9(2H), 2.3(3H) |
| 102 | $C_{26}H_{31}N_7O_4$ | 506 | 8.5(1H), 7.8(1H), 7.1(1HO,5.9(2H), 2.3(3H), 1.3(6H) |

TABLE 6-continued

Physical Data for Compounds of the Invention

| Ex.# | Formula | FABMS | Definitive $^1$H NMR (ppm) |
|---|---|---|---|
| 103 | $C_{27}H_{33}N_7O_5$ | 536 | 8.45(1H), 7.85(1H), 7.1(1H), 5.9 (2H), 2.4(3H), 1.4(9H) |
| 104 | $C_{29}H_{37}N_7O_5$ | 564 | 8.35(1H), 7.7(1H), 7.1(1H), 5.9(2H), 1.4(9H), 1.25(6H) |
| 105 | $C_{24}H_{24}F_3N_7O_4$ | 532 | 8.4(1H), 7.6(1H), 7.1(1H), 5.9(2H), 2.2(3H) |
| 106 | $C_{26}H_{31}N_7O_4$ | 506 | 8.5(1H), 7.8(1H), 7.05(1H), 5.9(2H), 1.25(6H) |
| 107 | $C_{25}H_{29}N_7O_4$ | 492 | 8.5(1H), 7.8(1H), 5.9(2H), 2.65(2H), 1.3(3H) |
| 108 | $C_{21}H_{21}ClN_6O_4$ | 457 | 8.5(1H), 7.8(1H), 7.1(1H), 6.8(3H), 6.4(1H), 5.9(2H), 4.4(2H) |
| 109 | $C_{22}H_{24}N_6O_4$ | | 8.5(1H), 7.8(1H), 7.1(1H), 6.8(3H), 6.2(1H), 5.9(2H), 4.4(2H), 2.4(3H) |
| 110 | $C_{24}H_{28}N_6O_4$ | 465 | 8.5(1H), 7.8(1H), 7.1(1H), 6.8(3H), 6.2(1H), 5.9(2H), 4.4(2H), 1.2(6H) |
| 111 | $C_{21}H_{21}ClN_6O_3S$ | 473.3 | 8.48(s,1H), 7.76(s,1H), 7.10(s,1H), 6.60(m,3H), 5.88(m,3H), 4.32(m, 2H), 2.6–3.1(m,6H). |
| 112 | $C_{22}H_{24}N_6O_3S$ | 453.3 | 8.45(s,1H), 7.79(s,1H), 7.07(s,1H), 6.60(m,3H), 6.40(bs,1H), 6.10(m, 1H), 5.90(s,2H), 4.30(d,2H), 2.5–3.1(m,6H), 3.40(s,3H). |
| 113 | $C_{24}H_{28}N_6O_3S$ | | 8.5(s,1H), 7.8(s,1H), 7.03(s,1H), 6.60(m,3H), 6.37(bs,1H), 6.10(bs, 1H), 5.83(s,2H), 4.28(m,2H), 2.45–3.1(7H),1.24(d,6H). |
| 114 | $C_{22}H_{23}ClN_5O_3S$ | 487.3 | 8.40(s,1H), 7.68(s,1H), 7.03(s,1H), 6.76(s,1H), 6.70(s,2H), 6.53(bs,1H), 6.45(bs,1H), 5.93(s,2H), 4.40(m,4H), 3.6(m,2H), 3.35(m,2H), 3.00(m,2H), 2.6–2.9(m,4H). |
| 115 | $C_{23}H_{26}N_6O_3S$ | 467.5 | 8.44(s,1H), 7.7(s,1H), 7.05(s,1H), 6.77(s,1H), 6.77(s,1H), 6.71(s,H), 6.50(bs,1H), 6.28(s,1H), 5.95(s,1H), 5.92(s,2H), 4.40(m,4H), 3.58(m,2H), 3.30(m,2H), 2.6–3.05(m,6H), 2.40(s, 3H). |
| 116 | $C_{25}H_{30}N_6O_3S$ | 495.4 | 8.45(s,1H), 7.77(s,1H), 7.06(s,1H), 6.86(s,1H), 6.70(s,2H), 6.55(bs,1H), 6.28(s,1H), 5.90(s,2H), 4.41(d,2H), 3.58(m,2H), 3.38(m,2H), 2.6–3.0 (m,7H), 1.25(d,6H). |
| 117 | $C_{21}H_{21}ClN_6O_3S$ | 473.4 | 8.41(s,1H), 7.78(s,1H), 7.03(s,1H), 6.75(m,2H), 6.43(s,1H), 6.30(bs,1H), 4.2–4.5(bs,4H), 3.76(m,2H), 3.4(m, 1H), 2.4–2.8(m;4H). |
| 118 | $C_{22}H_{24}N_6O_3S$ | 453.4 | 8.58(1H), 7.82(s,1H), 7.10(s,1H), 6.6–6.8(m,4H), 6.30(s,1H), 5.92(m, 2H), 6.76(m,1H), 4.25–4.45(m,4H), 3.76(m,3H), 3.4(m,1H), 2.4–2.8(7H), 2.4(s,3H). |
| 119 | $C_{24}H_{28}N_6O_3S$ | 481.4 | 8.47(s,1H), 7.82(s,1H), 7.08(s,1H), 6.71(m,2H), 6.30(s,1H), 6.03(m,1H), 5.90(s,2H), 4.22–4.44(m,4H), 3.75 (m,2H), 3.4(m,1H). |
| 120 | $C_{22}H_{23}ClN_6O_3S$ | 487.4 | 8.42(s,1H), 7.77(s,1H), 7.03(s,1H), 6.6–6.75(m,3H), 6.42(s,1H), 6.02(bs, 1H), 5.90(s,2H), 3.30–3.9(m,6H), 2.75(m,4H), 2.40(m,2H). |
| 121 | $C_{23}H_{26}N_6O_3S$ | 467.5 | 8.57(s,1H), 7.81(s,1H), 7.10(s,1H), 6.57–6.75(m,3H), 6.30(s,1H), 5.95(s, 2H), 5.47(m,1H), 4.37(m,4H), 3.25–3.8(m,5H), 2.77(m,4H), 2.40(s,3H). |
| 122 | $C_{23}H_{30}N_6O_3S$ | 495.5 | 8.55(s,1H), 7.82(s,1H), 7.08(s,1H), 6.58–6.76(m,3H), 6.30(s,1H), 5.90 (s,2H), 5.60(m,1H), 4.37(m,2H), 3.28–3.8(m,5H), 2.6–2.9(m,5H), 2.40(m,2H), 1.23(d,6H). |
| 123 | $C_{27}H_{34}ClN_7O_4$ | 556 | ND |
| 124 | $C_{27}H_{34}ClN_7O_5$ | 572 | 8.4(1H), 7.7(1H), 7.1(1H), 6.4(1H), 6.5–6.8(3H), 3.9(6H), 1.5(9H) |
| 125 | $C_{22}H_{26}ClN_7O_3$ | 472 | 9.0(1H), 7.9(1H), 7.2(1H), 6.4–6.8(4H) |
| 126 | $C_{24}H_{28}ClN_7O_4$ | 514 | 8.4(1H), 7.7(1H), 7.1(1H), 6.4–6.8(4H), 2.1(3H) |
| 127 | $C_4H_{28}ClN_7O_4$ | 514 | 8.5(1H), 7.7(1H), 7.1(1H), 6.4–6.8(4H), 3.8(6H) |
| 128 | $C_{22}H_{25}ClN_6O_4$ | 473.13 | 8.5(1H), 7.7(1H), 7.1(1H), 6.4(1H), 3.8(6H) |
| 129 | $C_{25}H_{32}N_6O_4$ | 481.26 | 8.5(1H), 7.8(1H), 7.1(1H), 6.2(1H), 1.3(6H) |
| 130 | $C_{21}H_{21}ClN_6O_4$ | 457.17 | 8.4(1H), 7.7(1H), 7.1(1H), 6.4(1H), 5.9(1H) |
| 131 | $C_{24}H_{28}N_6O_4$ | 465 | 8.5(1H), 7.8(1H), 7.1(1H), 6.2(1H), 5.9(2H), 1.2(6H) |
| 132 | $C_{22}H_{25}ClN_6O_4$ | 473.13 | 8.5(1H), 7.8(1H), 7.1(1H), 6.5(1H), 3.8(6H) |
| 133 | $C_{25}H_{32}N_6O_4$ | 480.63 | 8.5(1H), 7.8(1H), 7.1(1H), 6.3(1H), 3.9(6H), 1.2(6H) |
| 134 | $C_{21}H_{21}ClN_6O_4$ | 457.17 | 8.5(1H), 7.8(1H), 7.1(1H), 6.5(1H), 5.9(2H) |
| 135 | $C_{24}H_{28}N_6O_4$ | 465 | 8.6(1H), 7.8(1H), 7.1(1H), 6.3(1H), 5.9(2H), 1.2(6H) |
| 136 | $C_{23}H_{25}N_7O_4$ | 464 | 8.4(1H), 7.6(1H), 6.95(1H), 5.9(2H), 2.35(3H), 2.0(3H) |
| 137 | $C_{25}H_{29}N_7O_4$ | 492 | 8.4(1H), 7.6(1H), 6.95(1H), 5.9(2H), 2.0(3H), 1.25(6H) |
| 138 | $C_{22}H_{22}ClN_7O_4$ | 484 | 8.4(1H), 7.6(1H), 7.0(1H), 5.9(2H), 2.0(3H) |
| 139 | $C_{21}H_{22}N_6O_3$ | 407 | 8.4(1H), 7.7(1H), 7.05(1H), 5.9(2H) |
| 140 | $C_{22}H_{24}N_6O_3$ | 421 | 8.4(1H), 7.7(1H), 7.05(1H), 5.9(2H), 2.6(2H), 1.3(3H) |
| 141 | $C_{23}H_{26}N_6O_3$ | 435 | 8.4(1H), 7.7(1H), 7.05(1H), 5.9(2H), 1.3(6H) |
| 142 | $C_{20}H_{19}ClN_6O_3$ | 427 | 8.4(1H), 7.6(1H), 6.6(2H), 5.9(2H) |
| 143 | $C_{22}H_{24}N_6O_3$ | 421 | 8.45(1H), 7.7(1H), 7.05(1H), 5.9(2H) |
| 144 | $C_{23}H_{26}N_6O_3$ | 435 | 8.45(1H), 7.7(1H), 7.05(1H), 5.9 (2H), 2.65(2H), 1.3(3H) |
| 145 | $C_{24}H_{28}N_6O_3$ | 449 | 8.45(1H), 7.7(1H), 7.05(1H), 5.9(2H), 1.3(6H) |
| 146 | $C_{21}H_{21}ClN_6O_3$ | 441 | 8.45(1H), 7.7(1H), 7.05(1H), 5.9(2H) |

TABLE 7

Linker Groups (L)

| Linker Group (-L-) | Cleavage Reagent |
|---|---|
| 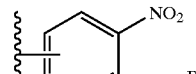 | Light |
| 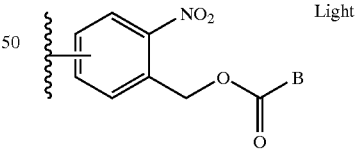 | Light |
| 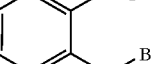 | Light |
| 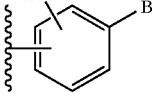 | $Ce(NH_4)_2(NO_3)_6$ |

TABLE 7-continued

Linker Groups (L)

| Linker Group (-L-) | Cleavage Reagent |
|---|---|
| 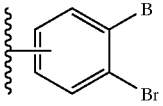 | Li, Mg, or BuLi |
| 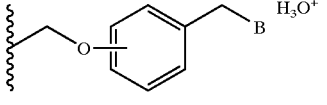 | H₃O⁺ |
| 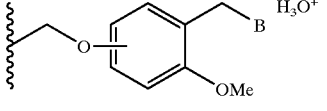 | H₃O⁺ |
| 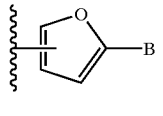 | 1) O₂ or Br₂, MeOH  2) H₃O⁺ |
| —CH=CH(CH₂)₂— | O₃, OsO₄/IO₄⁻, or KMnO₄ |
| —CH=CHCH₂— | O₃, OsO₄/IO₄⁻, or KMnO₄ |
| —CH₂CH=CH— | O₃, OsO₄/IO₄⁻, or KMnO₄ |
| —CH=CHCH₂B— | (Ph₃)PRhCl (H) |
| —SCH₂B— | Hg⁺² |
| 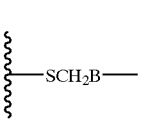 | Zn or Mg |
| 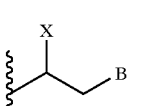 | Oxidation, e.g., Pb(OAc)₄ or H₅IO₆ |

["R" is H or alkyl; "B" is O or NH; X is an electron withdrawing group such as Br, Cl, or I; and  is the point of attachment to —C(O)—.]

In addition to the compounds specifically named in the Preferred Embodiments, the following compounds were made by the methods disclosed herein:

2-[[2-(1H-imidazol-1-yl)pyrimidin-4-yl]amino]-3-hydroxy-N-[(1,3-benzodioxol-5-yl)methyl]propanamide;
2-[[6-chloro-2-(1H-imidazol-1-yl)pyrimidin-4-yl]amino]-3-carboxy-N-(2-carboxyethyl)propanamide;
2-[[2-(1H-imidazol-1-yl)pyrimidin-4-yl]amino]-3-(thiophen-2-yl)-N-[3-(morpholin-4-yl)propyl]propanamide;
2-[[6-chloro-2-(1H-imidazol-1-yl)pyrimidin-4-yl]amino]-3-[(1,1-dimethylethyl)thio]-N-[3-(methylthio)propyl]propanamide;
2-[[6-chloro-2-(1H-imidazol-1-yl)pyrimidin-4-yl]amino]-3-[(1,1-dimethylethyl)thio]-N-[3-(phenyl)propyl]propanamide;
2-[[6-chloro-2-(1H-imidazol-1-yl)pyrimidin-4-yl]amino]-3-[(1,1-dimethylethyl)thio]-N-[2-(3,4-dimethoxyphenyl)ethyl]propanamide;
2-[[6-chloro-2-(1H-imidazol-1-yl)pyrimidin-4-yl]amino]-N-[2-(3,4-dimethoxyphenyl)ethyl-propanamide;
2-[[6-chloro-2-(1H-imidazol-1-yl)pyrimidin-4-yl]amino]-3-hydroxy-N-[(1,3-benzodioxol-5-yl)methyl]propanamide;
2-[[6-(1H-imidazol-1-yl)pyrimidin-4-yl]amino]-3-hydroxy-N-[(1,3-benzodioxol-5-yl)methyl]propanamide;
2-[[2-(1H-imidazol-1-yl)-6-methylpyrimidin-4-yl]amino]-3-[(3,4-dimethylphenyl)methylthio]-N-[(cyclopropyl)methyl]propanamide;
2-[[2-(1H-imidazol-1-yl)-6-methylpyrimidin-4-yl]amino]-3-[(3,4-dimethylphenyl)methylthio]-N-[(cyclopropyl)methyl]propanamide;
2-[[2-(1H-imidazol-1-yl)-6-methylpyrimidin-4-yl]amino]-3-(thiophen-2-yl)-N-[(4-chlorophenyl)methyl]propanamide;
3-[[2-(1H-imidazol-1-yl)-6-methylpyrimidin-4-yl]amino]-N-[(1,3-benzodioxol-5-yl)methyl]propanamide;
3-[[2-(1H-imidazol-1-yl)-6-methylpyrimidin-4-yl]amino]-N-[(4-trifluoromethylphenyl)methyl]propanamide;
3-[[2-(1H-imidazol-1-yl)-6-methylpyrimidin-4-yl]amino]-N-[2-(1,3-benzodioxol-5-yl)ethyl]propanamide;
3-[[2-(1H-imidazol-1-yl)-6-methylpyrimidin-4-yl](methyl)amino]-N-[(6-methoxypyridin-2-yl)methyl]propanamide;
3-[[2-(1H-imidazol-1-yl)-4-methylpyrimidin-4-yl](methyl)amino]-N-[(3,5-dimethoxyphenyl)methyl]propanamide;
3-[[2-(1H-imidazol-1-yl)-6-methylpyrimidin-4-yl](methyl)amino]-N-[(pyridin-2-yl)methyl]propanamide;
2-[[6-chloro-2-(1H-imidazol-1-yl)pyrimidin-4-yl]amino]-3-(methylthio)-N-[(1,3-benzodioxol-5-yl)methyl]butanamide;
2-[[6-chloro-2-(1H-imidazol-1-yl)pyrimidin-4-yl]amino]-4-(methylthio)-N-[(4-methoxyphenyl)methyl]butanamide;
2-[[6-chloro-2-(1H-imidazol-1-yl)pyrimidin-4-yl]amino]-4-(methylthio)-N-[2-(3,4-dimethoxyphenyl)ethyl]butanamide;
2-[[6-chloro-2-(1H-imidazol-1-yl)pyrimidin-4-yl]amino]-4-methylthio)-N-(methyl)butanamide;
2-[[2-(1H-imidazol-1-yl)-6-methylpyrimidin-4-yl]amino]-N-[2-(1,3-benzodioxol-5-yl)ethyl]-4-methylthiobutanamide;
2-[[2-(1H-imidazol-1-yl)-6-methylpyrimidin-4-yl]amino]-N-[(4-methoxyphenyl)methyl]-4-methylsulfonylbutanamide;
2-[[2-(1H-imidazol-1-yl)-4-methylpyrimidin-4-yl]amino]-N-[2-(1,3-benzodioxol-5-yl)ethyl]-4-(butylthio)butanamide;
2-[[2-(1H-imidazol-1-yl)-6-methylpyrimidin-4-yl]amino]-N-[(1,3-benzodioxol-5-yl)methyl]-4-methylthiobutanamide;
2-[[2-(1H-imidazol-1-yl)-6-methylpyrimidin-4-yl]amino]-N-[(2,5-dimethoxyphenyl)methyl]-3-methyl-3-[(phenylmethyl)thio]butanamide;
4-[[2-(1H-imidazol-1-yl)-6-methylpyrimidin-4-yl]amino]-N-[2-(1,3-benzodioxol-5-yl)ethyl]butanamide;

4-[[2-(1H-imidazol-1-yl)-methylpyrimidin-4-yl](methyl)
amino]-N-[(1,3-benzodioxol-5-yl)methyl]butanamide;
4-[[2-(1H-imidazol-1-yl)-6-methylpyrimidin-4-yl](methyl)
amino]-N-[(phenoxy)carbonylmethyl]butanamide;
2-[[2-(1H-imidazol-1-yl)pyrimidin-4-yl]amino]-N-[(1,3-benzodioxol-5-yl)methyl]pentane-1,5-diamide;
2-[[6-chloro-2-(1H-imidazol-1-yl)pyrimidin-4-yl]amino]-N-(4-methoxyphenyl)methyl]pentane-1,5-diamide;
2-[[6-chloro-2-(1H-imidazol-1-yl)pyrimidin-4-yl]amino]-N-[2-(3,4-dimethoxyphenyl)ethyl]pentane-1,5-diamide;
2-[[6-chloro-2-(1H-imidazol-1-yl)pyrimidin-4-yl]amino]-N-[(1,3-benzodioxol-5-yl)methyl]pentane-1,5-diamide;
2-[[6-(1H-imidazol-1-yl)pyrimidin-4-yl]amino]-N-[(1,3-benzodioxol-5-yl)methyl]pentane-1,5-diamide;
2-[[2-(1H-imidazol-1-yl)pyrimidin-4-yl]amino]-5-[[amino(nitroimino)methyl]amino]-N-[(1,3-benzodioxol-5-yl)methyl]pentanamide;
2-[[6-chloro-2-(1H-imidazol-1-yl)pyrimidin-4-yl]amino]-5-[[amino(nitroimino)methyl]amino]-N-[(1,3-benzodioxol-5-yl)methyl]pentanamide;
2-[[6-chloro-2-(1H-imidazol-1-yl)pyrimidin-4-yl]amino]-N-[(4-methoxyphenyl)methyl]-5-[[imino(amino)methyl]amino]pentanamide;
2-[[6-chloro-2-(1H-imidazol-1-yl)pyrimidin-4-yl]amino]-N-[(4-methoxyphenyl)methyl]-5-[[imino(nitroamino)methyl]amino]pentanamide;
2-[[6-chloro-2-(1H-imidazol-1-yl)pyrimidin-4-yl]amino]-5-[[amino(imino)methyl]amino]-N-[(1,3-benzodioxol-5-yl)methyl]pentanamide;
6-amino-2-[[6-chloro-2-(1H-imidazol-1-yl)pyrimidin-4-yl]amino]-N-[2-(3,4-dimethoxyphenyl)ethyl]hexanamide;
6-[[6-chloro-2-(1H-imidazol-1-yl)pyrimidin-4-yl]amino]-N-[(1,3-benzodioxol-5-yl)methyl]hexanamide;
5-amino-2-[[6-chloro-2-(1H-imidazol-1-yl)pyrimidin-4-yl]amino]-N-[(1,3-benzodioxol-5-yl)methyl]pentanamide;
5-amino-2-[[6-chloro-2-(1H-imidazol-1-yl)pyrimidin-4-yl]amino]-N-butyl-pentanamide;
2-[[6-(1H-imidazol-1-yl)pyrimidin-4-yl]amino]-4-methyl-N-[(1,3-benzodioxol-5-yl)methyl]pentanamide;
2-[[6-(1H-imidazol-1-yl)pyrimidin-4-yl]amino]-4-methyl-N-[2-(3,4-dimethoxyphenyl)ethyl]pentanamide;
5-[[amino(imino)methyl]amino]-6-(1H-imidazol-1-yl)pyrimidin-4-yl]-N-(phenylmethyl)pentanamide;
5-[[2-(1H-imidazol-1-yl)-6-methylpyrimidin-4-yl]amino]-N-[(1,3-benzodioxol-5-yl)methyl]pentanamide;
5-[[2-(1H-imidazol-1-yl)-6-methylpyrimidin-4-yl]amino]-N-[(1,4-benzodioxan-6-yl)ethyl]pentanamide; and
7-[[2-(1H-imidazol-1-yl)-6-methylpyrimidin-4-yl]amino]-N-(2-phenylcyclopropyl)heptanamide;
α-[[6-chloro-2-(1H-imidazol-1-yl)pyrimidin-4-yl]amino]-N-[2-(3,4-dimethoxyphenyl)ethyl]-2-thiophenepropanamide;
α-[[6-chloro-2-(1H-imidazol-1-yl)pyrimidin-4-yl]amino]-N-(butyl)-2-thiophenepropanamide;
α-[[6-chloro-2-(1H-imidazol-1-yl)pyrimidin-4-yl]amino]-N-[(1,3-benzodioxol-5-yl)methyl]-2-thiophenepropanamide;
N-[(1,3-benzodioxol-5-yl)methyl]-α-[[6-(1H-imidazol-1-yl)pyrimidin-4-yl]amino]benzenepropanamide;
α-[[6-chloro-2-(1H-imidazol-1-yl)pyrimidin-4-yl]amino]-N-[3-(methylsulfonyl)propyl]benzene-propanamide;
N-[2-(3,4-dimethoxyphenyl)ethyl]-α-[[6-(1H-imidazol-1-yl)pyrimidin-4-yl]amino]-2-thiophenepropanamide;
N-[(1,3-benzodioxol-5-oxy)ethyl]-2-(1H-imidazol-1-yl)pyrimidine-4-amine;
2-(1H-imidazol-1-yl)-6-fluoro-4-[[(3,4-dimethoxyphenyl)ethyl]amino]pyrimidine;
2-(1H-imidazol-1-yl)-6-fluoro-4-[[(phenyl)ethyl]amino]pyrimidine;
2-(1H-imidazol-1-yl)-6-methyl-4-[[3-[(1,3-benzodioxol-5-yl)methylcarbonyl]-aminopropyl]-(methyl)amino]pyrimidine;
2-(1H-imidazol-1-yl)-6-methyl-4-[[3-[2-(1,3-benzodioxol-5-yl)ethylcarbonyl]-aminopropyl]-(methyl)amino]pyrimidine;
2-(1H-imidazol-1-yl)-6-methyl-4-[[3-[(1,3-benzodioxol-5-yl)methyl]aminopropyl]-(methyl)amino]pyrimidine;
2-(1H-imidazol-1-yl)-6-methyl-4-[[3-[(1,4-benzodioxan-4-yl)methyl]aminopropyl]-(methyl)amino]pyrimidine;
2-(1H-imidazol-1-yl)-6-methyl-4-[[3-[(6-methoxynaphthyl)methyl]aminopropyl]-(methyl)amino]pyrimidine;
2-(1H-imidazol-1-yl)-6-methyl-4-[[3-(3,5-dimethylphenyl)methyl]aminopropyl]methyl)amino]pyrimidine;
2-(1H-imidazol-1-yl)-6-methyl-4-[[3-[(3,5-dimethoxyphenyl)methyl-aminopropyl]-methyl)amino]pyrimidine;
2-(1H-imidazol-1-yl)-6-methyl-4-[[3-[[3-(dimethylamino)phenyl]methyl]aminopropyl]-(methyl)amino]pyrimidine;
2-(1H-imidazol-1-yl)-6-methyl-4-[[3-[(3-methoxyphenyl)methyl]aminopropyl]-(methyl)amino]pyrimidine;
2-(1H-imidazol-1-yl)-6-methyl-4-[[3-[(n-undecanyl)amino]propyl](methyl)amino]pyrimidine;
2-(1H-imidazol-1-yl)-6-(1-methylethyl)-4-[[3-[2-(3-ethoxyphenyl)ethyl]aminopropyl]-(methyl)amino]pyrimidine;
2-(1H-imidazol-1-yl)-4-[[3-[(pyridin-1-yl)methyl]aminopropyl](methyl)amino]pyrimidine; 10997
2-(1H-imidazol-1-yl)-6-methyl-4-[[3-[(6-methoxypyridin-1-yl)methyl]aminopropyl]-(methyl)amino]pyrimidine;
2-(1H-imidazol-1-yl)-6-(1-methylethyl)-4-[[3-[(pyridin-2-yl)methyl]aminopropyl]-(methyl)amino]pyrimidine;
2-(1H-imidazol-1-yl)-6-methyl-4-[[3-[(6-methylpyridin-2-yl)methyl]aminopropyl]-(methyl)amino]pyrimidine;
N-[2-(1,3-benzodioxol-5-yl)ethyl]-6-chloro-2-(1H-imidazol-1-yl)pyrimidine-4-propionamide;
N-[(1,3-benzodioxol-5-yl)methyl]-2-(1H-imidazol-1-yl)pyrimidine-4-propionamide;
N-[2-(1,3-benzodioxol-5-yl)ethyl]-2-(1H-imidazol-1-yl)pyrimidine-4-propionamide;
N-[2-(1,3-benzodioxol-5-yl)ethyl]-2-[(2-(1H-imidazol-1-yl)pyrimidin-4-yl)oxy]acetamide;
N-[2-(1,3-benzodioxol-5-yl)ethyl]-2-[(2-(1H-imidazol-1-yl)pyrimidin-4-yl)thio]acetamide;
1-[2-(1H-imidazol-1-yl)pyrimidin-4-yl]-N-[(4-methoxyphenyl)methyl]piperazine-2-acetamide;
1-[2-(1H-imidazol-1-yl)pyrimidin-4-yl]-N-[(4-methylphenyl)-methyl]piperazine-2-acetamide;
1-[2-(1H-imidazol-1-yl)pyrimidin-4-yl]-N-[(1,3-benzodioxol-5-yl)methyl]piperazine-2-acetamide;
1-[6-chloro-2-(1H-imidazol-1-yl)pyrimidin-4-yl]-N-[(4-chlorophenyl)methyl]piperazine-2-acetamide;
1-[6-chloro-2-(1H-imidazol-1-yl)pyrimidin-4-yl]-N-[(4-methylphenyl)methyl]piperazine-2-acetamide;
1-[6-chloro-2-(1H-imidazol-1-yl)pyrimidin-4-yl]-N-[(1,3-benzodioxol-5-yl)methyl]piperazine-2-acetamide;
1-[6-chloro-2-(1H-imidazol-1-yl)pyrimidin-4-yl]-N-[(4-methoxyphenyl)methyl]piperazine-2-acetamide;
1-[6-chloro-2-(1H-imidazol-1-yl)pyrimidin-4-yl]-N-[phenylmethyl]piperazine-2-acetamide;
1-[6-chloro-2-(1H-imidazol-1-yl)pyrimidin-4-yl]-N-[2-(3,4-dimethoxyphenyl)ethyl]piperazine-2-acetamide;
1-[6-chloro-2-(1H-imidazol-1-yl)pyrimidin-4-yl]-N-[3-phenylpropyl]piperazine-2-acetamide;
1-[6-chloro-2-(1H-imidazol-1-yl)pyrimidin-4-yl]-N-[2-phenylethyl]piperazine-2-acetamide;

1-[6-chloro-2-(1H-imidazol-1-yl)pyrimidin-4-yl]-N-[(thiophene-2-yl)methyl]piperazine-2-acetamide;

1-[6-chloro-2-(1H-imidazol-1-yl)pyrimidin-4-yl]-N-(methyl)piperazine-2-acetamide;

N-[(1,3-benzodioxol-5-yl)methyl]-1,4-bis[6-chloro-2-(1H-imidazol-1-yl)pyrimidin-4-yl]piperazine-2-acetamide;

N-[(1,3-benzodioxol-5-yl)methyl]-1-[6-chloro-2-(1H-imidazol-1-yl)pyrimidin-4-yl]-4-[[(phenyl)amino]carbonyl]piperazine-2-acetamide;

N-[(1,3-benzodioxol-5-yl)methyl]-1-[6-chloro-2-(1H-imidazol-1-yl)pyrimidin-4-yl]-4-[(methoxy)carbonyl]piperazine-2-acetamide;

N-[(1,3-benzodioxol-5-yl)methyl]-1-[6-chloro-2-(1H-imidazol-1-yl)pyrimidin-4-yl]-4-[(4-methoxyphenyl)methyl]piperazine-2-acetamide;

4-[2-(1H-imidazol-1-yl)-6-methylpyrimidin-4-yl]-N-[(4-methylphenyl)methyl]-1-methylpiperazine-2-acetamide;

4-[6-chloro-2-(1H-imidazol-1-yl)pyrimidin-4-yl]-N-[(4-methylphenyl)methyl]-1-methylpiperazine-2-acetamide;

N-[(3-chloro-4-methoxyphenyl)methyl]-4-[2-(1H-imidazol-1-yl)-6-methylpyrimidin-4-yl]-1-methylpiperazine-2-acetamide;

4-[6-chloro-2-(1H-imidazol-1-yl)pyrimidin-4-yl]-N-[(3-chloro-4-methoxyphenyl)methyl]-1-methylpiperazine-2-acetamide;

4-[6-chloro-2-(1H-imidazol-1-yl)pyrimidin-4-yl]-N-(3,4,5-trimethoxyphenyl)methyl]-1-methylpiperazine-2-acetamide;

N-[2-(1,4-benzodioxan-6-yl)ethyl]-4-[2-(1H-imidazol-1-yl)pyrimidin-4-yl-1-methylpiperazine-2-acetamide;

1-butyl-4-[6-chloro-2-(1H-imidazol-1-yl)pyrimidin-4-yl]-N-[(furan-2-yl)methyl]piperazine-2-carboxamide;

N-[(1,4-benzodioxan-6-yl)methyl]-1-butyl-4-[6-chloro-2-(1H-imidazol-1-yl)pyrimidin-4-yl]piperazine-2-acetamide;

N-[2-(1,4-benzodioxan-6-yl)ethyl]-1-butyl-4-[6-chloro-2-(1H-imidazol-1-yl)pyrimidin-4-yl]piperazine-2-acetamide;

N-[(2,3-dimethoxyphenyl)methyl]-1-butyl-4-[2-(1H-imidazol-1-yl)pyrimidin-4-yl]piperazine-2-acetamide;

4-[6-chloro-2-(1H-imidazol-1-yl)pyrimidin-4-yl]-N-[(4-chlorophenyl)methyl]-1-[(4-methyoxyphenyl)methyl]piperazine-2-acetamide;

4-[6-methyl-2-(1H-imidazol-1-yl)pyrimidin-4-yl]-N-[(1,3-benzodioxol-5-yl)methyl]-1-[(4-methyoxyphenyl)methyl]piperazine-2-carboxamide;

4-[2-(1H-imidazol-1-yl)pyrimidin-4-yl]-N-[(4-chlorophenyl)methyl]-1-[(4-methyoxyphenyl)ethyl]piperazine-2-acetamide;

4-[6-(1H-imidazol-1-yl)pyrimidin-4-yl]-N-[(1,4-benzodioxan-6-yl)methyl]-1-[(4-methyoxyphenyl)methyl]piperazine-2-carboxamide;

4-[6-methyl-2-(1H-imidazol-1-yl)pyrimidin-4-yl]-N-[(4-methoxyphenyl)methyl-1-[(4-methyoxyphenyl)methyl]piperazine-2-acetamide;

4-[6-chloro-2-(1H-imidazol-1-yl)pyrimidin-4-yl]-N-[(4-methoxyphenyl)methyl]-1-[(4-methyoxyphenyl)methyl]piperazine-2-acetamide;

4-[6-methyl-2-(1H-imidazol-1-yl)pyrimidin-4-yl]-N-[(4-methoxyphenyl)ethyl]-1-[(4-methyoxyphenyl)methyl]piperazine-2-acetamide;

4-[6-methyl-2-(1H-imidazol-1-yl)pyrimidin-4-yl]-N-[(3,4-dimethoxyphenyl)methyl]-1-[(4-methyoxyphenyl)methyl]piperazine-2-acetamide;

4-[6-chloro-2-(1H-imidazol-1-yl)pyrimidin-4-yl]-N-[(indan-5-yl)methyl]-1-[(4-methyoxyphenyl)methyl]piperazine-2-acetamide;

N-[(1,3-benzodioxol-5-yl)methyl]-1-[(2,3-dichlorophenyl)methyl]-4-[2-(1H-imidazol-1-yl)pyrimidin-4-yl]piperazine-2-acetamide;

N-[(1,3-benzodioxol-5-yl)methyl]-1-[(3,4-dichlorophenyl)methyl]-4-[2-(1H-imidazol-1-yl)-6-methylpyrimidin-4-yl]piperazine-2-carboxamide;

N-[(1,3-benzodioxol-5-yl)methyl]-1-[(3,4-dichlorophenyl)methyl]-4-[2-(1H-imidazol-1-yl)pyrimidin-4-yl]piperazine-2-carboxamide;

4-[6-methyl-2-(1H-imidazol-1-yl)pyrimidin-4-yl]-N-[2-(1,3-benzodioxol-5-yl)ethyl]-1-[(3,4-dichlorophenyl)methyl]piperazine-2-acetamide;

N-[(1,3-benzodioxol-5-yl)methyl]-1-[(1,3-benzodioxol-5-yl)methyl]-4-[2-(1H-imidazol-1-yl)pyrimidin-4-yl]piperazine-2-acetamide;

N-[(1,3-benzodioxol-5-yl)methyl]-1-[(1,3-benzodioxol-5-yl)methyl]-4-[2-(1H-imidazol-1-yl)-4-methylpyrimidin-4-yl]piperazine-2-carboxamide;

N-[(1,3-benzodioxol-5-yl)methyl]-1-[(1,3-benzodioxol-5-yl)methyl]-4-[6-chloro-2-(1H-imidazol-1-yl)pyrimidin-4-yl]piperazine-2-carboxamide;

N-[(1,3-benzodioxol-5-yl)methyl]-1-[(1,3-benzodioxol-5-yl)methyl]-4-[6-(1H-imidazol-1-yl)pyrimidin-4-yl]piperazine-2-carboxamide;

N-[2-(1,3-benzodioxol-5-yl)ethyl]-1-[(1,3-benzodioxol-5-yl)methyl]-4-[2-(1H-imidazol-1-yl)-6-methylpyrimidin-4-yl]piperazine-2-acetamide;

N-[2-(1,3-benzodioxan-6-yl)ethyl]-1-[(1,3-benzodioxol-5-yl)methyl-4-[2-(1H-imidazol-1-yl)-6-methylpyrimidin-4-yl]piperazine-2-acetamide;

N-[(4-methoxyphenyl)methyl]-1-[(1,3-benzodioxol-5-yl)methyl]-4-[2-(1H-imidazol-1-yl)-6-methylpyrimidin-4-yl]piperazine-2-carboxamide;

N-[(4-methoxyphenyl)methyl]-1-[(1,3-benzodioxol-5-yl)methyl]-4-[2-(1H-imidazol-1-yl)-6-methylpyrimidin-4-yl]piperazine-2-acetamide;

N-[(4-methoxyphenyl)methyl]-1-[(1,3-benzodioxol-5-yl)methyl]-4-[2-(1H-imidazol-1-yl)-6-(iso-propyl)pyrimidin-4-yl]piperazine-2-acetamide;

N-[2-(4-methoxyphenyl)ethyl-1-[(1,3-benzodioxol-5-yl)methyl]-4-[2-(1H-imidazol-1-yl)-6-methylpyrimidin-4-yl]piperazine-2-acetamide;

N-[[2-(phenyl)cyclopropyl]amino]-1-[(1,3-benzodioxol-5-yl)methyl]-4-[6-chloro-2-(1H-imidazol-1-yl)pyrimidin-4-yl]piperazine-2-carboxamide;

N-[(4-ethoxyphenyl)methyl]-1-[(1,3-benzodioxan-6-yl)methyl]-4-[2-(1H-imidazol-1-yl)-6-methylpyrimidin-4-yl]piperazine-2-acetamide;

N-[(1,3-benzodioxol-5-yl)methyl]-1-[(1,3-benzodioxan-6-yl)methyl]-4-[2-(1H-imidazol-1-yl)-6-(iso-propyl)pyrimidin-4-yl]piperazine-2-acetamide;

N-[(1,3-benzodioxol-5-yl)methyl]-1-[(1,3-benzodioxan-6-yl)methyl]-4-[2-(1H-imidazol-1-yl)pyrimidin-4-yl]piperazine-2-acetamide;

N-[(1,3-benzodioxol-5-yl)methyl]-1-[(1,3-benzodioxan-6-yl)methyl]-4-[6-(1H-imidazol-1-yl)pyrimidin-4-yl]piperazine-2-carboxamide;

N-[2-(1,3-benzodioxol-5-yl)ethyl]-1-[(1,3-benzodioxan-6-yl)methyl]-4-[2-(1H-imidazol-1-yl)-6-methylpyrimidin-4-yl]piperazine-2-acetamide;

N-[2-(1,3-benzodioxol-5-yl)ethyl]-1-[(1,3-benzodioxan-6-yl)methyl]-4-[2-(1H-imidazol-1-yl)-6-methylpyrimidin-4-yl]piperazine-2-carboxamide;

N-[(4-methoxyphenyl)methyl]-1-[(1,3-benzodioxan-6-yl)methyl]-4-[2-(1H-imidazol-1-yl)-6-chloropyrimidin-4-yl]piperazine-2-acetamide;

N-[(3,4-dimethoxyphenyl)methyl]-1-[(1,3-benzodioxan-6-yl)methyl]-4-[2-(1H-imidazol-1-yl)-6-(iso-propyl)pyrimidin-4-yl]piperazine-2-acetamide;

N-[(3,4-dimethoxyphenyl)methyl]-1-[(1,3-benzodioxan-6-yl)methyl]-4-[2-(1H-imidazol-1-yl)-4-chloropyrimidin-4-yl]piperazine-2-acetamide;

N-[2-(1,3-benzodioxol-5-yl)ethyl]-1-[(pyridin-3-yl)methyl]-4-[2-(1H-imidazol-1-yl)-6-methylpyrimidin-4-yl]piperazine-2-acetamide;

N-[(1,4-benzodioxan-6-yl)methyl]-1-[(pyridin-3-yl)methyl]-4-[2-(1H-imidazol-1-yl)pyrimidin-4-yl]piperazine-2-carboxamide;

N-[2-(1,4-benzodioxan-6-yl)ethyl]-1-[(pyridin-3-yl)methyl]-4-[2-(1H-imidazol-1-yl)-6-methylpyrimidin-4-yl]piperazine-2-acetamide;

N-[(4-methoxyphenyl)methyl]-1-[(pyridin-3-yl)methyl]-4-[2-(1H-imidazol-1-yl)-4-chloropyrimidin-4-yl]piperazine-2-carboxamide;

N-[(3,4-dimethoxyphenyl)methyl]-1-[(pyridin-3-yl)methyl]-4-[2-(1H-imidazol-1-yl)-6-(iso-propyl)pyrimidin-4-yl]piperazine-2-acetamide;

N-[2-(3,4-dimethoxyphenyl)ethyl]-1-[(3-fluoro-4-methoxyphenyl)methyl]-4-[2-(1H-imidazol-1-yl)-6-(iso-propyl)pyrimidin-4-yl]piperazine-2-acetamide;

N-[3-(3,4-dimethoxyphenyl)propyl]-1-[(3-fluoro-4-methoxyphenyl)methyl]-4-[2-(1H-imidazol-1-yl)-6-(iso-propyl)pyrimidin-4-yl]piperazine-2-acetamide;

N-[(4-ethoxyphenyl)methyl]-1-[(3-fluoro-4-methoxyphenyl)methyl]-4-[2-(1H-imidazol-1-yl)-6-methylpyrimidin-4-yl]piperazine-2-acetamide;

N-[2-(4-methylphenoxy)ethyl]-1-[(3-fluoro-4-methoxyphenyl)methyl]-4-[2-(1H-imidazol-1-yl)-6-chloropyrimidin-4-yl]piperazine-2-acetamide;

N-[(4-methylphenyl)methyl]-1-[(3-fluoro-4-methoxyphenyl)methyl]-4-[2-(1H-imidazol-1-yl)-6-methylpyrimidin-4-yl]piperazine-2-acetamide;

N-[(4-chlorophenyl)methyl]-1-[(3-fluoro-4-methoxyphenyl)methyl]-4-[2-(1H-imidazol-1-yl)-6-methylpyrimidin-4-yl]piperazine-2-acetamide;

N-[(4-chlorophenyl)methyl]-1-[(3-fluoro-4-methoxyphenyl)methyl]-4-[2-(1H-imidazol-1-yl)-6-chloropyrimidin-4-yl]piperazine-2-acetamide;

N-[(1,3-benzodioxol-5-yl)methyl]-1-(3-fluoro-4-methoxyphenyl)methyl]-4-[2-(1H-imidazol-1-yl)-6-chloropyrimidin-4-yl]piperazine-2-acetamide;

N-[2-(1,3-benzodioxol-5-yl)ethyl]-1-[(3-fluoro-4-methoxyphenyl)methyl]-4-[2-(1H-imidazol-1-yl)-6-methylpyrimidin-4-yl]piperazine-2-acetamide;

N-[2-(1,3-benzodioxol-5-yl)ethyl]-1-[(3-fluoro-4-methoxyphenyl)methyl]-4-[2-(1H-imidazol-1-yl)pyrimidin-4-yl]piperazine-2-acetamide;

N-[2-(1,4-benzodioxan-6-yl)ethyl]-1-[(3-fluoro-4-methoxyphenyl)methyl]-4-[2-(1H-imidazol-1-yl)pyrimidin-4yl]piperazine-2-acetamide;

N-[2-(4-methoxyphenyl)ethyl]-1-[(3-fluoro-4-methoxyphenyl)methyl]-4-[2-(1H-imidazol-1-yl)-6-(iso-propyl)pyrimidin-4-yl]piperazine-2-acetamide;

N-[2-(3,4-dimethoxyphenyl)ethyl]-1-acetyl-4-[2-(1H-imidazol-1-yl)-6-(iso-propyl)pyrimidin-4-yl]piperazine-2-acetamide;

N-[(4-ethoxyphenyl)methyl]-1-acetyl-4-[2-(1H-imidazol-1-yl)-6-(iso-propyl)pyrimidin-4-yl]piperazine-2-carboxamide;

N-[2-(4-methylphenoxy)ethyl]-1-acetyl-4-[2-(1H-imidazol-1-yl)-4-chloropyrimidin-4-yl]piperazine-2-acetamide;

N-[2(3-chloro-4-methoxyphenyl)ethyl]-1-acetyl-4-[2-(1H-imidazol-1-yl)-6-chloroylpyrimidin-4-yl]piperazine-2-carboxamide;

N-[(1,3-benzodioxol-5-yl)methyl]-1-acetyl-4-[2-(1H-imidazol-1-yl)-6-methylpyrimidin-4-yl]piperazine-2-acetamide;

N-[(4-methoxyphenyl)methyl]-1-acetyl-4-[2-(1H-imidazol-1-yl)-6-methylpyrimidin-4-yl]piperazine-2-carboxamide;

N-[(4-methoxyphenyl)methyl]-1-acetyl-4-[2-(1H-imidazol-1-yl)chloropyrimidin-4-yl]piperazine-2-carboxamide;

N-[2-(3,4-dimethoxyphenyl)ethyl]-1-(3-methyl-1-oxobutyl)-4-[2-(1H-imidazol-1-yl)-6-(iso-propyl)pyrimidin-4-yl]piperazine-2-acetamide;

N-[2-(3,4-dimethoxyphenyl)ethyl]-1-(3-methyl-1-oxobutyl)-4-[2-(1H-imidazol-1-yl)-4-chloropyrimidin-4-yl]piperazine-2-carboxamide;

N-[2-(3-chloro-4-methoxyphenyl)ethyl]-1-(3-methyl-1-oxobutyl)-4-[2-(1H-imidazol-1-yl)-6-chloropyrimidin-4-yl]piperazine-2-carboxamide;

N-[2-(3-chloro-4-methoxyphenyl)ethyl]-1-(3-methyl-1-oxobutyl)-4-[2-(1H-imidazol-1-yl)-6-methylpyrimidin-4-yl]piperazine-2-acetamide;

N-(1,3-benzodioxol-5-yl)methyl]-1-(3-methyl-1-oxobutyl)-4-[2-(1H-imidazol-1-yl)pyrimidin-4-yl]piperazine-2-carboxamide;

N-[(1,3-benzodioxol-5-yl)methyl]-1-(3-methyl-1-oxobutyl)-4-[2-(1H-imidazol-1-yl)-6-methylpyrimidin-4-yl]piperazine-2-carboxamide;

N-[2-(1,3-benzodioxol-5-yl)ethyl]-1-(3-methyl-1-oxobutyl)-4-[2-(1H-imidazol-1-yl)-6-chloropyrimidin-4-yl]piperazine-2-carboxamide;

N-[(1,4-benzodioxan-6-yl)methyl]-1-(3-methyl-1-oxobutyl)-4-[2-(1H-imidazol-1-yl)-6-chloropyrimidin-4-yl]piperazine-2-carboxamide;

N-[2-(1,4-benzodioxan-6-yl)ethyl]-1-(3-methyl-1-oxobutyl)-4-[2-(1H-imidazol-1-yl)-6-chloropyrimidin-4-yl]piperazine-2-carboxamide;

N-[2-(1,4-benzodioxan-6-yl)ethyl]-1-(3-methyl-1-oxobutyl)-4-[2-(1H-imidazol-1-yl)-6-(trifluoromethyl)pyrimidin-4-yl]piperazine-2-acetamide;

N-[(2,6-dimethoxyphenyl)methyl]-1-(3-methyl-1-oxobutyl)-4-[2-(1H-imidazol-1-yl)-6-chloropyrimidin-4-yl]piperazine-2-acetamide;

N-[2-(3,4-dimethoxyphenyl)ethyl]-1-(methoxyacetyl)-4-[2-(1H-imidazol-1-yl)-6-(iso-propyl)pyrimidin-4-yl]piperazine-2-acetamide;

N-[2-(1,3-benzodioxol-5-yl)ethyl]-1-(methoxyacetyl)-4-[2-(1H-imidazol-1-yl)-6-methylpyrimidin-4-yl]piperazine-2-carboxamide;

N-[2-(1,3-benzodioxol-5-yl)ethyl]-1-(methoxyacetyl)-4-[2-(1H-imidazol-1-yl)-6-chloropyrimidin-4-yl]piperazine-2-acetamide;

N-[2-(1,3-benzodioxol-5-yl)ethyl]-1-(methoxyacetyl)-4-[2-(1H-imidazol-1-yl)-6-(trifluoromethyl)pyrimidin-4-yl]piperazine-2-acetamide;

N-[(3,4-dimethylphenyl)methyl]-1-(methoxyacetyl)-4-[6-(1H-imidazol-1-yl)-6-(trifluoromethyl)pyrimidin-4-yl]piperazine-2-carboxamide;

N-[(1,4-benzodioxan-6-yl)methyl]-1-(methoxyacetyl)-4-[2-(1H-imidazol-1-yl)-6-(iso-propyl)pyrimidin-4-yl]piperazine-2-acetamide;

N-[(1,4-benzodioxan-6-yl)methyl]-1-(methoxyacetyl)-4-[2-(1H-imidazol-1-yl)-6-(iso-propyl)pyrimidin-4-yl]piperazine-2-carboxamide;

N-[2-(1,4-benzodioxan-6-yl)ethyl]-1-(methoxyacetyl)-4-[2-(1H-imidazol-1-yl)-6-(trifluoromethyl)pyrimidin-4-yl]piperazine-2-acetamide;

N-[(4-methoxyphenyl)methyl]-1-(methoxyacetyl)-4-[2-(1H-imidazol-1-yl)-6-methylpyrimidin-4-yl]piperazine-2-acetamide;

N-[2–3,4-dimethoxyphenyl)ethyl]-1-[(tetrahydrofuran-2-yl)carbonyl]-4-[2-(1H-imidazol-1-yl)-6-chloropyrimidin-4-yl]piperazine-2-carboxamide;

N-[(4-methylphenyl)methyl]-1-[(tetrahydrofuran-2-yl)carbonyl-]-4-[2-(1H-imidazol-1-yl)-6-chloropyrimidin-4-yl]piperazine-2-acetamide;

N-[2-(4-chlorophenyl)ethyl]-1-[(tetrahydrofuran-2-yl)carbonyl]-4-[2-(1H-imidazol-1-yl)-6-methylpyrimidin-4-yl]piperazine-2-acetamide;

N-[(3-chloro-4-methoxyphenyl)methyl]-1-[(tetrahydrofuran-2-yl)carbonyl]-4-[2-(1H-imidazol-1-yl)-6chloropyrimidin-4-yl]piperazine-2-carboxamide;

N-[(1,3-benzodioxol-5-yl)methyl]-1-[(tetrahydrofuran-2-yl)carbonyl]-4-[2-(1H-imidazol-1-yl)pyrimidin-4-yl]piperazine-2-carboxamide;

N-[(1,3-benzodioxol-5-yl)methyl]-1-[(tetrahydrofuran-2-yl)carbonyl]-4-[6-(1H-imidazol-1-yl)pyrimidin-4-yl]piperazine-2-carboxamide;

N-[2-(1,3-benzodioxol-5-yl)ethyl]-1-(tetrahydrofuran-2-yl)carbonyl]-4-[2-(1H-imidazol-1-yl)-4-methylpyrimidin-4-yl]piperazine-2-acetamide;

N-[2-(1,3-benzodioxol-5-yl)ethyl]-1-(tetrahydrofuran-2-yl)carbonyl]-4-[2-(1H-imidazol-1-yl)pyrimidin-4-yl]piperazine-2-acetamide;

N-[2-(1,3-benzodioxol-5-yl)ethyl]-1-(tetrahydrofuran-2-yl)carbonyl-4-[2-(1H-imidazol-1-yl)-6-(iso-propyl)pyrimidin-4-yl]piperazine-2-acetamide;

N-[2-(1,3-benzodioxol-5-yl)ethyl]-1-[(tetrahydrofuran-2-yl)carbonyl]-4-[2-(1H-imidazol-1-yl)-6-methylpyrimidin-4-yl]piperazine-2-carboxamide;

N-[(1,4-benzodioxan-6-yl)methyl]-1-[(tetrahydrofuran-2-yl)carbonyl]-4-[2-(1H-imidazol-1-yl)-6-(iso-propyl)pyrimidin-4-yl]piperazine-2-acetamide;

N-[(1,4-benzodioxan-6-yl)methyl]-1-[(tetrahydrofuran-2-yl)carbonyl]-4-[2-(1H-imidazol-1-yl)-6-chloropyrimidin-4-yl]piperazine-2-acetamide;

N-[(1,4-benzodioxan-6-yl)methyl]-1-(tetrahydrofuran-2-yl)carbonyl]-4-[2-(1H-imidazol-1-yl)-6-chloropyrimidin-4-yl]piperazine-2-carboxamide;

N-[2-(1,4-benzodioxan-6-yl)ethyl]-1-[(tetrahydrofuran-2-yl)carbonyl]-4-[4-(1H-imidazol-1-yl)-6-methylpyrimidin-4-yl]piperazine-2-carboxamide;

N-[(4-methoxyphenyl)methyl]-1-[(tetrahydrofuran-2-yl)carbonyl]-4-[2-(1H-imidazol-1-yl)-6-chloropyrimidin-4-yl]piperazine-2-acetamide;

N-[2-(4-methoxyphenyl)ethyl]-1-[(tetrahydrofuran-2-yl)carbonyl]-4-[2-(1H-imidazol-1-yl)-6-chloropyrimidin-4-yl]piperazine-2-carboxamide;

N-[2-(3-methoxyphenyl)ethyl]-1-[(tetrahydrofuran-2-yl)carbonyl]-4-[2-(1H-imidazol-1-yl)-6-chloropyrimidin-4-yl]piperazine-2-carboxamide;

N-[(1,4-benzodioxan-2-yl)methyl]-1-[(tetrahydrofuran-2-yl)carbonyl]-4-[2-(1H-imidazol-1-yl)-6-iso-propyl)pyrimidin-4-yl]piperazine-2-carboxamide;

N-[(3,4-dimethoxyphenyl)methyl]-1-[(tetrahydrofuran-2-yl)carbonyl]-4-[2-(1H-imidazol-1-yl)-6-(iso-propyl)pyrimidin-4-yl]piperazine-2-acetamide;

N-[(3,5-dimethoxyphenyl)methyl]-1-[(tetrahydrofuran-2-yl)carbonyl]-4-[2-(1H-imidazol-1-yl)-6-chloropyrimidin-4-yl]piperazine-2-acetamide;

N-[(4-ethoxyphenyl)methyl]-1-[(2-hydroxy-2-oxoethoxy)acetyl]-4-[2-(1H-imidazol-1-yl)-6-chloropyrimidin-4-yl]piperazine-2-carboxamide;

N-[(3-chloro-4-methoxyphenyl)methyl]-1-[(2-hydroxy-2-oxoethoxy)acetyl]-4-[2-(1H-imidazol-1-yl)-6-chloropyrimidin-4-yl]piperazine-2-carboxamide;

N-[(1,3-benzodioxol-5-yl)methyl]-1-[(2-hydroxy-2-oxoethoxy)acetyl]-4-[2-(1H-imidazol-1-yl)-6-methylpyrimidin-4-yl]piperazine-2-carboxamide;

N-[2–3,4-dimethoxyphenyl)ethyl]-1-phenoxyacetyl)-4-[2-(1H-imidazol-1-yl)-6-methylpyrimidin-4-yl]piperazine-2-acetamide;

N-[3-(3,4-dimethoxyphenyl)propyl]-1-(phenoxyacetyl)-4-[2-(1H-imidazol-1-yl)-6-chloropyrimidin-4-yl]piperazine-2-acetamide;

N-[(4-methylphenyl)methyl]-1-phenoxyacetyl)-4-[2-(1H-imidazol-1-yl)-6-methylpyrimidin-4-yl]piperazine-2-acetamide;

N-[(1,3-benzodioxol-5-yl)methyl]-1-(phenoxyacetyl)-4-[2-(1H-imidazol-1-yl)pyrimidin-4-yl]piperazine-2-carboxamide;

N-[(1,3-benzodioxol-5-yl)methyl]-1-phenoxyacetyl)-4-[6-(1H-imidazol-1-yl)pyrimidin-4-yl]piperazine-2-acetamide;

N-[2-(1,3-benzodioxol-5-yl)ethyl]-1-(phenoxyacetyl)-4-[2-(1H-imidazol-1-yl)pyrimidin-4-yl]piperazine-2-acetamide;

N-[2-(1,3-benzodioxol-5-yl)ethyl]-1-(phenoxyacetyl)-4-[2-(1H-imidazol-1-yl)-6-chloropyrimidin-4-yl]piperazine-2-carboxamide;

N-[(1,4-benzodioxan-6-yl)methyl]-1-(phenoxyacetyl)-4-[2-(1H-imidazol-1-yl)-6-chloropyrimidin-4-yl]piperazine-2-acetamide;

N-[2-(1,4-benzodioxan-6-yl)ethyl]-1-(phenoxyacetyl)-4-[2-(1H-imidazol-1-yl)pyrimidin-4-yl]piperazine-2-acetamide;

N-[(4-methoxyphenyl)methyl]-1-phenoxyacetyl)-4-[2-(1H-imidazol-1-yl)pyrimidin-4-yl]piperazine-2-acetamide;

N-[(4-methoxyphenyl)methyl]-1-phenoxyacetyl)-4-[2-(1H-imidazol-1-yl)-6-chloropyrimidin-4-yl]piperazine-2-carboxamide;

N-[2-(4-methoxyphenyl)ethyl]-1-(phenoxyacetyl)-4-[2-(1H-imidazol-1-yl)-6-methylpyrimidin-4-yl]piperazine-2-acetamide;

N-[2-(4-methoxyphenyl)ethyl]-1-phenoxyacetyl)-4-[2-(1H-imidazol-1-yl)pyrimidin-4-yl]piperazine-2-acetamide;

N-[2-(3,4-dimethoxyphenyl)ethyl]-1-[(4-methoxyphenyl)carbonyl]-4-[2-(1H-imidazol-1-yl)-6-chloropyrimidin-4-yl]piperazine-2-acetamide;

N-[(1,3-benzodioxol-5-yl)methyl]-4-(6-fluoropyridin-2-yl)-1-[2-(1H-imidazol-1-yl)pyrimidin-4-yl]piperazine-2-acetamide;

1-(acetyl)-4-[2-(1H-imidazol-1-yl)pyrimidin-4-yl]-N-[(4-methylsulfonylphenyl)methyl]piperazine-2-acetamide;

N-[(1,3-benzodioxol-5-yl)methyl]-4-[[2-(ethoxycarbonyl)methyl-1-[2-(1H-imidazol-1-yl)pyrimidin-4-yl]piperazine-2-acetamide;

4-[amino(imino)methyl]-N-[(1,3-benzodioxol-5-yl)methyl]-1-[2-(1H-imidazol-1-yl)pyrimidin-4-yl]piperazine-2-acetamide;

1-methylsulfonyl-4-[6-methyl-2-(1H-imidazol-1-yl)pyrimidin-4-yl]-N-[2-(1,4-benzodioxan-6-yl)ethyl]piperazine-2-acetamide;

1-methylsulfonyl-4-[2-(1H-imidazol-1-yl)pyrimidin-4-yl]-N-[2-(1,4-benzodioxan-6-yl)ethyl]piperazine-2-acetamide;

1-methylsulfonyl-4-[6-methyl-2-(1H-imidazol-1-yl)pyrimidin-4-yl]-N-[2-(4-methoxyphenyl)ethyl]piperazine-2-acetamide;

1-methylsulfonyl-4-[6-iso-propyl-2-(1H-imidazol-1-yl)pyrimidin-4-yl]-N-[(3,4-dimethoxyphenyl)methyl]piperazine-2-acetamide;

1-(n-octyl)sulfonyl-4-[6-methyl-2-(1H-imidazol-1-yl)pyrimidin-4-yl]-N-[2-(3,4-dimethoxyphenyl)ethyl]piperazine-2-acetamide;

1-(n-octyl)sulfonyl-4-[6-chloro-2-(1H-imidazol-1-yl)pyrimidin-4-yl]-N-[(3-chloro-4-methoxyphenyl)methyl]piperazine-2-acetamide;

1-(n-octyl)sulfonyl-4-[6-(1H-imidazol-1-yl)pyrimidin-4-yl]-N-[(1,3-benzodioxol-5-yl)methyl]piperazine-2-acetamide;

1-(n-octyl)sulfonyl-4-[6-methyl-2-(1H-imidazol-1-yl)pyrimidin-4-yl]-N-[2-(1,3-benzodioxol-5-yl)ethyl]piperazine-2-acetamide;
1-(n-octyl)sulfonyl-4-[6-methyl-2-(1H-imidazol-1-yl)pyrimidin-4-yl]-N-2-(1,4-benzodioxan-6-yl)ethyl]piperazine-2-acetamide;
1-(n-octyl)sulfonyl-4-[6-methyl-2-(1H-imidazol-1-yl)pyrimidin-4-yl]-N-[(3-methoxyphenyl)methyl]piperazine-2-acetamide;
1-(n-octyl)sulfonyl-4-[6-methyl-2-(1H-imidazol-1-yl)pyrimidin-4-yl]-N-[(4-fluorophenyl)sulfonyl]piperazine-2-acetamide;
1-(4-methylphenyl)sulfonyl-4-[6-chloro-2-(1H-imidazol-1-yl)pyrimidin-4-yl]-N-[(pyridin-3-yl)methyl]piperazine-2-carboxamide;
1-(4-methylphenyl)sulfonyl-4-[6-chloro-2-(1H-imidazol-1-yl)pyrimidin-4-yl]-N-[(4-methoxyphenyl)methyl]piperazine-2-carboxamide;
1-(4-methylphenyl)sulfonyl-4-[6-chloro-2-(1H-imidazol-1-yl)pyrimidin-4-yl]-N-[(3,4-dimethoxyphenyl)methyl]piperazine-2-carboxamide;
1-(4-methoxyphenyl)sulfonyl-4-[6-methyl-2-(1H-imidazol-1-yl)pyrimidin-4-yl]-N-[2-(3,4-dimethoxyphenyl)ethyl]piperazine-2-acetamide;
1-(4-methoxyphenyl)sulfonyl-4-[6-chloro-2-(1H-imidazol-1-yl)pyrimidin-4-yl]-N-[(1,3-benzodioxol-5-yl)methyl]piperazine-2-carboxamide;
1-(4-methoxyphenyl)sulfonyl-4-[2-(1H-imidazol-1-yl)pyrimidin-4-yl]-N-[2-(1,3-benzodioxol-5-yl)ethyl]piperazine-2-carboxamide;
1-(4-methoxyphenyl)sulfonyl-4-[2-(1H-imidazol-1-yl)pyrimidin-4-yl]-N-[2-(1,3-benzodioxol-5-yl)ethyl]piperazine-2-acetamide;
1-(4-methoxyphenyl)sulfonyl-4-[6-methyl-2-(1H-imidazol-1-yl)pyrimidin-4-yl]-N-[(3,4-dimethoxyphenyl)methyl]piperazine-2-acetamide;
1-(4-methoxyphenyl)sulfonyl-4-[6-methyl-2-(1H-imidazol-1-yl)pyrimidin-4-yl]-N-[2-(1,4-benzodioxan-6-yl)ethyl]piperazine-2-carboxamide;
1-(4-methoxyphenyl)sulfonyl-4-[6-iso-propyl-2-(1H-imidazol-1-yl)pyrimidin-4-yl]-N-[(4-methoxyphenyl)methyl]piperazine-2-carboxamide;
1-(4-methoxyphenyl)sulfonyl-4-[2-(1H-imidazol-1-yl)pyrimidin-4-yl]-N-[(2-methoxyphenyl)methyl]piperazine-2-carboxamide;
1-(4-methoxyphenyl)sulfonyl-4-[6-methyl-2-(1H-imidazol-1-yl)pyrimidin-4-yl]-N-[2-(4-methoxyphenyl)ethyl]piperazine-2-acetamide;
1-(4-methoxyphenyl)sulfonyl-4-[6-chloro-2-(1H-imidazol-1-yl)pyrimidin-4-yl]-N-[2-(4-methoxyphenyl)ethyl]piperazine-2-carboxamide;
1-(4-methoxyphenyl)sulfonyl-4-[6-methyl-2-(1H-imidazol-1-yl)pyrimidin-4-yl]-N-[(3,4-dimethoxyphenyl)methyl]piperazine-2-carboxamide;
1-(4-methoxyphenyl)sulfonyl-4-[6-iso-propyl-2-(1H-imidazol-1-yl)pyrimidin-4-yl]-N-[(3,4-dimethoxyphenyl)methyl]piperazine-2-carboxamide;
1-(4-methoxyphenyl)sulfonyl-4-[6-chloro-2-(1H-imidazol-1-yl)pyrimidin-4-yl]-N-[(3,4-dimethoxyphenyl)methyl]piperazine-2-carboxamide;
1-(4-fluorophenyl)sulfonyl-4-[6-chloro-2-(1H-imidazol-1-yl)pyrimidin-4-yl]-N-[2-(1,3-benzodioxol-5-yl)ethyl]piperazine-2-acetamide;
1-(4-fluorophenyl)sulfonyl-4-[2-(1H-imidazol-1-yl)pyrimidin-4-yl]-N-[2-(1,4-benzodioxan-6-yl)ethyl]piperazine-2-acetamide;
1-(dimethylamino)sulfonyl-4-[6-methyl-2-(1H-imidazol-1-yl)pyrimidin-4-yl]-N-[(4-methylphenyl)methyl]piperazine-2-acetamide;
1-(dimethylamino)sulfonyl-4-[2-(1H-imidazol-1-yl)pyrimidin-4-yl]-N-[2-(3-chloro-4-methoxyphenyl)ethyl]piperazine-2-acetamide;
1-(dimethylamino)sulfonyl-4-[6-methyl-2-(1H-imidazol-1-yl)pyrimidin-4-yl]-N-[(1,3-benzodioxol-5-yl)methyl]piperazine-2-acetamide;
1-(dimethylamino)sulfonyl-4-[2-(1H-imidazol-1-yl)pyrimidin-4-yl]-N-[(1,3-benzodioxol-5-yl)methyl]piperazine-2-carboxamide;
1-(dimethylamino)sulfonyl-4-[6-chloro-2-(1H-imidazol-1-yl)pyrimidin-4-yl]-N-[2-(1,3-benzodioxol-5-yl)ethyl]piperazine-2-acetamide;
1-(dimethylamino)sulfonyl-4-[2-(1H-imidazol-1-yl)pyrimidin-4-yl]-N-[(1,4-benzodioxan-6-yl)methyl]piperazine-2-acetamide;
1-(dimethylamino)sulfonyl-4-[6-trifluoromethyl-2-(1H-imidazol-1-yl)pyrimidin-4-yl]-N-[(1,4-benzodioxan-6-yl)methyl]piperazine-2-acetamide;
1-(dimethylamino)sulfonyl-4-[6-iso-propyl-2-(1H-imidazol-1-yl)pyrimidin-4-yl]-N-[2-(1,4-benzodioxan-6-yl)ethyl]piperazine-2-acetamide;
1-(dimethylamino)sulfonyl-4-[6-chloro-2-(1H-imidazol-1-yl)pyrimidin-4-yl]-N-[2-(1,4-benzodioxan-6-yl)ethyl]piperazine-2-acetamide;
1-(dimethylamino)sulfonyl-4-[6-methyl-2-(1H-imidazol-1-yl)pyrimidin-4-yl]-N-[2–4-methoxyphenyl)ethyl]piperazine-2-acetamide;
1-(dimethylamino)sulfonyl-4-[6-iso-propyl-2-(1H-imidazol-1-yl)pyrimidin-4-yl]-N-[(3,4-dimethoxyphenyl)methyl]piperazine-2-acetamide;
1-n-propyl)aminocarbonyl-4-[6-methyl-2-(1H-imidazol-1-yl)pyrimidin-4-yl]-N-[2-(3,4-dimethoxyphenyl)ethyl]piperazine-2-acetamide;
1-(n-propyl)aminocarbonyl-4-[6-methyl-2-(1H-imidazol-1-yl)pyrimidin-4-yl]-N-[2-(4-methylphenoxy)ethyl]piperazine-2-carboxamide;
1-(n-propyl)aminocarbonyl-4-[6-chloro-2-(1H-imidazol-1-yl)pyrimidin-4-yl]-N-[2-(4-chlorophenyl)ethyl]piperazine-2-carboxamide;
1-n-propyl)aminocarbonyl-4-[6-methyl-2-(1H-imidazol-1-yl)pyrimidin-4-yl]-N-[(3-chloro-4-methoxyphenyl)methyl]piperazine-2-acetamide;
1n-propyl)aminocarbonyl-4-[6-chloro-2-(1H-imidazol-1-yl)pyrimidin-4-yl]-N-[2-(3-chloro-4-methoxyphenyl)ethyl]piperazine-2-carboxamide;
1-(n-propyl)aminocarbonyl-4-[6-iso-propyl-2-(1H-imidazol-1-yl)pyrimidin-4-yl]-N-[(1,3-benzodioxol-5-yl)methyl]piperazine-2-carboxamide;
1-(n-propyl)aminocarbonyl-4-[6-chloro-2-(1H-imidazol-1-yl)pyrimidin-4-yl]-N-[(1,3-benzodioxol-5-yl)methyl]piperazine-2-carboxamide;
1-(n-propyl)aminocarbonyl-4-[6-chloro-2-(1H-imidazol-1-yl)pyrimidin-4-yl]-N-[(1,3-benzodioxol-5-yl)methyl]piperazine-2-acetamide;
1-(n-propyl)aminocarbonyl-4-[6-chloro-2-(1H-imidazol-1-yl)pyrimidin-4-yl]-N-[2-(1,3-benzodioxol-5-yl)ethyl]piperazine-2-carboxamide;
1-(n-propyl)aminocarbonyl-4-[6-chloro-2-(1H-imidazol-1-yl)pyrimidin-4-yl]-N-[2-(1,3-benzodioxol-5-yl)ethyl]piperazine-2-acetamide;
1-(n-propyl)aminocarbonyl-4-[6-(1H-imidazol-1-yl)pyrimidin-4-yl]-N-[2-(1,3-benzodioxol-5-yl)ethyl]piperazine-2-carboxamide;
1-(n-propyl)aminocarbonyl-4-[6-iso-propyl-2-(1H-imidazol-1-yl)pyrimidin-4-yl]-N-[(1,4-benzodioxan-6-yl)methyl]piperazine-2-carboxamide;
1-(n-propyl)aminocarbonyl-4-[2-(1H-imidazol-1-yl)pyrimidin-4-yl]-N-[2-(1,4-benzodioxan-6-yl)ethyl]piperazine-2-carboxamide;

1-(n-propyl)aminocarbonyl-4-[6-chloro-2-(1H-imidazol-1-yl)pyrimidin-4-yl]-N-[(3,4-dimethoxyphenyl)methyl]piperazine-2-acetamide;
1-(cyclohexyl)aminocarbonyl-4-[6-chloro-2-(1H-imidazol-1-yl)pyrimidin-4-yl]-N-[2-(3,4-dimethoxyphenyl)ethyl]piperazine-2-acetamide;
1-(cyclohexyl)aminocarbonyl-4-[6-methyl-2-(1H-imidazol-1-yl)pyrimidin-4-yl]-N-[(4-ethoxyphenyl)methyl]piperazine-2-carboxamide;
1-(cyclohexyl)aminocarbonyl-4-[2-(1H-imidazol-1-yl)pyrimidin-4-yl]-N-[2-(3-chloro-4-methoxyphenyl)ethyl]piperazine-2-acetamide;
1-(cyclohexyl)aminocarbonyl-4-[6-iso-propyl-2-(1H-imidazol-1-yl)pyrimidin-4-yl]-N-[2-(3-chloro-4-methoxyphenyl)ethyl]piperazine-2-acetamide;
1-(cyclohexyl)aminocarbonyl-4-[6-chloro-2-(1H-imidazol-1-yl)pyrimidin-4-yl]-N-[2-(1,3-benzodioxol-5-yl)methyl]piperazine-2-acetamide;
1-(cyclohexyl)aminocarbonyl-4-[2-(1H-imidazol-1-yl)pyrimidin-4-yl]-N-[2-(1,3-benzodioxol-5-yl)ethyl]piperazine-2-acetamide;
1-cyclohexyl)aminocarbonyl-4-[6-(1H-imidazol-1-yl)pyrimidin-4-yl]-N-[2-(1,3-benzodioxol-5-yl)ethyl]piperazine-2-carboxamide;
1-(cyclohexyl)aminocarbonyl-4-[6-iso-propyl-2-(1H-imidazol-1-yl)pyrimidin-4-yl]-N-[(1,4-benzodioxan-6-yl)methyl]piperazine-2-carboxamide;
1-cyclohexyl)aminocarbonyl-4-[6-methyl-2-(1H-imidazol-1-yl)pyrimidin-4-yl]-N-[(1,4-benzodioxan-6-yl)methyl]piperazine-2-carboxamide;
1-(cyclohexyl)aminocarbonyl-4-[6-chloro-2-(1H-imidazol-1-yl)pyrimidin-4-yl]-N-[(1,4-benzodioxan-6-yl)methyl]piperazine-2-carboxamide;
1-(cyclohexyl)aminocarbonyl-4-[6-chloro-2-(1H-imidazol-1-yl)pyrimidin-4-yl]-N-[(1,4-benzodioxan-6-yl)methyl]piperazine-2-acetamide;
1-(cyclohexyl)aminocarbonyl-4-[6-trifluoromethyl-2-(1H-imidazol-1-yl)pyrimidin-4-yl]-N-[2-(1,4-benzodioxan-6-yl)ethyl]piperazine-2-acetamide;
1-(cyclohexyl)aminocarbonyl-4-[6-chloro-2-(1H-imidazol-1-yl)pyrimidin-4-yl]-N-[2-(4-methoxyphenyl)ethyl]piperazine-2-carboxamide;
1-(cyclohexyl)aminocarbonyl-4-[6-methyl-2-(1H-imidazol-1-yl)pyrimidin-4-yl]-N-[(1,4-benzodioxan-2-yl)methyl]piperazine-2-carboxamide;
1-(cyclohexyl)aminocarbonyl-4-[6-iso-propyl-2-(1H-imidazol-1-yl)pyrimidin-4-yl]-N-[(1,4-benzodioxan-2-yl)methyl]piperazine-2-carboxamide;
1-(cyclohexyl)aminocarbonyl-4-[6-iso-propyl-2-(1H-imidazol-1-yl)pyrimidin-4-yl]-N-[(2,3-dimethoxyphenyl)methyl]piperazine-2-carboxamide;
1-(cyclohexyl)aminocarbonyl-4-[6-chloro-2-(1H-imidazol-1-yl)pyrimidin-4-yl]-N-[(2,3-dimethoxyphenyl)methyl]piperazine-2-carboxamide;
1-(phenylsulfonyl)aminocarbonyl-4-[6-chloro-2-(1H-imidazol-1-yl)pyrimidin-4-yl]-N-[2-(3,4-dimethoxyphenyl)ethyl]piperazine-2-acetamide;
1-(phenylsulfonyl)aminocarbonyl-4-[6-methyl-2-(1H-imidazol-1-yl)pyrimidin-4-yl]-N-[(4-ethoxyphenyl)methylpiperazine-2-acetamide;
1-(phenylsulfonyl)aminocarbonyl-4-[2-(1H-imidazol-1-yl)pyrimidin-4-yl]-N-[(4-ethoxyphenyl)methyl]piperazine-2-acetamide;
1-(phenylsulfonyl)aminocarbonyl-4-[6-chloro-2-(1H-imidazol-1-yl)pyrimidin-4-yl]-N-[2-(4-methylphenoxy)ethyl]piperazine-2-acetamide;
1-(phenylsulfonyl)aminocarbonyl-4-[6-chloro-2-(1H-imidazol-1-yl)pyrimidin-4-yl]-N-[(4-methylphenyl)methyl]piperazine-2-acetamide;
1-(phenylsulfonyl)aminocarbonyl-4-[6-methyl-2-(1H-imidazol-1-yl)pyrimidin-4-yl]-N-[2-(3-chloro-4-methoxyphenyl)ethyl]piperazine-2-acetamide;
1-(phenylsulfonyl)aminocarbonyl-4-[6-methyl-2-(1H-imidazol-1-yl)pyrimidin-4-yl]-N-[(1,3-benzodioxol-5-yl)methyl]piperazine-2-acetamide;
1-(phenylsulfonyl)aminocarbonyl-4-[6-methyl-2-(1H-imidazol-1-yl)pyrimidin-4-yl]-N-[(1,3-benzodioxol-5-yl)methyl]piperazine-2-carboxamide;
1-phenylsulfonyl)aminocarbonyl-4-[6-chloro-2-(1H-imidazol-1-yl)pyrimidin-4-yl]-N-[(1,3-benzodioxol-5-yl)methyl]piperazine-2-carboxamide;
1-(phenylsulfonyl)aminocarbonyl-4-[6-methyl-2-(1H-imidazol-1-yl)pyrimidin-4-yl]-N-[(1,4-benzodioxan-6-yl)methyl]piperazine-2-acetamide;
1-(phenylsulfonyl)aminocarbonyl-4-[6-methyl-2-(1H-imidazol-1-yl)pyrimidin-4-yl]-N-[2-(1,4-benzodioxan-6-yl)ethyl]piperazine-2-acetamide;
1-(phenylsulfonyl)aminocarbonyl-4-[2-(1H-imidazol-1-yl)pyrimidin-4-yl]-N-[2-(1,4-benzodioxan-6-yl)ethyl]piperazine-2-acetamide;
1-(phenylsulfonyl)aminocarbonyl-4-[6-methyl-2-(1H-imidazol-1-yl)pyrimidin-4-yl]-N-[(4-methoxyphenyl)methyl]piperazine-2-acetamide;
1-(phenylsulfonyl)aminocarbonyl-4-[6-chloro-2-(1H-imidazol-1-yl)pyrimidin-4-yl]-N-[(2,5-dimethoxyphenyl)methyl]piperazine-2-acetamide;
1-[2-(thien-2-yl)ethyl]-4-[2-(1H-imidazol-1-yl)pyrimidin-4-yl]-N-[(1,3-benzodioxol-5-yl)methyl]piperazine-2-carboxamide;
1-[2-(thien-2-yl)ethyl]-4-[6-methyl-2-(1H-imidazol-1-yl)pyrimidin-4-yl]-N-[(1,3-benzodioxol-5-yl)methyl]piperazine-2-carboxamide;
1-[2-(thien-2-yl)ethyl]-4-[6-iso-propyl-2-(1H-imidazol-1-yl)pyrimidin-4-yl]-N-(1,4-benzodioxan-6-yl)methyl]piperazine-2-acetamide;
1-[2-(thien-2-yl)ethyl]-4-[6-chloro-2-(1H-imidazol-1-yl)pyrimidin-4-yl]-N-[(1,4-benzodioxan-4-yl)methyl]piperazine-2-carboxamide;
1-[2-(thien-2-yl)ethyl]-4-[6-chloro-2-(1H-imidazol-1-yl)pyrimidin-4-yl]-N-[(2,3-dimethoxyphenyl)methyl]piperazine-2-acetamide;
1-[2-(thien-2-yl)ethyl]-4-[6-iso-propyl-2-(1H-imidazol-1-yl)pyrimidin-4-yl]-N-[(cyclopropyl)methyl]piperazine-2-acetamide;
1-(4-methoxyphenyl)aminocarbonyl-4-[6-chloro-2-(1H-imidazol-1-yl)pyrimidin-4-yl]-N-[(4-chlorophenyl)methyl]piperazine-2-carboxamide;
1-(4-methoxyphenyl)aminocarbonyl-4-[2-(1H-imidazol-1-yl)pyrimidin-4-yl]-N-[2-(2,4-dimethoxyphenyl)ethyl]piperazine-2-carboxamide;
1-(4-methoxyphenyl)aminocarbonyl-4-[6-methyl-2-(1H-imidazol-1-yl)pyrimidin-4-yl]-N-[(1,3-benzodioxol-5-yl)methyl]piperazine-2-carboxamide;
1–4-methoxyphenyl)aminocarbonyl-4-[2-(1H-imidazol-1-yl)pyrimidin-4-yl]-N-[2-(1,3-benzodioxol-5-yl)ethyl]piperazine-2-acetamide;
1-(4-methoxyphenyl)aminocarbonyl-4-[2-(1H-imidazol-1-yl)pyrimidin-4-yl]-N-[(1,4-benzodioxan-6-yl)methyl]piperazine-2-carboxamide;
1-(4-methoxyphenyl)aminocarbonyl-4-[6-chloro-2-(1H-imidazol-1-yl)pyrimidin-4-yl]-N-[(1,4-benzodioxan-6-yl)methyl]piperazine-2-carboxamide;
1-(4-methoxyphenyl)aminocarbonyl-4-[6-methyl-2-(1H-imidazol-1-yl)pyrimidin-4-yl]-N-[2-(1,4-benzodioxan-6-yl)ethyl]piperazine-2-acetamide;
1-(4-methoxyphenyl)aminocarbonyl-4-[2-(1H-imidazol-1-yl)pyrimidin-4-yl]-N-[(4-methoxyphenyl)methyl]piperazine-2-acetamide;

1-(3,4-dichlorophenyl)aminocarbonyl-4-[6-methyl-2-(1H-imidazol-1-yl)pyrimidin-4-yl]-N-[2-3,4-dimethoxyphenyl)ethyl]piperazine-2-acetamide;

1-(3,4-dichlorophenyl)aminocarbonyl-4-[2-(1H-imidazol-1-yl)pyrimidin-4-yl]-N-[2-(1,3-benzodioxol-5-yl)ethyl]piperazine-2-acetamide;

1-(3,4-dichlorophenyl)aminocarbonyl-4-[2-(1H-imidazol-1-yl)pyrimidin-4-yl]-N-(1,4-benzodioxan-6-yl)methyl)piperazine-2-acetamide;

1-(3,4-dichlorophenyl)aminocarbonyl-4-[6-chloro-2-(1H-imidazol-1-yl)pyrimidin-4-yl]-N-[(4-methoxyphenyl)methyl]piperazine-2-carboxamide;

1-(3,4-dichlorophenyl)aminocarbonyl-4-[2-(1H-imidazol-1-yl)pyrimidin-4-yl]-N-[(3,5-dimethoxyphenyl)methyl]piperazine-2-carboxamide;

1-(methoxy)carbonyl-4-[6-methyl-2-(1H-imidazol-1-yl)pyrimidin-4-yl]-N-[2-(3,4-dimethoxyphenyl)ethyl]piperazine-2-acetamide;

1-(methoxy)carbonyl-4-[6-chloro-2-(1H-imidazol-1-yl)pyrimidin-4-yl]-N-[2-(3,4-dimethoxyphenyl)ethyl]piperazine-2-carboxamide;

1-(methoxy)carbonyl-4-[6-chloro-2-(1H-imidazol-1-yl)pyrimidin-4-yl]-N-[(3-chloro-4-methoxyphenyl)methyl]piperazine-2-acetamide;

1-(methoxy)carbonyl-4-[6-iso-propyl-2-(1H-imidazol-1-yl)pyrimidin-4-yl]-N-[2-(3-chloro-4-methoxyphenyl)ethyl]piperazine-2-acetamide;

1-(methoxy)carbonyl-4-[6-iso-propyl-2-(1H-imidazol-1-yl)pyrimidin-4-yl]-N-[2-(1,3-benzodioxol-5-yl)ethyl]piperazine-2-acetamide;

1-(methoxy)carbonyl-4-[6-chloro-2-(1H-imidazol-1-yl)pyrimidin-4-yl]-N-[2-(1,3-benzodioxol-5-yl)ethyl]piperazine-2-acetamide;

1-(methoxy)carbonyl-4-[2-(1H-imidazol-1-yl)pyrimidin-4-yl]-N-[2-(1,4-benzodioxan-6-yl)ethyl]piperazine-2-carboxamide;

1-(methoxy)carbonyl-4-[2-(1H-imidazol-1-yl)pyrimidin-4-yl]-N-[2-(1,4-benzodioxan-6-yl)ethyl]piperazine-2-acetamide;

1-(methoxy)carbonyl-4-[6-chloro-2-(1H-imidazol-1-yl)pyrimidin-4-yl]-N-[2-(1,4-benzodioxan-6-yl)ethyl]piperazine-2-carboxamide;

1-(methoxy)carbonyl-4-[6-iso-propyl-2-(1H-imidazol-1-yl)pyrimidin-4-yl]-N-[(4-methoxyphenyl)methyl]piperazine-2-carboxamide;

1-(methoxy)carbonyl-4-[6-chloro-2-(1H-imidazol-1-yl)pyrimidin-4-yl]-N-[(cyclopropyl)methyl]piperazine-2-carboxamide;

1-(iso-propoxy)carbonyl-4-[6-methyl-2-(1H-imidazol-1-yl)pyrimidin-4-yl]-N-[2-(4-methylphenoxy)ethyl]piperazine-2-carboxamide;

1-(iso-propoxy)carbonyl-4-[6-chloro-2-(1H-imidazol-1-yl)pyrimidin-4-yl]-N-[(4-methylphenyl)methyl]piperazine-2-carboxamide;

1-(iso-propoxy)carbonyl-4-[6-methyl-2-(1H-imidazol-1-yl)pyrimidin-4-yl]-N-[(1,3-benzodioxol-5-yl)methyl]piperazine-2-carboxamide;

1-(iso-propoxy)carbonyl-4-[2-(1H-imidazol-1-yl)pyrimidin-4-yl]-N-[(1,3-benzodioxol-5-yl)methyl]piperazine-2-acetamide;

1-(isopropoxy)carbonyl-4-[6-methyl-2-(1H-imidazol-1-yl)pyrimidin-4-yl]-N-[2-(1,4-benzodioxane-yl)ethyl]piperazine-2-carboxamide;

1-(iso-propoxy)carbonyl-4-[6-methyl-2-(1H-imidazol-1-yl)pyrimidin-4-yl]-N-[(3,4-dimethoxyphenyl)methyl]piperazine-2-carboxamide;

1-(iso-propoxy)carbonyl-4-[6-iso-propyl-2-(1H-imidazol-1-yl)pyrimidin-4-yl]-N-[(3,4-dimethoxyphenyl)methyl]piperazine-2-carboxamide;

1-(iso-propoxy)carbonyl-4-[6-chloro-2-(1H-imidazol-1-yl)pyrimidin-4-yl]-N-(cyclopropyl)piperazine-2-acetamide;

1-(n-butoxy)carbonyl-4-[2-(1H-imidazol-1-yl)pyrimidin-4-yl]-N-[(1,3-benzodioxol-5-yl)methyl]piperazine-2-acetamide;

1-(n-butoxy)carbonyl-4-[6-chloro-2-(1H-imidazol-1-yl)pyrimidin-4-yl]-N-[(1,3-benzodioxol-5-yl)methyl]piperazine-2-acetamide;

1-(n-butoxy)carbonyl-4-[2-(1H-imidazol-1-yl)pyrimidin-4-yl]-N-[2-(1,3-benzodioxol-5-yl)ethyl]piperazine-2-acetamide;

1-(n-butoxy)carbonyl-4-[6-iso-propyl-2-(1H-imidazol-1-yl)pyrimidin-4-yl]-N-[(1,4-benzodioxan-6-yl)methyl]piperazine-2-acetamide;

1-(n-butoxy)carbonyl-4-[6-chloro-2-(1H-imidazol-1-yl)pyrimidin-4-yl]-N-[(1,4-benzodioxan-6-yl)methyl]piperazine-2-acetamide;

1-(n-butoxy)carbonyl-4-[6-methyl-2-(1H-imidazol-1-yl)pyrimidin-4-yl]-N-[2-(1,4-benzodioxan-4-yl)ethyl]piperazine-2-acetamide;

1-(n-butoxy)carbonyl-4-[6-methyl-2-(1H-imidazol-1-yl)pyrimidin-4-yl]-N-[(3,4-dimethoxyphenyl)methylpiperazine-2-acetamide;

1-(n-butoxy)carbonyl-4-[6-chloro-2-(1H-imidazol-1-yl)pyrimidin-4-yl]-N-[(3,4-dimethoxyphenyl)methyl]piperazine-2-carboxamide;

1-(2-(methoxy)ethoxy)carbonyl-4-[6-iso-propyl-2-(1H-imidazol-1-yl)pyrimidin-4-yl)-N-[3-(,4-dimethoxyphenyl)propyl]piperazine-2-carboxamide;

1-(2-(methoxy)ethoxy)carbonyl-4-[6-iso-propyl-2-(1H-imidazol-1-yl)pyrimidin-4-yl]-N-2-(1,3-benzodioxol-5-yl)ethyl]piperazine-2-carboxamide;

1-(2-methoxy)ethoxy)carbonyl-4-[6-iso-propyl-2-(1H-imidazol-1-yl)pyrimidin-4-yl]-N-[(1,4-benzodioxan-6-yl)methyl]piperazine-2-carboxamide;

1-(2-(methoxy)ethoxy)carbonyl-4-[6-(1H-imidazol-1-yl)pyrimidin-4-yl]-N-(1,4-benzodioxan-6-yl)methyl]piperazine-2-carboxamide;

1-(2-(methoxy)ethoxy)carbonyl-4-[6-methyl-2-(1H-imidazol-1-yl)pyrimidin-4-yl]-N-[2-(1,4-benzodioxan-6-yl)ethyl]piperazine-2-acetamide;

1-(2-(methoxy)ethoxy)carbonyl-4-[6-chloro-2-(1H-imidazol-1-yl)pyrimidin-4-yl]-N-[2-(4-methoxyphenyl)ethyl]piperazine-2-acetamide;

1-(2-(methoxy)ethoxy)carbonyl-4-[6-chloro-2-(1H-imidazol-1-yl)pyrimidin-4-yl]-N-[2-(3-methoxyphenyl)ethyl]piperazine-2-carboxamide;

1-(1-methylpropoxy)carbonyl-4-[6-chloro-2-(1H-imidazol-1-yl)pyrimidin-4-yl]-N-[2-(4-methylphenoxy)ethyl]piperazine-2-acetamide;

1-(1-methylpropoxy)carbonyl-4-[6-methyl-2-(1H-imidazol-1-yl)pyrimidin-4-yl]-N-[(1,3-benzodioxol-5-yl)methyl]piperazine-2-acetamide;

1-(1-methylpropoxy)carbonyl-4-[6-chloro-2-(1H-imidazol-1-yl)pyrimidin-4-yl]-N-[(1,3-benzodioxol-5-yl)methyl]piperazine-2-acetamide;

1-(1-methylpropoxy)carbonyl-4-[6-(1H-imidazol-1-yl)pyrimidin-4-yl]-N-[(1,3-benzodioxol-5-yl)methyl]piperazine-2-carboxamide;

1-(1-methylpropoxy)carbonyl-4-[6-chloro-2-(1H-imidazol-1-yl)pyrimidin-4-yl]-N-[(1,4-benzodioxan-6-yl)methyl]piperazine-2-acetamide;

1-(1-methylpropoxy)carbonyl-4-[6-chloro-2-(1H-imidazol-1-yl)pyrimidin-4-yl]-N-[(1,4-benzodioxan-6-yl)methyl]piperazine-2-carboxamide;

1-(1-methylpropoxy)carbonyl-4-[6-(1H-imidazol-1-yl)pyrimidin-4-yl]-N-[(1,4-benzodioxan-6-yl)methyl]piperazine-2-carboxamide;

1-(1-methylpropoxy)carbonyl-4-[2-(1H-imidazol-1-yl)pyrimidin-4-yl]-N-[2-(1,4-benzodioxan-6-yl)ethyl]piperazine-2-acetamide;
1-(1-methylpropoxy)carbonyl-4-[6-chloro-2-(1H-imidazol-1-yl)pyrimidin-4-yl]-N-[(4-methoxyphenyl)methyl]piperazine-2-carboxamide;
1(1-methylpropoxy)carbonyl-4-[6-methyl-2-(1H-imidazol-1-yl)pyrimidin-4-yl]-N-[(3,4-dimethoxyphenyl)methyl]piperazine-2-acetamide;
1-(phenoxy)carbonyl-4-[6-iso-propyl-2-(1H-imidazol-1-yl)pyrimidin-4-yl]-N-[2-(3,4-dimethoxyphenyl)ethyl]piperazine-2-acetamide;
1-(phenoxy)carbonyl-4-[6-methyl-2-(1H-imidazol-1-yl)pyrimidin-4-yl]-N-[2-(3,4-dimethoxyphenyl)ethyl]piperazine-2-acetamide;
1-(phenoxy)carbonyl-4-[6-chloro-2-(1H-imidazol-1-yl)pyrimidin-4-yl]-N-[2-(3,4-dimethoxyphenyl)ethyl]piperazine-2-acetamide;
1-(phenoxy)carbonyl-4-[6-(1H-imidazol-1-yl)pyrimidin-4-yl]-N-[(1,3-benzodioxol-5-yl)methyl]piperazine-2-carboxamide;
1-(phenoxy)carbonyl-4-[2-(1H-imidazol-1-yl)pyrimidin-4-yl]-N-[(furan-2-yl)methyl]piperazine-2-acetamide;
1-(phenoxy)carbonyl-4-[6-methyl-2-(1H-imidazol-1-yl)pyrimidin-4-yl]-N-[(1,4-benzodioxan-6-yl)methyl]piperazine-2-carboxamide;
1-(phenoxy)carbonyl-4-[6-chloro-2-(1H-imidazol-1-yl)pyrimidin-4-yl]-N-[(1,4-benzodioxan-6-yl)methyl]piperazine-2-carboxamide;
1-(phenoxy)carbonyl-4-[2-(1H-imidazol-1-yl)pyrimidin-4-yl]-N-[2-(1,4-benzodioxanyl)ethyl]piperazine-2-carboxamide;
1-(phenoxy)carbonyl-4-[6-chloro-2-(1H-imidazol-1-yl)pyrimidin-4-yl]-N-[(4-methoxyphenyl)methyl]piperazine-2-carboxamide;
1-(phenoxy)carbonyl-4-[6-iso-propyl-2-(1H-imidazol-1-yl)pyrimidin-4-yl]-N-[(3,4-dimethoxyphenyl)methyl]piperazine-2-carboxamide;
1-(4-methoxyphenoxy)carbonyl-4-[2-(1H-imidazol-1-yl)pyrimidin-4-yl]-N-[(1,3-benzodioxol-5-yl)methyl]piperazine-2-carboxamide;
1-(4-methoxyphenoxy)carbonyl-4-[6-methyl-2-(1H-imidazol-1-yl)pyrimidin-4-yl]-N-[(1,3-benzodioxol-5-yl)methyl]piperazine-2-carboxamide;
1-(4-methoxyphenoxy)carbonyl-4-[2-(1H-imidazol-1-yl)pyrimidin-4-yl]-N-[2-(1,3-benzodioxol-5-yl)ethyl]piperazine-2-acetamide;
1-(4-methoxyphenoxy)carbonyl-4-[6-chloro-2-(1H-imidazol-1-yl)pyrimidin-4-yl]-N-[2-(1,3-benzodioxol-5-yl)ethyl]piperazine-2-carboxamide;
1-(4-methoxyphenoxy)carbonyl-4-[6-(1H-imidazol-1-yl)pyrimidin-4-yl]-N-[(1,4-benzodioxan-6-yl)methyl]piperazine-2-carboxamide;
1-(4-methoxyphenoxy)carbonyl-4-[2-(1H-imidazol-1-yl)pyrimidin-4-yl]-N-[2-(1,4-benzodioxan-6yl)ethyl]piperazine-2-carboxamide;
1-(4-methoxyphenoxy)carbonyl-4-[6-chloro-2-(1H-imidazol-1-yl)pyrimidin-4-yl]-N-[2-(4-methoxyphenyl)ethyl]piperazine-2-acetamide;
1-(4-methoxyphenoxy)carbonyl-4-[6-chloro-2-(1H-imidazol-1-yl)pyrimidin-4-yl]-N-[(2,4-dimethoxyphenyl)methyl]piperazine-2-carboxamide;
1-(4-methoxyphenoxy)carbonyl-4-[6-methyl-2-(1H-imidazol-1-yl)pyrimidin-4-yl]-N-[(3,4-dimethoxyphenyl)methyl]piperazine-2-carboxamide;
1-((phenyl)methoxy)carbonyl-4-[6-iso-propyl-2-(1H-imidazol-1-yl)pyrimidin-4-yl]-N-[2-(4-methylphenoxy)ethyl]piperazine-2-carboxamide;
1-((phenyl)methoxy)carbonyl-4-[6-chloro-2-(1H-imidazol-1-yl)pyrimidin-4-yl]-N-[2-(4-methylphenoxy)ethyl]piperazine-2-carboxamide;
1-((phenyl)methoxy)carbonyl-4-[2-(1H-imidazol-1-yl)pyrimidin-4-yl]-N-[(1,3-benzodioxol-5-yl)methyl]piperazine-2-carboxamide;
1-((phenyl)methoxy)carbonyl-4-[6-iso-propyl-2-(1H-imidazol-1-yl)pyrimidin-4-yl]-N-[(1,3-benzodioxol-5-yl)methyl]piperazine-2-acetamide;
1-((phenyl)methoxy)carbonyl-4-[6-chloro-2-(1H-imidazol-1-yl)pyrimidin-4-yl]-N-[(1,3-benzodioxol-5-yl)methyl]piperazine-2-carboxamide;
1-((phenyl)methoxy)carbonyl-4-[6-methyl-2-(1H-imidazol-1-yl)pyrimidin-4-yl]-N-[2-(1,3-benzodioxol-5-yl)ethyl]piperazine-2-carboxamide;
1-((phenyl)methoxy)carbonyl-4-[6-iso-propyl-2-(1H-imidazol-1-yl)pyrimidin-4-yl]-N-[(1,4-benzodioxan-6-yl)methyl]piperazine-2-carboxamide;
1-((phenyl)methoxy)carbonyl-4-[6-chloro-2-(1H-imidazol-1-yl)pyrimidin-4-yl]-N-[(1,4-benzodioxan-6-yl)methyl]piperazine-2-acetamide;
1-((phenyl)methoxy)carbonyl-4-[6-chloro-2-(1H-imidazol-1-yl)pyrimidin-4-yl]-N-[2-(1,4-benzodioxan-6-yl)ethyl]piperazine-2-carboxamide;
1-((phenyl)methoxy)carbonyl-4-[2-(1H-imidazol-1-yl)pyrimidin-4-yl]-N-[(4-methoxyphenyl)methyl]piperazine-2-carboxamide;
1-((phenyl)methoxy)carbonyl-4-[6-methyl-2-(1H-imidazol-1-yl)pyrimidin-4-yl]-N-[2-(4-methoxyphenyl)ethyl]piperazine-2-acetamide;
1-((phenyl)methoxy)carbonyl-4-[6-methyl-2-(1H-imidazol-1-yl)pyrimidin-4-yl]-N-[(3,4-dimethoxyphenyl)methyl]piperazine-2-carboxamide;
1-((phenyl)methoxy)carbonyl-4-[6-iso-propyl-2-(1H-imidazol-1-yl)pyrimidin-4-yl]-N-[(3,4-dimethoxyphenyl)methyl]piperazine-2-acetamide;
1-(4-methoxyphenyl)carbonyl-4-[2-(1H-imidazol-1-yl)pyrimidin-4-yl]-N-[2-(1,3-benzodioxol-5-yl)ethyl]piperazine-2-acetamide;
1-(4-methoxyphenyl)carbonyl-4-[6-chloro-2-(1H-imidazol-1-yl)pyrimidin-4-yl]-N-[2-(1,3-benzodioxol-5-yl)ethyl]piperazine-2-acetamide;
1-(4-methoxyphenyl)carbonyl-4-[6-chloro-2-(1H-imidazol-1-yl)pyrimidin-4-yl]-N-[2-(1,3-benzodioxol-5-yl)ethyl]piperazine-2-carboxamide;
1-(4-methoxyphenyl)carbonyl-4-[6-(1H-imidazol-1-yl)pyrimidin-4-yl]-N-[2-(1,3-benzodioxol-5-yl)ethyl]piperazine-2-acetamide;
1-(4-methoxyphenyl)carbonyl-4-[6-methyl-2-(1H-imidazol-1-yl)pyrimidin-4-yl]-N-[(1,4-benzodioxan-6-yl)methyl]piperazine-2-carboxamide;
1-(4-methoxyphenyl)carbonyl-4-[6-methyl-2-(1H-imidazol-1-yl)pyrimidin-4-yl]-N-[(4-methoxyphenyl)methyl]piperazine-2-acetamide;
1-(4-methoxyphenyl)carbonyl-4-[6-chloro-2-(1H-imidazol-1-yl)pyrimidin-4-yl]-N-[(1,4-benzodioxan-2-yl)methyl]piperazine-2-carboxamide;
1-(pyridin-3-yl)carbonyl-4-[6-methyl-2-(1H-imidazol-1-yl)pyrimidin-4-yl]-N-[2-(3,4-dimethoxyphenyl)ethyl]piperazine-2-acetamide;
1-(pyridin-3-yl)carbonyl-4-[6-chloro-2-(1H-imidazol-1-yl)pyrimidin-4-yl]-N-[(1,3-benzodioxol-5-yl)methyl]piperazine-2-carboxamide;
1-(pyridin-3-yl)carbonyl-4-[2-(1H-imidazol-1-yl)pyrimidin-4-yl]-N-[2-(1,3-benzodioxol-5-yl)ethyl]piperazine-2-acetamide;
1-(pyridin-3-yl)carbonyl-4-[6-iso-propyl-2-(1H-imidazol-1-yl)pyrimidin-4-yl]-N-[2-(1,3-benzodioxol-5-yl)ethyl]piperazine-2-acetamide;

1-(pyridin-3-yl)carbonyl-4-[6-chloro-2-(1H-imidazol-1-yl)pyrimidin-4-yl]-N-[(1,4-benzodioxan-6-yl)methyl]piperazine-2-acetamide;

1-(pyridin-3-yl)carbonyl-4-[6-chloro-2-(1H-imidazol-1-yl)pyrimidin-4-yl]-N-[2-(1,4-benzodioxan-6-yl)ethyl]piperazine-2-acetamide;

1-(pyridin-3-yl)carbonyl-4-[6-chloro-2-(1H-imidazol-1-yl)pyrimidin-4-yl]-N-[2-(4-methoxyphenyl)ethyl]piperazine-2-carboxamide;

1-[2-(4-methoxyphenyl)ethyl]-4-[2-(1H-imidazol-1-yl)pyrimidin-4-yl]-N-[2-3-chloro-4-methoxyphenyl)ethyl]piperazine-2-carboxamide;

1-[2-4-methoxyphenyl)ethyl]-4-[6-methyl-2-(1H-imidazol-1-yl)pyrimidin-4-yl]-N-[(1,3-benzodioxol-5-yl)methyl]piperazine-2-carboxamide;

1-[2-4-methoxyphenyl)ethyl]-4-[6-iso-propyl-2-(1H-imidazol-1-yl)pyrimidin-4-yl]-N-[(1,3-benzodioxol-5-yl)methyl]piperazine-2-acetamide;

1-[2-(4-methoxyphenyl)ethyl]-4-[6-chloro-2-(1H-imidazol-1-yl)pyrimidin-4-yl]-N-[(1,3-benzodioxol-5-yl)methyl]piperazine-2-acetamide;

1-[2-(4-methoxyphenyl)ethyl]-4-[2-(1H-imidazol-1-yl)pyrimidin-4-yl]-N-[2-(1,3-benzodioxol-5-yl)ethyl]piperazine-2-carboxamide;

1-[2-(4-methoxyphenyl)ethyl]-4-[6-iso-propyl-2-(1H-imidazol-1-yl)pyrimidin-4-yl]-N-[(1,4-benzodioxan-6-yl)methyl]piperazine-2-acetamide;

1-[2-(4-methoxyphenyl)ethyl]-4-[2-(1H-imidazol-1-yl)pyrimidin-4-yl]-N-[(1,4-benzodioxan-6-yl)methyl]piperazine-2-carboxamide;

1-[2-(4-methoxyphenyl)ethyl]-4-[6-methyl-2-(1H-imidazol-1-yl)pyrimidin-4-yl]-N-[(4-methoxyphenyl)methyl]piperazine-2-carboxamide;

1-[2-(4-methoxyphenyl)ethyl]-4-[6-chloro-2-(1H-imidazol-1-yl)pyrimidin-4-yl]-N-[2-(4-methoxyphenyl)ethyl]piperazine-2-carboxamide;

1-[2-(4-methoxyphenyl)ethyl]-4-[2-(1H-imidazol-1-yl)pyrimidin-4-yl]-N-[(3,4-dimethoxyphenyl)methyl]piperazine-2-carboxamide;

1-[(3,4-dichlorophenyl)methyl]carbonyl-4-[6-iso-propyl-2-(1H-imidazol-1-yl)pyrimidin-4-yl]-N-[2-(3,4-dimethoxyphenyl)ethyl]piperazine-2-acetamide;

1-[(3,4-dichlorophenyl)methyl]carbonyl-4-[6-chloro-2-(1H-imidazol-1-yl)pyrimidin-4-yl]-N-[(4-methylphenyl)methyl]piperazine-2-carboxamide;

1-[(3,4-dichlorophenyl)methyl]carbonyl-4-[6-methyl-2-(1H-imidazol-1-yl)pyrimidin-4-yl]-N-[2-(1,3-benzodioxol-5-yl)ethyl]piperazine-2-acetamide;

1-[(3,4-dichlorophenyl)methyl]carbonyl-4-[6-chloro-2-(1H-imidazol-1-yl)pyrimidin-4-yl]-N-[(3,4,5-trimethoxyphenyl)methyl]piperazine-2 carboxamide;

1-[(3,4-dichlorophenyl)methyl]carbonyl-4-[6-chloro-2-(1H-imidazol-1-yl)pyrimidin-4-yl]-N-[(3,4-dimethoxyphenyl)methyl]piperazine-2-carboxamide;

1-[(1,3-benzodioxol-5-yl)methyl]carbonyl-4-[6-chloro-2-(1H-imidazol-1-yl)pyrimidin-4-yl]-N-[2-(3,4-dimethoxyphenyl)ethyl]piperazine-2-carboxamide;

1-[(1,3-benzodioxol-5-yl)methyl]carbonyl-4-[6-iso-propyl-2-(1H-imidazol-1-yl)pyrimidin-4-yl]-N-[3-(3,4-dimethoxyphenyl)propyl]piperazine-2-carboxamide;

1-[(1,3-benzodioxol-5-yl)methyl]carbonyl-4-[6-iso-propyl-2-(1H-imidazol-1-yl)pyrimidin-4-yl]-N-[3-(3,4-dimethoxyphenyl)propyl]piperazine-2-acetamide;

1-[(1,3-benzodioxol-5-yl)methyl]carbonyl-4-[2-(1H-imidazol-1-yl)pyrimidin-4-yl]-N-[(1,3-benzodioxol-5-yl)methyl]piperazine-2-carboxamide;

1-[(1,3-benzodioxol-5-yl)methyl]carbonyl-4-[6-iso-propyl-2-(1H-imidazol-1-yl)pyrimidin-4-yl]-N-[(1,3-benzodioxol-5-yl)methyl]piperazine-2-carboxamide;

1-[(1,3-benzodioxol-5-yl)methyl]carbonyl-4-[2-(1H-imidazol-1-yl)pyrimidin-4-yl]-N-[2-(1,3-benzodioxol-5-yl)ethyl]piperazine-2-acetamide;

1-[(1,3-benzodioxol-5-yl)methyl]carbonyl-4-[6-(1H-imidazol-1-yl)pyrimidin-4-yl]-N-[2-(1,3-benzodioxol-5-yl)ethyl]piperazine-2-acetamide;

1-[(1,3-benzodioxol-5-yl)methyl]carbonyl-4-[6-(1H-imidazol-1-yl)pyrimidin-4-yl]-N-[2-(1,3-benzodioxol-5-yl)ethyl]piperazine-2-carboxamide;

1-[(1,3-benzodioxol-5-yl)methyl]carbonyl-4-[2-(1H-imidazol-1-yl)pyrimidin-4-yl]-N-[(1,4-benzodioxan-5-yl)methyl]piperazine-2-carboxamide;

1-[(1,3-benzodioxol-5-yl)methyl]carbonyl-4-[6-methyl-2-(1H-imidazol-1-yl)pyrimidin-4-yl]-N-[(4-methoxyphenyl)methyl]piperazine-2carboxamide;

1-[(1,3-benzodioxol-5-yl)methyl]carbonyl-4-[6-iso-propyl-2-(1H-imidazol-1-yl)pyrimidin-4-yl]-N-[(4-methoxyphenyl)methyl]piperazine-2-carboxamide;

1-[(1,3-benzodioxol-5-yl)methyl]carbonyl-4-[6-(1H-imidazol-1-yl)pyrimidin-4-yl]-N-[(4-methoxyphenyl)methyl]piperazine-2-carboxamide;

1-[(1,3-benzodioxol-5-yl)methyl]carbonyl-4-[6-chloro-2-(1H-imidazol-1-yl)pyrimidin-4-yl]-N-(2-phenylcyclopropyl)piperazine-2-carboxamide;

1-methylsulfonyl-4-[2-(1H-imidazol-1-yl)pyrimidin-4-yl]-N-[2-(1,3-benzodioxol-5-yl)ethyl]piperazine-2-carboxamide;

N-[(4-methoxyphenyl)ethyl]-4-[2-(1H-imidazol-1-yl)-6-methylpyrimidin-4-yl]-1-(2-methyl-1-oxopropyl)piperazine-2-acetamide;

N-[(1,3-benzodioxol-5-yl)methyl]-1-[2-(1H-imidazol-1-yl)pyrimidin-4-yl-4-(1-oxopropyl)piperazine-2-acetamide;

N-[(1,3-benzodioxol-5-yl)methyl]-1-2-(1H-imidazol-1-yl)-5-methylpyrimidin-4-yl]-4-(phenylmethyl)piperazine-3-acetamide;

4-[(dimethylethoxy)carbonyl]-1-[2-(1H-imidazol-1-yl)-6-methylpyrimidin-4-yl]-N-[(3-chloro-4-methoxyphenyl)methyl]piperazine-2-acetamide;

4-[(dimethylethoxy)carbonyl]-1-[2-(1H-imidazol-1-yl)-6-methylpyrimidin-4-yl]-N-[(1,3-benzodioxol-5-yl)methyl]piperazine-2-acetamide;

4-[(dimethylethoxy)carbonyl]-1-[2-(1H-imidazol-1-yl)-6-methylpyrimidin-4-yl]-N-[2-(1,3-benzodioxol-5-yl)ethyl]piperazine-2-acetamide;

4-[(dimethylethoxy)carbonyl]-1-[2-(1H-imidazol-1-yl)-6-methylpyrimidin-4-yl]-N-[(1,4-benzodioxan-6-yl)methyl]piperazine-2-acetamide;

4-[(dimethylethoxy)carbonyl]-1-[2-(1H-imidazol-1-yl)-6-methylpyrimidin-4-yl]-N-[2-1,4-benzodioxan-6-yl)ethyl]piperazine-2-acetamide;

4-[(dimethylethoxy)carbonyl]-1-[2-(1H-imidazol-1-yl)-6-methylpyrimidin-4-yl]-N-[(4-methoxyphenyl)methyl]piperazine-2-acetamide;

4-[(dimethylethoxy)carbonyl]-1-[2-(1H-imidazol-1-yl)-6-methylpyrimidin-4-yl]-N-[(3,4-dimethoxyphenyl)methyl]piperazine-2-acetamide;

1-[6-chloro-2-(1H-imidazol-1-yl)pyrimidin-4-yl]-N-[2-(3,4-dimethoxyphenyl)ethyl]-4-methylpiperazine-2-acetamide;

1-[6-chloro-2-(1H-imidazol-1-yl)pyrimidin-4-yl]-N-[(4-ethoxyphenyl)methyl]-4-methylpiperazine-2-acetamide;

1-[6-chloro-2-(1H-imidazol-1-yl)pyrimidin-4-yl]-N-[(4-methylphenyl)ethyl]-4-methylpiperazine-2-acetamide;

1-[6-chloro-2-(1H-imidazol-1-yl)pyrimidin-4-yl]-N-[(4-chlorophenyl)methyl]-4-methylpiperazine-2-acetamide;

1-[2-(1H-imidazol-1-yl)-6-methylpyrimidin-4-yl]-N-[(4-chlorophenyl)methyl]-4-methylpiperazine-2-acetamide;

1-[2-(1H-imidazol-1-yl)-6-methylpyrimidin-4-yl]-N-[(4-chlorophenyl)ethyl]-4-methylpiperazine-2-acetamide;

1-[6-chloro-2-(1H-imidazol-1-yl)pyrimidin-4-yl]-N-[(3-chloro-4-methoxyphenyl)methyl]-4-methylpiperazine-2-acetamide;

1-[2-(1H-imidazol-1-yl)pyrimidin-4-yl]-N-[(3-chloro-4-methoxyphenyl)ethyl]-4-methylpiperazine-2-carboxamide;

1-[6-chloro-2-(1H-imidazol-1-yl)pyrimidin-4-yl]-N-[2-(3,4-dimethoxyphenyl)ethyl]-4-methylpiperazine-2-carboxamide;

1-[6-chloro-2-(1H-imidazol-1-yl)pyrimidin-4-yl]-N-[(3,5-dimethoxyphenyl)ethyl]-4-methylpiperazine-2-acetamide;

1-[2-(1H-imidazol-1-yl)-6-methylpyrimidin-4-yl]-N-[2-(1,3-benzodioxol-5-yl)ethyl]-4-methylpiperazine-2-acetamide;

1-[6-chloro-2-(1H-imidazol-1-yl)pyrimidin-4-yl]-N-[(1,4-benzodioxan-6-yl))methyl]-4-methylpiperazine-2-acetamide;

1-[2-(1H-imidazol-1-yl)-6-methylpyrimidin-4-yl]-N-[(1,4-benzodioxan-6-yl))methyl]-4-methylpiperazine-2-carboxamide;

1-[2-(1H-imidazol-1-yl)-6-methylpyrimidin-4-yl]-N-[2-(1,4-benzodioxan-6-yl)ethyl]-4-methylpiperazine-2-acetamide;

1-[6-chloro-2-(1H-imidazol-1-yl)pyrimidin-4-yl]-N-[(4-methoxyphenyl)methyl]-4-methylpiperazine-2-acetamide;

1-[6-chloro-2-(1H-imidazol-1-yl)pyrimidin-4-yl]-N-[(3-methoxyphenyl)methyl]-4-methylpiperazine-2-acetamide;

1-[2-(1H-imidazol-1-yl)pyrimidin-4-yl]-N-[(2-methoxyphenyl))methyl-4-methylpiperazine-2-carboxamide;

1-[6-chloro-2-(1H-imidazol-1-yl)pyrimidin-4-yl]-N-[(3-methoxyphenyl)ethyl]-4-methylpiperazine-2-acetamide;

1-[2-(1H-imidazol-1-yl)-6-trifluoromethylpyrimidin-4-yl]-N-[[4-(2-methoxyethoxy)phenyl))methyl]-4-methylpiperazine-2-carboxamide;

1-[2-(1H-imidazol-1-yl)-6-methylpyrimidin-4-yl]-N-[(3,4-dimethoxyphenyl)methyl]-4-methylpiperazine-2-acetamide;

1-[2-(1H-imidazol-1-yl)pyrimidin-4-yl]-N-[(3,4-dimethoxyphenyl)methyl]-4-methylpiperazine-2-acetamide;

1-[6-(1H-imidazol-1-yl)pyrimidin-4-yl]-N-[(cyclopropyl)methyl]-4-methylpiperazine-2-acetamide;

1-[6-chloro-2-(1H-imidazol-1-yl)pyrimidin-4-yl]-N-[(indan-5-yl)methyl]-4-methylpiperazine-2-acetamide;

1-[2-(1H-imidazol-1-yl)-6-methylpyrimidin-4-yl]-N-(4-ethoxyphenyl)methyl]-4-butylpiperazine-2-acetamide;

1-[6-chloro-2-(1H-imidazol-1-yl)pyrimidin-4-yl]-N-[(4-methylphenyl)methyl]-4-butylpiperazine-2-acetamide;

1-[6-chloro-2-(1H-imidazol-1-yl)pyrimidin-4-yl]-N-[(3-chloro-4-methoxyphenyl)methyl]-4-butylpiperazine-2-acetamide;

1-[2-(1H-imidazol-1-yl)-6-methylethylpyrimidin-4-yl]-N-[(3-chloro-4-methoxyphenyl)methyl]-4-butylpiperazine-2-acetamide;

1-[6-chloro-2-(1H-imidazol-1-yl)pyrimidin-4-yl]-N-[(1,3-benzodioxol-5-yl)methyl]-4-butylpiperazine-2-acetamide;

1-[2-(1H-imidazol-1-yl)-6-methylethylpyrimidin-4-yl]-N-[(1,3-benzodioxol-5-yl)methyl]-4-butylpiperazine-2-acetamide;

1-[2-(1H-imidazol-1-yl)-6-methylpyrimidin-4-yl]-N-[2-(1,3-benzodioxol-5-yl)ethyl]-4-butylpiperazine-2-acetamide;

1-[6-chloro-2-(1H-imidazol-1-yl)pyrimidin-4-yl]-N-[2-(1,3-benzodioxol-5-yl)ethyl]-4-butylpiperazine-2-carboxamide;

1-[2-(1H-imidazol-1-yl)pyrimidin-4-yl]-N-[2-(1,3-benzodioxol-5-yl)ethyl]-4-butylpiperazine-2-acetamide;

1-[6-chloro-2-(1H-imidazol-1-yl)pyrimidin-4-yl]-N-[2-(1,4-benzodioxan-6-yl)ethyl]-4-butylpiperazine-2-acetamide;

1-[2-(1H-imidazol-1-yl)-6-methylpyrimidin-4-yl]-N-[2-(1,4-benzodioxan-6-yl)ethyl]-4-butylpiperazine-2-acetamide;

1-[2-(1H-imidazol-1-yl)pyrimidin-4-yl]-N-[1,4-benzodioxan-6-yl)ethyl]-4-butylpiperazine-2-acetamide;

1-[6-chloro-2-(1H-imidazol-1-yl)pyrimidin-4-yl]-N-[2-1,4-benzodioxan-6-yl)ethyl]-4-butylpiperazine-2-acetamide;

1-[2-(1H-imidazol-1-yl)-6-(methylethyl)pyrimidin-4-yl]-N-(4-methoxyphenyl)methyl]-4-butylpiperazine-2-acetamide;

1-[6-chloro-2-(1H-imidazol-1-yl)pyrimidin-4-yl]-N-[(4-methoxyphenyl)methyl]-4-butylpiperazine-2-acetamide;

1-[2-(1H-imidazol-1-yl)-6-methylpyrimidin-4-yl]-N-[(4-methoxyphenyl)methyl]-4-butylpiperazine-2-acetamide;

1-[2-(1H-imidazol-1-yl)pyrimidin-4-yl]-N-[(4-methoxyphenyl)methyl]-4-butylpiperazine-2-acetamide;

1-[2-(1H-imidazol-1-yl)pyrimidin-4-yl]-N-[(3,4-dimethoxyphenyl)methyl]-4-butylpiperazine-2-acetamide;

1-[6-chloro-2-(1H-imidazol-1-yl)pyrimidin-4-yl]-N-[(4-methylphenyl)methyl]-4-[(4-methoxyphenyl)methyl]piperazine-2-acetamide;

1-[6-chloro-2-(1H-imidazol-1-yl)pyrimidin-4-yl]-N-[(4-chlorophenyl)methyl]-4-[(4-methoxyphenyl)methyl]piperazine-2-acetamide;

1-[6-chloro-2-(1H-imidazol-1-yl)pyrimidin-4-yl]-N-[(3-chloro-4-methoxyphenyl)methyl]-4-[(4-methoxyphenyl)methyl]piperazine-2-acetamide;

1-[6-chloro-2-(1H-imidazol-1-yl)pyrimidin-4-yl]-N-[(3-chloro-4-methoxyphenyl)ethyl]-4-[(4-methoxyphenyl)methyl]piperazine-2-acetamide;

1-[2-(1H-imidazol-1-yl)pyrimidin-4-yl]-N-[(1,3-benzodioxol-5-yl)methyl]-4-[(4-methoxyphenyl)methyl]piperazine-2-acetamide;

1-[2-(1H-imidazol-1-yl)-6-methylpyrimidin-4-yl]-N-[2-(1,3-benzodioxol-5-yl)ethyl]-4-[(4-methoxyphenyl)methyl]piperazine-2-acetamide;

1-[6-chloro-2-(1H-imidazol-1-yl)pyrimidin-4-yl]-N-[2-(1,3-benzodioxol-5-yl)ethyl]-4-[(4-methoxyphenyl)methyl]piperazine-2-acetamide;

1-[6-chloro-2-(1H-imidazol-1-yl)pyrimidin-4-yl]-N-[(1,4-benzodioxan-6-yl)ethyl]-4-[(4-methoxyphenyl)methyl]piperazine-2-acetamide;

1-[2-(1H-imidazol-1-yl)-6-(methylethyl)pyrimidin-4-yl]-N-[(1,4-benzodioxan-yl)methyl]-4-[(4-methoxyphenyl)methyl]piperazine-2-acetamide;

1-[2-(1H-imidazol-1-yl)pyrimidin-4-yl]-N-[2-(1,4-benzodioxan-6-yl)ethyl]-4-[(4-methoxyphenyl)methyl]piperazine-2-acetamide;

1-[6-chloro-2-(1H-imidazol-1-yl)pyrimidin-4-yl]-N-[2-(1,4-benzodioxan-6-yl)ethyl]-4-[(4-methoxyphenyl)methyl]piperazine-2-acetamide;

1-[2-(1H-imidazol-1-yl)pyrimidin-4-yl]-N-[2-(1,4-benzodioxan-6-yl)ethyl]-4-[(4-methoxyphenyl)methyl]piperazine-2-acetamide;

1-[2-(1H-imidazol-1-yl)-6-(methylethyl)pyrimidin-4-yl]-N-[(4-methoxyphenyl)methyl]-4-[(4-methoxyphenyl)methyl]piperazine-2-acetamide;

1-[2-(1H-imidazol-1-yl)-6-trifluoromethylpyrimidin-4-yl]-N-(2-phenylcyclopropyl)-4-[(4-methoxyphenyl)methyl]piperazine-2-acetamide;

1-[2-(1H-imidazol-1-yl)-6-methylpyrimidin-4-yl]-N-[(3,4-dimethoxyphenyl)methyl]-4-[(4-methoxyphenyl)methyl]piperazine-2-acetamide;

1-[6-chloro-2-(1H-imidazol-1-yl)pyrimidin-4-yl]-N-[(4-methylphenyl)methyl]-4-[(3,4-dichlorphenyl)methyl]piperazine-2-acetamide;

1-[2-(1H-imidazol-1-yl)-6-methylpyrimidin-4-yl]-N-[(1,3-benzodioxol-5-yl)methyl]-4-[(3,4-dichlorphenyl)methyl]piperazine-2-acetamide;

1-[6-chloro-2-(1H-imidazol-1-yl)pyrimidin-4-yl]-N-[2-1,3-benzodioxol-5-yl)ethyl]-4-[(3,4-dichlorphenyl)methyl]piperazine-2-acetamide;

1-[6-chloro-2-(1H-imidazol-1-yl)pyrimidin-4-yl]-N-[(1,4-benzodioxan-6-yl)methyl]-4-[(3,4-dichlorphenyl)methyl]piperazine-2-acetamide;

1-[2-(1H-imidazol-1-yl)-6-methylpyrimidin-4-yl]-N-[(1,4-benzodioxan-6-yl)methyl]-4-[(3,4-dichlorphenyl)methyl]piperazine-2-acetamide;

1-[2-(1H-imidazol-1-yl)pyrimidin-4-yl]-N-[2-(1,4-benzodioxan-6-yl)ethyl]-4-[(3,4-dichlorphenyl)methyl]piperazine-2-acetamide;

1-[6-chloro-2-(1H-imidazol-1-yl)pyrimidin-4-yl]-N-[(4-methoxyphenyl)ethyl]-4-[(3,4-dichlorphenyl)methyl]piperazine-2-acetamide;

1-[6-chloro-2-(1H-imidazol-1-yl)pyrimidin-4-yl]-N-[(4-chloroxyphenyl)methyl]-4-[(1,3-benzodioxol-5-yl)methyl]piperazine-2-acetamide;

1-[2-(1H-imidazol-1-yl)pyrimidin-4-yl]-N-[(-[(1,3-benzodioxol-5-yl)methyl]-4-[(1,3-benzodioxol-5-yl)methyl]piperazine-2-acetamide;

1-[6-chloro-2-(1H-imidazol-1-yl)pyrimidin-4-yl]-N-[(-[(1,3-benzodioxol-5-yl)methyl]-4-[(1,3-benzodioxol-5-yl)methyl]piperazine-2-acetamide;

1-[2-(1H-imidazol-1-yl)pyrimidin-4-yl]-N-[(-[2-(1,3-benzodioxol-5-yl)ethyl]-4-[(1,3-benzodioxol-5-yl)methyl]piperazine-2-acetamide;

1-[2-(1H-imidazol-1-yl)-6-methylpyrimidin-4-yl]-N-[2-(1,3-benzodioxol-5-yl)ethyl]-4-[(1,3-benzodioxol-5-yl)methyl]piperazine-2-acetamide;

1-[6-chloro-2-(1H-imidazol-1-yl)pyrimidin-4-yl]-N-[(1,4-benzodioxan-6-yl)methyl]-4-[(1,3-benzodioxol-5-yl)methyl]piperazine-2-acetamide;

1-[2-(1H-imidazol-1-yl)-6-methylpyrimidin-4-yl]-N-[(1,4-benzodioxan-6-yl)methyl]-4-[(1,3-benzodioxol-5-yl)methyl]piperazine-2-acetamide;

1-[2-(1H-imidazol-1-yl)pyrimidin-4-yl]-N-[(1,4-benzodioxan-6-yl)methyl]-4-[(1,3-benzodioxol-5-yl)methyl]piperazine-2-acetamide;

1-[6-chloro-2-(1H-imidazol-1-yl)pyrimidin-4-yl]-N-[2-(1,4-benzodioxan-6-yl)ethyl]-4-[(1,3-benzodioxol-5-yl)methyl]piperazine-2-acetamide;

1-[2-(1H-imidazol-1-yl)pyrimidin-4-yl]-N-[2-(1,4-benzodioxan-6-yl)ethyl]-4-[(1,3-benzodioxol-5-yl)methyl]piperazine-2-acetamide;

1-[2-(1H-imidazol-1-yl)-6-methylpyrimidin-4-yl]-N-[2-(1,4-benzodioxan-6-yl)ethyl]-4-[(1,3-benzodioxol-5-yl)methyl]piperazine-2-acetamide;

1-[2-(1H-imidazol-1-yl)pyrimidin-4-yl]-N-[(3,4-dimethoxyphenyl)methyl]-4-[(1,3-benzodioxol-5-yl)methyl]piperazine-2-acetamide;

1-[2-(1H-imidazol-1-yl)-6-(methylethyl)pyrimidin-4-yl]-N-[(4-methylphenyl)methyl]-4-[(1,4-benzodioxan-6-yl)methyl]piperazine-2-acetamide; 1-[6-chloro-2-(1H-imidazol-1-yl)pyrimidin-4-yl]-N-[(4-methylphenyl)methyl]-4-[(1,4-benzodioxan-6-yl)methyl]piperazine-2-acetamide;

1-[6-(1H-imidazol-1-yl)pyrimidin-4-yl]-N-[(3-chloro-4-methoxyphenyl)ethyl]-4-[(1,4-benzodioxan-6-yl)methyl]piperazine-2-acetamide;

1-[2-(1H-imidazol-1-yl)-6-methylpyrimidin-4-yl]-N-[(3,5-dimethoxyphenyl)methyl]-4-[(1,4-benzodioxan-6-yl)methyl]piperazine-2-acetamide;

1-[2-(1H-imidazol-1-yl)-6-methylpyrimidin-4-yl]-N-[(1,3-benzodioxol-5-yl)methyl]-4-(1,4-benzodioxan-6-yl)methylpiperazine-2-acetamide;

1-[6-chloro-2-(1H-imidazol-1-yl)pyrimidin-4-yl]-N-[(1,-benzodioxan-6-yl)methyl]-4-[(1,4-benzodioxan-6-yl)methyl]piperazine-2-acetamide;

1-[2-(1H-imidazol-1-yl)-6-methylpyrimidin-4-yl]-N-[(4-methoxyphenyl)methyl]-4-[(1,4-benzodioxan-4-yl)methyl]piperazine-2-acetamide;

1-[6-(1H-imidazol-1-yl)pyrimidin-4-yl]-N-[(4-methoxyphenyl)methyl]-4-[(1,4-benzodioxan-6-yl)methyl]piperazine-2-acetamide;

1-[2-(1H-imidazol-1-yl)-6-methylpyrimidin-4-yl]-N-[(3-methoxyphenyl)ethyl]-4-[(1,4-benzodioxan-6-yl)methyl]piperazine-2-carboxamide;

1-[2-(1H-imidazol-1-yl)pyrimidin-4-yl]-N-[(2-thiophenyl)ethyl]-4-[(1,4-benzodioxan-6-yl)methyl]piperazine-2-acetamide;

1-[2-(1H-imidazol-1-yl)-6-trifluoromethylpyrimidin-4-yl]-N-[(3,5-dimethoxyphenyl)methyl]-4-[(1,4-benzodioxan-6-yl)methyl]piperazine-2-carboxamide;

1-[2-(1H-imidazol-1-yl)-6-methylpyrimidin-4-yl]-N-[(1-adamantyl)methyl]-4-[(1,4-benzodioxan-6-yl)methyl]piperazine-2-carboxamide;

1-[2-(1H-imidazol-1-yl)pyrimidin-4-yl]-N-[(5-indanyl)methyl]-4-[(1,4-benzodioxan-6-yl)methyl]piperazine-2-acetamide;

1-[6-chloro-2-(1H-imidazol-1-yl)pyrimidin-4-yl]-N-[2-(3,4-dimethoxyphenyl)ethyl]-4-(pyridin-3-yl)methyl]piperazine-2-acetamide;

1-[2-(1H-imidazol-1-yl)-6-methylethyl)pyrimidin-4-yl]-N-[(3,4-dimethoxyphenyl)propyl]-4-[(pyridin-3-yl)methyl]piperazine-2-acetamide;

1-[6-chloro-2-(1H-imidazol-1-yl)pyrimidin-4-yl]-N-(4-ethoxyphenyl)methyl]-4-[(pyridin-3-yl)methyl]piperazine-2-acetamide;

1-[2-(1H-imidazol-1-yl)-6-methylpyrimidin-4-yl]-N-[(4-ethoxyphenyl)methyl]-4-[(pyridin-3-yl)methyl]piperazine-2-acetamide;

1-[6-chloro-2-(1H-imidazol-1-yl)pyrimidin-4-yl]-N-[(4-methylphenoxy)ethyl]-4-[(pyridin-3-yl)methyl]piperazine-2-acetamide;

1-[6-chloro-2-(1H-imidazol-1-yl)pyrimidin-4-yl]-N-[(4-methylphenyl)methyl]-4-[(pyridin-3-yl)methyl]piperazine-2-acetamide;

1-[6-chloro-2-(1H-imidazol-1-yl)pyrimidin-4-yl]-N-[(3-chloro-4-methoxyphenyl)methyl]-4-[(pyridin-3-yl)methyl]piperazine-2-acetamide;

1-[2-(1H-imidazol-1-yl)-6-methylpyrimidin-4-yl]-N-[(1,3-benzodioxol-5-yl)methyl]-4-[(pyridin-3-yl)methyl]piperazine-2-acetamide;

1-[6-chloro-2-(1H-imidazol-1-yl)pyrimidin-4-yl]-N-[(1,3-benzodioxol-5-yl)methyl]-4-[(pyridin-3-yl)methyl]piperazine-2-acetamide;

1-[6-chloro-2-(1H-imidazol-1-yl)pyrimidin-4-yl]-N-[2-(1,3-benzodioxol-5-yl)ethyl]-4-[(pyridin-3-yl)methyl]piperazine-2-acetamide;

1-[2-(1H-imidazol-1-yl)-6-methylpyrimidin-4-yl]-N-[(1,4-benzodioxan-6-yl)methyl]-4-[(pyridin-3-yl)methyl]piperazine-2-acetamide;

1-[2-(1H-imidazol-1-yl)-6-(methylethyl)pyrimidin-4-yl]-N-[(1,4-benzodioxan-6-yl)methyl]-4-(pyridin-3-yl)methyl]piperazine-2-acetamide;

1-[6-chloro-2-(1H-imidazol-1-yl)pyrimidin-4-yl]-N-[(1,4-benzodioxan-6-yl)methyl]-4-[(pyridin-3-yl)methyl]piperazine-2-acetamide;

1-[2-(1H-imidazol-1-yl)pyrimidin-4-yl]-N-[(1,4-benzodioxan-6-yl)methyl]-4-[(pyridin-3-yl)methyl]piperazine-2-acetamide;

1-[2-(1H-imidazol-1-yl)-6-methylpyrimidin-4-yl]-N-[(1,4benzodioxan-6-yl)methyl]-4-[(pyridin-3-yl)methyl]piperazine-2-acetamide;

1-[6-chloro-2-(1H-imidazol-1-yl)pyrimidin-4-yl]-N-[(4-methoxyphenyl)methyl]-4-[(pyridin-3-yl)methyl]piperazine-2-acetamide;

1-[2-(1H-imidazol-1-yl)-6-methylpyrimidin-4-yl]-N-[(4-methoxyphenyl)methyl]-4-[(pyridin-3-yl)methyl]piperazine-2-acetamide;

1-[6-chloro-2-(1H-imidazol-1-yl)pyrimidin-4-yl]-N-[(3-methoxyphenyl)methyl]-4-[(pyridin-3-yl)methyl]piperazine-2-acetamide;

1-[6-chloro-2-(1H-imidazol-1-yl)pyrimidin-4-yl]-N-[(4-methoxyphenyl)ethyl]-4-[(pyridin-3-yl)methyl]piperazine-2-acetamide;

1-[2-(1H-imidazol-1-yl)-6-(methylethyl)pyrimidin-4-yl]-N-[(2,6-dimethoxyphenyl)methyl]-4-[(pyridin-3-yl)methyl]piperazine-2-carboxamide;

1-[2-(1H-imidazol-1-yl)-6-(methylethyl)pyrimidin-4-yl]-N-[(3,4-dimethoxyphenyl)methyl]-4-[-pyridin-3-yl)methyl]piperazine-2-acetamide;

1-[2-(1H-imidazol-1-yl)pyrimidin-4-yl]-N-[(cyclopropyl)methyl]-4-[(pyridin-3-yl)methyl]piperazine-2-carboxamide;

1-[2-(1H-imidazol-1-yl)-6-methylpyrimidin-4-yl]-N-[(1,3-benzodioxol-5-yl)methyl]-4-[(3-fluoro-4-methoxyphenyl)methyl]piperazine-2-acetamide;

1-[6-chloro-2-(1H-imidazol-1-yl)pyrimidin-4-yl]-N-[2-(1,3-benzodioxol-5-yl)ethyl]-4-[(3-fluoro-4-methoxyphenyl)methyl]piperazine-2-acetamide;

1-[2-(1H-imidazol-1-yl)pyrimidin-4-yl]-N-[2-(1,3-benzodioxol-5-yl)ethyl]-4-[(3-fluoro-4-methoxyphenyl)methyl]piperazine-2-acetamide;

1-[2-(1H-imidazol-1-yl)-6-methylpyrimidin-4-yl]-N-[(1,4-benzodioxan-6-yl)methyl]-4-[(3-fluoro-4-methoxyphenyl)methyl]piperazine-2-acetamide;

1-[2-(1H-imidazol-1-yl)pyrimidin-4-yl]-N-[2-(1,4-benzodioxan-6-yl)ethyl]-4-[(3-fluoro-4-methoxyphenyl)methyl]piperazine-2-acetamide;

1-[2-(1H-imidazol-1-yl)pyrimidin-4-yl]-N-[(4-methoxyphenyl)ethyl]-4-[(3-fluoro-4-methoxyphenyl)methyl]piperazine-2-acetamide;

1-[2-(1H-imidazol-1-yl)-6-methylpyrimidin-4-yl]-N-[(4-methoxyphenyl)ethyl]-4-[(3-fluoro-4-methoxyphenyl)methyl]piperazine-2-acetamide;

1-[2-(1H-imidazol-1-yl)pyrimidin-4-yl]-N-[(3,4-dimethoxyphenyl)methyl]-4-[(3-fluoro-4-methoxyphenyl)methyl]piperazine-2-acetamide;

1-[2-(1H-imidazol-1-yl)pyrimidin-4-yl]-N-[(1-adamantyl)methyl]-4-[(3-fluoro-4-methoxyphenyl)methyl]piperazine-2-acetamide;

1-[6-chloro-2-(1H-imidazol-1-yl)pyrimidin-4-yl]-N-[(cyclopropyl)methyl]-4-[(3-fluoro-4-methoxyphenyl)methyl]piperazine-2-acetamide;

1-[6-chloro-2-(1H-imidazol-1-yl)pyrimidin-4-yl]-N-[2-(3,4-dimethoxyphenyl)ethyl]-4-acetylpiperazine-2-acetamide;

1-[2-(1H-imidazol-1-yl)-6-methylpyrimidin-4-yl]-N-[2-(3,4-dimethoxyphenyl)ethyl]-4-acetylpiperazine-2-acetamide;

1-[6-chloro-2-(1H-imidazol-1-yl)pyrimidin-4-yl]-N-[(4-ethoxyphenyl)methyl]-4-acetylpiperazine-2-acetamide;

1-[2-(1H-imidazol-1-yl)-6-methylpyrimidin-4-yl]-N-[(4-ethoxyphenyl)methyl]-4-acetylpiperazine-2-acetamide;

1-[6-chloro-2-(1H-imidazol-1-yl)pyrimidin-4-yl]-N-[(4-methylphenyl)methyl]-4-acetylpiperazine-2-acetamide;

1-[2-(1H-imidazol-1-yl)-6-(methylethyl)pyrimidin-4-yl]-N-[(4-methylphenyl)methyl]-4-acetylpiperazine-2-acetamide;

1-[2-(1H-imidazol-1-yl)pyrimidin-4-yl)-N-[(4-methylphenyl)methyl]-4-acetylpiperazine-2-acetamide;

1-[6-chloro-2-(1H-imidazol-1-yl)pyrimidin-4-yl]-N-[(4-chlorophenyl)ethyl]-4-acetylpiperazine-2-acetamide;

1-[6-chloro-2-(1H-imidazol-1-yl)pyrimidin-4-yl]-N-[(4-methoxy-3-chlorophenyl)methyl]-4-acetylpiperazine-2-acetamide;

1-[2-(1H-imidazol-1-yl)-6-methylpyrimidin-4-yl]-N-[(4-methoxy-3-chlorophenyl)methyl]-4-acetylpiperazine-2-acetamide;

1-[2-(1H-imidazol-1-yl)-(methylethyl)pyrimidin-4-yl]-N-[(4-methoxy-3-chlorophenyl)methyl]-4-acetylpiperazine-2-acetamide;

1-[2-(1H-imidazol-1-yl)pyrimidin-4-yl]-N-[(4-methoxy-3-chlorophenyl)methyl]-4-acetylpiperazine-2-acetamide;

1-[6-chloro-2-(1H-imidazol-1-yl)pyrimidin-4-yl]-N-[(4-methoxy-3-chlorophenyl)ethyl]-4-acetylpiperazine-2-acetamide;

1-[2-(1H-imidazol-1-yl)-6-(methylethyl)pyrimidin-4-yl]-N-[(3,5-dimethoxyphenyl)ethyl]-4-acetylpiperazine-2-carboxamide;

1-[2-(1H-imidazol-1-yl)pyrimidin-4-yl]-N-[(1,3-benzodioxol-5-yl)methyl]-4-acetylpiperazine-2-acetamide;

1-[6-chloro-2-(1H-imidazol-1-yl)pyrimidin-4-yl]-N-[2-(1,3-benzodioxol-5-yl)ethyl]-4-acetylpiperazine-2-acetamide;

1-[2-(1H-imidazol-1-yl)-6-(methylethyl)pyrimidin-4-yl]-N-[2-(1,3-benzodioxol-5-yl)ethyl]-4-acetylpiperazine-2-acetamide;

1-[6-chloro-2-(1H-imidazol-1-yl)pyrimidin-4-yl]-N-[(3,4,5-trimethoxyphenyl)methyl)-4-acetylpiperazine-2-acetamide;

1-[6-chloro-2-(1H-imidazol-1-yl)pyrimidin-4-yl]-N-[(1,4-benzodioxan-6-yl)methyl]-4-acetylpiperazine-2-acetamide;

1-[6-chloro-2-(1H-imidazol-1-yl)pyrimidin-4-yl]-N-[2-(1,4-benzodioxan-yl)ethyl]-4-acetylpiperazine-2-acetamide;

1-[2-(1H-imidazol-1-yl)-6-methylpyrimidin-4-yl]-N-[2-(1,4-benzodioxanyl)ethyl]-4-acetylpiperazine-2-acetamide;

1-[6-(1H-imidazol-1-yl)pyrimidin-4-yl]-N-[2-(1,4-benzodioxan-6-yl)ethyl]-4-acetylpiperazine-2-acetamide;

1-[2-(1H-imidazol-1-yl)-6-(methylethyl)pyrimidin-4-yl]-N-[(4-methoxyphenyl)methyl]-4-acetylpiperazine-2-acetamide;

1-[6-chloro-2-(1H-imidazol-1-yl)pyrimidin-4-yl]-N-[(4-methoxyphenyl)methyl]-4-acetylpiperazine-2-acetamide;

1-[2-(1H-imidazol-1-yl)pyrimidin-4-yl]-N-[(4-methoxyphenyl)methyl-4-acetylpiperazine-2-acetamide;

1-[2-(1H-imidazol-1-yl)-6-(methylethyl)pyrimidin-4-yl]-N-[(3-methoxyphenyl)methyl-4-acetylpiperazine-2-acetamide;

1-[6-chloro-2-(1H-imidazol-1-yl)pyrimidin-4-yl]-N-[(3-methoxyphenyl)methyl]-4-acetylpiperazine-2-acetamide;

1-[2-(1H-imidazol-1-yl)-methylpyrimidin-4-yl]-N-[(4-methoxyphenyl)ethyl]-4-acetylpiperazine-2-acetamide;

1-[6-chloro-2-(1H-imidazol-1-yl)pyrimidin-4-yl]-N-[(3-methoxyphenyl)ethyl]-4-acetylpiperazine-2-acetamide;

1-[6-chloro-2-(1H-imidazol-1-yl)pyrimidin-4-yl]-N-[(3,4-difluoroxyphenyl)ethyl]-4-acetylpiperazine-2-acetamide;

1-[6-chloro-2-(1H-imidazol-1-yl)pyrimidin-4-yl]-N-[(1,4-benzodioxan-2-yl)methyl]-4-acetylpiperazine-2-acetamide;

1-[6-chloro-2-(1H-imidazol-1-yl)pyrimidin-4-yl]-N-(2-phenylcyclopropyl)-4-acetylpiperazine-2-acetamide;
1-[6-(1H-imidazol-1-yl)pyrimidin-4-yl]-N-[(3,4-dimethoxyphenyl)methyl]-4-acetylpiperazine-2-acetamide;
1-[2-(1H-imidazol-1-yl)-6-methylpyrimidin-4-yl]-N-[(3,4-dimethoxyphenyl)methyl]-4-acetylpiperazine-2-acetamide;
1-[6-chloro-2-(1H-imidazol-1-yl)pyrimidin-4-yl]-N-(cyclopropyl)-4-acetylpiperazine-2-acetamide;
1-[6-chloro-2-(1H-imidazol-1-yl)pyrimidin-4-yl]-N-[(indan-5-yl)methyl]-4-acetylpiperazine-2-acetamide;
1-[6-chloro-2-(1H-imidazol-1-yl)pyrimidin-4-yl]-N-[2-(3,4-dimethoxyphenyl)ethyl]-4-(3-methyl-1-oxobutyl)piperazine-2-acetamide;
1-[6-chloro-2-(1H-imidazol-1-yl)pyrimidin-4-yl]-N-[(4-methoxyphenyl)methyl]-4-(3-methyl-1-oxobutyl)piperazine-2-acetamide;
1-[6-chloro-2-(1H-imidazol-1-yl)pyrimidin-4-yl]-N-[(4-methylphenyl)methyl]-4-(3-methyl-1-oxobutyl)piperazine-2-acetamide;
1-[6-chloro-2-(1H-imidazol-1-yl)pyrimidin-4-yl]-N-[(4-chlorophenyl)methyl]-4-(3-methyl-1-oxobutyl)piperazine-2-acetamide;
1-[6-(1H-imidazol-1-yl)pyrimidin-4-yl]-N-[(4-chlorophenyl)ethyl]-4-(3-methyl-1-oxobutyl)piperazine-2-acetamide;
1-[6-chloro-2-(1H-imidazol-1-yl)pyrimidin-4-yl]-N-[(4-chlorophenyl)ethyl]-4-(3-methyl-1-oxobutyl)piperazine-2-acetamide;
1-[6-chloro-2-(1H-imidazol-1-yl)pyrimidin-4-yl]-N-[(4-methoxy-3-chlorophenyl)methyl]-4-(3-methyl-1-oxobutyl)piperazine-2-acetamide;
1-[2-(1H-imidazol-1-yl)-6-methylpyrimidin-4-yl]-N-[(4-methoxy-3-chlorophenyl)ethyl]-4-(3-methyl-1-oxobutyl)piperazine-2-acetamide;
1-6-chloro-2-(1H-imidazol-1-yl)pyrimidin-4-yl-N-[(4-methoxy-3-chlorophenyl)ethyl]-4-(3methyl-1-oxobutyl)piperazine-2-acetamide;
1-[6-chloro-2-(1H-imidazol-1-yl)pyrimidin-4-yl]-N-[(1,3-benzodioxol-5-yl)methyl]-4-(3-methyl-1-oxobutyl)piperazine-2-acetamide;
1-[6-(1H-imidazol-1-yl)pyrimidin-4-yl]-N-[(1,3-benzodioxol-5-yl)methyl]-4-(3-methyl-1-oxobutyl)piperazine-2-acetamide;
1-[2-(1H-imidazol-1-yl)-6-methylethyl)pyrimidin-4-yl]-N-[(1,3-benzodioxol-5-yl)methyl]-4-(3-methyl-1-oxobutyl)piperazine-2-carboxamide;
1-[6-(1H-imidazol-1-yl)pyrimidin-4-yl]-N-[2-(1,3-benzodioxol-5-yl)ethyl]-4-(3-methyl-1-oxobutyl)piperazine-2-acetamide;
1-[2-(1H-imidazol-1-yl)pyrimidin-4-yl]-N-[2-(1,3-benzodioxol-5-yl)ethyl]-4-(3-methyl-1 oxobutyl)piperazine-2-acetamide;
1-[6-chloro-2-(1H-imidazol-1-yl)pyrimidin-4-yl]-N-[2-(1,3-benzodioxol-5-yl)ethyl]-4-(3-methyl-1-oxobutyl)piperazine-2-acetamide;
1-[2-(1H-imidazol-1-yl)pyrimidin-4-yl]-N-[2-(1,3-benzodioxol-5-yl)ethyl]-4-(3methyl-1-oxobutyl)piperazine-2-acetamide;
1-[6-chloro-2-(1H-imidazol-1-yl)pyrimidin-4-yl]-N-[(1,4-benzodioxan-yl)methyl]-4-(3-methyl-1-oxobutyl)piperazine-2-acetamide;
1-[6-chloro-2-(1H-imidazol-1-yl)pyrimidin-4-yl]-N-[2-(1,4-benzodioxan-6-yl)ethyl]-4-(3-methyl-1-oxobutyl)piperazine-2-acetamide;
1-[6-chloro-2-(1H-imidazol-1-yl)pyrimidin-4-yl]-N-[(4-methoxyphenyl)methyl]-4-(3-methyl-1-oxobutyl)piperazine-2-acetamide;
1-[2-(1H-imidazol-1-yl)-6-methylpyrimidin-4-yl]-N-[(4-methoxyphenyl)methyl]-4-(3-methyl-1-oxobutyl)piperazine-2-acetamide;
1-[6-chloro-2-(1H-imidazol-1-yl)pyrimidin-4-yl]-N-[(3-methoxyphenyl)methyl]-4-(3-methyl-1-oxobutyl)piperazine-2-acetamide;
1-[6-chloro-2-(1H-imidazol-1-yl)pyrimidin-4-yl]-N-[(4-methoxyphenyl)ethyl]-4-(3-methyl-1-oxobutyl)piperazine-2-acetamide;
1-[6-chloro-2-(1H-imidazol-1-yl)pyrimidin-4-yl]-N-[(3-methoxyphenyl)ethyl]-4-(3-methyl-1-oxobutyl)piperazine-2-acetamide;
1-[6-chloro-2-(1H-imidazol-1-yl)pyrimidin-4-yl]-N-[(2-thienyl)ethyl]-4-(3-methyl-1-oxobutyl)piperazine-2-acetamide;
1-[2-(1H-imidazol-1-yl)pyrimidin-4-yl]-N-[[4-(2-methoxyethoxy)phenyl]ethyl]-4-(3-methyl-1-oxobutyl)piperazine-2-carboxamide;
1-[6-chloro-2-(1H-imidazol-1-yl)pyrimidin-4-yl]-N-[(1,4-benzodioxan-2-yl)ethyl]-4-(3-methyl-1-oxobutyl)piperazine-2-acetamide;
1-[6(1H-imidazol-1-yl)pyrimidin-4-yl]-N-(2-phenylcyclopropyl)4-(3-methyl-1-oxobutyl)piperazine-2-carboxamide;
1-[6-chloro-2-(1H-imidazol-1-yl)pyrimidin-4-yl]-N-[(2,5-dimethoxyphenyl)methyl]-4-(3-methyl-1-oxobutyl)piperazine-2-acetamide;
1-[2-(1H-imidazol-1-yl)pyrimidin-4-yl]-N-(indan-2-yl)-4-(3-methyl-1-oxobutyl)piperazine-2-carboxamide;
1-[6-chloro-2-(1H-imidazol-1-yl)pyrimidin-4-yl]-N-(indan-5-yl)-4-(3-methyl-1-oxobutyl)piperazine-2-acetamide;
1-[2-(1H-imidazol-1-yl)-6-(methylethyl)pyrimidin-4-yl]-N-[2-(3,4-dimethoxyphenyl)ethyl]-4-(2-methoxy-1-oxoethyl)piperazine-2-acetamide;
1-[2-(1H-imidazol-1-yl)-methylpyrimidin-4-yl]-N-[2-(3,4-dimethoxyphenyl)ethyl]-4-(2-methoxy-1-oxoethyl)piperazine-2-acetamide;
1-[2-(1H-imidazol-1-yl)-(methylethyl)pyrimidin-4-yl]-N-[(4-ethoxyphenyl)ethyl]-4-(2-methoxy-1-oxoethyl)piperazine-2-acetamide;
1-[6-chloro-2-(1H-imidazol-1-yl)pyrimidin-4-yl]-N-[(4-ethoxyphenyl)ethyl]-4-(2-methoxy-1-oxoethyl)piperazine-2-acetamide;
1-[2-(1H-imidazol-1-yl)-6-methylpyrimidin-4-yl]-N-[(4-ethoxyphenyl)ethyl]-4-(2-methoxy-1-oxoethyl)piperazine-2-acetamide;
1-6-chloro-2-(1H-imidazol-1-yl)pyrimidin-4-yl]-N-[(4-methylphenyl)methyl]-4-(2-methoxy-1-oxoethyl)piperazine-2-acetamide;
1-[6-chloro-2-(1H-imidazol-1-yl)pyrimidin-4-yl]-N-[(4-chlorophenyl)methyl]-4-(2-methoxy-1-oxoethyl)piperazine-2-acetamide;
1-[2-(1H-imidazol-1-yl)-6-methylpyrimidin-4-yl]-N-[(4-chlorophenyl)methyl]-4-(2-methoxy-1-oxoethyl)piperazine-2-acetamide;
1-[6-chloro-2-(1H-imidazol-1-yl)pyrimidin-4-yl]-N-[(4-methoxy-3-chlorophenyl)methyl]-4-(2-methoxy-1-oxoethyl)piperazine-2-acetamide;
1-[6-chloro-2-(1H-imidazol-1-yl)pyrimidin-4-yl]-N-[(4-methoxy-3-chlorophenyl)ethyl]-4-(2-methoxy-1-oxoethyl)piperazine-2-acetamide;
1-[6-chloro-2-(1H-imidazol-1-yl)pyrimidin-4-yl]-N-[(1,3-benzodioxol-5-yl)methyl]-4-(2-methoxy-1-oxoethyl)piperazine-2-acetamide;
1-[2-(1H-imidazol-1-yl)-6-methylpyrimidin-4-yl]-N-[(1,3-benzodioxol-5-yl)methyl]-4-(2-methoxy-1-oxoethyl)piperazine-2-acetamide;

1-[2-(1H-imidazol-1-yl)-6-(methylethyl)pyrimidin-4-yl]-N-[(1,3-benzodioxol-5-yl)methyl]-4-(2-methoxy-1-oxoethyl)piperazine-2-acetamide;

1-[2-(1H-imidazol-1-yl)pyrimidin-4-yl]-N-[(1,3-benzodioxol-5-yl)methyl]-4-(2-methoxy-1-oxoethyl)piperazine-2-acetamide;

1-[6-chloro-2-(1H-imidazol-1-yl)pyrimidin-4-yl]-N-[2-(1,3-benzodioxol-5-yl)ethyl]-4-(2-methoxy-1-oxoethyl)piperazine-2-acetamide;

1-[2-(1H-imidazol-1-yl)-6-methylpyrimidin-4-yl]-N-[2-(1,3-benzodioxol-5-yl)ethyl]-4-(2-methoxy-1-oxoethyl)piperazine-2-acetamide;

1-[2-(1H-imidazol-1-yl)-6-(methylethyl)pyrimidin-4-yl]-N-[2-(1,3-benzodioxol-5-yl)ethyl]-4-(2-methoxy-1-oxoethyl)piperazine-2-acetamide;

1-[2-(1H-imidazol-1-yl)pyrimidin-4-yl]-N-[2-(1,3-benzodioxol-5-yl)ethyl]-4-(2-methoxy-1-oxoethyl)piperazine-2-acetamide;

1-[6-chloro-2-(1H-imidazol-1-yl)pyrimidin-4-yl]-N-[(1,4-benzodioxan-6-yl)methyl]-4-(2-methoxy-1-oxoethyl)piperazine-2-acetamide;

1-[2-(1H-imidazol-1-yl)-6-methylpyrimidin-4-yl]-N-[2-(1,4-benzodioxan-6-yl)ethyl]-4-(2-methoxy-1-oxoethyl)piperazine-2-acetamide;

1-[6-chloro-2-(1H-imidazol-1-yl)pyrimidin-4-yl]-N-[(4-methoxyphenyl)methyl]-4-(2-methoxy-1-oxoethyl)piperazine-2-acetamide;

1-[2-(1H-imidazol-1-yl)-6-methylpyrimidin-4-yl]-N-[(4-methoxyphenyl)methyl]-4-(2-methoxy-1-oxoethyl)piperazine-2-acetamide;

1-[2-(1H-imidazol-1-yl)-6-(methylethyl)pyrimidin-4-yl]-N-[(4-methoxyphenyl)methyl]-4-(2-methoxy-1-oxoethyl)piperazine-2-acetamide;

1-[6-chloro-2-(1H-imidazol-1-yl)pyrimidin-4-yl]-N-[(3-methoxyphenyl)methyl]-4-(2-methoxy-1-oxoethyl)piperazine-2-acetamide;

1-[2-(1H-imidazol-1-yl)-6-methylpyrimidin-4-yl]-N-[(4-methoxyphenyl)ethyl]-4-2-methoxy-1-oxoethyl)piperazine-2-acetamide;

1-[2-(1H-imidazol-1-yl)-6-(methylethyl)pyrimidin-4-yl]-N-[(3,4-dimethoxyphenyl)methyl]-4-(2-methoxy-1-oxoethyl)piperazine-2-acetamide;

1-[6-chloro-2-(1H-imidazol-1-yl)pyrimidin-4-yl]-N-(indan-5-yl)-4-(2-methoxy-1-oxoethyl)piperazine-2-acetamide;

1-[2-(1H-imidazol-1-yl)-6-(methylethyl)pyrimidin-4-yl]-N-[2-(3,4-dimethoxyphenyl)ethyl]-4-(tetrahydro-3-furanoyl)piperazine-2-acetamide; 1-[2-(1H-imidazol-1-yl)-6-(methylethyl)pyrimidin-4-yl]N-[(3,4-dimethoxyphenyl)propyl]-4-tetrahydro-3-furanoyl)piperazine-2-acetamide;

1-[2-(1H-imidazol-1-yl)-6-methylpyrimidin-4-yl]-N-[(4-ethoxyphenyl)methyl]-4-(tetrahydro-3-furanoyl)piperazine-2-acetamide;

1-[2-(1H-imidazol-1-yl)-6-(methylethyl)pyrimidin-4-yl]-N-[(4-ethoxyphenyl)ethyl]-4-(tetrahydro-3-furanoyl)piperazine-2-acetamide;

1-[6-chloro-2-(1H-imidazol-1-yl)pyrimidin-4-yl]-N-[(4-methylphenyl)ethyl]-4-(tetrahydro-3-furanoyl)piperazine-2-acetamide;

1-2-(1H-imidazol-1-yl)-6-methylpyrimidin-4-yl]-N-[(4-methylphenyl)ethyl]-4-(tetrahydro-3-furanoyl)piperazine-2-acetamide;

1-[2-(1H-imidazol-1-yl)-6-methylpyrimidin-4-yl]-N-[(4-methylphenyl)methyl]-4-(tetrahydro-3-furanoyl)piperazine-2-acetamide;

1-[2-(1H-imidazol-1-yl)pyrimidin-4-yl]-N-[(4-methylphenyl)methyl]-4-(tetrahydro-3-furanoyl)piperazine-2-acetamide;

1-[2-(1H-imidazol-1-yl)-6-(methylethyl)pyrimidin-4-yl]-N-[(4-methylphenyl)methyl]-4-(tetrahydro-3-furanoyl)piperazine-2-acetamide;

1-[2-(1H-imidazol-1-yl)-6-(methylethyl)pyrimidin-4-yl]-N-[(4-chlorophenyl)methyl]-4-(tetrahydro-3-furanoyl)piperazine-2-acetamide;

1-[2-(1H-imidazol-1-yl)-6-methylpyrimidin-4-yl]-N-[(4-chlorophenyl)methyl]-4-(tetrahydro-3-furanoyl)piperazine-2-acetamide;

1-[2-(1H-imidazol-1-yl)-6-methylpyrimidin-4-yl]-N-[(4-chlorophenyl)ethyl]-4-(tetrahydro-3-furanoyl)piperazine-2-acetamide;

1-[6-chloro-2-(1H-imidazol-1-yl)pyrimidin-4-yl]-N-[(4-methoxy-3-chlorophenyl)ethyl]-4-(tetrahydro-3-furanoyl)piperazine-2-acetamide;

1-2-(1H-imidazol-1-yl)-6-methylpyrimidin-4-yl]-N-[(4-methoxy-3-chlorophenyl)ethyl]-4-(tetrahydro-3-furanoyl)piperazine-2-acetamide;

1-2-(1H-imidazol-1-yl)pyrimidin-4-yl]-N-[(1,3-benzodioxol-5-yl)methyl]-4-(tetrahydro-3-furanoyl)piperazine-2-acetamide;

1-[6-chloro-2-(1H-imidazol-1-yl)pyrimidin-4-yl]-N-[(1,3-benzodioxol-5-yl)methyl]-4-(tetrahydro-3-furanoyl)piperazine-2-acetamide;

1-[6-chloro-2-(1H-imidazol-1-yl)pyrimidin-4-yl]-N-[2-(1,3-benzodioxol-5-yl)ethyl]-4-(tetrahydro-3-furanoyl)piperazine-2-acetamide;

1-[2-(1H-imidazol-1-yl)pyrimidin-4-yl]-N-[2-(1,3-benzodioxol-5-yl)ethyl]-4-(tetrahydro-3-furanoyl)piperazine-2-acetamide;

1-[6-chloro-2-(1H-imidazol-1-yl)pyrimidin-4-yl]-N-[(3,4-dimethylphenyl)methyl]-4-(tetrahydro-3-furanoyl)piperazine-2-acetamide;

1-[2-(1H-imidazol-1-yl)-6-(methylethyl)pyrimidin-4-yl]-N-[(1,4-benzodioxan-6-yl)methyl]-4-(tetrahydro-3-furanoyl)piperazine-2-acetamide; 1-[6-chloro-2-(1H-imidazol-1-yl)pyrimidin-4-yl]-N-[(1,4-benzodioxan-6-yl)methyl]-4-(tetrahydro-3-furanoyl)piperazine-2-acetamide;

1-[6-chloro-2-(1H-imidazol-1-yl)pyrimidin-4-yl]-N-[(4-methoxyphenyl)methyl-4-(tetrahydro-3-furanoyl)piperazine-2-acetamide;

1-[2-(1H-imidazol-1-yl)pyrimidin-4-yl]-N-[(3-methoxyphenyl)methyl]-4-(tetrahydro-3-furanoyl)piperazine-2-acetamide;

1-[6-chloro-2-(1H-imidazol-1-yl)pyrimidin-4-yl]-N-[(4-methoxyphenyl)ethyl]-4-(tetrahydro-3-furanoyl)piperazine-2-acetamide;

1-[2-(1H-imidazol-1-yl)-6-methylpyrimidin-4-yl]-N-[(3-methoxyphenyl)ethyl]-4-(tetrahydro-3-furanoyl)piperazine-2-acetamide;

1-[2-(1H-imidazol-1-yl)pyrimidin-4-yl]-N-[(3,4-difluorophenyl)ethyl]-4-(tetrahydro-3-furanoyl)piperazine-2-carboxamide;

1-[6-chloro-2-(1H-imidazol-1-yl)pyrimidin-4-yl]-N-[(2,5-dimethoxyphenyl)methyl]-4-(tetrahydro-3-furanoyl)piperazine-2-acetamide;

1-[6-chloro-2-(1H-imidazol-1-yl)pyrimidin-4-yl]-N-[(3,4-dimethoxyphenyl)methyl]-4-tetrahydro-3-furanoyl)piperazine-2-acetamide;

1-[6-(1H-imidazol-1-yl)pyrimidin-4-yl]-N-[(3,5-dimethoxyphenyl)methyl]-4-(tetrahydro-3-furanoyl)piperazine-2-acetamide;

1-[6-chloro-2-(1H-imidazol-1-yl)pyrimidin-4-yl]-N-[2-(3,4-dimethoxyphenyl)ethyl]-4-(2-carboxymethoxy-1-oxoethyl)piperazine-2-acetamide;

1-[6-chloro-2-(1H-imidazol-1-yl)pyrimidin-4-yl]-N-[(3,4-dimethoxyphenyl)butyl]-4-(2-carboxymethoxy-1-oxoethyl)piperazine-2-acetamide;

1-[6-chloro-2-(1H-imidazol-1-yl)pyrimidin-4-yl]-N-[(3-chloro-4-methoxyphenyl)methyl]-4-(2-carboxymethoxy-1-oxoethyl)piperazine-2-acetamide;

1-[6-chloro-2-(1H-imidazol-1-yl)pyrimidin-4-yl]-N-[(3-chloro-4-methoxyphenyl)ethyl]-4-(2-carboxymethoxy-1-oxoethyl)piperazine-2-acetamide;

1-[2-(1H-imidazol-1-yl)pyrimidin-4-yl]-N-[(1,3-benzodioxol-5-yl)methyl]-4-(2-carboxymethoxy-1-oxoethyl)piperazine-2-acetamide;

1-[2-(1H-imidazol-1-yl)pyrimidin-4-yl]-N-[2-(1,3-benzodioxol-5-yl)ethyl]-4-(2-carboxymethoxy-1-oxoethyl)piperazine-2-acetamide;

1-[6-chloro-2-(1H-imidazol-1-yl)pyrimidin-4-yl]-N-[(1,3-benzodioxol-5-yl)methyl]-4-(2-carboxymethoxy-1-oxoethyl)piperazine-2-acetamide;

1-[6-chloro-2-(1H-imidazol-1-yl)pyrimidin-4-yl]-N-[2-(1,3-benzodioxol-5-yl)ethyl]-4-(2-carboxymethoxy-1-oxoethyl)piperazine-2-acetamide;

1-[2-(1H-imidazol-1-yl)-6-methylpyrimidin-4-yl]-N-[(4-methoxyphenyl)ethyl]-4-(2-carboxymethoxy-1-oxoethyl)piperazine-2-acetamide;

1-[6-chloro-2-(1H-imidazol-1-yl)pyrimidin-4-yl]-N-[(3-methoxyphenyl)ethyl]-4-(2-carboxymethoxy-1-oxoethyl)piperazine-2-acetamide;

1-[6-(1H-imidazol-1-yl)pyrimidin-4-yl)-N-[(2,4-dimethoxyphenyl)methyl]-4-(2-carboxymethoxy-1-oxoethyl)piperazine-2-carboxamide;

1-[2-(1H-imidazol-1-yl)-6-(methylethyl)pyrimidin-4-yl]-N-[(2,6-dimethoxyphenyl)methyl]-4-(2-carboxymethoxy-1-oxoethyl)piperazine-2-carboxamide;

1-[2-(1H-imidazol-1-yl)pyrimidin-4-yl]-N-[(2,6-dimethoxyphenyl)methyl]-4-(2-carboxymethoxy-1-oxoethyl)piperazine-2-carboxamide;

1-[4-(1H-imidazol-1-yl)-6-(methylethyl)pyrimidin-4-yl]-N-[2-(3,4-dimethoxyphenyl)ethyl]-4-(2-phenoxy-1-oxoethyl)piperazine-2-acetamide;

1-[6-chloro-2-(1H-imidazol-1-yl)pyrimidin-4-yl]-N-[(3,4-dimethoxyphenyl)propyl]-4-(2-phenoxy-1-oxoethyl)piperazine-2-carboxamide;

1-[2-(1H-imidazol-1-yl)-6-methylpyrimidin-4-yl]-N-[(1,3-benzodioxol-5-yl)methyl]-4-(2-phenoxy-1-oxoethyl)piperazine-2-acetamide;

1-[2-(1H-imidazol-1-yl)-6-methylpyrimidin-4-yl]-N-[2-(1,3-benzodioxol-5-yl)ethyl]-4-(2-phenoxy-1-oxoethyl)piperazine-2-acetamide;

1-[2-(1H-imidazol-1-yl)-6-trifluoromethylpyrimidin-4-yl]-N-[(3,4-dimethylphenyl)methyl]-4-(2-phenoxy-1-oxoethyl)piperazine-2-acetamide;

1-[2-(1H-imidazol-1-yl)-6-methylpyrimidin-4-yl]-N-[(4-methoxyphenyl)methyl]-4-(2-phenoxy-1-oxoethyl)piperazine-2-acetamide;

1-[6-chloro-2-(1H-imidazol-1-yl)pyrimidin-4-yl]-N-[(3,4-dimethoxyphenyl)methyl]-4-(2-phenoxy-1-oxoethyl)piperazine-2-acetamide;

1-[6-chloro-2-(1H-imidazol-1-yl)pyrimidin-4-yl]-N-[2-(3,4-dimethoxyphenyl)ethyl]-4-(pyridin-3-ylcarbonyl)piperazine-2-acetamide;

1-[2-(1H-imidazol-1-yl)pyrimidin-4-yl]-N-[2-(3,4-dimethoxyphenyl)ethyl]-4-(pyridin-3-ylcarbonyl)piperazine-2-acetamide;

1-[2-(1H-imidazol-1-yl)pyrimidin-4-yl]-N-[(3,4-dimethoxyphenyl)propyl]-4-(pyridin-3-ylcarbonyl)piperazine-2-carboxamide;

1-[6-chloro-2-(1H-imidazol-1-yl)pyrimidin-4-yl]-N-[(3,4-dimethoxyphenyl)butyl]-4-(pyridin-3-ylcarbonyl)piperazine-2-acetamide;

1-[2-(1H-imidazol-1-yl)-6-(methylethyl)pyrimidin-4-yl]-N-[(4-ethoxyphenyl)methyl]-4-(pyridin-3-ylcarbonyl)piperazine-2-acetamide;

1-[6-chloro-2-(1H-imidazol-1-yl)pyrimidin-4-yl]-N-[(4-methylphenoxy)ethyl]-4-(pyridin-3-ylcarbonyl)piperazine-2-acetamide;

1-[2-(1H-imidazol-1-yl)-6-methylpyrimidin-4-yl]-N-[(4-methylphenyl)methyl]-4-(pyridin-3-ylcarbonyl)piperazine-2-acetamide;

1-[6-chloro-2-(1H-imidazol-1-yl)pyrimidin-4-yl]-N-[(4-chlorophenyl)methyl]-4-(pyridin-3-ylcarbonyl)piperazine-2-acetamide;

1-[6-chloro-2-(1H-imidazol-1-yl)pyrimidin-4-yl]-N-[(4-methoxy-3-chlorophenyl)methyl]-4-(pyridin-3-ylcarbonyl)piperazine-2-acetamide;

1-[6-chloro-2-(1H-imidazol-1-yl)pyrimidin-4-yl]-N-[(4-methoxy-3-chlorophenyl)ethyl]-(pyridin-3-ylcarbonyl)piperazine-2-acetamide;

1-[2-(1H-imidazol-1-yl)-6-methylpyrimidin-4-yl]-N-[(4-methoxy-3-chlorophenyl)ethyl]-4-(pyridin-3-ylcarbonyl)piperazine-2-acetamide;

1-[2-(1H-imidazol-1-yl)-6-methylpyrimidin-4-yl]-N-[(2,5-dimethoxyphenyl)ethyl]-4-(pyridin-3-ylcarbonyl)piperazine-2-carboxamide;

1-[2-(1H-imidazol-1-yl)-6-methylpyrimidin-4-yl]-N-[(1,3-benzodioxol-5-yl)methyl]-4-(pyridin-3-ylcarbonyl)piperazine-2-acetamide;

1-[2-(1H-imidazol-1-yl)pyrimidin-4-yl]-N-[2-(1,3-benzodioxol-5-yl)ethyl]-4-(pyridin-3-ylcarbonyl)piperazine-2-acetamide;

1-[2-(1H-imidazol-1-yl)-6-methylpyrimidin-4-yl]-N-[2-(1,3-benzodioxol-5-yl)ethyl]-4-(pyridin-3-ylcarbonyl)piperazine-2-carboxamide;

1-[2-(1H-imidazol-1-yl)-6-methylpyrimidin-4-yl]-N-[(2,5-dimethylphenyl)methyl]-4-(pyridin-3-ylcarbonyl)piperazine-2-carboxamide;

1-[2-(1H-imidazol-1-yl)-methylpyrimidin-4-yl]-N-[(1,4-benzodioxan-6-yl)methyl]-4-(pyridin-3-ylcarbonyl)piperazine-2-acetamide;

1-[6-chloro-2-(1H-imidazol-1-yl)pyrimidin-4-yl]-N-[2-(1,4-benzodioxan-6-yl)ethyl]-4-(pyridin-3-ylcarbonyl)piperazine-2-acetamide;

1-[2-(1H-imidazol-1-yl)-6-methylpyrimidin-4-yl]-N-[2-(1,4-benzodioxan-6-yl)ethyl]-4-pyridin-3-ylcarbonyl)piperazine-2-acetamide;

1-[2-(1H-imidazol-1-yl)-6-methylethyl)pyrimidin-4-yl]-N-[2-(1,4-benzodioxan-6-yl)ethyl]-4-(pyridin-3-ylcarbonyl)piperazine-2-acetamide;

1-[2-(1H-imidazol-1-yl)-6-methylpyrimidin-4-yl]-N-[(4-methoxyphenyl)methyl]-4-(pyridin-3-ylcarbonyl)piperazine-2-acetamide;

1-[2-(1H-imidazol-1-yl)-6-(methylethyl)pyrimidin-4-yl]-N-[(4-methoxyphenyl)methyl]-4-pyridin-3-ylcarbonyl)piperazine-2-acetamide;

1-[2-(1H-imidazol-1-yl)-6-methylpyrimidin-4-yl]-N-[(4-methoxyphenyl)ethyl]-4-(pyridin-3-ylcarbonyl)piperazine-2-acetamide;

1-[6-chloro-2-(1H-imidazol-1-yl)pyrimidin-4-yl]-N-[(2-methoxyphenyl)ethyl]-4-(pyridin-3-ylcarbonyl)piperazine-2-carboxamide;

1-[6-chloro-2-(1H-imidazol-1-yl)pyrimidin-4-yl]-N-[(2-thienyl)ethyl]-4-(pyridin-3-ylcarbonyl)piperazine-2-acetamide;

1-[6-(1H-imidazol-1-yl)pyrimidin-4-yl]-N-[2-thienyl)ethyl]-4-(pyridin-3-ylcarbonyl)piperazine-2-carboxamide;

1-6-(1H-imidazol-1-yl)pyrimidin-4-yl]-N-[(3,4-difluorophenyl)ethyl]-4-(pyridin-3-ylcarbonyl)piperazine-2-acetamide;

1-[2-(1H-imidazol-1-yl)-6-(methylethyl)pyrimidin-4-yl]-N-[(3,4-dimethoxyphenyl)methyl]-4-(pyridin-3-ylcarbonyl)piperazine-2-acetamide;

1-[6-chloro-2-(1H-imidazol-1-yl)pyrimidin-4-yl]-N-[(5-indanyl)methyl]-4-(pyridin-3-ylcarbonyl)piperazine-2-acetamide;

1-[2-(1H-imidazol-1-yl)-6-(methylethyl)pyrimidin-4-yl]-N-[2-(3,4-dimethoxyphenyl)ethyl]-4-[2-(4-methoxyphenyl)-1-oxoethyl]piperazine-2-acetamide;

1-[2-(1H-imidazol-1-yl)-6-(methylethyl)pyrimidin-4-yl]-N-[(4-chlorophenyl)methyl]-4-[2-(4-methoxyphenyl)-1-oxoethyl]piperazine-2-carboxamide;

1-[6-chloro-2-(1H-imidazol-1-yl)pyrimidin-4-yl]-N-[(4-methoxy-3-chlorophenyl)methyl]-4-[2-4-methoxyphenyl)-1-oxoethyl]piperazine-2-acetamide;

1-[2-(1H-imidazol-1-yl)-6-methylpyrimidin-4-yl]-N-[(4-methoxy-3-chlorophenyl)methyl]-4-[2-(4-methoxyphenyl)-1-oxoethyl]piperazine-2-acetamide;

1-[2-(1H-imidazol-1-yl)pyrimidin-4-yl]-N-[(4-methoxy-3-chlorophenyl)methyl]-4-[2-(4-methoxyphenyl)-1-oxoethyl]piperazine-2-acetamide;

1-[6-(1H-imidazol-1-yl)pyrimidin-4-yl]-N-[(3,5-dimethoxyphenyl)ethyl]-4-[2-(4-methoxyphenyl)-1-oxoethyl]piperazine-2-acetamide;

1-[2-(1H-imidazol-1-yl)-6-trifluoromethylpyrimidin-4-yl]-N-[2-(1,3-benzodioxol-5-yl)ethyl]-4-[2-(4-methoxyphenyl)-1-oxoethyl]piperazine-2-acetamide;

1-[2-(1H-imidazol-1-yl)-6-methylpyrimidin-4-yl]-N-[(3,4-dimethylphenyl)methyl]-4-[2-(4-methoxyphenyl)-1-oxoethyl]piperazine-2-acetamide;

1-[2-(1H-imidazol-1-yl)pyrimidin-4-yl]-N-[3,4-dimethylphenyl)methyl]-4-[2-(4-methoxyphenyl)-1-oxoethyl]piperazine-2-acetamide;

1-[2-(1H-imidazol-1-yl)-6-(methylethyl)pyrimidin-4-yl]-N-[(3,4-dimethylphenyl)ethyl]-4-[2-(4-methoxyphenyl)-1-oxoethyl]piperazine-2-acetamide;

1-[2-(1H-imidazol-1-yl)-6-trifluoromethylpyrimidin-4-yl]-N-[(3-pyridinyl)methyl]-4-[2-(4-methoxyphenyl)-1-oxoethyl]piperazine-2-carboxamide;

1-6-chloro-2-(1H-imidazol-1-yl)pyrimidin-4-yl]-N-[(1,4-benzodioxan-6-yl)methyl]-4-[2-(4-methoxyphenyl)-1-oxoethyl]piperazine-2-acetamide;

1-[2-(1H-imidazol-1-yl)-6-methylethyl)pyrimidin-4-yl]-N-[(1,4-benzodioxan-6-yl)methyl]-4-[2-(4-methoxyphenyl)-1-oxoethyl]piperazine-2-acetamide;

1-[6-chloro-2-(1H-imidazol-1-yl)pyrimidin-4-yl]-N-[(4-methoxyphenyl)methyl]-4-[2-(4-methoxyphenyl)-1-oxoethyl]piperazine-2-acetamide;

1-[2-(1H-imidazol-1-yl)-6-(methylethyl)pyrimidin-4-yl]-N-[(4-methoxyphenyl)methyl]-4-[2-(4methoxyphenyl)-1-oxoethyl]piperazine-2-acetamide;

1-[2-(1H-imidazol-1-yl)-6-(methylethyl)pyrimidin-4-yl]-N-[(3-methoxyphenyl)ethyl]-4-[2-(4-methoxyphenyl)-1-oxoethyl]piperazine-2-acetamide;

1-[2-(1H-imidazol-1-yl)pyrimidin-4-yl]-N-[(2-thienyl)ethyl]-4-[2-(4-methoxyphenyl)-1-oxoethyl]piperazine-2-acetamide;

1-[6-(1H-imidazol-1-yl)pyrimidin-4-yl]-N-[(1H-methylpyrrol-2-yl)ethyl]-4-[2-(4-methoxyphenyl)-1-oxoethyl]piperazine-2-carboxamide;

1-[6-chloro-2-(1H-imidazol-1-yl)pyrimidin-4-yl]-N-[(3,4-dimethoxyphenyl methyl-4-[2-(4-methoxyphenyl)-1-oxoethyl]piperazine-2-acetamide;

1-[2-(1H-imidazol-1-yl)-6-trifluoromethylpyrimidin-4-yl]-N-[(3,4-dimethoxyphenyl)methyl]-4-[2-(4-methoxyphenyl)-1-oxoethyl]piperazine-2-acetamide;

1-[2-(1H-imidazol-1-yl)-6-methylpyrimidin-4-yl]-N-[(2,5-dimethoxyphenyl)methyl]-4-[2-(1,3-benzodioxol-5-yl)-1-oxoethyl]piperazine-2-carboxamide;

1-6-chloro-2-(1H-imidazol-1-yl)pyrimidin-4-yl]-N-[(2,5-dimethoxyphenyl)methyl]-4-[2-(1,3-benzodioxol-5-yl)-1-oxoethyl]piperazine-2-acetamide;

1-[6-chloro-2-(1H-imidazol-1-yl)pyrimidin-4-yl]-N-[(4-methoxyphenyl)methyl]-4-[2-(1,3-benzodioxol-5-yl)-1-oxoethyl]piperazine-2-acetamide;

1-[6-chloro-2-(1H-imidazol-1-yl)-6-(methylethyl)pyrimidin-4-yl]-N-[(4-methoxyphenyl)methyl]-4-[2-(1,3-benzodioxol-5-yl)-1-oxoethyl]piperazine-2-acetamide;

1-[6-(1H-imidazol-1-yl)pyrimidin-4-yl]-N-[(4-methylphenoxy)ethyl]-4-[2-(1,3-benzodioxol-5-yl)-1-oxoethyl]piperazine-2-acetamide;

1-[2-(1H-imidazol-1-yl)pyrimidin-4-yl]-N-[(4-chlorophenyl)methyl]-4-[2-(1,3-benzodioxol-5-yl)-1-oxoethyl]piperazine-2-acetamide;

1-[6-chloro-2-(1H-imidazol-1-yl)pyrimidin-4-yl]-N-(4-chlorophenyl)methyl-4-[2-(1,3-benzodioxol-5-yl)-1-oxoethyl]piperazine-2-acetamide;

1-[6-chloro-2-(1H-imidazol-1-yl)pyrimidin-4-yl]-N-[(4-chlorophenyl)ethyl]-4-[2-(1,3-benzodioxol-5-yl)-1-oxoethyl]piperazine-2-acetamide;

1-[2-(1H-imidazol-1-yl)-6-methylpyrimidin-4-yl]-N-[(4-methoxy-3-chlorophenyl)ethyl]-4-[2-(1,3-benzodioxol-5-yl)-1-oxoethyl]piperazine-2-acetamide;

1-[2-(1H-imidazol-1-yl)-6-methylethyl)pyrimidin-4-yl]-N-[(3,5-dimethoxyphenyl)ethyl]-4-[2-(1,3-benzodioxol-5-yl)-1-oxoethyl]piperazine-2-carboxamide;

1-[2-(1H-imidazol-1-yl)-6-methylpyrimidin-4-yl]-N-[(1,3-benzodioxol-5-yl)methyl]-4-[2-(1,3-benzodioxol-5-yl)-1-oxoethyl]piperazine-2-acetamide;

1-[6-chloro-2-(1H-imidazol-1-yl)pyrimidin-4-yl]-N-[(1,3-benzodioxol-5-yl)methyl]-4-[2-(1,3-benzodioxol-5-yl)-1-oxoethyl]piperazine-2-acetamide;

1-[2-(1H-imidazol-1-yl)pyrimidin-4-yl]-N-[2-(1,3-benzodioxol-5-yl)ethyl]-4-[2-(1,3-benzodioxol-5-yl)-1-oxoethyl]piperazine-2-acetamide;

1-[6-(1H-imidazol-1-yl)pyrimidin-4-yl]-N-[(3,4-dimethylphenyl)ethyl]-4-[2-(1,3-benzodioxol-5-yl)-1-oxoethyl]piperazine-2-acetamide;

1-[6-chloro-2-(1H-imidazol-1-yl)pyrimidin-4-yl]-N-[(1,4-benzodioxan-6-yl)methyl]-4-[2-(1,3-benzodioxol-5-yl)-1-oxoethyl]piperazine-2-acetamide;

1-[2-(1H-imidazol-1-yl)pyrimidin-4-yl]-N-[2-(1,4-benzodioxan-6-yl)ethyl]-4-[2-(1,3-benzodioxol-5-yl)-1-oxoethyl]piperazine-2-acetamide;

1-[2-(1H-imidazol-1-yl)-6-methylpyrimidin-4-yl]-N-[(4-methoxyphenyl)methyl]-4-[2-(1,3-benzodioxol-5-yl)-1-oxoethyl]piperazine-2-acetamide;

1-[6-chloro-2-(1H-imidazol-1-yl)pyrimidin-4-yl]-N-[(3-methoxyphenyl)methyl]-4-[2-(1,3-benzodioxol-5-yl)-1-oxoethyl]piperazine-2-acetamide;

1-[2-(1H-imidazol-1-yl)-6-trifluoromethylpyrimidin-4-yl]-N-[(3-methoxyphenyl)ethyl]-4-[2-(1,3-benzodioxol-5-yl)-1-oxoethyl]piperazine-2-acetamide;

1-[6-chloro-2-(1H-imidazol-1-yl)pyrimidin-4-yl]-N-[(3-methoxyphenyl)ethyl]-4-[2-(1,3-benzodioxol-5-yl)-1-oxoethyl]piperazine-2-acetamide;

1-[2-(1H-imidazol-1-yl)-6-methylethyl)pyrimidin-4-yl]-N-[(2-thienyl)ethyl]-4-[2-(1,3-benzodioxol-5-yl)-1-oxoethyl]piperazine-2-acetamide;

1-[2-(1H-imidazol-1-yl)-6-methylpyrimidin-4-yl]-N-[(1,4-benzodioxan-2-yl)methyl]-4-[2-(1,3-benzodioxol-5-yl)-1-oxoethyl]piperazine-2-acetamide;

1-[2-(1H-imidazol-1-yl)-6-(methylethyl)pyrimidin-4-yl]-N-[(3,4-dimethoxyphenyl)methyl]-4-[2-(1,3-benzodioxol-5-yl)-1-oxoethyl]piperazine-2-acetamide;

1-[2-(1H-imidazol-1-yl)-6-methylpyrimidin-4-yl]-N-[(3,4-dimethoxyphenyl)methyl]-4-[2-(1,3-benzodioxol-5-yl)-1-oxoethyl]piperazine-2-acetamide;

1-[2-(1H-imidazol-1-yl)-6-methylpyrimidin-4-yl]-N-(2-indanyl)-4-[2-(1,3-benzodioxol-5-yl)-1-oxoethyl]piperazine-2-acetamide;

1-[6-chloro-2-(1H-imidazol-1-yl)pyrimidin-4-yl]-N-[(5-indanyl)methyl]-4-[2-(1,3-benzodioxol-5-yl)-1-oxoethyl]piperazine-2-acetamide;

1-[2-(1H-imidazol-1-yl)-6-methylpyrimidin-4-yl]-N-[(5-indanyl)methyl]-4-[2-(1,3-benzodioxol-5-yl)-1-oxoethyl]piperazine-2-carboxamide;

1-[6-chloro-2-(1H-imidazol-1-yl)pyrimidin-4-yl]-N-[(4-methylphenyl)methyl]-4-(methylsulfonyl)piperazine-2-acetamide;

1-[6-chloro-2-(1H-imidazol-1-yl)pyrimidin-4-yl]-N-[(4-chlorophenyl)methyl]-4-(methylsulfonyl)piperazine-2-acetamide;

1-[6-chloro-2-(1H-imidazol-1-yl)pyrimidin-4-yl]-N-[(1,3-benzodioxol-5-yl)methyl]-4-(methylsulfonyl)piperazine-2-acetamide;

1-[2-(1H-imidazol-1-yl)pyrimidin-4-yl]-N-[(1,3-benzodioxol-5-yl)methyl]-4-(methylsulfonyl)piperazine-2-acetamide;

1-[2-(1H-imidazol-1-yl)-6-methylpyrimidin-4-yl]-N-[(1,3-benzodioxol-5-yl)methyl]-4-(methylsulfonyl)piperazine-2-acetamide;

1-[2-(1H-imidazol-1-yl)-6-methylpyrimidin-4-yl]-N-[2-(1,3-benzodioxol-5-yl)ethyl]-4-(methylsulfonyl)piperazine-2-acetamide;

1-[6-chloro-2-(1H-imidazol-1-yl)pyrimidin-4-yl]-N-[2-(1,3-benzodioxol-5-yl)ethyl]-4-(methylsulfonyl)piperazine-2-acetamide;

1-[-2-(1H-imidazol-1-yl)pyrimidin-4-yl]-N-[2-(1,3-benzodioxol-5-yl)ethyl]-4-(methylsulfonyl)piperazine-2-acetamide;

1-[6-chloro-2-(1H-imidazol-1-yl)pyrimidin-4-yl]-N-[(1,4-benzodioxan-6-yl)methyl]-4-(methylsulfonyl)piperazine-2-acetamide;

1-[2-(1H-imidazol-1-yl)pyrimidin-4-yl]-N-[(1,4-benzodioxan-6-yl)methyl]-4-(methylsulfonyl)piperazine-2-acetamide;

1-[2-(1H-imidazol-1-yl)-6-methylpyrimidin-4-yl]-N-[(1,4-benzodioxan-6-yl)methyl]-4-(methylsulfonyl)piperazine-2-acetamide;

1-[2-(1H-imidazol-1-yl)-6-(methylethyl)pyrimidin-4-yl]-N-[(1,4-benzodioxan-yl)methyl]-4-(methylsulfonyl)piperazine-2-acetamide;

1-[6-chloro-2-(1H-imidazol-1-yl)pyrimidin-4-yl]-N-[(4-methoxyphenyl)ethyl]-4-(methylsulfonyl)piperazine-2acetamide;

1-[2(1H-imidazol-1-yl)pyrimidin-4-yl]-N-[(4-methoxyphenyl)ethyl]-4-(methylsulfonyl)piperazine-2-acetamide;

1-[2-(1H-imidazol-1-yl)-6-methylpyrimidin-4-yl]-N-[(2-methoxyphenyl)ethyl]-4-(methylsulfonyl)piperazine-2-carboxamide;

1-[2-(1H-imidazol-1-yl)-6-(methylethyl)pyrimidin-4-yl]-N-[(3,4-dimethoxyphenyl)methyl]-4-(methylsulfonyl)piperazine-2-acetamide;

1-[2-(1H-imidazol-1-yl)-6-methylpyrimidin-4-yl]-N-[(3,4-dimethoxyphenyl)methyl]-4-(methylsulfonyl)piperazine-2-acetamide;

1-[6-chloro-2-(1H-imidazol-1-yl)pyrimidin-4-yl]-N-[(4-methylphenyl)methyl]-4-(octylsulfonyl)piperazine-2-acetamide;

1-[6-chloro-2-(1H-imidazol-1-yl)pyrimidin-4-yl]-N-[(3-chloro-4-methoxyphenyl)methyl]-4-(octylsulfonyl)piperazine-2-acetamide;

1-[6-chloro-2-(1H-imidazol-1-yl)pyrimidin-4-yl]-N-[(3-chloro-4-methoxyphenyl)ethyl]-4-(octylsulfonyl)piperazine-2-acetamide;

1-[2-(1H-imidazol-1-yl)-6-(methylethyl)pyrimidin-4-yl]-N-[(1,3-benzodioxol-5-yl)methyl-4-(octylsulfonyl)piperazine-2-acetamide;

1-[2-(1H-imidazol-1-yl)-6-methylpyrimidin-4-yl]-N-[2-(1,3-benzodioxol-5-yl)ethyl]-4-octylsulfonyl)piperazine-2-acetamide;

1-[2-(1H-imidazol-1-yl)pyrimidin-4-yl]-N-[2-(1,3-benzodioxol-5-yl)ethyl]-4-(octylsulfonyl)piperazine-2-acetamide;

1-6-chloro-2-(1H-imidazol-1-yl)pyrimidin-4-yl]-N-[(1,4-benzodioxan-6-yl)methyl]-4-(octylsulfonyl)piperazine-2-acetamide;

1-[6-chloro-2-(1H-imidazol-1-yl)pyrimidin-4-yl]-N-[(4-methoxyphenyl)methyl]-4-(octylsulfonyl)piperazine-2-acetamide;

1-[2-(1H-imidazol-1-yl)-6-methylpyrimidin-4-yl]-N-[4-methoxyphenyl)methyl]-4-(octylsulfonyl)piperazine-2-acetamide;

1-[6-chloro-2-(1H-imidazol-1-yl)pyrimidin-4-yl]-N-[(3-methoxyphenyl)ethyl]-4-(octylsulfonyl)piperazine-2-acetamide;

1-[6-chloro-2-(1H-imidazol-1-yl)pyrimidin-4-yl]-N-[(3,4-dimethoxyphenyl)methyl]-4-(octylsulfonyl)piperazine-2-acetamide;

1-[6-chloro-2-(1H-imidazol-1-yl)pyrimidin-4-yl]-N-[2-(3,4-dimethoxyphenyl)ethyl]-4-(dimethylaminosulfonyl)piperazine-2-acetamide;

1-[2-(1H-imidazol-1-yl)-6-trifluoromethylpyrimidin-4-yl]-N-[(4-chlorophenyl)methyl]-4-(dimethylaminosulfonyl)piperazine-2-carboxamide;

1-[6-chloro-2-(1H-imidazol-1-yl)pyrimidin-4-yl]-N-[(3-chloro-4-methoxyphenyl)methyl]-4-(dimethylaminosulfonyl)piperazine-2-acetamide;

1-[6-chloro-2-(1H-imidazol-1-yl)pyrimidin-4-yl]-N-[(3-chloro-4-methoxyphenyl)ethyl]-4-(dimethylaminosulfonyl)piperazine-2-acetamide;

1-[2-(1H-imidazol-1-yl)-6-methylpyrimidin-4-yl]-N-[(1,3-benzodioxol-5-yl)methyl]-4-(dimethylaminosulfonyl)piperazine-2-acetamide;

1-[6-chloro-2-(1H-imidazol-1-yl)pyrimidin-4-yl]-N-[(1,3-benzodioxol-5-yl)methyl]-4-(dimethylaminosulfonyl)piperazine-2-acetamide;

1-[6-chloro-2-(1H-imidazol-1-yl)pyrimidin-4-yl]-N-[2-(1,3-benzodioxol-5-yl)ethyl]-4-(dimethylaminosulfonyl)piperazine-2-acetamide;

1-[2-(1H-imidazol-1-yl)-6-(methylethyl)pyrimidin-4-yl]-N-[2-(1,3-benzodioxol-5-yl)ethyl]-4-(dimethylaminosulfonyl)piperazine-2-acetamide;

1-[2-(1H-imidazol-1-yl)-6-methylpyrimidin-4-yl]-N-[2-(1,3-benzodioxol-5-yl)ethyl]-4-(dimethylaminosulfonyl)piperazine-2-acetamide;

1-[2-(1H-imidazol-1-yl)pyrimidin-4-yl]-N-[2-(1,3-benzodioxol-5-yl)ethyl]-4-(dimethylaminosulfonyl)piperazine-2-acetamide;

1-[6-chloro-2-(1H-imidazol-1-yl)pyrimidin-4-yl]-N-[(1,4-benzodioxan-6-yl)methyl]-4-(dimethylaminosulfonyl)piperazine-2-acetamide;

1-[2-(1H-imidazol-1-yl)-6-methylpyrimidin-4-yl]-N-[(1,4-benzodioxan-6-yl)methyl]-4-(dimethylaminosulfonyl)piperazine-2-acetamide;

1-[2-(1H-imidazol-1-yl)-6-(methylethyl)pyrimidin-4-yl]-N-[(1,4-benzodioxan-6-yl)methyl]-4-(dimethylaminosulfonyl)piperazine-2-carboxamide;

1-[2-(1H-imidazol-1-yl)pyrimidin-4-yl]-N-[(1,4-benzodioxan-6-yl)methyl]-4-(dimethylaminosulfonyl)piperazine-2-acetamide;

1-[6-chloro-2-(1H-imidazol-1-yl)pyrimidin-4-yl]-N-[2-(1,4-benzodioxan-6-yl)ethyl]-4-(dimethylaminosulfonyl)piperazine-2-acetamide;

1-[6-chloro-2-(1H-imidazol-1-yl)pyrimidin-4-yl]-N-[(4-methoxyphenyl)methyl]-4-(dimethylaminosulfonyl)piperazine-2-acetamide;

1-[2-(1H-imidazol-1-yl)pyrimidin-4-yl]-N-[(4-methoxyphenyl)methyl]-4-(dimethylaminosulfonyl)piperazine-2-acetamide;
1-[6-chloro-2-(1H-imidazol-1-yl)pyrimidin-4-yl]-N-[(3-methoxyphenyl)methyl]-4-(dimethylaminosulfonyl)piperazine-2-acetamide;
1-[6-chloro-2-(1H-imidazol-1-yl)pyrimidin-4-yl]-N-[(1,4-benzodioxan-2-yl)methyl]-4-(dimethylaminosulfonyl)piperazine-2-carboxamide;
1-[2-(1H-imidazol-1-yl)-6-methylpyrimidin-4-yl]-N-[(2,6-dimethoxyphenyl)methyl]-4-(dimethylaminosulfonyl)piperazine-2-acetamide;
1-[6-chloro-2-(1H-imidazol-1-yl)pyrimidin-4-yl]-N-[(3,4-dimethoxyphenyl)methyl]-4-(dimethylaminosulfonyl)piperazine-2-acetamide;
1-[2-(1H-imidazol-1-yl)-6-(methylethyl)pyrimidin-4-yl]-N-[(3,4-dimethoxyphenyl)methyl]-4-(dimethylaminosulfonyl)piperazine-2-acetamide;
1-[2-(1H-imidazol-1-yl)-6-methylpyrimidin-4-yl]-N-[(3,4-dimethoxyphenyl)methyl]-4-(dimethylaminosulfonyl)piperazine-2-acetamide;
1-[2-(1H-imidazol-1-yl)-6-methylpyrimidin-4-yl]-N-[(3,5-dimethoxyphenyl)methyl]-4-(dimethylaminosulfonyl)piperazine-2-carboxamide;
1-[6-chloro-2-(1H-imidazol-1-yl)pyrimidin-4-yl]-N-[(2-adamantyl)methyl]-4-(dimethylaminosulfonyl)piperazine-2-carboxamide;
1-[6-(1H-imidazol-1-yl)pyrimidin-4-yl]-N-[(2,3-dimethoxyphenyl)methyl]-4-(propylaminocarbonyl)piperazine-2-acetamide;
1-[6-chloro-2-(1H-imidazol-1-yl)pyrimidin-4-yl]-N-[2-(3,4-dimethoxyphenyl)ethyl]-4-(propylaminocarbonyl)piperazine-2-acetamide;
1-[2-(1H-imidazol-1-yl)-6-methylpyrimidin-4-yl]-N-[2-(3,4-dimethoxyphenyl)ethyl]-4-(propylaminocarbonyl)piperazine-2-acetamide;
1-[6-chloro-2-(1H-imidazol-1-yl)pyrimidin-4-yl]-N-[(3,4-dimethoxyphenyl)propyl]-4-(propylaminocarbonyl)piperazine-2-acetamide;
1-[2-(1H-imidazol-1-yl)pyrimidin-4-yl]-N-[(3,4-dimethoxyphenyl)butyl]-4-(propylaminocarbonyl)piperazine-2-acetamide;
1-[6-chloro-2-(1H-imidazol-1-yl)pyrimidin-4-yl]-N-(4-ethoxyphenyl)methyl-4-(propylaminocarbonyl)piperazine-2-acetamide;
1-[2-(1H-imidazol-1-yl)pyrimidin-4-yl]-N-[(4-ethoxyphenyl)methyl]-4-(propylaminocarbonyl)piperazine-2-acetamide;
1-[2-(1H-imidazol-1-yl)-6-methylethyl)pyrimidin-4-yl]-N-[(4-ethoxyphenyl)methyl]-4-(propylaminocarbonyl)piperazine-2-acetamide;
1-[6-chloro-2-(1H-imidazol-1-yl)pyrimidin-4-yl]-N-[(4-methylphenoxy)ethyl]-4-(propylaminocarbonyl)piperazine-2-acetamide;
1-[2-(1H-imidazol-1-yl)-6-methylpyrimidin-4-yl]-N-[(4-methylphenoxy)ethyl]-4-(propylaminocarbonyl)piperazine-2-acetamide;
1-[2-(1H-imidazol-1-yl)-6-trifluoromethylpyrimidin-4-yl]-N-[(4-methylphenoxy)ethyl]-4-(propylaminocarbonyl)piperazine-2-carboxamide;
1-[6-chloro-2-(1H-imidazol-1-yl)pyrimidin-4-yl]-N-[(4-methylphenyl)methyl]-4-(propylaminocarbonyl)piperazine-2-acetamide;
1-[2-(1H-imidazol-1-yl)-6-methylpyrimidin-4-yl]-N-[(4-methylphenyl)methyl]-4-(propylaminocarbonyl)piperazine-2-acetamide;
1-[2-(1H-imidazol-1-yl)pyrimidin-yl]-N-[(4-methylphenyl)ethyl]-4-(propylaminocarbonyl)piperazine-2-acetamide;
1-[2-(1H-imidazol-1-yl)-6-(methylethyl)pyrimidin-4-yl]-N-[(4-methylphenyl)methyl]-4-(propylaminocarbonyl)piperazine-2-acetamide;
1-[6-chloro-2-(1H-imidazol-1-yl)pyrimidin-4-yl]-N-[(4-chlorophenyl)methyl]-4-(propylaminocarbonyl)piperazine-2-acetamide;
1-[2-(1H-imidazol-1-yl)-6-methylpyrimidin-4-yl]-N-[(4-chlorophenyl)methyl]-4-(propylaminocarbonyl)piperazine-2-acetamide;
1-[2-(1H-imidazol-1-yl)pyrimidin-4-yl]-N-[(4-chlorophenyl)methyl]-4-propylaminocarbonyl)piperazine-2-acetamide;
1-[6-chloro-2-(1H-imidazol-1-yl)pyrimidin-4-yl]-N-[(4-chorophenyl)ethyl]-4-(propylaminocarbonyl)piperazine-2-acetamide;
1-[6-chloro-2-(1H-imidazol-1-yl)pyrimidin-4-yl]-N-[(3-chloro-4-methoxyphenyl)methyl]-4-(propylaminocarbonyl)piperazine-2-acetamide;
1-[2-(1H-imidazol-1-yl)-6-methylpyrimidin-4-yl]-N-[(3-chloro-4-methoxyphenyl)methyl]-4-(propylaminocarbonyl)piperazine-2-acetamide;
1-[2-(1H-imidazol-1-yl)pyrimidin-4-yl]-N-[(3-chloro-4-methoxyphenyl)methyl]-4-(propylaminocarbonyl)piperazine-2-acetamide;
1-[2-(1H-imidazol-1-yl)methylpyrimidin-4-yl]-N-[(3-chloro-4-methoxyphenyl)ethyl]-4-(propylaminocarbonyl)piperazine-2-acetamide;
1-[6-chloro-2-(1H-imidazol-1-yl)pyrimidin-4-yl]-N-[(3-chloro-4-methoxyphenyl)ethyl]-4-(propylaminocarbonyl)piperazine-2-acetamide;
1-[2-(1H-imidazol-1-yl)pyrimidin-4-yl]-N-[(3-chloro-4-methoxyphenyl)ethyl]-4-(propylaminocarbonyl)piperazine-2-acetamide;
1-[6-chloro-2-(1H-imidazol-1-yl)pyrimidin-4-yl]-N-[(2,5-dimethoxyphenyl)ethyl]-4-(propylaminocarbonyl)piperazine-2-acetamide;
1-[2-(1H-imidazol-1-yl)pyrimidin-4-yl]-N-[(1,3-benzodioxol-5-yl)methyl]-4-(propylaminocarbonyl)piperazine-2-acetamide;
1-[2-(1H-imidazol-1-yl)-6-methylpyrimidin-4-yl]-N-[(1,3-benzodioxol-5-yl)methyl]-4-(propylaminocarbonyl)piperazine-2-acetamide;
1-[2-(1H-imidazol-1-yl)-6-(methylethyl)pyrimidin-4-yl]-N-[(1,3-benzodioxol-5-yl)methyl]-4-(propylaminocarbonyl)piperazine-2-acetamide;
1-[6-chloro-2-(1H-imidazol-1-yl)pyrimidin-4-yl]-N-[2-(1,3-benzodioxol-5-yl)ethyl]-4-(propylaminocarbonyl)piperazine-2-acetamide;
1-[2-(1H-imidazol-1-yl)-6-methylpyrimidin-4-yl]-N-[2-(1,3-benzodioxol-5-yl)ethyl]-4(propylaminocarbonyl)piperazine-2-acetamide;
1-[2-(1H-imidazol-1-yl)pyrimidin-4-yl]-N-[2-(1,3-benzodioxol-5-yl)ethyl]-4-(propylaminocarbonyl)piperazine-2-acetamide;
1-[2-(1H-imidazol-1-yl)pyrimidin-4-yl]-N-[2-(1,3-benzodioxol-5-yl)ethyl]-4-(propylaminocarbonyl)piperazine-2-carboxamide;
1-[6-chloro-2-(1H-imidazol-1-yl)pyrimidin-4-yl]-N-[(3,4-dimethylphenyl)methyl]-4-(propylaminocarbonyl)piperazine-2-acetamide;
1-[2-(1H-imidazol-1-yl)pyrimidin-4-yl]-N-[(1,4-benzodioxan-6-yl)methyl]-4-(propylaminocarbonyl)piperazine-2-acetamide;
1-[2-(1H-imidazol-1-yl)-6-methylethyl)pyrimidin-4-yl]-N-[(1,4-benzodioxan-6-yl)methyl]-4-(propylaminocarbonyl)piperazine-2-acetamide;
1-[2-(1H-imidazol-1-yl)-methylpyrimidin-4-yl]-N-[(1,4-benzodioxan-6-yl)methyl]-4-(propylaminocarbonyl)piperazine-2-acetamide;

1-[6-chloro-2-(1H-imidazol-1-yl)pyrimidin-4-yl]-N-[(1,4-benzodioxan-6-yl)methyl]-4-(propylaminocarbonyl)piperazine-2-acetamide;
1-[6-chloro-2-(1H-imidazol-1-yl)pyrimidin-4-yl]-N-[2-(1,4-benzodioxan-6-yl)ethyl]-4-(propylaminocarbonyl)piperazine-2-acetamide;
1-[2-(1H-imidazol-1-yl)-6-methylpyrimidin-4-yl]-N-[2-(1,4-benzodioxan-6-yl)ethyl]-4-(propylaminocarbonyl)piperazine-2-acetamide;
1-[2-(1H-imidazol-1-yl)pyrimidin-4-yl]-N-[2-(1,4-benzodioxan-6-yl)ethyl]-4-(propylaminocarbonyl)piperazine-2-acetamide;
1-[2-(1H-imidazol-1-yl)-6-(methylethyl)pyrimidin-4-yl]-N-[(1,4-benzodioxan-6-yl)methyl]-4-(propylaminocarbonyl)piperazine-2-acetamide;
1-[2-(1H-imidazol-1-yl)pyrimidin-4-yl]-N-[(4-methoxyphenyl)methyl]-4-(propylaminocarbonyl)piperazine-2-acetamide;
1-[6-chloro-2-(1H-imidazol-1-yl)pyrimidin-4-yl]-N-[(4-methoxyphenyl)methyl]-4-(propylaminocarbonyl)piperazine-2-acetamide;
1-[2-(1H-imidazol-1-yl)-6-methylpyrimidin-4-yl]-N-[(4-methoxyphenyl)methyl]-4-(propylaminocarbonyl)piperazine-2-acetamide;
1-[6-chloro-2-(1H-imidazol-1-yl)pyrimidin-4-yl]-N-[(3-methoxyphenyl)methyl]-4-(propylaminocarbonyl)piperazine-2-acetamide;
1-[2-(1H-imidazol-1-yl)-6-methylpyrimidin-4-yl]-N-[(3-methoxyphenyl methyl]-4-(propylaminocarbonyl)piperazine-2-acetamide;
1-[6-chloro-2-(1H-imidazol-1-yl)pyrimidin-4-yl]-N-[(4-methoxyphenyl)ethyl]-4-(propylaminocarbonyl)piperazine-2-acetamide;
1-[2-(1H-imidazol-1-yl)-6-methylpyrimidin-4-yl]-N-[(4-methoxyphenyl)ethyl]-4-(propylaminocarbonyl)piperazine-2-acetamide;
1-[2-(1H-imidazol-1-yl)pyrimidin-4-yl]-N-[(4-methoxyphenyl)ethyl]-4-(propylaminocarbonyl)piperazine-2-acetamide;
1-[6-chloro-2-(1H-imidazol-1-yl)pyrimidin-4-yl]-N-[(3-methoxyphenyl)ethyl]-4-(propylaminocarbonyl)piperazine-2-acetamide;
1-[2-(1H-imidazol-1-yl)-6-methylpyrimidin-4-yl]-N-[(3-methoxyphenyl)ethyl]-4-(propylaminocarbonyl)piperazine-2-acetamide;
1-[6-chloro-2-(1H-imidazol-1-yl)pyrimidin-4-yl]-N-[(2-methoxyphenyl)ethyl]-4-(propylaminocarbonyl)piperazine-2-acetamide;
1-[6-chloro-2-(1H-imidazol-1-yl)pyrimidin-4-yl]-N-[(2-thienyl)ethyl]-4-(propylaminocarbonyl)piperazine-2-acetamide;
1-[2-(1H-imidazol-1-yl)pyrimidin-4-yl]-N-[(2-thienyl)ethyl]-4-(propylaminocarbonyl)piperazine-2-carboxamide;
1-[6-chloro-2-(1H-imidazol-1-yl)pyrimidin-4-yl]-N-[(3,4-difluorophenyl)ethyl]-4-(propylaminocarbonyl)piperazine-2-acetamide;
1-[6-chloro-2-(1H-imidazol-1-yl)pyrimidin-4-yl]-N-[(1,4-benzodioxan-2-yl)methyl]-4-(propylaminocarbonyl)piperazine-2-acetamide;
1-[2-(1H-imidazol-1-yl)-6-methylpyrimidin-4-yl]-N-[(1,4-benzodioxan-2-yl)methyl]-4-(propylaminocarbonyl)piperazine-2-acetamide;
1-[2-(1H-imidazol-1-yl)-6-(methylethyl)pyrimidin-4-yl]-N-[(1,4-benzodioxan-2-yl)methyl]-4-(propylaminocarbonyl)piperazine-2-acetamide;
1-[6-chloro-2-(1H-imidazol-1-yl)pyrimidin-4-yl]-N-[(2,5-dimethoxyphenyl)methyl-4-(propylaminocarbonyl)piperazine-2-acetamide;
1-[2-(1H-imidazol-1-yl)pyrimidin-4-yl]-N-[(3,4-dimethoxyphenyl)methyl]-4-(propylaminocarbonyl)piperazine-2-acetamide;
1-[2-(1H-imidazol-1-yl)-6-(methylethyl)pyrimidin-4-yl]-N-[(3,4-dimethoxyphenyl)methyl]-4-(propylaminocarbonyl)piperazine-2-acetamide;
1-[6-chloro-2-(1H-imidazol-1-yl)pyrimidin-4-yl]-N-[(3,4-dimethoxyphenyl)methyl]-4-(propylaminocarbonyl)piperazine-2-acetamide;
1-[2-(1H-imidazol-1-yl)-6-methylpyrimidin-4-yl]-N-[(3,4-dimethoxyphenyl)methyl]-4-(propylaminocarbonyl)piperazine-2-acetamide;
1-[6-chloro-2-(1H-imidazol-1-yl)pyrimidin-4-yl]-N-[(3,5-dimethoxyphenyl)methyl]-4-(propylaminocarbonyl)piperazine-2-acetamide;
1-[2-(1H-imidazol-1-yl)pyrimidin-4-yl]-N-[(3,5-dimethoxyphenyl)methyl]-4-(propylaminocarbonyl)-piperazine-2-acetamide;
1-[2-(1H-imidazol-1-yl)-6-trifluoromethylpyrimidin-4-yl]-N-(cyclopropyl)-4(propylaminocarbonyl)piperazine-2-acetamide;
1-[2-(1H-imidazol-1-yl)pyrimidin-4-yl]-N-(2-indanyl)-4-(propylaminocarbonyl)piperazine-2-acetamide;
1-[6-chloro-2-(1H-imidazol-1-yl)pyrimidin-4-yl]-N-[(5-indanyl)methyl]-4-(propylaminocarbonyl)piperazine-2-acetamide;
1-[2-(1H-imidazol-1-yl)-6-methylpyrimidin-4-yl]-N-[2-(3,4-dimethoxyphenyl)ethyl]-4-(cyclohexylaminocarbonyl)piperazine-2-acetamide;
1-[6-chloro-2-(1H-imidazol-1-yl)pyrimidin-4-yl]-N-[(4-ethoxyphenyl)methyl]-4-(cyclohexylaminocarbonyl)piperazine-2-acetamide;
1-[2-(1H-imidazol-1-yl)-6-methylpyrimidin-4-yl]-N-[(4-ethoxyphenyl)methyl]-4-(cyclohexylaminocarbonyl)piperazine-2-acetamide;
1-[2-(1H-imidazol-1-yl)pyrimidin-4-yl]-N-[(4-ethoxyphenyl)methyl]-4-(cyclohexylaminocarbonyl)piperazine-2-acetamide;
1-[2-(1H-imidazol-1-yl)-6-methylpyrimidin-4-yl]-N-[(4-methylphenoxy)ethyl]-4-(cyclohexylaminocarbonyl)piperazine-2-acetamide;
1-[6-chloro-2-(1H-imidazol-1-yl)pyrimidin-4-yl]-N-[(4-chlorophenyl)methyl]-4-(cyclohexylaminocarbonyl)piperazine-2-acetamide;
1-[6-chloro-2-(1H-imidazol-1-yl)pyrimidin-4-yl]-N-[(4-chlorophenyl)ethyl]-4-(cyclohexylaminocarbonyl)piperazine-2-acetamide;
1-[2-(1H-imidazol-1-yl)pyrimidin-4-yl]-N-[(3-chloro-4-methoxyphenyl)methyl-4-(cyclohexylaminocarbonyl)piperazine-2-acetamide;
1-[2-(1H-imidazol-1-yl)-6-methylpyrimidin-4-yl]-N-[(3-chloro-4-methoxyphenyl)methyl]-4-(cyclohexylaminocarbonyl)piperazine-2-acetamide;
1-[2-(1H-imidazol-1-yl)-6-methylpyrimidin-4-yl]-N-[(3-chloro-4-methoxyphenyl)ethyl]-4-(cyclohexylaminocarbonyl)piperazine-2-carboxamide;
1-[2-(1H-imidazol-1-yl)pyrimidin-4-yl]-N-[(3-chloro-4-methoxyphenyl)ethyl]-4-(cyclohexylaminocarbonyl)piperazine-2-acetamide;
1-[2-(1H-imidazol-1-yl)pyrimidin-4-yl]-N-[(3,4-dimethoxyphenyl)methyl]-4-(cyclohexylaminocarbonyl)piperazine-2-acetamide;
1-[6-chloro-2-(1H-imidazol-1-yl)pyrimidin-4-yl]-N-[(1,3-benzodioxol-5-yl)methyl]-4-(cyclohexylaminocarbonyl)piperazine-2-acetamide;
1-[2-(1H-imidazol-1-yl)pyrimidin-4-yl]-N-[(1,3-benzodioxol-5-yl)methyl]-4-(cyclohexylaminocarbonyl)piperazine-2-acetamide;

1-[6-chloro-2-(1H-imidazol-1-yl)pyrimidin-4-yl]-N-[2-(1,3-benzodioxol-5-yl)ethyl]-4-(cyclohexylaminocarbonyl)piperazine-2-acetamide;
1-[2-(1H-imidazol-1-yl)-6-methylpyrimidin-4-yl]-N-[2-(1,3-benzodioxol-5-yl)ethyl]-4-(cyclohexylaminocarbonyl)piperazine-2-acetamide;
1-[6-chloro-2-(1H-imidazol-1-yl)pyrimidin-4-yl]-N-[(1,4-benzodioxan-4-yl)methyl]-4-(cyclohexylaminocarbonyl)piperazine-2-acetamide;
1-[2-(1H-imidazol-1-yl)-6-(methylethyl)pyrimidin-4-yl]-N-[(1,4-benzodioxan-6-yl)methyl]-4-(cyclohexylaminocarbonyl)piperazine-2-acetamide;
1-[2-(1H-imidazol-1-yl)-6-methylpyrimidin-4-yl]-N-[2-(1,4-benzodioxan-6-yl)ethyl]-4-(cyclohexylaminocarbonyl)piperazine-2-acetamide;
1-[2-(1H-imidazol-1-yl)pyrimidin-4-yl]-N-[(4-methoxyphenyl)methyl]-4-(cyclohexylaminocarbonyl)piperazine-2-acetamide;
1-[2-(1H-imidazol-1-yl)-6-methylpyrimidin-4-yl]-N-[(4-methoxyphenyl)methyl]-4-(cyclohexylaminocarbonyl)piperazine-2-acetamide;
1-[2-(1H-imidazol-1-yl)-6-(methylethyl)pyrimidin-4-yl]-N-[(4-methoxyphenyl)methyl]-4-(cyclohexylaminocarbonyl)piperazine-2-acetamide;
1-[2-(1H-imidazol-1-yl)pyrimidin-4-yl]-N-[(3-methoxyphenyl)methyl]-4-(cyclohexylaminocarbonyl)piperazine-2-acetamide;
1-[6-chloro-2-(1H-imidazol-1-yl)pyrimidin-4-yl]-N-[(4-methoxyphenyl)ethyl]-4-(cyclohexylaminocarbonyl)piperazine-2-acetamide;
1-[2-(1H-imidazol-1-yl)pyrimidin-4-yl]-N-[(4-methoxyphenyl)ethyl]-4(cyclohexylaminocarbonyl)piperazine-2-acetamide;
1-[6-chloro-2-(1H-imidazol-1-yl)pyrimidin-4-yl]-N-[(3-methoxyphenyl)ethyl]-4-(cyclohexylaminocarbonyl)piperazine-2-acetamide;
1-[6-chloro-2-(1H-imidazol-1-yl)pyrimidin-4-yl]-N-[(2-methoxyphenyl)ethyl]-4-(cyclohexylaminocarbonyl)piperazine-2-acetamide;
1-[6-chloro-2-(1H-imidazol-1-yl)pyrimidin-4-yl]-N-[(2-thienyl)ethyl]-4-(cyclohexylaminocarbonyl)piperazine-2-acetamide;
1-[6-chloro-2-(1H-imidazol-1-yl)pyrimidin-4-yl]-N-[(3,4-difluorophenyl)methyl]-4-(cyclohexylaminocarbonyl)piperazine-2-acetamide;
1-[2-(1H-imidazol-1-yl)pyrimidin-4-yl]-N-[(2,5-dimethoxyphenyl)methyl]-4-(cyclohexylaminocarbonyl)piperazine-2-acetamide;
1-[2-(1H-imidazol-1-yl)-6-(methylethyl)pyrimidin-4-yl]-N-[(2,5-dimethoxyphenyl)methyl]-4-(cyclohexylaminocarbonyl)piperazine-2-acetamide;
1-[6-chloro-2-(1H-imidazol-1-yl)pyrimidin-4-yl]-N-[(2,5-dimethoxyphenyl)methyl]-4-(cyclohexylaminocarbonyl)piperazine-2-acetamide;
1-[6-chloro-2-(1H-imidazol-1-yl)pyrimidin-4-yl]-N-[(3,4-dimethoxyphenyl)methyl]-4-(cyclohexylaminocarbonyl)piperazine-2-acetamide;
1-[6-chloro-2-(1H-imidazol-1-yl)pyrimidin-4-yl]-N-(2-indanyl)-4-(cyclohexylaminocarbonyl)piperazine-2-acetamide;
1-[6-chloro-2-(1H-imidazol-1-yl)pyrimidin-4-yl]-N-[(4-ethoxyphenyl)methyl]-4-(phenylsulfonylaminocarbonyl)piperazine-2-acetamide;
1-[6-chloro-2-(1H-imidazol-1-yl)pyrimidin-4-yl]-[N-(1,3-benzodioxol-5-yl)methyl]-4-(phenylsulfonylaminocarbonyl)piperazine-2-acetamide;
1-[6-chloro-2-(1H-imidazol-1-yl)pyrimidin-4-yl]-N-[2-(1,3-benzodioxol-5-yl)ethyl]-4-(phenylsulfonylaminocarbonyl)piperazine-2-acetamide;
1-[6-chloro-2-(1H-imidazol-1-yl)pyrimidin-4-yl]-N-[(1,4-benzodioxan-6-yl)methyl-4-(phenylsulfonylaminocarbonyl)piperazine-2-acetamide;
1-[2-(1H-imidazol-1-yl)-6-trifluoromethylpyrimidin-4-yl]-N-[(2,3-dimethoxyphenyl)methyl]-4-(phenylaminocarbonyl)piperazine-2-carboxamide;
1-[2-(1H-imidazol-1-yl)-6-(methylethyl)pyrimidin-4-yl]-N-[2-(3,4-dimethoxyphenyl)ethyl]-4-(phenylaminocarbonyl)piperazine-2-acetamide;
1-[2-(1H-imidazol-1-yl)-6-(methylethyl)pyrimidin-4-yl]-N-[(3,4-dimethoxyphenyl)propyl]-4-(phenylaminocarbonyl)piperazine-2-acetamide;
1-[6-chloro-2-(1H-imidazol-1-yl)pyrimidin-4-yl]-N-[(4-ethoxyphenyl)methyl]-4-(phenylaminocarbonyl)piperazine-2-acetamide;
1-[2-(1H-imidazol-1-yl)pyrimidin-4-yl]-N-[(4-ethoxyphenyl)methyl]-4-(phenylaminocarbonyl)piperazine-2-acetamide;
1-[2-(1H-imidazol-1-yl)-6-methylpyrimidin-4-yl]-N-[(4-methylphenoxy)ethyl]-4-(phenylaminocarbonyl)piperazine-2-acetamide;
1-[6-chloro-2-(1H-imidazol-1-yl)pyrimidin-4-yl]-N-[(4-methylphenyl)methyl]-4-(phenylaminocarbonyl)piperazine-2-acetamide;
1-[2-(1H-imidazol-1-yl)-6-methylpyrimidin-4-yl]-N-[(4-methylphenyl)methyl]-4-(phenylaminocarbonyl)piperazine-2-acetamide;
1-[2-(1H-imidazol-1-yl)-6-methylpyrimidin-4-yl]-N-[(4-chlorophenyl)methyl]-4-(phenylaminocarbonyl)piperazine-2-acetamide;
1-[6-chloro-2-(1H-imidazol-1-yl)pyrimidin-4-yl]-N-[(4-chlorophenyl)methyl]-4-(phenylaminocarbonyl)piperazine-2-acetamide;
1-[2-(1H-imidazol-1-yl)pyrimidin-4-yl]-N-[(4-chlorophenyl)methyl]-4-(phenylaminocarbonyl)piperazine-2-acetamide;
1-[2-(1H-imidazol-1-yl)-6-methylpyrimidin-4-yl]-N-[(4-chlorophenyl)ethyl]-4-(phenylaminocarbonyl)piperazine-2-carboxamide;
1-[6-chloro-2-(1H-imidazol-1-yl)pyrimidin-4-yl]-N-[(3-chloro-4-methoxyphenyl)methyl]-4-(phenylaminocarbonyl)piperazine-2-acetamide;
1-[2-(1H-imidazol-1-yl)-6-trifluoromethylpyrimidin-4-yl]-N-[(3-chloro-4-methoxyphenyl)ethyl]-4-(phenylaminocarbonyl)piperazine-2-carboxamide;
1-[6-chloro-2-(1H-imidazol-1-yl)pyrimidin-4-yl]-N-[(2,5-dimethoxyphenyl)ethyl]-4-(phenylaminocarbonyl)piperazine-2-acetamide;
1-[6-chloro-2-(1H-imidazol-1-yl)pyrimidin-4-yl]-N-[(1,3-benzodioxol-5-yl)methyl]-4-(phenylaminocarbonyl)piperazine-2-acetamide;
1-[2-(1H-imidazol-1-yl)pyrimidin-4-yl]-N-[2-(1,3-benzodioxol-5-yl)ethyl]-4-(phenylaminocarbonyl)piperazine-2-acetamide;
1-[2-(1H-imidazol-1-yl)-6-methylpyrimidin-yl]-N-[(1,4-benzodioxan-6-yl)methyl]-4-(phenylaminocarbonyl)piperazine-2-acetamide;
1-[6-chloro-2-(1H-imidazol-1-yl)pyrimidin-4-yl]-N-[(1,4-benzodioxan-6-yl)methyl]-4-(phenylaminocarbonyl)piperazine-2-acetamide;
1-[6-(1H-imidazol-1-yl)pyrimidin-4-yl]-N-[(1,4-benzodioxan-6-yl)methyl]-4-(phenylaminocarbonyl)piperazine-2-acetamide;
1-[2-(1H-imidazol-1-yl)-6-(methylethyl)pyrimidin-4-yl]-N-[(4-methoxyphenyl)methyl]-4-(phenylaminocarbonyl)piperazine-2-acetamide;
1-[6-chloro-2-(1H-imidazol-1-yl)pyrimidin-4-yl]-N-[(4-methoxyphenyl)methyl-4-phenylaminocarbonyl)piperazine-2-acetamide;

1-[6-chloro-2-(1H-imidazol-1-yl)pyrimidin-4-yl]-N-[(3-methoxyphenyl)methyl]-4-phenylaminocarbonyl)piperazine-2-acetamide;

1-[2-(1H-imidazol-1-yl)-6-methylpyrimidin-4-yl]-N-[(4-methoxyphenyl)ethyl-4-phenylaminocarbonyl)piperazine-2-acetamide;

1-[2-(1H-imidazol-1-yl)pyrimidin-4-yl]-N-[(4-methoxyphenyl)ethyl]-4-(phenylaminocarbonyl)piperazine-2-acetamide;

1-[2-(1H-imidazol-1-yl)pyrimidin-4-yl]-N-[(3-methoxyphenyl)ethyl]-4-phenylaminocarbonyl)piperazine-2-acetamide;

1-[2-(1H-imidazol-1-yl)pyrimidin-4-yl]-N-[(3-thienyl)ethyl]-4-(phenylaminocarbonyl)piperazine-2-acetamide;

1-[6-chloro-2-(1H-imidazol-1-yl)pyrimidin-4-yl]-N-[(3,4-difluorophenyl)methyl]-4-(phenylaminocarbonyl)piperazine-2-acetamide;

1-[6-chloro-2-(1H-imidazol-1-yl)pyrimidin-4-yl]-N-[(2,5-dimethoxyphenyl)methyl]-4-(phenylaminocarbonyl)piperazine-2-acetamide;

1-[6-chloro-2-(1H-imidazol-1-yl)pyrimidin-4-yl]-N-[(3,4-dimethoxyphenyl)methyl]-4-(phenylaminocarbonyl)piperazine-2-acetamide;

1-[2-(1H-imidazol-1-yl)-6-(methylethyl)pyrimidin-4-yl]-N-[(3,4-dimethoxyphenyl)methyl]-4-(phenylaminocarbonyl)piperazine-2-acetamide;

1-[6-(1H-imidazol-1-yl)pyrimidin-4-yl]-N-[(cyclopropyl)methyl]-4-(phenylaminocarbonyl)piperazine-2-carboxamide;

1-[6-chloro-2-(1H-imidazol-1-yl)pyrimidin-4-yl]-N-[(5-indanyl)methyl]-4-phenylaminocarbonylpiperazine-2-acetamide;

1-[6-(1H-imidazol-1-yl)pyrimidin-4-yl]-N-[(2,3-dimethoxyphenyl)ethyl]-4-[(4-methoxyphenyl)aminocarbonyl]piperazine-2-carboxamide;

1-[2-(1H-imidazol-1-yl)-6-(methylethyl)pyrimidin-4-yl]-N-[(2,3-dimethoxyphenyl)ethyl]-4-[(4-methoxyphenyl)aminocarbonyl]piperazine-2-carboxamide;

1-[6-chloro-2-(1H-imidazol-1-yl)pyrimidin-4-yl]-N-[(3,4-dimethoxyphenyl)methyl]-4-[(4-methoxyphenyl)aminocarbonyl]piperazine-2-acetamide;

1-[2-(1H-imidazol-1-yl)pyrimidin-4-yl]-N-[(3,4-dimethoxyphenyl)methyl]-4-[(4-methoxyphenyl)aminocarbonyl]piperazine-2-acetamide;

1-[2-(1H-imidazol-1-yl)pyrimidin-4-yl]-N-[(4-ethoxyphenyl)methyl]-4-[(4-methoxyphenyl)aminocarbonyl]piperazine-2-acetamide;

1-[6-chloro-2-(1H-imidazol-1-yl)pyrimidin-4-yl]-N-[(4-methylphenoxy)ethyl]-4-[(4-methoxyphenyl)aminocarbonyl]piperazine-2-acetamide;

1-[2-(1H-imidazol-1-yl)pyrimidin-4-yl]-N-[(4-methylphenoxy)ethyl]-4-[(4-methoxyphenyl)aminocarbonyl]piperazine-2-acetamide;

1-[2-(1H-imidazol-1-yl)-6-trifluoromethylpyrimidin-4-yl]-N-[(4-methylphenyl)methyl]-4-[(4-methoxyphenyl)aminocarbonyl]piperazine-2-acetamide;

1-[2-(1H-imidazol-1-yl)pyrimidin-4-yl]-N-[(4-chlorophenyl)methyl]-4-[(4-methoxyphenyl)aminocarbonyl]piperazine-2-acetamide;

1-[2-(1H-imidazol-1-yl)pyrimidin-4-yl]-N-[(3-chloro-4-methoxyphenyl)methyl]-4-[(4-methoxyphenyl)aminocarbonyl]piperazine-2-carboxamide;

1-[2-(1H-imidazol-1-yl)pyrimidin-4-yl]-N-[(3-chloro-4-methoxyphenyl)methyl]-4-[(4-methoxyphenyl)aminocarbonyl]piperazine-2-acetamide;

1-[2-(1H-imidazol-1-yl)-6-methylpyrimidin-4-yl]-N-[(3-chloro-4-methoxyphenyl)methyl]-4-[(4-methoxyphenyl)aminocarbonyl]piperazine-2-acetamide;

1-[6-chloro-2-(1H-imidazol-1-yl)pyrimidin-4-yl]-N-[(3-chloro-4-methoxyphenyl)ethyl]-4-[(4-methoxyphenyl)aminocarbonyl]piperazine-2-acetamide;

1-[6-chloro-2-(1H-imidazol-1-yl)pyrimidin-4-yl]-N-[(2,5-dimethoxyphenyl)ethyl]-4-[(4-methoxyphenyl)aminocarbonyl]piperazine-2-acetamide;

1-[2-(1H-imidazol-1-yl)pyrimidin-4-yl]-N-[(2,5-dimethoxyphenyl)ethyl]-4-[(4-methoxyphenyl)aminocarbonyl]piperazine-2-carboxamide;

1-[2-(1H-imidazol-1-yl)pyrimidin-4-yl]-N-[(1,3-benzodioxol-5-yl)methyl]-4-[(4-methoxyphenyl)aminocarbonyl]piperazine-2-acetamide;

1-[2-(1H-imidazol-1-yl)-6-(methylethyl)pyrimidin-4-yl]-N-[(1,3-benzodioxol-5-yl)methyl]-4-[(4-methoxyphenyl)aminocarbonyl]piperazine-2-acetamide;

1-[2-(1H-imidazol-1-yl)-6-methylpyrimidin-4-yl]-N-[(1,3-benzodioxol-5-yl)methyl]-4-[(4-methoxyphenyl)aminocarbonyl]piperazine-2-carboxamide;

1-[6-chloro-2-(1H-imidazol-1-yl)pyrimidin-4-yl]-N-[(1,3-benzodioxol-5-yl)methyl]-4-[(4-methoxyphenyl)aminocarbonyl]piperazine-2-acetamide;

1-[2-(1H-imidazol-1-yl)pyrimidin-4-yl]-N-[2-(1,3-benzodioxol-5-yl)ethyl]-4-[(4-methoxyphenyl)aminocarbonyl]piperazine-2-acetamide;

1-[6-chloro-2-(1H-imidazol-1-yl)pyrimidin-4-yl]-N-[2-(1,3-benzodioxol-5-yl)ethyl]-4-[(4-methoxyphenyl)aminocarbonyl]piperazine-2-acetamide;

1-[2-(1H-imidazol-1-yl)-6-methylpyrimidin-4-yl]-N-[2-(1,3-benzodioxol-5-yl)ethyl]-4-[(4-methoxyphenyl)aminocarbonyl]piperazine-2-acetamide;

1-[6-chloro-2-(1H-imidazol-1-yl)pyrimidin-4-yl]-N-[(3,4-dimethylphenyl)methyl]-4-[(4-methoxyphenyl)aminocarbonyl]piperazine-2-acetamide;

1-[6-(1H-imidazol-1-yl)pyrimidin-4-yl]-N-[(3,4-dimethylphenyl)methyl]-4-[(4-methoxyphenyl)aminocarbonyl]piperazine-2-acetamide;

1-[2-(1H-imidazol-1-yl)pyrimidin-4-yl]-N-[(2-furyl)methyl]-4-[(4-methoxyphenyl)aminocarbonyl]piperazine-2-acetamide;

1-[2-(1H-imidazol-1-yl)pyrimidin-4-yl]-N-[(1,4-benzodioxan-6-yl)methyl]-4-[(4-methoxyphenyl)aminocarbonyl]piperazine-2-acetamide;

1-[6-chloro-2-(1H-imidazol-1-yl)pyrimidin-4-yl]-N-[(1,4-benzodioxan-6-yl)methyl]-4-[(4-methoxyphenyl)aminocarbonyl]piperazine-2-acetamide;

1-[2-(1H-imidazol-1-yl)-6-(methylethyl)pyrimidin-4-yl]-N-[(1,4-benzodioxan-6-yl)methyl]-4-[(4-methoxyphenyl)aminocarbonyl]piperazine-2-acetamide;

1-[2-(1H-imidazol-1-yl)-6-methylpyrimidin-4-yl]-N-[2-(1,4-benzodioxan-6-yl)ethyl]-4-[(4-methoxyphenyl)aminocarbonyl]piperazine-2-acetamide;

1-[2-(1H-imidazol-1-yl)pyrimidin-4-yl]-N-[2-(1,4-benzodioxan-6-yl)ethyl]-4-[(4-methoxyphenyl)aminocarbonyl]piperazine-2-acetamide;

1-[6-chloro-2-(1H-imidazol-1-yl)pyrimidin-4-yl]-N-[(1,4-benzodioxan-6-yl)methyl]-4-[(4-methoxyphenyl)aminocarbonyl]piperazine-2-carboxamide;

1-[2-(1H-imidazol-1-yl)-6-methylpyrimidin-4-yl]-N-[(4-methoxyphenyl)methyl]-4-[(4-methoxyphenyl)aminocarbonyl]piperazine-2-acetamide;

1-[2-(1H-imidazol-1-yl)pyrimidin-4-yl]-N-[(3-methoxyphenyl)methyl]-4-1(4-methoxyphenyl)aminocarbonyl]piperazine-2-acetamide;

1-[2-(1H-imidazol-1-yl)-6-methylpyrimidin-4-yl]-N-[(3-methoxyphenyl)methyl]-4-[(4-methoxyphenyl)aminocarbonyl]piperazine-2-acetamide;

1-[6-chloro-2-(1H-imidazol-1-yl)pyrimidin-4-yl]-N-[(3-methoxyphenyl)ethyl]-4-[(4-methoxyphenyl)aminocarbonyl]piperazine-2-acetamide;

1-[2-(1H-imidazol-1-yl)pyrimidin-4-yl]-N-[(3-methoxyphenyl)ethyl]-4-[(4-methoxyphenyl)aminocarbonyl]piperazine-2-acetamide;
1-[2-(1H-imidazol-1-yl)-6-methylethyl)pyrimidin-4-yl]-N-[(1,4-benzodioxan-2-yl)ethyl]-4-[(4-methoxyphenyl)aminocarbonyl]piperazine-2-acetamide;
1-[6-chloro-2-(1H-imidazol-1-yl)pyrimidin-4-yl]-N-[(2,3-dimethoxyphenyl)methyl]-4-[(4-methoxyphenyl)aminocarbonyl]piperazine-2-acetamide;
1-[6-chloro-2-(1H-imidazol-1-yl)pyrimidin-4-yl]-N-[(2,5-dimethoxyphenyl)methyl]-4-[(4-methoxyphenyl)aminocarbonyl]piperazine-2-acetamide;
1-[2-(1H-imidazol-1-yl)-6-methylpyrimidin-4-yl]-N-[(3,4-dimethoxyphenyl)methyl]-4-[(4-methoxyphenyl)aminocarbonyl]piperazine-2-acetamide;
1-[6-chloro-2-(1H-imidazol-1-yl)pyrimidin-4-yl]-N-[(3,4-dimethoxyphenyl)methyl]-4-[(4-methoxyphenyl)aminocarbonyl]piperazine-2-acetamide;
1-[6-chloro-2-(1H-imidazol-1-yl)pyrimidin-4-yl]-N-[(cyclopropyl)methyl]-4-[(4-methoxyphenyl)aminocarbonyl]piperazine-2-acetamide;
1-[6-chloro-2-(1H-imidazol-1-yl)pyrimidin-4-yl]-N-(2-indanyl)-4-[(4-methoxyphenyl)aminocarbonyl]piperazine-2-acetamide; 1-[2-(1H-imidazol-1-yl)-6-methylpyrimidin-4-yl]-N-[(5-indanyl)methyl]-4-[(4-methoxyphenyl)aminocarbonyl]piperazine-2-acetamide;
1-[2-(1H-imidazol-1-yl)-6-methylpyrimidin-4-yl]-N-[2-(3,4-dimethoxyphenyl)ethyl]-4-[(3,4-dichlorophenyl)aminocarbonyl]piperazine-2-acetamide;
1-[6-chloro-2-(1H-imidazol-1-yl)pyrimidin-4-yl]-N-[(3,4-dimethoxyphenyl)propyl]-4-[(3,4-dichlorophenyl)aminocarbonyl]piperazine-2-acetamide;
1-[6-chloro-2-(1H-imidazol-1-yl)pyrimidin-4-yl]-N-[(3,4-dimethoxyphenyl)butyl]-4-[(3,4-dichlorophenyl)aminocarbonyl]piperazine-2-acetamide;
1-[2-(1H-imidazol-1-yl)-6-(methylethyl)pyrimidin-4-yl]-N-[(4-ethoxyphenyl)ethyl]-4-[(3,4-dichlorophenyl)aminocarbonyl]piperazine-2-acetamide;
1-[2-(1H-imidazol-1-yl)-6-methylpyrimidin-4-yl]-N-[(4-ethoxyphenyl)methyl]-4-[(3,4-dichlorophenyl)aminocarbonyl]piperazine-2-acetamide;
1-[6-chloro-2-(1H-imidazol-1-yl)pyrimidin-4-yl]-N-[(4-methylphenoxy)ethyl]-4-[(3,4-dichlorophenyl)aminocarbonyl]piperazine-2-acetamide;
1-[2-(1H-imidazol-1-yl)-6-methylpyrimidin-4-yl]-N-[(4-methylphenyl)methyl]-4-[(3,4-dichlorophenyl)aminocarbonyl]piperazine-2-acetamide;
1-[6-chloro-2-(1H-imidazol-1-yl)pyrimidin-4-yl]-N-[(4-methylphenyl)methyl]-4-[(3,4-dichlorophenyl)aminocarbonyl]piperazine-2-acetamide;
1-[2-(1H-imidazol-1-yl)pyrimidin-4-yl]-N-[(4-chlorophenyl)methyl]-4-[(3,4-dichlorophenyl)aminocarbonyl]piperazine-2-acetamide;
1-[6-chloro-2-(1H-imidazol-1-yl)pyrimidin-4-yl]-N-[(4-chlorophenyl)methyl]-4-[(3,4-dichlorophenyl)aminocarbonyl]piperazine-2-acetamide;
1-2-(1H-imidazol-1-yl)pyrimidin-4-yl]-N-[(3-chloro-4-methoxyphenyl)methyl]-4-[(3,4-dichlorophenyl)aminocarbonyl]piperazine-2-acetamide;
1-[6-chloro-2-(1H-imidazol-1-yl)pyrimidin-4-yl]-N-[(2,5-dimethoxyphenyl)methyl]-4-[(3,4-dichlorophenyl)aminocarbonyl]piperazine-2-acetamide;
1-[6-chloro-2-(1H-imidazol-1-1-yl)pyrimidin-4-yl]-N-[(1,3-benzodioxol-5-yl)methyl]-4-[(3,4-dichlorophenyl)aminocarbonyl]piperazine-2-acetamide;
1-[2-(1H-imidazol-1-yl)-6-methylpyrimidin-4-yl]-N-[(1,3-benzodioxol-5-yl)methyl]-4-[(3,4-dichlorophenyl)aminocarbonyl]piperazine-2-acetamide;
1-[2-(1H-imidazol-1-yl)pyrimidin-4-yl]-N-[(1,3-benzodioxol-5-yl)methyl]-4-[(3,4-dichlorophenyl)aminocarbonyl]piperazine-2-acetamide;
1-6-chloro-2-(1H-imidazol-1-yl)pyrimidin-4-yl]-N-[2-(1,3-benzodioxol-5-yl)ethyl]-4-[(3,4-dichlorophenyl)aminocarbonyl]piperazine-2-acetamide;
1-[2-(1H-imidazol-1-yl)-6-methylpyrimidin-4-yl]-N-[2-(1,3-benzodioxol-5-yl)ethyl]-4-[(3,4-dichlorophenyl)aminocarbonyl]piperazine-2-acetamide;
1-[6-chloro-2-(1H-imidazol-1-yl)pyrimidin-4-yl]-N-[(3,4dimethylphenyl)methyl]-4-[(3,4-dichlorophenyl)aminocarbonyl]piperazine-2-acetamide;
1-[2-(1H-imidazol-1-yl)pyrimidin-4-yl]-N-[(1,4-benzodioxan-6-yl)methyl]-4-[-3,4-dichlorophenyl)aminocarbonyl]piperazine-2-acetamide;
1-[6-chloro-2-(1H-imidazol-1-yl)pyrimidin-4-yl]-N-[(1,4-benzodioxan-6-yl)methyl]-4-[(3,4dichlorophenyl)aminocarbonyl]piperazine-2-acetamide;
1-[2-(1H-imidazol-1-yl)-6-methylpyrimidin-4-yl]-N-[2-(1,4-benzodioxan-6-yl)ethyl]-4-[(3,4-dichlorophenyl)aminocarbonyl]piperazine-2-acetamide;
1-[2-(1H-imidazol-1-yl)pyrimidin-4-yl]-N-[(4-methoxyphenyl)methyl]-4-[(3,4-dichlorophenyl)aminocarbonyl]piperazine-2-acetamide;
1-[2-(1H-imidazol-1-yl)-6-methylpyrimidin-4-yl]-N-[(4-methoxyphenyl)methyl]-4-[(3,4-dichlorophenyl)aminocarbonyl]piperazine-2-acetamide;
1-[6-chloro-2-(1H-imidazol-1-yl)pyrimidin-4-yl]-N-[(4-methoxyphenyl)methyl]-4-[(3,4-dichlorophenyl)aminocarbonyl]piperazine-2-acetamide;
1-[2-(1H-imidazol-1-yl)pyrimidin-4-yl]-N-[(3-methoxyphenyl)methyl]-4-[(3,4-dichlorophenyl)aminocarbonyl]piperazine-2-acetamide;
1-[2-(1H-imidazol-1-yl)-6-methylpyrimidin-4-yl]-N-[(3-methoxyphenyl)methyl-4-[(3,4-dichlorophenyl)aminocarbonyl]piperazine-2-acetamide;
1-[6-chloro-2-(1H-imidazol-1-yl)pyrimidin-4-yl]-N-[(4-methoxyphenyl)ethyl]-4-[1(3,4-dichlorophenyl)aminocarbonyl]piperazine-2-acetamide;
1-[2-(1H-imidazol-1-yl)-6-(methylethyl)pyrimidin-4-yl]-N-[(2,5-dimethoxyphenyl)methyl]-4-[(3,4-dichlorophenyl)aminocarbonyl]piperazine-2-acetamide;
1-[2-(1H-imidazol-1-yl)-6-methylpyrimidin-4-yl]-N-[(2,5-dimethoxyphenyl)methyl]-4-[(3,4-dichlorophenyl)aminocarbonyl]piperazine-2-acetamide;
1-[6-chloro-2-(1H-imidazol-1-yl)pyrimidin-4-yl]-N-[(2,5-dimethoxyphenyl)methyl]-4-[(3,4-dichlorophenyl)aminocarbonyl]piperazine-2-acetamide;
1-[2-(1H-imidazol-1-yl)-6-methylpyrimidin-4-yl]-N-[(3,4-dimethoxyphenyl)methyl]-4-[(3,4-dichlorophenyl)aminocarbonyl]piperazine-2-acetamide;
1-[2-(1H-imidazol-1-yl)pyrimidin-4-yl]-N-[(3,4-dimethoxyphenyl)methyl]-4-[(3,4-dichlorophenyl)aminocarbonyl]piperazine-2-acetamide;
1-[2-(1H-imidazol-1-yl)-6-methylpyrimidin-4-yl]-N-[2-3,4-dimethoxyphenyl)ethyl]-4-(methoxycarbonyl)piperazine-2-acetamide;
1-[6-chloro-2-(1H-imidazol-1-yl)pyrimidin-4-yl]-N-[(4-ethoxyphenyl)methyl]-4-(methoxycarbonyl)piperazine-2-acetamide;
1-[6-chloro-2-(1H-imidazol-1-yl)pyrimidin-4-yl]-N-[(4-methylphenyl)methyl]-4-(methoxycarbonyl)piperazine-2-acetamide;
1-[6-chloro-2-(1H-imidazol-1-yl)pyrimidin-4-yl]-N-[(4-chlorophenyl)methyl]-4-(methoxycarbonyl)piperazine-2-acetamide;
1-[6-chloro-2-(1H-imidazol-1-yl)pyrimidin-4-yl]-N-[(3-chloro-4-methoxyphenyl)methyl]-4-(methoxycarbonyl)piperazine-2-acetamide;

1-[2-(1H-imidazol-1-yl)-6-methylpyrimidin-4-yl]-N-[(3-chloro-4-methoxyphenyl)ethyl]-4-(methoxycarbonyl)piperazine-2-acetamide;

1-[6-chloro-2-(1H-imidazol-1-yl)pyrimidin-4-yl]-N-[(1,3-benzodioxol-5-yl)methyl]-4-(methoxycarbonyl)piperazine-2-acetamide;

1-[6-chloro-2-(1H-imidazol-1-yl)pyrimidin-4-yl]-N-[2-(1,3-benzodioxol-5-yl)ethyl]-4-(methoxycarbonyl)piperazine-2-acetamide;

1-[2-(1H-imidazol-1-yl)-6-methylpyrimidin-4-yl]-N-[2-(1,3-benzodioxol-5-yl)ethyl]-4-(methoxycarbonyl)piperazine-2-acetamide;

1-[2-(1H-imidazol-1-yl)pyrimidin-4-yl]-N-[2-(1,3-benzodioxol-5-yl)ethyl]-4-(methoxycarbonyl)piperazine-2-acetamide;

1-[6-chloro-2-(1H-imidazol-1-yl)pyrimidin-4-yl]-N-[(1,4-benzodioxan-yl)methyl]-4-(methoxycarbonyl)piperazine-2-acetamide;

1-[2-(1H-imidazol-1-yl)pyrimidin-4-yl]-N-[(1,4-benzodioxan-6-yl)methyl]-4-(methoxycarbonyl)piperazine-2-acetamide;

1-[2-(1H-imidazol-1-yl)-6-methylpyrimidin-4-yl]-N-[(1,4-benzodioxan-6-yl)methyl]-4-(methoxycarbonyl)piperazine-2-acetamide;

1-[2-(1H-imidazol-1-yl)-6-(methylethyl)pyrimidin-4-yl]-N-[(4-methoxyphenyl)methyl]-4-(methoxycarbonyl)piperazine-2-acetamide;

1-[6-chloro-2-(1H-imidazol-1-yl)pyrimidin-4-yl]-N-[(4-methoxyphenyl)methyl]-4-(methoxycarbonyl)piperazine-2-acetamide;

1-[2-(1H-imidazol-1-yl)-6-methylpyrimidin-4-yl]-N-[(4-methoxyphenyl)methyl]-4-(methoxycarbonyl)piperazine-2-acetamide;

1-[6-chloro-2-(1H-imidazol-1-yl)pyrimidin-4-yl]-N-[(4-methoxyphenyl)ethyl]-4-(methoxycarbonyl)piperazine-2-acetamide;

1-[2-(1H-imidazol-1-yl)-6-methylpyrimidin-4-yl]-N-[(4-methoxyphenyl)ethyl]-4-(methoxycarbonyl)piperazine-2-acetamide;

1-[6-chloro-2-(1H-imidazol-1-yl)pyrimidin-4-yl]-N-[(3-methoxyphenyl)ethyl]-4-(methoxycarbonyl)piperazine-2-acetamide;

1-[6-chloro-2-(1H-imidazol-1-yl)pyrimidin-4-yl]-N-[(1,4-benzodioxan-2-yl)methyl]-4-(methoxycarbonyl)piperazine-2-acetamide;

1-[2-(1H-imidazol-1-yl)-6-(methylethyl)pyrimidin-4-yl]-N-[(3,4-dimethoxyphenyl)methyl]-4-(methoxycarbonyl)piperazine-2-acetamide;

1-[2-(1H-imidazol-1-yl)-6-methylpyrimidin-4-yl]-N-[(1,3-benzodioxol-5-yl)methyl]-4-(methylethoxycarbonyl)piperazine-2-acetamide;

1-2-(1H-imidazol-1-yl)-pyrimidin-4-yl]-N-[(4-methoxyphenyl)methyl]-4-methylethoxycarbonyl)piperazine-2-acetamide;

1-[2-(1H-imidazol-1-yl)pyrimidin-4-yl]-N-[(1,4-benzodioxan-6-yl)methyl]-4-(butoxycarbonyl)piperazine-2-acetamide;

1-[2-(1H-imidazol-1-yl)-6-methylpyrimidin-4-yl]-N-[(1,4-benzodioxan-6-yl)methyl]-4-(butoxycarbonyl)piperazine-2-acetamide;

1-[2-(1H-imidazol-1-yl)-6-methylpyrimidin-4-yl]N-[(4-methoxyphenyl)methyl]-4-(butoxycarbonyl)piperazine-2-acetamide;

1-[2-(1H-imidazol-1-yl)pyrimidin-4-yl]-N-[(4-methoxyphenyl)methyl]-4-(butoxycarbonyl)piperazine-2-acetamide;

1-[2-(1H-imidazol-1-yl)-6-(methylethyl)pyrimidin-4-yl]-N-[(3,4-difluorophenyl)methyl]-4-(butoxycarbonyl)piperazine-2-carboxamide;

1-[6-chloro-2-(1H-imidazol-1-yl)pyrimidin-4-yl]-N-[(4-chlorophenyl)methyl]-4-[(2-methoxyethoxy)carbonyl]piperazine-2-acetamide;

1-[2-(1H-imidazol-1-yl)-6-methylpyrimidin-4-yl]-N-[(3-chloro-4-methoxyphenyl)methyl]-4-[(2-methoxyethoxy)carbonyl]piperazine-2-acetamide;

1-[2-(1H-imidazol-1-yl)-6-(methylethyl)pyrimidin-4-yl]-N-[(1,3-benzodioxol-5-yl)methyl]-4-[(2-methoxyethoxy)carbonyl]piperazine-2-acetamide;

1-[2-(1H-imidazol-1-yl)-6-methylpyrimidin-4-yl]-N-[(1,3-benzodioxol-5-yl)methyl]-4-[(2-methoxyethoxy)carbonyl]piperazine-2-acetamide;

1-[6-chloro-2-(1H-imidazol-1-yl)pyrimidin-4-yl]-N-[(1,3-benzodioxol-5-yl)methyl]-4-[(2-methoxyethoxy)carbonyl]piperazine-2-acetamide;

1-[6-chloro-2-(1H-imidazol-1-yl)pyrimidin-4-yl]-N-[2-(1,3-benzodioxol-5-yl)ethyl]-4-[(2-methoxyethoxy)carbonyl]piperazine-2-acetamide;

1-[2-(1H-imidazol-1-yl)pyrimidin-4-yl]-N-[(1,4-benzodioxan-6-yl)methyl]-4-[(2-methoxyethoxy)carbonyl]piperazine-2-acetamide;

1-[2-(1H-imidazol-1-yl)-6-methylpyrimidin-4-yl]-N-[(1,4-benzodioxan-6-yl)methyl]-4-[(2-methoxyethoxy)carbonyl]piperazine-2-acetamide;

1-[2-(1H-imidazol-1-yl)pyrimidin-4-yl]-N-[2-(1,4-benzodioxan-6-yl)ethyl]-4-[(2-methoxyethoxy)carbonyl]piperazine-2-acetamide;

1-[2-(1H-imidazol-1-yl)-6-methylpyrimidin-4-yl]-N-[2-(1,4-benzodioxan-6-yl)ethyl]-4-[(2-methoxyethoxy)carbonyl]piperazine-2-acetamide;

1-[6-chloro-2-(1H-imidazol-1-yl)pyrimidin-4-yl]-N-[(4-methoxyphenyl)methyl]-4-[(2-methoxyethoxy)carbonyl]piperazine-2-acetamide;

1-[2-(1H-imidazol-1-yl)-6-methylpyrimidin-4-yl]-N-[2-(3,4-dimethoxyphenyl)ethyl]-4-[(2-methoxyethoxy)carbonyl]piperazine-2-acetamide;

1-[6-chloro-2-(1H-imidazol-1-yl)pyrimidin-4-yl]-N-[(3,5-dimethoxyphenyl)methyl]-4-[(2-methoxyethoxy)carbonyl]piperazine-2-acetamide;

1-[6-chloro-2-(1H-imidazol-1-yl)pyrimidin-4-yl]-N-[(4-chlorophenyl)methyl]-4-[(phenylmethoxy)carbonyl]piperazine-2-acetamide;

1-[2-(1H-imidazol-1-yl)pyrimidin-4-yl]-N-[(1,3-benzodioxol-5-yl)methyl]-4-[(phenylmethoxy)carbonyl]piperazine-2-acetamide;

1-[2-(1H-imidazol-1-yl)pyrimidin-4-yl]-N-[2-(1,3-benzodioxol-5-yl)ethyl]-4-[(phenylmethoxy)carbonyl]piperazine-2-acetamide;

1-[6-chloro-2-(1H-imidazol-1-yl)pyrimidin-4-yl]-N-[2-(1,3-benzodioxol-5-yl)ethyl]-4-[(phenylmethoxy)carbonyl]piperazine-2-acetamide;

1-2-(1H-imidazol-1-yl)pyrimidin-4-yl]-N-[(1,4-benzodioxan-yl)methyl]-4-[(phenylmethoxy)carbonyl]piperazine-2-acetamide;

1-[2-(1H-imidazol-1-yl)-6-(methylethyl)pyrimidin-4-yl]-N-[(1,4-benzodioxan-6-yl)methyl]-4-[(phenylmethoxy)carbonyl]piperazine-2-acetamide;

1-[2-(1H-imidazol-1-yl)-6-methylpyrimidin-4-yl]-N-[(1,4-benzodioxan-6-yl)methyl]-4-[(phenylmethoxy)carbonyl]piperazine-2-acetamide;

1-6-chloro-2-(1H-imidazol-1-yl)pyrimidin-4-yl]-N-[(1,4-benzodioxan-6-yl)methyl]-4-[(phenylmethoxy)carbonyl]piperazine-2-acetamide;

1-[6-(1H-imidazol-1-yl)pyrimidin-4-yl]-N-[2-(1,4-benzodioxan-6-yl)ethyl]-4-[(phenylmethoxy)carbonyl]piperazine-2-carboxamide;

1-[2-(1H-imidazol-1-yl)pyrimidin-4-yl]-N-[(4-methoxyphenyl)methyl]-4-[(phenylmethoxy)carbonyl]piperazine-2-acetamide;

1-[6-chloro-2-(1H-imidazol-1-yl)pyrimidin-4-yl]-N-[(4-methoxyphenyl)ethyl]-4-[(phenylmethoxy)carbonyl]piperazine-2-acetamide;

1-[2-(1H-imidazol-1-yl)-6-methylpyrimidin-4-yl]-N-[(4-methoxyphenyl)ethyl]-4-[(phenylmethoxy)carbonyl]piperazine-2-acetamide;

1-[6-(1H-imidazol-1-yl)pyrimidin-4-yl]-N-[(2-thienyl)ethyl]-4-[(phenylmethoxy)carbonyl]piperazine-2-acetamide;

1-[2-(1H-imidazol-1-yl)-6-methylpyrimidin-4-yl]-N-[2-(3,4-dimethoxyphenyl)ethyl]-4-[(phenylmethoxy)carbonyl]piperazine-2-acetamide;

1-[6-chloro-2-(1H-imidazol-1-yl)pyrimidin-4-yl]-N-[2-(3,4-dimethoxyphenyl)ethyl]-4-[(phenylmethoxy)carbonyl]piperazine-2-acetamide;

1-[2-(1H-imidazol-1-yl)pyrimidin-4-yl]-N-[2-(3,4-dimethoxyphenyl)ethyl]-4-[(phenylmethoxy)carbonyl]piperazine-2-acetamide;

1-[2-(1H-imidazol-1-yl)-6-(methylethyl)pyrimidin-4-yl]-N-[2-(3,4-dimethoxyphenyl)ethyl]-4-[(phenylmethoxy)carbonyl]piperazine-2-acetamide;

1-[2-(1H-imidazol-1-yl)pyrimidin-4-yl]-N-[(1,3-benzodioxol-5-yl)methyl]-4-[(1-methylpropoxy)carbonyl]piperazine-2-acetamide;

1-[2-(1H-imidazol-1-yl)pyrimidin-4-yl]-N-[2-(1,3-benzodioxol-5-yl)ethyl]-4-[(1-methylpropoxy)carbonyl]piperazine-2-acetamide;

1-6-chloro-2-(1H-imidazol-1-yl)pyrimidin-4-yl]-N-[(4-methoxyphenyl)methyl]-4-[(1-methylpropoxy)carbonyl]piperazine-2-acetamide;

1-[6-chloro-2-(1H-imidazol-1-yl)pyrimidin-4-yl]-N-[(3-chloro-4-methoxyphenyl)methyl]-4-[(4-methoxyphenoxy)carbonyl]piperazine-2-carboxamide;

1-[2-(1H-imidazol-1-yl)-6-(methylethyl)pyrimidin-4-yl]-N-[(3,4,5-trimethoxyphenyl)methyl]-4-[(4-methoxyphenoxy)carbonyl]piperazine-2-acetamide;

1-[2-(1H-imidazol-1-yl)-6-trifluoromethylpyrimidin-4-yl]-N-[(1,4-benzodioxan-6-yl)methyl]-4-[(4-methoxyphenoxy)carbonyl]piperazine-2-carboxamide;

1-[2-(1H-imidazol-1-yl)pyrimidin-4-yl]-N-[(1,4-benzodioxan-6-yl)methyl]-4-[(4-methoxyphenoxy)carbonyl]piperazine-2-acetamide;

1-[2-(1H-imidazol-1-yl)-6-methylpyrimidin-4-yl]-N-[2-(1,4-benzodioxan-6-yl)ethyl]-4-[(4-methoxyphenoxy)carbonyl]piperazine-2-acetamide;

1-[6-(1H-imidazol-1-yl)pyrimidin-4-yl]-N-[(3-methoxyphenyl)methyl]-4-[(4-methoxyphenoxy)carbonyl]piperazine-2-carboxamide;

1-[2-(1H-imidazol-1-yl)-6-methylpyrimidin-4-yl]-N-[(1-methylpyrrol-2-yl)ethyl]-4-[(4-methoxyphenoxy)carbonyl]piperazine-2-carboxamide;

1-[2-(1H-imidazol-1-yl)-6-methylethyl)pyrimidin-4-yl]-N-[(2,4-dimethoxyphenyl)methyl]-4-[(4-methoxyphenoxy)carbonyl]piperazine-2-carboxamide;

1-[6-chloro-2-(1H-imidazol-1-yl)pyrimidin-4-yl]-N-[(2,6-dimethoxyphenyl)methyl]-4-[(4-methoxyphenoxy)carbonyl]piperazine-2-carboxamide;

1-[2-(1H-imidazol-1-yl)-6-methylpyrimidin-4-yl]-N-[(3,4-dimethoxyphenyl)methyl]-4-[(4-methoxyphenoxy)carbonyl]piperazine-2-carboxamide;

N-[(1,3-benzodioxol-5-yl)methyl]-4-[6-[bis(ethoxycarbonyl)methyl]-2-(1H-imidazol-1-yl)lpyrimidin-4-yl]-1-](methoxy)carbonyl]piperazine-2-acetamide;

N-[(1,3-benzodioxol-5-yl)methyl]-4-[6-(aminocarbonyl)-2-(1H-imidazol-1-yl)lpyrimidin-4-yl]-1-[(methoxy)carbonyl]piperazine-2-acetamide;

1-[6-chloro-2-(1H-imidazol-1-yl)pyrimidin-4-yl]-N-methylpiperidine-2-carboxamide;

N-[(2-methoxypyridin-5-yl)methyl]-1-[2-(1H-imidazol-1-yl)-6-methylpyrimidin-4-yl]piperidine-2-carboxamide;

N-[(2-methylpyridin-5-yl)methyl]-1-[2-(1H-imidazol-1-yl)-6-methylpyrimidin-4-yl]piperidine-2-carboxamide;

N-[(4-nitrophenyl)methyl]-1-[2-(1H-imidazol-1-yl)-6-methylpyrimidin-4-yl]piperidine-2-acetamide;

N-[[4-(acetylamino)phenyl]methyl]-1-[2(1H-imidazol-1-yl)-6-methylpyrimidin-4-yl]piperidine-2-acetamide;

N-[[4-(methylsulfonylamino)phenyl]methyl]-1-[2-(1H-imidazol-1-yl)-6-methylpyrimidin-4-yl]piperidine-2-acetamide;

N-[(2,3-dihydrobenzofuran-5-yl)methyl]-1-[2-(1H-imidazol-1-yl)-6-methylpyrimidin-4-yl]piperidine-2-acetamide;

N-[(indan-5-yl)methyl]-1-[2-(1H-imidazol-1-yl)-6-methylpyrimidin-4-yl]piperidine-2-acetamide;

N-[(3-chloro-4-methoxyphenyl)methyl]-1-[2-(1H-imidazol-1-yl)pyrimidin-4-yl]piperidine-2-acetamide;

N-[(4-methoxyphenyl)aminocarbonyl]-1-[2-(1H-imidazol-1-yl)pyrimidin-4-yl]piperidine-2-methaneamine;

N-[(1,3-benzodioxol-5-yl)methylcarbonyl]-1-[2-(1H-imidazol-1-yl)pyrimidin-4-yl]piperidine-2-methaneamine;

N-[(4-methoxyphenoxy)carbonyl]-1-[2-(1H-imidazol-1-yl)pyrimidin-4-yl]piperidine-2-methaneamine;

N-[(4-methoxyphenyl)methylcarbonyl]-1-[2-(1H-imidazol-1-yl)pyrimidin-4-yl]piperidine-2-methaneamine;

N-[[(1,3-benzodioxol-5-yl)methyl]aminocarbonyl]-1-[2-(1H-imidazol-1-yl)pyrimidin-4-yl]piperidine-2-methaneamine;

N-[(1,3-benzodioxol-5-yl)methyl]-1-[2-(1H-imidazol-1-yl)pyrimidin-4-yl]piperidine-2-methaneamine;

N-[(1,3-benzodioxol-5-yl)carbonyl]-1-[2-(1H-imidazol-1-yl)-6-methylpyrimidin-4-yl]piperidine-2-ethaneamine;

1-[2-(1H-imidazol-1-yl)-6-methylpyrimidin-4-yl]-N-[2-(3,4-dimethoxyphenyl)ethyl]piperidine-2-acetamide;

1-[2-(1H-imidazol-1-yl)-6-methylpyrimidin-4-yl]-N-[(4-ethoxyphenyl)methyl]piperidine-2-acetamide;

1-[2-(1H-imidazol-1-yl)-6-methylpyrimidin-4-yl]-N-[(4-methylphenoxy)ethyl]piperidine-2-acetamide;

1-[2-(1H-imidazol-1-yl)-6-methylpyrimidin-4-yl]-N-[(4-methylphenyl)methyl]piperidine-2-acetamide;

1-[2-(1H-imidazol-1-yl)-6-methylpyrimidin-4-yl]-N-[(4-chlorophenyl)methyl]piperidine-2-acetamide;

1-[2-(1H-imidazol-1-yl)-6-methylpyrimidin-4-yl]-N-[(3-chloro-4-methoxyphenyl)methyl]piperidine-2-acetamide;

1-[2-(1H-imidazol-1-yl)-6-methylpyrimidin-4-yl]-N-[(3-chloro-4-methoxyphenyl)ethyl]piperidine-2-acetamide;

1-[2-(1H-imidazol-1-yl)pyrimidin-4-yl]-N-[(1,3-benzodioxol-5-yl)methyl]piperidine-2-acetamide;

1-[2-(1H-imidazol-1-yl)-6-methylpyrimidin-4-yl]-N-[(1,3-benzodioxol-5-yl)methyl]piperidine-2-acetamide;

1-[2-(1H-imidazol-1-yl)-6-methylpyrimidin-4-yl]-N-[2-(1,3-benzodioxol-5-yl)ethyl]piperidine-2-acetamide;

1-[2-(1H-imidazol-1-yl)pyrimidin-4-yl]-N-[2-(1,3-benzodioxol-5-yl)ethyl]piperidine-2-acetamide;

1-[2-(1H-imidazol-1-yl)pyrimidin-4-yl]-N-[(1,4-benzodioxan-6-yl)methyl]piperidine-2-acetamide;

1-[2-(1H-imidazol-1-yl)-6-methylpyrimidin-4-yl]-N-[(1,4-benzodioxan-6-yl)methyl]piperidine-2-acetamide;

1-[2-(1H-imidazol-1-yl)-6-methylpyrimidin-4-yl]-N-[(4-methoxyphenyl)methyl]piperidine-2-acetamide;

1-[2-(1H-imidazol-1-yl)-6-methylpyrimidin-4-yl]-N-[(4-methoxyphenyl)ethyl]piperidine-2-acetamide;

1-[2-(1H-imidazol-1-yl)-6-methylpyrimidin-4-yl]-N-[(2,4-dimethoxyphenyl)methyl]piperidine-2-acetamide;

1-[2-(1H-imidazol-1-yl)-6-methylpyrimidin-4-yl]-N-[(3,4-dimethoxyphenyl)methyl]piperidine-2-acetamide;
1-[2-(1H-imidazol-1-yl)pyrimidin-4-yl]-N-[(3,4-dimethoxyphenyl)methyl]piperidine-2-acetamide;
1-[2-(1H-imidazol-1-yl)-6-methylpyrimidin-4-yl]-N-[(1,3-benzodioxol-5-yl)methyl]piperidine-3-carboxamide;
1-[2-(1H-imidazol-1-yl)-6-methylpyrimidin-4-yl]-N-[2-(1,3-benzodioxol-5-yl)ethyl]piperidine-3-carboxamide;
1-[2-(1H-imidazol-1-yl)-6-methylpyrimidin-4-yl]-N-[(1,4-benzodioxan-6-yl)methyl]piperidine-3-carboxamide;
1-[2-(1H-imidazol-1-yl)-6-methylpyrimidin-4-yl]-N-[(4-methoxyphenyl)methyl]piperidine-3-carboxamide;
1-[2-(1H-imidazol-1-yl)-6-methylpyrimidin-4-yl]-N-[(3,4-dimethoxyphenyl)methyl]piperidine-3-carboxamide;
1-[2-(1H-imidazol-1-yl)-6-methylpyrimidin-4-yl]-N-[(3-chloro-4-methoxyphenyl)methyl]piperidine-3-acetamide;
1-[2-(1H-imidazol-1-yl)-6-methylpyrimidin-4-yl]-N-[(1,3-benzodioxol-5-yl)methyl]piperidine-3-acetamide;
1-[2-(1H-imidazol-1-yl)-6-methylpyrimidin-4-yl]-N-[2-(1,3-benzodioxol-5-yl)ethyl]piperidine-3-acetamide;
1-[2-(1H-imidazol-1-yl)-6-methylpyrimidin-4-yl]-N-[(1,4-benzodioxan-6-yl)methyl]piperidine-3-acetamide;
1-[2-(1H-imidazol-1-yl)-6-methylpyrimidin-4-yl]-N-[2-(1,4-benzodioxan-6-yl)ethyl]piperidine-3-acetamide;
1-[2-(1H-imidazol-1-yl)-6-methylpyrimidin-4-yl]-N-[(4-methoxyphenyl)methyl]piperidine-3-acetamide;
1-[2-(1H-imidazol-1-yl)-6-methylpyrimidin-4-yl]-N-[(4-methoxyphenyl)ethyl]piperidine-3-acetamide;
1-[2-(1H-imidazol-1-yl)-6-methylpyrimidin-4-yl]-N-[(2,4-dimethoxyphenyl)methyl]piperidine-3-acetamide;
1-[2-(1H-imidazol-1-yl)-6-methylpyrimidin-4-yl]-N-[(3,4-dimethoxyphenyl)methyl]piperidine-3-acetamide;
1-[2-(1H-imidazol-1-yl)-6-methylethylpyrimidin-4-yl]-N-[1-(phenylmethyl)piperidin-4-yl]piperidine-2-acetamide;
1-[2-(1H-imidazol-1-yl)-6-methylpyrimidin-4-yl]-N-(1-cyanocyclohexyl)piperidine-2-acetamide;
1-[2-(1H-imidazol-1-yl)-6-methylethylpyrimidin-4-yl]-N-(2,2-dimethoxyethyl)piperidine-2-acetamide;
1-[2-(1H-imidazol-1-yl)-6-methylethylpyrimidin-4-yl]-N-tridecylpiperidine-2-acetamide;
1-[2-(1H-imidazol-1-yl)pyrimidin-4-yl]-N-(2-hydroxy-4-methylthiobutyl)piperidine-2-acetamide;
1-[2-(1H-imidazol-1-yl)-6-methylethylpyrimidin-4-yl]-N,N-[bis(2-cyanoethyl)]piperidine-2-acetamide;
1-[2-(1H-imidazol-1-yl)-6-methylpyrimidin-4-yl]-N,N-[bis(2-cyanomethyl)]piperidine-2-acetamide;
1-[2-(1H-imidazol-1-yl)-6-methylethylpyrimidin-4-yl]-N-(4,4-diethoxybutyl)piperidine-2-acetamide;
1-[2-(1H-imidazol-1-yl)-6-methylpyrimidin-4-yl]-N-[(2,3-dihydrobenzofuran-5-yl)methyl]piperidine-2-acetamide;
1-[2-(1H-imidazol-1-yl)-6-methylpyrimidin-4-yl]-N-[(indan-5-yl)methyl]piperidine-2-acetamide;
1-[2-(1H-imidazol-1-yl)-6-methylpyrimidin-4-yl]-N-[(cyclohexyl)methyl]piperidine-2-acetamide;
1-[2-(1H-imidazol-1-yl)pyrimidin-4-yl]-N-(1,2,3,4-tetrahydronaphthalen-1-yl)piperidine-2-acetamide;
1-[2-(1H-imidazol-1-yl)pyrimidin-4-yl]-N-[(naphthalen-1-yl)methyl]piperidine-2-acetamide;
1-[2-(1H-imidazol-1-yl)-6-methylethylpyrimidin-4-yl]-N-[(1,3-benzodioxol-5-yl)methyl]piperidine-2-acetamide;
1-[2-(1H-imidazol-1-yl)-6-methylethylpyrimidin-4-yl]-N-[(4-chlorophenyl)methyl]piperidine-2-acetamide;
1-[2-(1H-imidazol-1-yl)-6-methylethylpyrimidin-4-yl]-N-(2-ethylhexyl)piperidine-2-acetamide;
1-[2-(1H-imidazol-1-yl)pyrimidin-4-yl]-N-(2-ethylhexyl)piperidine-2-acetamide;
1-[2-(1H-imidazol-1-yl)-6-methylpyrimidin-4-yl]-N-(2-ethylhexyl)piperidine-2-acetamide;
1-[2-(1H-imidazol-1-yl)-6-methylethylpyrimidin-4-yl]-N-(1-methylhexyl)piperidine-2-acetamide;
1-[2-(1H-imidazol-1-yl)pyrimidin-4-yl]-N-(1-methylhexyl)piperidine-2-acetamide;
1-[2-(1H-imidazol-1-yl)pyrimidin-4-yl]-N-[(2-methylphenyl)methyl]piperidine-2-acetamide;
1-[2-(1H-imidazol-1-yl)-6-methylethylpyrimidin-4-yl]-N-[(4-methoxyphenyl)methyl]piperidine-2-acetamide;
1-[2-(1H-imidazol-1-yl)-6-methylpyrimidin-4-yl]-N-[(4-methoxyphenyl)methyl]piperidine-2-acetamide;
1-[2-(1H-imidazol-1-yl)-6-methylethylpyrimidin-4-yl]-N-(cyclooctyl)piperidine-2-acetamide;
1-[2-(1H-imidazol-1-yl)-6-methylpyrimidin-4-yl]-N-(1-ethyl-3-hydroxy-1-hydroxyethylpropyl)piperidine-2-acetamide;
1-[2-(1H-imidazol-1-yl)-6-methylethylpyrimidin-4-yl]-N-[3-(morpholin-4-yl)propyl]piperidine-2-acetamide;
1-[2-(1H-imidazol-1-yl)-6-methylethylpyrimidin-4-yl]-N-(1-methyl-3-phenylpropyl)piperidine-2-acetamide;
1-[2-(1H-imidazol-1-yl)pyrimidin-4-yl]-N-(1-methyl-3-phenylpropyl)piperidine-2-acetamide;
1-[2-(1H-imidazol-1-yl)-6-methylpyrimidin-4-yl]-N-(1-methyl-3-phenylpropyl)piperidine-2-acetamide;
1-[2-(1H-imidazol-1-yl)-6-methylethylpyrimidin-4-yl]-N-(1-methylheptyl)piperidine-2-acetamide;
1-[2-(1H-imidazol-1-yl)pyrimidin-4-yl]-N-(1-methylheptyl)piperidine-2-acetamide;
1-[2-(1H-imidazol-1-yl)-6-methylpyrimidin-4-yl]-N-(1-methylheptyl)piperidine-2-acetamide;
1-[2-(1H-imidazol-1-yl)pyrimidin-4-yl]-N-[(3-fluorophenyl)methyl]piperidine-2-acetamide;
1-[2-(1H-imidazol-1-yl)-6-methylpyrimidin-4-yl]-N-[(3-fluorophenyl)methyl]piperidine-2-acetamide;
1-[2-(1H-imidazol-1-yl)-6-methylpyrimidin-4-yl]-N-[(4-methylphenyl)methyl]piperidine-2-acetamide;
1-[2-(1H-imidazol-1-yl)pyrimidin-4-yl]-N-(1-phenylethyl)piperidine-2-acetamide;
1-[2-(1H-imidazol-1-yl)-6-methylpyrimidin-4-yl]-N-phenylmethylpiperidine-2-acetamide;
1-[2-(1H-imidazol-1-yl)-6-methylpyrimidin-4-yl]-N-[(3,4-dichlorophenyl)methyl]piperidine-2-acetamide;
piperidine-2-acetamide;
1-[2-(1H-imidazol-1-yl)pyrimidin-4-yl]-N-(2-phenylethyl)piperidine-2-acetamide;
1-[2-(1H-imidazol-1-yl)-6-methylpyrimidin-4-yl]-N-(2-phenylethyl)piperidine-2-acetamide;
1-[2-(1H-imidazol-1-yl)-6-methylethylpyrimidin-4-yl]-N-[3-(pyrrolidinon-1-yl)propyl]piperidine-2-acetamide;
1-[2-(1H-imidazol-1-yl)pyrimidin-4-yl]-N-(1,5-dimethylhexyl)piperidine-2-acetamide;
1-[2-(1H-imidazol-1-yl)-6-methylpyrimidin-4-yl]-N-(1,5-dimethylhexyl)piperidine-2-acetamide;
1-[2-(1H-imidazol-1-yl)-6-methylethylpyrimidin-4-yl]-N-(1,5-dimethylhexyl)piperidine-2-acetamide;
1-[2-(1H-imidazol-1-yl)pyrimidin-4-yl]-N-[(2-fluorophenyl)methyl]piperidine-2-acetamide;
1-[2-(1H-imidazol-1-yl)-6-methylpyrimidin-4-yl]-N-[(2-fluorophenyl)methyl]piperidine-2-acetamide;
1-[2-(1H-imidazol-1-yl)-6-methylethylpyrimidin-4-yl]-N-[(3,4-dimethoxyphenyl)methyl]piperidine-2-acetamide;
1-[2-(1H-imidazol-1-yl)-6-methylpyrimidin-4-yl]-N-[(3,4-dimethoxyphenyl)methyl]piperidine-2-acetamide;
1-[2-(1H-imidazol-1-yl)-methylpyrimidin-4-yl]-N-[2-(2-chlorophenyl)ethyl]piperidine-2-acetamide;
1-[2-(1H-imidazol-1-yl)pyrimidin-4-yl]-N-[(furan-2-yl)methyl]piperidine-2-acetamide;
1-[2-(1H-imidazol-1-yl)-6-methylpyrimidin-4-yl]-N-[(furan-2-yl)methyl]piperidine-2-acetamide;

1-[2-(1H-imidazol-1-yl)-6-methylethylpyrimidin 4-yl]-N-[(furan-2-yl)methyl]piperidine-2-acetamide;
1-[2-(1H-imidazol-1-yl)-6-methylethylpyrimidin-4-yl]-N-[(pyridin-2-yl)methyl]piperidine-2-acetamide;
1-[2-(1H-imidazol-1-yl)pyrimidin-4-yl]-N-[(pyridin-2-yl)methyl]piperidine-2-acetamide;
1-[2-(1H-imidazol-1-yl)-6-methylpyrimidin-4-yl]-N-[pyridin-2-yl)methyl]piperidine-2-acetamide;
1-[2-(1H-imidazol-1-yl)-6-methylpyrimidin-4-yl]-N-[(3-trifluoromethylphenyl)methyl]piperidine-2-acetamide;
1-[2-(1H-imidazol-1-yl)pyrimidin-4-yl]-N-[(3-trifluoromethylphenyl)methyl]piperidine-2-acetamide;
1-[2-(1H-imidazol-1-yl)-6-methylpyrimidin-4-yl]-N-(2-phenylpropyl)piperidine-2-acetamide;
1-[2-(1H-imidazol-1-yl)-6-methylpyrimidin-4-yl]-N-(2-phenylpropyl)piperidine-2-acetamide;
1-[2-(1H-imidazol-1-yl)-6-methylpyrimidin-4-yl]-N-[2-(2-methoxyphenyl)ethyl]piperidine-2-acetamide;
1-[2-(1H-imidazol-1-yl)-pyrimidin-4-yl]-N-[2-(2-methoxyphenyl)ethyl]piperidine-2-acetamide;
1-[2-(1H-imidazol-1-yl)-6-methylpyrimidin-4-yl]-N-(2-hydroxy-4-methylthiobutyl)piperidine-2-acetamide;
1-[2-(1H-imidazol-1-yl)-6-methylethylpyrimidin-4-yl]-N-(2-hydroxy-4-methylthiobutyl)piperidine-2-acetamide;
1-[2-(1H-imidazol-1-yl)-6-methylpyrimidin-4-yl-N-[(2,4-dichlorophenyl)methylpiperidine-2-acetamide;
1-[2-(1H-imidazol-1-yl)-6-methylethylpyrimidin-4-yl]-N-[(3-methylphenyl)methyl]piperidine-2-acetamide;
1-[2-(1H-imidazol-1-yl)pyrimidin-4-yl]-N-[(3-methylphenyl)methyl]piperidine-2-acetamide;
1-[2-(1H-imidazol-1-yl)-6-methylpyrimidin-yl]-N-[(3-methylphenyl)methyl]piperidine-2-acetamide;
1-[2-(1H-imidazol-1-yl)-6-methylethylpyrimidin-4-yl]-N-[2-(3-methoxyphenyl)ethyl]piperidine-2-acetamide;
1-[2-(1H-imidazol-1-yl)pyrimidin-4-yl]-N-[2-(3-methoxyphenyl)ethyl]piperidine-2-acetamide;
1-[2-(1H-imidazol-1-yl)-6-methylpyrimidin-4-yl]-N-[2-(3-methoxyphenyl)ethyl]piperidine-2-acetamide;
1-[2-(1H-imidazol-1-yl)-6-methylethylpyrimidin-4-yl]N-[2-(3,4-dimethoxyphenyl)ethyl]piperidine-2-acetamide;
1-[2-(1H-imidazol-1-yl)pyrimidin-4-yl]-N-[2-(3,4-dimethoxyphenyl)ethyl]piperidine-2-acetamide;
1-[2-(1H-imidazol-1-yl)-6-methylpyrimidin-4-yl]-N-[2-(3,4-dimethoxyphenyl)ethyl]piperidine-2-acetamide;
1-[2-(1H-imidazol-1-yl)-6-methylethylpyrimidin-4-yl]-N-(phenylbutyl)piperidine-2-acetamide
1-[2-(1H-imidazol-1-yl)-pyrimidin-4-yl)-N-(phenylbutyl)piperidin-6-2-acetamide;
1-[2-(1H-imidazol-1-yl)pyrimidin-4-yl]-N-(1-hydroxymethylpentyl)piperidine-2-acetamide;
1-[2-(1H-imidazol-1-yl)-6-methylpyrimidin-4-yl]-N-(1-hydroxymethylpentyl)piperidine-2-acetamide;
1-[2-(1H-imidazol-1-yl)-6-methylethylpyrimidin-4-yl]-N-[(3,5-dimethoxyphenyl)methyl]piperidine-2-acetamide;
1-[2-(1H-imidazol-1-yl]pyrimidin-4-yl]-N-[(3,5-dimethoxyphenyl)methyl]piperidine-2-acetamide;
1-[2-(1H-imidazol-1-yl)-6-methylpyrimidin-4-yl]-N-[(3,5-dimethoxyphenyl)methyl-piperidine-2-acetamide;
1-[2-(1H-imidazol-1-yl)-6-methylethylpyrimidin-4-yl]-N-[2-(4-ethoxyphenyl)ethyl]piperidine-2-acetamide;
1-[2-(1H-imidazol-1-yl)pyrimidin-4-yl]-N-[2-(4-ethoxyphenyl)ethyl]piperidine-2-acetamide;
1-[2-(1H-imidazol-1-yl)-6-methylpyrimidin-4-yl]-N-[2-(4-ethoxyphenyl)ethyl]piperidine-2-acetamide;
1-[2-(1H-imidazol-1-yl)-6-methylethylpyrimidin-4-yl]-N-[2-(4-bromophenyl)ethyl]piperidine-2-acetamide;
1-[2-(1H-imidazol-1-yl)pyrimidin-4-yl]-N-[2-4-bromophenyl)ethyl]piperidine-2-acetamide;
1-[2-(1H-imidazol-1-yl)-6-methylpyrimidin-4-yl]-N-[2-(4-bromophenyl)ethyl]piperidine-2-acetamide;
1-[2-(1H-imidazol-1-yl)-6-methylethylpyrimidin-4-yl]-N-pentylpiperidine-2-acetamide;
1-[2-(1H-imidazol-1-yl)pyrimidin-4-yl]-N-pentylpiperidine-2-acetamide;
1-[2-(1H-imidazol-1-yl)-6-methylpyrimidin-4-yl]-N-pentylpiperidine-2-acetamide;
1-[2-(1H-imidazol-1-yl)-6-methylpyrimidin-4-yl]-N-[3-(1H-imidazol-1-yl)propyl]piperidine-2-acetamide;
1-[2-(1H-imidazol-1-yl)-6-methylpyrimidin-4-yl]-N-[3-(1H-imidazol-1-yl)propyl]piperidine-2-acetamide;
1-[2-(1H-imidazol-1-yl)-6-methylpyrimidin-4-yl]-N-[(3-chlorophenyl)methyl]piperidine-2-acetamide;
1-[2-(1H-imidazol-1-yl)pyrimidin-4-yl]-N-[(3-chlorophenyl)methyl]piperidine-2-acetamide;
1-[2-(1H-imidazol-1-yl)-6-methylpyrimidin-4-yl]-N-[(2,4-dichlorophenyl)methyl]piperidine-2-acetamide;
1-[2-(1H-imidazol-1-yl)pyrimidin-4-yl]-N-[(2,4-dichlorophenyl)methyl]piperidine-2-acetamide;
1-[2-(1H-imidazol-1-yl)-6-methylpyrimidin-4-yl]-N-2-(1-phenyl)ethyl]piperidine-2-acetamide;
1-[2-(1H-imidazol-1-yl)pyrimidin-4-yl]-N-[1-(phenyl)ethyl]piperidine-2-acetamide;
1-[2-(1H-imidazol-1-yl)-6-methylpyrimidin-4-yl]-N-[2-(3-fluorophenyl)ethyl]piperidine-2-acetamide;
1-[2-(1H-imidazol-1-yl-)methylethylpyrimidin-4-yl]-N-[2-(3-ethoxy-4-methoxyphenyl)ethyl]piperidine-2-acetamide;
1-[2-(1H-imidazol-1-yl)pyrimidin-4-yl-N-[2-(3-ethoxy-4-methoxyphenyl)ethyl]piperidine-2-acetamide;
1-[2-(1H-imidazol-1-yl)-6-methylpyrimidin-4-yl]-N-[2-(3-ethoxy-4-methoxyphenyl)ethyl]piperidine-2-acetamide;
1-[2-(1H-imidazol-1-yl)pyrimidin-4-yl]-N-[2-(4-chlorophenyl)ethyl]piperidine-2-acetamide;
1-[2-(1H-imidazol-1-yl)-6-methylpyrimidin-4-yl]-N-[2-(4-chlorophenyl)ethyl]piperidine-2-acetamide;
1-2-(1H-imidazol-1-yl)-6-methylpyrimidin-4-yl]-N-(5-hydroxypentyl)piperidine-2-acetamide;
1-[2-(1H-imidazol-1-yl)pyrimidin-4-yl]-N-butylpiperidine-2-acetamide;
1-[2-(1H-imidazol-1-yl)-6-methylpyrimidin-4-yl]-N-[(4-fluorophenyl)(methyl)methyl]piperidine-2-acetamide;
1-[2-(1H-imidazol-1-yl)pyrimidin-4-yl]-N-[(4-fluorophenyl)(methyl)methyl]piperidine-2-acetamide;
1-[2-(1H-imidazol-1-yl)pyrimidin-4-yl]-N-[2-(2,5-dimethoxyphenyl)ethyl]piperidine-2-acetamide;
1-[2-(1H-imidazol-1-yl)-6-methylpyrimidin-4-yl-N-[2-(2,5-dimethoxyphenyl)ethyl]piperidine-2-acetamide;
1-[2-(1H-imidazol-1-yl)-6-methylethylpyrimidin-4-yl]-N-[2-(4-ethoxy-3-methoxyphenyl)ethyl]piperidine-2-acetamide;
1-[2-(1H-imidazol-1-yl)pyrimidin-4-yl]-N-[2-(4-ethoxy-3-methoxyphenyl)ethyl]piperidine-2-acetamide;
1-[2-(1H-imidazol-1-yl)-6-methylpyrimidin-4-yl]-N-2-(4-ethoxy-3-methoxyphenyl)ethyl]piperidine-2-acetamide;
1-[2-(1H-imidazol-1-yl)-6-methylethylpyrimidin-4-yl]-N-[2-(4-methoxyphenyl)ethyl]piperidine-2-acetamide;
1-[2-(1H-imidazol-1-yl)-6-methylpyrimidin-4-yl]-N-[2-(4-methoxyphenyl)ethyl]piperidine-2-acetamide;
1-[2-(1H-imidazol-1-yl)-6-methylethylpyrimidin-4-yl]-N-[(3-methylethoxy)propyl]piperidine-2-acetamide;
1-[2-(1H-imidazol-1-yl)-6-methylethylpyrimidin-4-yl]-N-hexylpipenidine-2-acetamide;
1-[2-(1H-imidazol-1-yl)pyrimidin-4-yl]-N-hexylpipenidine-2-acetamide;
1-[2-(1H-imidazol-1-yl)-6-methylpyrimidin-4-yl]-N-hexylpiperidin-2-acetamide;

1-[2-(1H-imidazol-1-yl)pyrimidin-4-yl]-N-[2-cyclohexen-1-yl)ethyl]piperidine-2-acetamide;
1-[2-(1H-imidazol-1-yl)-6-methylpyrimidin-4-yl]-N-[2-cyclohexen-1-yl)ethyl]piperidine-2-acetamide;
1-[2-(1H-imidazol-1-yl)-6-methylpyrimidin-4-yl]-N-[(3-fluoro-5-trifluoromethylphenyl)methyl]piperidine-2-acetamide;
1-[2-(1H-imidazol-1-yl)pyrimidin-4-yl]-N-[(3-fluoro-5-trifluoromethylphenyl)methyl]piperidine-2-acetamide;
1-[2-(1H-imidazol-1-yl)-pyrimidin-4-yl]-N-[2-(4-methylphenyl)ethyl]piperidine-2-acetamide;
1-[2-(1H-imidazol-1-yl)-6-methylpyrimidin-4-yl]-N-[2-(4-methylphenyl)ethyl]piperidine-2-acetamide;
1-[2-(1H-imidazol-1-yl)-methylethylpyrimidin-4-yl]-N-3-ethoxypropyl)piperidine-2-acetamide;
1-[2-(1H-imidazol-1-yl)-6-methylpyrimidin-4-yl]-N-(3-ethoxypropyl)piperidine-2-acetamide;
1-[2-(1H-imidazol-1-yl)-6-methylethylpyrimidin-4-yl]-N-heptylpiperidine-2-acetamide;
1-[2-(1H-imidazol-1-yl)pyrimidin-4-yl]-N-heptylpiperidine-2-acetamide;
1-[2-(1H-imidazol-1-yl)-6-methylpyrimidin-4-yl]-N-heptylpiperidine-2-acetamide;
1-[2-(1H-imidazol-1-yl)-6-methylpyrimidin-4-yl]-N-(3-methoxypropyl)piperidine-2-acetamide;
1-[2-(1H-imidazol-1-yl)pyrimidin-4-yl]-N-(1-cyclohexylethyl)piperidine-2-acetamide;
1-[2-(1H-imidazol-1-yl)-6-methylpyrimidin-4-yl]-N-(1-cyclohexylethyl)piperidine-2-acetamide;
1-[2-(1H-imidazol-1-yl)-6-methylethylpyrimidin-4-yl]-N-[(4-trifluoromethoxyphenyl)methyl]piperidine-2-acetamide;
1-[2-(1H-imidazol-1-yl)-6-methylpyrimidin-4-yl]-N-[(4-trifluoromethoxyphenyl)methyl]piperidine-2-acetamide;
1-[2-(1H-imidazol-1-yl)pyrimidin-4-yl]-N-[2-(4-flurophenyl)ethyl]piperidine-2-acetamide;
1-2-(1H-imidazol-1-yl)-6-methylpyrimidin-4-yl]-N-[2-(4-flurophenyl)ethyl]piperidine-2-acetamide;
1-[2-(1H-imidazol-1-yl)-6-methylethylpyrimidin-4-yl]-N-[2-(3-bromo-4-methoxyphenyl)ethyl]piperidine-2-acetamide;
1-[2-(1H-imidazol-1-yl)pyrimidin-4-yl]-N-[2-(3-bromo-4-methoxyphenyl)ethyl]piperidine-2-acetamide;
1-[2-(1H-imidazol-1-yl)-6-methylpyrimidin-4-yl]-N-[2-(3-bromo-4-methoxyphenyl)ethyl]piperidine-2-acetamide;
1-[2-(1H-imidazol-1-yl)-6-methylethylpyrimidin-4-yl]-N-(3-phenylpropyl)piperidine-2-acetamide;
1-[2-(1H-imidazol-1-yl)pyrimidin-4-yl]-N-(3-phenylpropyl)piperidine-2-acetamide;
1-[2-(1H-imidazol-1-yl)-6-methylpyrimidin-4-yl]-N-(3-phenylpropyl)piperidine-2-acetamide;
1-[2-(1H-imidazol-1-yl)-6-methylethylpyrimidin-4-yl]-N-octylpiperidine-2-acetamide;
1-[2-(1H-imidazol-1-yl)-6-methylpyrimidin-4-yl]-N-octylpiperidine-2-acetamide;
1-[2-(1H-imidazol-1-yl)-6-methylpyrimidin-4-yl]-N-(1-hydroxy-3-methylbutyl)piperidine-2-acetamide;
1-[2-(1H-imidazol-1-yl)-6-methylethylpyrimidin-4-yl]-N-[1-(4-methylphenyl)ethyl]piperidine-2-acetamide;
1-[2-(1H-imidazol-1-yl)pyrimidin-4-yl]-N-[1-(4-methylphenyl)ethyl]piperidine-2-acetamide;
1-[2-(1H-imidazol-1-yl)-6-methylpyrimidin-4-yl]-N-[1-(4-methylphenyl)ethyl]piperidine-2-acetamide;
1-[2-(1H-imidazol-1-yl)-6-methylpyrimidin-4-yl]-N-(4,4-diethoxybutyl)piperidine-2-acetamide;
1-[2-(1H-imidazol-1-yl)-6-methylethylpyrimidin-4-yl]-N-[(4-trifluoromethylphenyl)methyl]piperidine-2-acetamide;
1-[2-(1H-imidazol-1-yl)-pyrimidin-4-yl]-N-](4-trifluoromethylphenyl)methyl]piperidine-2-acetamide;
1-[2-(1H-imidazol-1-yl)-6-methylpyrimidin-4-yl]-N-[(4-trifluoromethylphenyl)methyl]piperidine-2-acetamide;
1-[2-(1H-imidazol-1-yl)-6-methylethylpyrimidin-4-yl]-N-(3-butoxypropyl)piperidine-2-acetamide;
1-[2-(1H-imidazol-1-yl)-4-methylpyrimidin-4-yl]-N-(3-butoxypropyl)piperidine-2-acetamide;
1-[2-(1H-imidazol-1-yl)-6-methylethylpyrimidin-4-yl]-N-[2-(thiophen-2-yl)ethyl]piperidine-2-acetamide;
1-[2-(1H-imidazol-1-yl)-6-methylpyrimidin-4-yl]-N-[2-(thiophen-2-yl)ethyl]piperidine-2-acetamide;
1-[2-(1H-imidazol-1-yl)-6-methylethylpyrimidin-4-yl]-N-[3-(pyrrolidin-1-yl)propyl]piperidine-2-acetamide;
1-2-(1H-imidazol-1-yl)-6-methylethylpyrimidin-4-yl]-N-[(cyclohexyl)methyl]piperidine-2-acetamide;
1-[2-(1H-imidazol-1-yl)pyrimidin-4-yl]-N-[(cyclohexyl)methyl]piperidine-2-acetamide;
1-[2-(1H-imidazol-1-yl)-6-methylpyrimidin-4-yl]-N-[(4-fluorophenyl)methyl]piperidine-2-acetamide;
N-[(1,3-benzodioxol-5-yl)methyl]-1-[3-(1H-imidazol-1-yl)phenyl]piperidine-2-acetamide;
N-[(1,3-benzodioxol-5-yl)methyl]-1-chloro-5-(1H-imidazol-1-yl)triazin-1-yl]piperidine-2-acetamide;
N-[(1,3-benzodioxol-5-yl)methyl]-1-[6-(1H-imidazol-1-yl)pyrazin-2-yl]piperidine-2-acetamide;
N-[(1,3-benzodioxol-5-yl)methyl]-1-[6-(morpholin-4-yl)-2-(1H-imidazol-1-yl)pyrimidin-4-yl]piperidine-2-acetamide;
1-[6-chloro-2-(1H-imidazol-1-yl)pyrimidin-4-yl]-N-[2-(3,4-dimethoxyphenyl)ethyl]pyrrolidine-2-carboxamide;
1-[6-chloro-2-(1H-imidazol-1-yl)pyrimidin-4-yl]-4-hydroxy-N-[4-(hydroxycarbonyl)phenyl]methyl]pyrrolidine-2-carboxamide;
N-[(3,4-dimethoxyphenyl)methyl]-1-[2-(1H-imidazol-1-yl)pyrimidin-4-yl]pyrrolidine-2-carboxamide;
N-[2-(3,4-dimethoxyphenyl)ethyl]-1-[2-(1H-imidazol-1-yl)pyrimidin-4-yl]pyrrolidine-2-acetamide;
N-[(1,3-benzodioxol-5-yl)methyl]-1-[2-(1H-imidazol-1-yl)pyrimidin-4-yl]pyrrolidine-2-acetamide;
N-[2-(1,3-benzodioxol-5-yl)ethyl]-1-[2-(1H-imidazol-1-yl)pyrimidin-4-yl]pyrrolidine-2-carboxamide;
N-[(1,3-benzodioxol-5-yl)methyl]-1-[2-(1H-imidazol-1-yl)-6-methylpyrimidin-4-yl]pyrrolidine-2-acetamide;
N-[(1,3-benzodioxol-5-yl)methyl]-1-[2-(1H-imidazol-1-yl)-6-(methylethyl)pyrimidin-4-yl]pyrrolidine-2-acetamide;
N-[(3-chloro-4-methoxyphenyl)methyl]-1-[2-(1H-imidazol-1-yl)pyrimidin-4-yl]pyrrolidine-2-acetamide;
N-[(3-chloro-4-methoxyphenyl)ethyl]-1-[2-(1H-imidazol-1-yl)-6-ethylpyrimidin-4-yl]pyrrolidine-2-carboxamide;
N-[(3,4-dihydroxyphenyl)ethyl-1-[2-(1H-imidazol-1-yl)-6-methylpyrimidin-4-yl]pyrrolidine-2-carboxamide;
N-octyl-1-[2-(1H-imidazol-1-yl)-6-methylpyrimidin-4-yl]pyrrolidine-2-carboxamide;
N-(phenylpropyl)-1-[2-(1H-imidazol-1-yl)-6-methylpyrimidin-4-yl]pyrrolidine-2-carboxamide;
N-[(pyridin-3-yl)ethyl]-1-[2-(1H-imidazol-1-yl)-6-methylpyrimidin-4-yl]pyrrolidine-2-carboxamide;
N-[(morpholin-4-yl)ethyl]-1-[2-(1H-imidazol-1-yl)-6-methylpyrimidin-4-yl]pyrrolidine-2-carboxamide;
1-[2-(1H-imidazol-1-yl)-6-methylpyrimidin-4-yl]-N-[2-1,4-benzodioxan-4-yl)ethyl]pyrrolidine-2-carboxamide;
1-[2-(1H-imidazol-1-yl)pyrimidin-4-yl]-N-[2-(1,4-benzodioxan-6-yl)ethyl]pyrrolidine-2-carboxamide;
1-2-(1H-imidazol-1-yl)-6-methylpyrimidin-4-yl]-N-[(4-methoxyphenyl)ethyl]pyrrolidine-2-carboxamide;
1-[2-(1H-imidazol-1-yl)pyrimidin-4-yl]-N-[2-(3-methoxyphenyl)ethyl]pyrrolidine-2-carboxamide;

1-[2-(1H-imidazol-1-yl)pyrimidin-4-yl]-N-[2-(3,4-dimethoxyphenyl)ethyl]pyrrolidine-2-carboxamide;
1-[2-(1H-imidazol-1-yl)pyrimidin-4-yl]-N-[2-(4-ethoxyphenyl)ethyl]pyrrolidine-2-carboxamide;
1-[2-(1H-imidazol-1-yl)pyrimidin-4-yl]-N-[2-(4-bromophenyl)ethyl]pyrrolidine-2-carboxamide;
1-[2-(1H-imidazol-1-yl)pyrimidin yl]-N-[2-(3-ethoxy-4-methoxyphenyl)ethyl]pyrrolidine-2-carboxamide;
1-[2-(1H-imidazol-1-yl)pyrimidin-4-yl]-N-[2-(2,5-dimethoxyphenyl)ethyl]pyrrolidine-2-carboxamide;
1-[2-(1H-imidazol-1-yl)pyrimidin-4-yl]-N-[2-(4-ethoxy-3-methoxyphenyl)ethyl]pyrrolidine-2-carboxamide;
1-[2-(1H-imidazol-1-yl)pyrimidin-4-yl]-N-[2-(4-methoxyphenyl)ethyl]pyrrolidine-2-carboxamide;
1-[2-(1H-imidazol-1-yl)pyrimidin-4-yl]-N-[2-(3-bromo-4-methoxyphenyl)ethyl]pyrrolidine-2-carboxamide;
N-[2-(1,3-benzodioxol-5-yl)ethyl]-1-[2-(1H-imidazol-1-yl)pyrimidin-4-yl]pyrrolidine-2-propionamide;
N-[2-(1,3-benzodioxol-5-yl)ethyl]-1-[2-(1H-imidazol-1-yl)-6-methylpyrimidin-4-yl]pyrrolidine-2-propionamide;
N-[2-(3,4-dimethoxyphenyl)ethyl]-1-[2-(1H-imidazol-1-yl)pyrimidin-4-yl]pyrrolidine-3-carboxamide;
N-[2-(3,4-dimethoxyphenyl)ethyl]-1-[2-(1H-imidazol-1-yl)-6-methylpyrimidin-4-yl]pyrrolidine-3-carboxamide;
N-[2-(3,4-dimethoxyphenyl)ethyl]-1-[2-(1H-imidazol-1-yl)pyrimidin-4-yl]pyrrolidine-3-acetamide;
4-[2-[[4-(methoxy)phenoxy]propyl]pyrrolidin-1-yl]-2-(1H-imidazol-1-yl)pyrimidine;
4-[2-[[4-(methoxy)phenoxy]propyl]pyrrolidin-1-yl]-2-(1H-imidazol-1-yl)-6-methylpyrimidine;
4-[2-[(1,3-benzodioxol-5-yl)propyl]pyrrolidin-1-yl]-2-(1H-imidazol-1-yl)pyrimidine;
4-[2-[(1,3-benzodioxol-5-yl)prop-2-enyl]pyrrolidin-1-yl]-2-(1H-imidazol-1-yl)pyrimidine;
N-[2-(3,4-dimethoxyphenyl)ethyl]-1-[2-(1H-imidazol-1-yl)-6-methylpyrimidin-4-yl]pyrrolidine-3-acetamide;
N-[2-(3,4-dimethoxyphenyl)ethyl]-1-[2-(1H-imidazol-1-yl)-6-ethylpyrimidin-4-yl]pyrrolidine-3-acetamide;
4-[2-(1H-imidazol-1-yl)pyrimidin-4-yl]-N-[(1,3-benzodioxol-5-yl)ethyl]morpholine-2-carboxamide;
4-[2-(1H-imidazol-1-yl)-6-methylprimidin-4-yl]-N-[(4-methoxyphenyl)ethyl]-thiomorpholine-2-acetamide;
N-[(1,3-dioxolan-5-yl)methyl]-1-[2-(1H-imidazol-1-yl)pyrimidin-4-yl]perhydroazepine-2-acetamide;
N-[(3,4-dimethoxyphenyl)ethyl]-1-[2-(1H-imidazol-1-yl)-6-methylpyrimidin-4-yl]azetidine-2-carboxamide;
4-[2-(1H-imidazol-1-yl)pyrimidin-4-yl]-N-[(1,4-benzodioxan-6-yl)ethyl]morpholine-2-carboxamide;
4-[2-(1H-imidazol-1-yl)-6-methylpyrimidin-4-yl]-N-[2-(1,3-benzodioxol-5-yl)ethyl]thiomorpholine-2-acetamide;
N-[(1,3-benzodioxol-5-yl)methyl]-1-[2-(1H-imidazol-1-yl)pyrimidin-4-yl]indole-6-carboxamide;
N-[2-(1,3-benzodioxol-5-yl)ethyl]-1-[2-(1H-imidazol-1-yl)pyrimidin-4-yl]pyrrole-2-carboxamide;
N-[2-(3,4-dimethoxyphenyl)ethyl]-2-[2-(1H-imidazol-1-yl)pyrimidin-4-yl]-1,2,3,4-tetrahydroisoquinoline-3-carboxamide;
4-[2-(1H-imidazol-1-yl)-6-methylpyrimidin-4-yl]-N-[2-(1,3-benzodioxol-5-yl)ethyl]morpholine-2-carboxamide;
4-[2-(1H-imidazol-1-yl)-6-methylpyrimidin-4-yl]-N-[2-(1,4-benzodioxan-6-yl)ethyl]morpholine-2-carboxamide;
4-[2-(1H-imidazol-1-yl)pyrimidin-4-yl]-N-[(4-methoxyphenyl)ethyl]morpholine-2-carboxamide;
4-[2-(1H-imidazol-1-yl)-6-methylpyrimidin-4-yl]-N-[(4-methoxyphenyl)ethyl]morpholine-2-carboxamide;
4-[2-(1H-imidazol-1-yl)pyrimidin-4-yl]-N-[2-(3,4-dimethoxyphenyl)ethyl]morpholine-2-carboxamide;
4-[2-(1H-imidazol-1-yl)-6-methylpyrimidin-4-yl]-N-[2-(3,4-dimethoxyphenyl)ethyl]morpholine-2-carboxamide;
4-[2-(1H-imidazol-1-yl)pyrimidin-4-yl]-N-[(4-methoxyphenyl)methyl]morpholine-2-carboxamide;
4-[2-(1H-imidazol-1-yl)-6-methylpyrimidin-4-yl]-N-[(4-methoxyphenyl)methyl]morpholine-2-carboxamide;
4-[2-(1H-imidazol-1-yl)pyrimidin-4-yl]-N-[(1,3-benzodioxol-5-yl)methyl]morpholine-2-acetamide;
4-[2-(1H-imidazol-1-yl)-6-methylpyrimidin-4-yl]-N-[(1,3-benzodioxol-5-yl)methyl]morpholine-2-acetamide;
N-[(1,3-benzodioxol-5-yl)methyl]-4-[2-(1H-imidazol-1-yl)pyrimidin-4-yl]morpholine-3-carboxamide;
N-[(1,3-benzodioxol-5-yl)methyl]-4-[2-(1H-imidazol-1-yl)-6-(methylethyl)pyrimidin-4-yl]morpholine-3-carboxamide;
N-[2-(1,3-benzodioxol-5-yl)ethyl]-4-[6-ethyl-2-(1H-imidazol-1-yl)pyrimidin-4-yl]morpholine-3-carboxamide;
N-[2-(1,3-benzodioxol-5-yl)ethyl]-4-[2-(1H-imidazol-1-yl)pyrimidin-4-yl]morpholine-3-carboxamide;
N-[(4-methoxyphenyl)methyl]-4-[2-(1H-imidazol-1-yl)-methylpyrimidin-4-yl]morpholine-3-carboxamide;
N-[(4-chlorophenyl)methyl]-4-[2-(1H-imidazol-1-yl)-6-methylpyrimidin-4-yl]morpholine-3-carboxamide;
N-[(3,4-dichlorophenyl)methyl]-4-[2-(1H-imidazol-1-yl)-6-methylpyrimidin-4-yl]morpholine-3-carboxamide;
N-[(4-methylphenyl)methyl]-4-[2-(1H-imidazol-1-yl)-6-methylpyrimidin-4-yl]morpholine-3-carboxamide;
N-[(3,4-dimethylphenyl)methyl]-4-[2-(1H-imidazol-1-yl)-6-methylpyrimidin-4-yl]morpholine-3-carboxamide;
N-[(1,3-benzodioxol-5-yl)methyl]-1-[2-(1H-imidazol-1-yl)pyrimidin-4-yl]perhydroazepine-2-carboxamide;
N-[(1,3-benzodioxol-5-yl)methyl]-1-[2-(1H-imidazol-1-yl)-6-methylpyrimidin-4-yl]perhydroazepine-2-carboxamide;
N-[(1,3-benzodioxol-5-yl)methyl]-1-[2-(1H-imidazol-1-yl)-6-(methylethyl)pyrimidin-4-yl]perhydroazepine-2-carboxamide;
N-[(1,4-benzodioxan-6-yl)methyl]-1-[2-(1H-imidazol-1-yl)pyrimidin-4-yl]perhydroazepine-2-carboxamide;
N-[(1,4-benzodioxan-6-yl)methyl]-1-[2-(1H-imidazol-1-yl)-6-methylpyrimidin-4-yl]perhydroazepine-2-carboxamide;
N-[2-(1,3-benzodioxol-5-yl)ethyl]-1-[2-(1H-imidazol-1-yl)pyrimidin-4-yl]perhydroazepine-2-carboxamide;
N-[2-(1,3-benzodioxol-6-yl)ethyl]-1-[2-(1H-imidazol-1-yl)-6-methylpyrimidin-4-yl]perhydroazepine-2-carboxamide;
N-[2-(1,3-benzodioxol-5-yl)ethyl]-1-[2-(1H-imidazol-1-yl)-6-ethylpyrimidin-4-yl]perhydroazepine-2-carboxamide;
N-[2-(1,3-benzodioxol-5-yl)ethyl]-1-[6-chloro-2-(1H-imidazol-1-yl)pyrimidin-4-yl]perhydroazepine-2-carboxamide;
N-[2-(1,4-benzodioxan-6-yl)ethyl]-1-[2-(1H-imidazol-1-yl)pyrimidin-4-yl]perhydroazepine-2-carboxamide;
N-[2-(1,4-benzodioxan-6-yl)ethyl]-1-[2-(1H-imidazol-1-yl)-6-methylpyrimidin-4-yl]perhydroazepine-2-carboxamide;
N-[2-(3,4-dimethoxyphenyl)ethyl]-1-[2-(1H-imidazol-1-yl)pyrimidin-4-yl]perhydroazepine-2-carboxamide;
N-[2-(3,4-dimethoxyphenyl)ethyl]-1-[2-(1H-imidazol-1-yl)-6-methylpyrimidin-4-yl]perhydroazepine-2-carboxamide;
N-[2-(3,4-dimethoxyphenyl)ethyl]-1-[2-(1H-imidazol-1-yl)-6-ethylpyrimidin-4-yl]perhydroazepine-2-carboxamide;

N-[(3,4-dimethoxyphenyl)methyl]-1-[2-(1H-imidazol-1-yl)-6-(methylethyl)pyrimidin-4-yl]perhydroazepine-2-carboxamide;
N-[2-(3,4-dimethoxyphenyl)ethyl]-1-[6-chloro-2-(1H-imidazol-1-yl)pyrimidin-4-yl]perhydroazepine-2-carboxamide;
N-[(1,3-benzodioxol-5-yl)methyl]-1-[2-(1H-imidazol-1-yl)pyrimidin-4-yl]perhydroazepine-2-acetamide;
N-[(1,3-benzodioxol-5-yl)methyl]-1-[2-(1H-imidazol-1-yl)-6-methylpyrimidin-4-yl]perhydroazepine-2-acetamide;
N-[(1,3-benzodioxol-5-yl)methyl]-1-[2-(1H-imidazol-1-yl)-6-ethylpyrimidin-4-yl]perhydroazepine-2-acetamide;
N-[(1,4-benzodioxan-6-yl)methyl]-1-[2-(1H-imidazol-1-yl)pyrimidin-4-yl]perhydroazepine-2-acetamide;
N-[(1,4-benzodioxan-6-yl)methyl]-1-[2-(1H-imidazol-1-yl)-6-methylpyrimidin-4-yl]perhydroazepine-2-acetamide;
N-[(3,4-dimethoxyphenyl)methyl]-1-[2-(1H-imidazol-1-yl)-6-methylpyrimidin-4-yl]perhydroazepine-2-acetamide;
N-[(3,4-dimethoxyphenyl)methyl]-1-[2-(1H-imidazol-1-yl)-6-(methylethyl)pyrimidin-4-yl]perhydroazepine-2-acetamide;
N-[2-(3,4-dimethoxyphenyl)ethyl]-1-[2-(1H-imidazol-1-yl)-6-methylpyrimidin-4-yl]perhydroazepine-2-acetamide;
N-[2-(3,4-dimethoxyphenyl)ethyl]-1-[2-(1 H-imidazol-1-yl)-6-(methylethyl)pyrimidin-4-yl]perhydroazepine-2-acetamide;
N-[(4-methoxyphenyl)methyl]-1-[2-(1H-imidazol-1-yl)pyrimidin-4-yl]perhydroazepine-2-acetamide;
N-[(4-methoxyphenyl)methyl]-1-[2-(1H-imidazol-1-yl)-6-methylpyrimidin-4-yl]perhydroazepine-2-acetamide;
N-[(4-trifluoromethoxyphenyl)methyl]-1-[2-(1H-imidazol-1-yl)pyrimidin-4-yl]perhydroazepine-2-acetamide;
N-[(4-trifluoromethoxyphenyl)methyl]-1-[2-(1H-imidazol-1-yl)-6-methylpyrimidin-4-yl]perhydroazepine-2-acetamide;
2-[[2-(1H-imidazol-1-yl)-6-methylpyrimidin-4-yl]amino]-N-[(4-chlorophenyl)ethyl]pyridine-3-propanamide;
4-chloro-2-(1H-imidazol-1-yl)-6-(perhydroazepin-1-yl)pyrimidine;
2,4-bis(1H-imidazol-1-yl)-6-methylpyrimidine;
N-[(3,4-dimethoxyphenyl)ethyl]-6-[2-(1H-imidazol-1-yl)pyrimidin-4-yl]-N-methyl-5,6,7,8,-tetrahydropyrido[5,6-c]pyrimidine-4-amine;
2-[2-(1H-imidazol-1-yl)-6-methylpyrimidin-4-yl]-N-[(1,4-benzodioxan-6-yl)ethyl]isoquinoline-3carboxamide; and
4-chloro-2-(1H-imidazol-1-yl)-6-[(2-methoxyphenyl)amino]pyrimidine.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of formula (Vb):

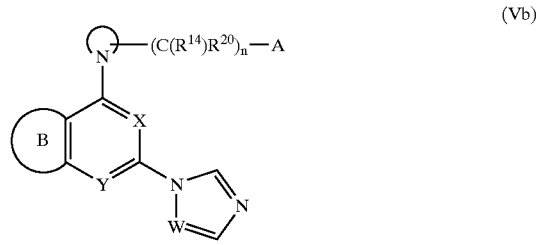

(Vb)

wherein B is a fused imidazolyl; and wherein:
A is $-R^1$, $-OR^1$, $-C(O)N(R^1)R^2$, $-P(O)[N(R^1)R^2]_2$, $-N(R^1)C(O)R^2$, $-N(R^{16})C(O)OR^2$, $-N(R^1)R^{21}$, $-N(R^{16})C(O)N(R^1)R^{16}$, $-S(O)_tR^1$, $-SO_2NHC(O)R^1$, $-N(R^1)SO_2R^{22}$, $-SO_2N(R^1)H$, $-C(O)NHSO_2R^{22}$, or $-CH=NOR^1$;
each X and Y are N;
each W is N or CH;
n is zero or an integer from 1 to 3;
t is zero, one or two;

is an optionally substituted N-heterocyclyl;
each $R^1$ and $R^2$ are independently chosen from the group consisting of hydrogen, optionally substituted $C_1$–$C_{20}$ alkyl, optionally substituted cycloalkyl, $-[C_0$–$C_8$ alkyl]$-R^9$, $-[C_2$–$C_8$ alkenyl]$-R^9$, $-[C_2$–$C_8$ alkynyl]$-R^9$, $-[C_2$–$C_8$ alkyl]$-R^{10}$ (optionally substituted by hydroxy), $-[C_1$–$C_8]-R^{11}$ (optionally substituted by hydroxy), and optionally substituted heterocyclyl;
or $R^1$ and $R^2$ together with the nitrogen atom to which they are attached is an optionally substituted N-heterocyclyl;
$R^9$ is chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);
each $R^{10}$ is independently chosen from the group consisting of halo, alkoxy, optionally substituted aryloxy, optionally substituted aralkoxy, optionally substituted $-S(O)_t-R^{22}$, acylamino, amino, monoalkylamino, dialkylamino, (triphenylmethyl)amino, hydroxy, mercapto, and alkylsulfonamido;
each $R^{11}$ is independently chosen from the group consisting of cyano, di(alkoxy)alkyl, carboxy, alkoxycarbonyl, aminocarbonyl, monoalkylaminocarbonyl and dialkylaminocarbonyl;
each $R^{14}$, and $R^{20}$ are independently hydrogen or alkyl;
each $R^{16}$ is independently hydrogen, alkyl, optionally substituted aryl, optionally substituted aralkyl or cycloalkyl;
each $R^{21}$ is independently hydrogen, alkyl, cycloalkyl, optionally substituted aryl, optionally substituted aralkyl, $-C(O)R^{22}$ or $-SO_2R^{22}$;
or $R^{21}$ taken together with $R^1$ and the nitrogen to which they are attached is an optionally substituted N-heterocyclyl;

or R²¹ taken together with R¹⁶ and the nitrogen to which they are attached is an optionally substituted N-heterocyclyl;
each R²² is independently alkyl, cycloalkyl, optionally substituted aryl or optionally substituted aralkyl; and as a single stereoisomer or mixture thereof, or a pharmaceutically acceptable salt thereof.

2. The compound of claim 1 wherein each W is CH.
3. The compound of claim 2 of the formula (Vba):

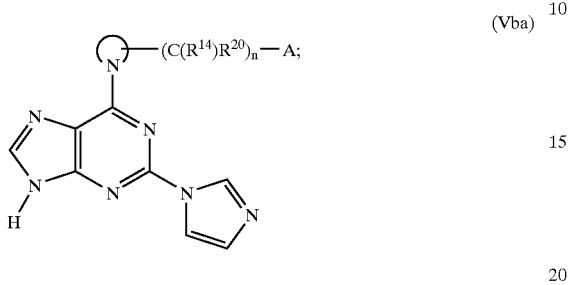

where A is —OR¹, —C(O)N(R¹)R², —N(R¹⁶)C(O)N(R¹)R¹⁶, —NR¹C(O)R² or —N(R¹)R²¹; and

is an N-heterocyclyl selected from group consisting of piperidinyl, piperazinyl, pyrrolidinyl or morpholinyl.

4. The compound of claim 3, i.e., N-[(1,3-benzodioxol-5-yl)methyl]-1-[2-(1H-imidazol-1-yl)purin-6-yl]piperidine-2-acetamide.

5. A compound of formula (Va):

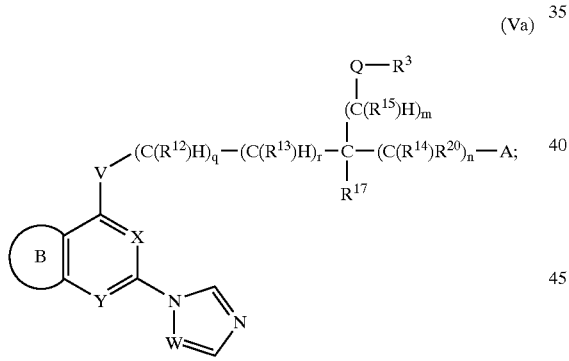

wherein B is a fused optionally substituted imidazolyl; and wherein:
A is —R¹, —OR¹, —C(O)N(R¹)R², —P(O)[N(R¹)R²]₂, —N(R¹)C(O)R², —N(R¹⁶)C(O)OR², —N(R¹)R²¹, —N(R¹⁶)C(O)N(R¹)R¹⁶, —S(O)ₜR¹, —SO₂NHC(O)R¹, —N(R¹)SO₂R²², —SO₂N(R¹)H, —C(O)NHSO₂R²², or —CH=NOR¹;
each X and Y are N;
V is N(R⁴), S, O or C(R⁴)H;
each W is N or OH;
Q is chosen from the group consisting of a direct bond, —C(O)—, —O—, —C(=N-R¹)—, —S(O)ₜ, and —N(R⁶)—;
m is zero or an integer from 1 to 4;
n is zero or an integer from 1 to 3;
q is zero or one;
r is zero or one, provided that when Q and V are heteroatoms, m, q, and r cannot all be zero; when A is —OR¹, —N(R¹)C(O)R², —N(R¹⁸)C(O)OR², —N(R¹)R²¹, —N(R¹⁶)C(O)N(R¹)R¹⁶, —S(O)ₜR¹ (where t is zero), or —N(R¹)SO₂R²², n, q, and r cannot all be zero; and when Q is a heteroatom and A is —OR¹, —N(R¹)C(O)R², —N(R¹⁸)C(O)OR², —N(R¹⁶)C(O)N(R¹)R¹⁶, —S(O)ₜR¹ (when t is zero) or —N(R¹)SO₂R²², m and n cannot both be zero;
t is zero, one or two;
each R¹ and R² are independently chosen from the group consisting of hydrogen, optionally substituted C₁–C₂₀ alkyl, optionally substituted cycloalkyl, —[C₀–C₈ alkyl]—R⁹, —[C₂–C₈ alkenyl]—R⁹, —[C₂–C₈ alkynyl]—R⁹, —[C₂–C₈ alkyl], R¹⁰ (optionally substituted by hydroxy), —[C₁–C₈]—R¹¹ (optionally substituted by hydroxy), and optionally substituted heterocyclyl;
or R¹ and R² together with the nitrogen atom to which they are attached is an optionally substituted N-heterocyclyl;
R³ is chosen from the group consisting of hydrogen, alkyl, cycloalkyl, optionally substituted aryl, —[C₂–C₈ alkyl]—R¹⁰, —[C₁–C₈ alkyl]—R¹¹, and heterocyclyl (optionally substituted by one or more substituents selected from the group consisting of halo, alkyl, alkoxy and imidazolyl);
or when Q is —N(R⁶)—or a direct bond to R³, R³ may additionally be aminocarbonyl, alkoxycarbonyl, alkylsulfonyl, monoalkylaminocarbonyl, dialkylaminocarbonyl and —C(=NR¹⁸)—NH₂;
or —Q—R³ taken together represents —C(O)OH, —C(O)N(R¹)R², —C(=NH)—N(r¹)R² or

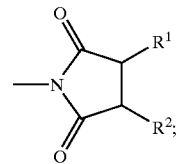

R⁴ is chosen from the group consisting of hydrogen, alkyl, aryl, aralkyl and cycloalkyl;
provided that when A is —R¹or —OR¹, R⁴ cannot be hydrogen, and when V is CH, R⁴ may additionally be hydroxy;
R⁶ is chosen from the group consisting of hydrogen, alkyl, cycloalkyl, —[C₁–C₈ alkyl]-R⁸, alkoxycarbonyl, optionally substituted aryloxycarbonyl, optionally substituted aralkoxycarbonyl, alkylsulfonyl, optionally substituted aryl, optionally substituted heterocyclyl, alkoxycarbonylalkyl, carboxyalkyl, optionally substituted arylsulfonyl, aminocarbonyl, monoalkylaminocarbonyl, dialkylaminocarbonyl, optionally substituted arylaminocarbonyl, aminosulfonyl, monoalkylaminosulfonyl, dialkylaminosulfonyl, arylaminosulfonyl, arylsulfonylaminocarbonyl, optionally substituted N-heterocyclyl, —C(=NH)—N(CN)R¹, —C(O)—R²³ —N(R¹)R², —C(O)—R²³ —N(R¹)C(O)-R²³ —N(R¹)R², and —C(O)—N(R¹)—R²³ —C(O)OR¹;
each R⁸ and R⁹ are independently chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each $R^{10}$ is independently chosen from the group consisting of halo, alkoxy, optionally substituted aryloxy, optionally substituted aralkoxy, optionally substituted —S(O)$_t$—R$^{22}$, acylamino, amino, monoalkylamino, dialkylamino, (triphenylmethyl) amino, hydroxy, mercapto, and alkylsulfonamido;

each $R^{11}$ is independently chosen from the group consisting of cyano, di(alkoxy)alkyl, carboxy, alkoxycarbonyl, aminocarbonyl, monoalkylaminocarbonyl and dialkylaminocarbonyl; each $R^{12}$, $R^{13}$, $R^{14}$, $R^{15}$, $R^{17}$, and $R^{20}$ are independently hydrogen or alkyl;

each $R^{16}$ is independently hydrogen, alkyl, optionally substituted aryl, optionally substituted aralkyl or cycloalkyl;

$R^{18}$ is hydrogen, NO$_2$, or toluenesulfonyl;

each $R^{21}$ is independently hydrogen, alkyl, cycloalkyl, optionally substituted aryl, optionally substituted aralkyl, —C(O)R$^{22}$ or —SO$_2$R$^{22}$;

or $R^{21}$ taken together with $R^1$ and the nitrogen to which they are attached is an optionally substituted N-heterocyclyl;

or $R^{21}$ taken together with $R^{16}$ and the nitrogen to which they are attached is an optionally substituted N-heterocyclyl;

each $R^{22}$ is independently alkyl, cycloalkyl, optionally substituted aryl or optionally substituted aralkyl; and $R^{23}$ is an amino acid residue; as a single stereoisomer or mixture thereof, or a pharmaceutically acceptable salt thereof.

6. A compound of formula (Vc):

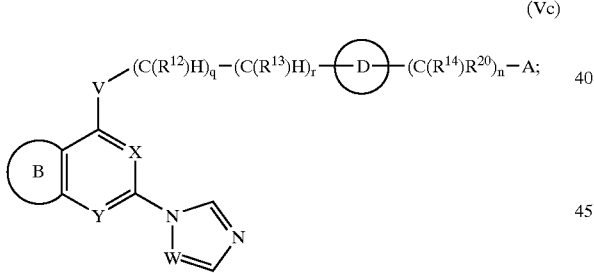

(Vc)

wherein B is a fused optionally substituted imidazolyl; and wherein:

A is —R$^1$, —OR$^1$, —C(O)N(R$^1$)R$^2$, —P(O)[N(R$^1$)R$^2$]$_2$, —N(R$^1$)C(O)R$^2$, —N(R$^{16}$)C(O)OR$^2$, —N(R$^1$)R$^{21}$, —N(R$^{16}$)C(O)N(R$^1$)R$^{16}$, —S(O)$_t$R$^1$, —SO$_2$NHC(O)R$^1$, —N(R$^1$)SO$_2$R$^{22}$, —SO$_2$N(R$^1$)H, —C(O)NHSO$_2$R$^{22}$, or —CH=NOR$^1$;

each X and Y are N;

V is S, O or C(R$^4$)H;

each W is N or CH;

n is zero or an integer from 1 to 3;

q is zero or one;

r is zero or one, provided that when V is a heteroatom, q and r cannot both be zero; and when A is —OR$^1$, —N(R$^1$)C(O)R$^2$, —N(R$^{18}$)C(O)OR$^2$, —N(R$^1$)R$^{21}$, —N(R$^{16}$)C(O)N(R$^1$)R$^{16}$, —S(O)$_t$R$^1$ (where t is zero), or —N(R$^1$)SO$_2$R$^{22}$, n, q, and r cannot all be zero;

t is zero, one or two;

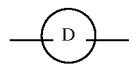

is an optionally substituted carbocyclyl or optionally substituted N-heterocyclyl;

each $R^1$ and $R^2$ are independently chosen from the group consisting of hydrogen, optionally substituted $C_1$–$C_{20}$ alkyl, optionally substituted cycloalkyl, —[$C_{0-C8}$ alkyl]—R$^9$, —[$C_2$–$C_8$ alkenyl]—R$^9$, —[$C_2$–$C_8$ alkynyl]—R$^9$, —[$C_2$–$C_8$ alkyl]—R$^{10}$ (optionally substituted by hydroxy), -[$C_1$–$C_8$]–R$^{11}$ (optionally substituted by hydroxy), and optionally substituted heterocyclyl;

or $R^1$ and $R^2$ together with the nitrogen atom to which they are attached is an optionally substituted N-heterocyclyl;

$R^4$ is chosen from the group consisting of hydrogen, alkyl, aryl, aralkyl and cycloalkyl; provided that when A is —R$^1$ or —OR$^1$, R$^4$ cannot be hydrogen, and when V is OH, R$^4$ may additionally be hydroxy;

$R^9$ is chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each $R^{10}$ is independently chosen from the group consisting of halo, alkoxy, optionally substituted aryloxy, optionally substituted aralkoxy, optionally substituted —S(O)$_t$—R$^{22}$, acylamino, amino, monoalkylamino, dialkylamino, (triphenylmethyl)amino, hydroxy, mercapto, and alkylsulfonamido;

each $R^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each $R^{12}$, $R^{13}$, $R^{14}$, and $R^{20}$ are independently hydrogen or alkyl;

each $R^{16}$ is independently hydrogen, alkyl, optionally substituted aryl, optionally substituted aralkyl or cycloalkyl;

each $R^{21}$ is independently hydrogen, alkyl, cycloalkyl, optionally substituted aryl, optionally substituted aralkyl, —C(O)R$^{22}$ or —SO$_2$R$^{22}$;

or $R^{21}$ taken together with R$^1$ and the nitrogen to which they are attached is an optionally substituted N-heterocyclyl;

or $R^{21}$ taken together with R$^{16}$ and the nitrogen to which they are attached is an optionally substituted N-heterocyclyl; and each $R^{22}$ is independently alkyl, cycloalkyl, optionally substituted aryl or optionally substituted aralkyl;

as a single stereoisomer or mixture thereof, or a pharmaceutically acceptable salt thereof.

7. A compound of formula (Vc):

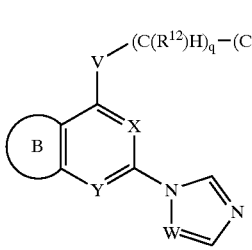

wherein B is a fused optionally substituted imidazolyl; and wherein:

A is —$R^1$, —$OR^1$, —$C(O)N(R^1)R^2$, —$P(O)[N(R^1)R^2]_2$, —$N(R^1)C(O)R^2$, —$N(R^{16})C(O)OR^2$, —$N(R^{16})C(O)N(R^1)R^{16}$, —$S(O)_tR^1$, —$SO_2NHC(O)R^1$, —$N(R^1)SO_2R^{22}$, —$SO_2N(R^1)H$, —$C(O)NHSO_2R^{22}$, or —$CH=NOR^1$;

each X and Y are N;
V is $N(R^4)$;
each W is N or CH;
n is zero or an integer from 1 to 3;
q is zero or one;
r is zero or one, provided that when V is a heteroatom, q and r cannot both be zero; and when A is —$OR^1$, —$N(R^1)C(O)R^2$, —$N(R^{16})C(O)OR^2$, —$N(R^1)R^{21}$, —$N(R^{16})C(O)N(R^1)R^{16}$, —$S(O)_tR^1$ (where t is zero), or —$N(R^1)SO_2R^{22}$, n, q, and r cannot all be zero;
t is zero, one or two;

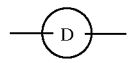

is an optionally substituted N-heterocyclyl;

each $R^1$ and $R^2$ are independently chosen from the group consisting of hydrogen, optionally substituted $C_1$-$C_{20}$ alkyl, optionally substituted cycloalkyl, —[$C_0$-$C_8$ alkyl]—$R^9$, —[$C_2$-$C_8$ alkenyl]—$R^9$, —[$C_2$-$C_8$ alkynyl]—$R^9$, —[$C_2$-$C_8$ alkyl]—$R^{10}$ (optionally substituted by hydroxy), —[$C_1$-$C_8$]—$R^{11}$ (optionally substituted by hydroxy), and optionally substituted heterocyclyl;

or $R^1$ and $R^2$ together with the nitrogen atom to which they are attached is an optionally substituted N-heterocyclyl;

$R^4$ is chosen from the group consisting of hydrogen, alkyl, aryl, aralkyl and cycloalkyl; provided that when A is —$R^1$ or —$OR^1$, $R^4$ cannot be hydrogen, and when V is CH, $R^4$ may additionally be hydroxy;

$R^9$ is chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each $R^{10}$ is independently chosen from the group consisting of halo, alkoxy, optionally substituted aryloxy, optionally substituted aralkoxy, optionally substituted —$S(O)_t$—$R^{22}$, acylamino, amino, monoalkylamino, dialkylamino, (triphenylmethyl) amino, hydroxy, mercapto, and alkylsulfonamido;

each $R^{11}$ is independently chosen from the group consisting of cyano, di(alkoxy)alkyl, carboxy, alkoxycarbonyl, aminocarbonyl, monoalkylaminocarbonyl and dialkylaminocarbonyl;

each $R^{12}$, $R^{13}$, $R^{14}$, and $R^{20}$ are independently hydrogen or alkyl;

each $R^{16}$ is independently hydrogen, alkyl, optionally substituted aryl, optionally substituted aralkyl or cycloalkyl;

each $R^{21}$ is independently hydrogen, alkyl, cycloalkyl, optionally substituted aryl, optionally substituted aralkyl, —$C(O)R^{22}$ or or $R^{21}$ taken together with $R^1$ and the nitrogen to which they are attached is an optionally substituted N-heterocyclyl;

or $R^{21}$ taken together with $R^{16}$ and the nitrogen to which they are attached is an optionally substituted N-heterocyclyl; and each $R^{22}$ is independently alkyl, cycloalkyl, optionally substituted aryl or optionally substituted aralkyl;

as a single stereoisomer or mixture thereof, or a pharmaceutically acceptable salt thereof.

8. A compound of formula (Vc):

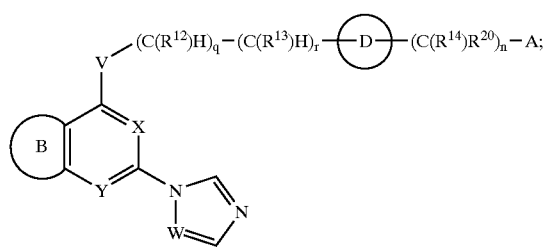

wherein B is a fused optionally substituted imidazolyl; and wherein:

A is —$R^1$, —$OR^1$, —$C(O)N(R^1)R^2$, —$P(O)[N(R^1)R^2]_2$, —$N(R^1)C(O)R^2$, —$N(R^{16})C(O)OR^2$, —$N(R^1)R^{21}$, —$N(R^{16})C(O)N(R^1)R^{16}$, —$S(O)_2R^1$, —$SO_2NHC(O)R^1$, —$N(R^1)SO_2R^{22}$, —$SO_2N(R^1)H$, —$C(O)NHSO_2R^{22}$, or —$CH=NOR^1$;

each X and Y are N;
V is $N(R^4)$;
each W is N or CH;
n is zero or an integer from 1 to 3;
q is zero or one;
r is zero or one, provided that when V is a heteroatom, q and r cannot both be zero; and when A is —$OR^1$, —$N(R^1)C(O)R^2$, —$N(R^{18})C(O)OR^2$, —$N(R^1)R^{21}$, —$N(R^{16})C(O)N(R^1)R^{16}$, —$S(O)_tR^1$ (where t is zero), or —$N(R^1)SO_2R^{22}$, n, q, and r cannot all be zero;
t is zero, one or two;

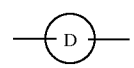

is an optionally substituted carbocyclyl;

each $R^1$ and $R^2$ are independently chosen from the group consisting of hydrogen, optionally substituted $C_1$-$C_{20}$ alkyl, optionally substituted cycloalkyl, —[$C_0$-$C_8$ alkyl]—$R^9$, —[$C_2$-$C_8$ alkenyl]—$R^9$, —[$C_2$-$C_8$ alkynyl]—$R^9$, —[$C_2$-$C_8$ alkyl]—$R^{10}$ (optionally substituted by hydroxy), —[$C_1$–$C_8$]—$R^{11}$ (optionally substituted by hydroxy), and optionally substituted heterocyclyl;

or $R^1$ and $R^2$ together with the nitrogen atom to which they are attached is an optionally substituted N-heterocyclyl;

$R^4$ is chosen from the group consisting of hydrogen, alkyl, aryl, aralkyl and cycloalkyl; provided that when A is —$R^1$ or —$OR^1$, $R^4$ cannot be hydrogen, and when V is CH, $R^4$ may additionally be hydroxy;

$R^9$ is chosen from the group consisting of haloalkyl, cycloalkyl (optionally substituted with halo, cyano, alkyl or alkoxy), carbocyclyl (optionally substituted with one or more substituents selected from the group consisting of halo, alkyl and alkoxy), and heterocyclyl (optionally substituted with alkyl, aralkyl or alkoxy);

each $R^{10}$ is independently chosen from the group consisting of halo, alkoxy, optionally substituted aryloxy, optionally substituted aralkoxy, optionally substituted —S(O)$_t$—$R^{22}$, acylamino, amino, monoalkylamino, dialkylamino, (triphenylmethyl)amino, hydroxy, mercapto, and alkylsulfonamido;

each $R^{11}$ is independently chosen from the group consisting of cyano, di(alkoxy)alkyl, carboxy, alkoxycarbonyl, aminocarbonyl, monoalkylaminocarbonyl and dialalxylaminocarbonyl;

each $R^{12}$, $R^{13}$, $R^{14}$, and $R^{20}$ are independently hydrogen or alkyl;

each $R^{16}$ is independently hydrogen, alkyl, optionally substituted aryl, optionally substituted aralkyl or cycloalkyl;

each $R^{21}$ is independently hydrogen, alkyl, cycloalkyl, optionally substituted aryl, optionally substituted aralkyl, —C(O)$R^{22}$ or —SO$_2R^{22}$;

or $R^{21}$ taken together with $R^1$ and the nitrogen to which they are attached is an optionally substituted N-heterocyclyl;

or $R^{21}$ taken together with $R^{16}$ and the nitrogen to which they are attached is an optionally substituted N-heterocyclyl; and each $R^{22}$ is independently alkyl, cycloalkyl, optionally substituted aryl or optionally substituted aralkyl; and as a single stereoisomer or mixture thereof, or a pharmaceutically acceptable salt thereof.

* * * * *